(12) United States Patent
Voronina et al.

(10) Patent No.: US 11,576,984 B2
(45) Date of Patent: Feb. 14, 2023

(54) GENETICALLY MODIFIED MOUSE WITH HUMANIZED IMMUNOGLOBULIN HEAVY CHAIN CONSTANT REGION GENES AND METHOD OF USING

(71) Applicant: Regeneron Pharmaceuticals, Inc., Tarrytown, NY (US)

(72) Inventors: Vera Voronina, Sleepy Hollow, NY (US); Corey Momont, White Plains, NY (US); John McWhirter, Hastings-on-Hudson, NY (US); Naxin Tu, Pleasantville, NY (US); Lynn MacDonald, Harrison, NY (US); Andrew J. Murphy, Croton-On-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 386 days.

(21) Appl. No.: 16/363,774

(22) Filed: Mar. 25, 2019

(65) Prior Publication Data
US 2019/0290783 A1    Sep. 26, 2019

Related U.S. Application Data

(60) Provisional application No. 62/689,628, filed on Jun. 25, 2018, provisional application No. 62/648,197, filed on Mar. 26, 2018.

(51) Int. Cl.
*A01K 67/027*    (2006.01)
*A61K 49/00*    (2006.01)

(52) U.S. Cl.
CPC ...... *A61K 49/0008* (2013.01); *A01K 67/0278* (2013.01); *A01K 2207/15* (2013.01); *A01K 2217/072* (2013.01); *A01K 2217/15* (2013.01); *A01K 2227/105* (2013.01); *A01K 2267/03* (2013.01)

(58) Field of Classification Search
CPC .......... A01K 67/0278; A01K 2217/072; A01K 2217/15; A01K 2227/105; A01K 2207/15
USPC .................................................. 800/8, 18, 3
See application file for complete search history.

(56) References Cited

U.S. PATENT DOCUMENTS

| | | | |
|---|---|---|---|
| 5,624,821 | A | 4/1997 | Winter et al. |
| 5,648,260 | A | 7/1997 | Winter et al. |
| 5,658,853 | A | 8/1997 | Kassebaum et al. |
| 5,731,168 | A | 3/1998 | Carter et al. |
| 5,770,429 | A | 6/1998 | Lonberg et al. |
| 5,807,706 | A | 9/1998 | Carter et al. |
| 5,814,318 | A | 9/1998 | Lonberg et al. |
| 5,821,333 | A | 10/1998 | Carter et al. |
| 5,859,312 | A | 1/1999 | Littman et al. |
| 5,877,396 | A | 3/1999 | Ravetch et al. |
| 6,111,166 | A | 8/2000 | van de Winkel |
| 6,114,598 | A | 9/2000 | Kucherlapati et al. |
| 6,294,347 | B1 | 9/2001 | Peltz et al. |
| 6,528,624 | B1 | 3/2003 | Idusogie et al. |
| 6,586,251 | B2 | 7/2003 | Economides et al. |
| 6,596,541 | B2 | 7/2003 | Murphy et al. |
| 6,676,927 | B1 | 1/2004 | Ravetch |
| 6,737,056 | B1 | 5/2004 | Presta |
| 6,998,514 | B2 | 2/2006 | Bruggemann |
| 7,105,348 | B2 | 9/2006 | Murphy et al. |
| 7,122,637 | B2 | 10/2006 | Presta |
| 7,183,387 | B1 | 2/2007 | Presta |
| 7,265,261 | B2 | 9/2007 | Takai et al. |
| 7,294,754 | B2 | 11/2007 | Poueymirou et al. |
| 7,297,775 | B2 | 11/2007 | Idusogie et al. |
| 7,309,810 | B2 | 12/2007 | Takai et al. |
| 7,317,091 | B2 | 1/2008 | Lazar et al. |

(Continued)

FOREIGN PATENT DOCUMENTS

| | | |
|---|---|---|
| EP | 2123754 A1 | 11/2009 |
| EP | 2 064 325 B1 | 12/2011 |

(Continued)

OTHER PUBLICATIONS

Macdonald (PNAS, 2014, vol. 111, No. 14, p. 5142-5153).*

(Continued)

*Primary Examiner* — Michael C Wilson

(74) *Attorney, Agent, or Firm* — Foley Hoag LLP; Brendan T. Jones; Mi Cai

(57) ABSTRACT

Provided herein are methods and compositions related to the in vivo testing of therapeutic agents comprising a human Fc in genetically modified rodents (e.g., the testing of the pharmacokinetic and/or pharmacodynamic properties of such a therapeutic agent in genetically modified rodents). In some embodiments the genetically modified rodents express antibodies comprising a human Fc (e.g., a human IgG1 Fc, a human IgG4 Fc). In some embodiments, the rodents express fully human antibodies (i.e., antibodies having human heavy chains and human light ($\gamma$ or $\kappa$) chains). In certain embodiments the genetically modified rodents comprise one or more Fc receptors with a human extracellular domain (e.g., a Neonatal Fc Receptor (FcRn), a $\beta$-2-microglobulin polypeptide ($\beta$2M), a Fc $\epsilon$ receptor 1$\alpha$ (Fc$\epsilon$R1$\alpha$), a Fc $\gamma$ receptor 1 alpha (Fc$\gamma$R1a), a Fc gamma receptor 2a (Fc$\gamma$R2a), a Fc gamma receptor 2b (Fc$\gamma$R2b), a Fc gamma receptor 3a (Fc$\gamma$R3a), a Fc gamma receptor 3b (Fc$\gamma$R3b), a Fc gamma receptor 2c (Fc$\gamma$R2c)). The transmembrane and cytoplasmic domain of such receptors can be human or non-human (e.g., rodent).

20 Claims, 24 Drawing Sheets

Specification includes a Sequence Listing.

(56) References Cited

U.S. PATENT DOCUMENTS

| | | |
|---|---|---|
| 7,332,581 B2 | 2/2008 | Presta |
| 7,351,875 B2 | 4/2008 | Hogarth et al. |
| 7,358,416 B2 | 4/2008 | Roopenian |
| 7,402,728 B2 | 7/2008 | Chan et al. |
| 7,579,170 B2 | 8/2009 | Beliard et al. |
| 7,632,497 B2 | 12/2009 | Stavenhagen |
| 7,642,228 B2 | 1/2010 | Carter et al. |
| 7,662,925 B2 | 2/2010 | Lazar et al. |
| 7,695,936 B2 | 4/2010 | Carter et al. |
| 7,713,524 B2 | 5/2010 | Bourel et al. |
| 7,754,482 B2 | 7/2010 | Riley et al. |
| 7,816,082 B2 | 10/2010 | Han et al. |
| 8,093,359 B2 | 1/2012 | Lazar et al. |
| 8,216,805 B2 | 7/2012 | Carter et al. |
| 8,232,449 B2 | 7/2012 | Tanamachi et al. |
| 8,388,955 B2 | 3/2013 | Lazar et al. |
| 8,502,018 B2 | 8/2013 | Murphy et al. |
| 8,642,835 B2 | 2/2014 | MacDonald et al. |
| 8,658,154 B2 | 2/2014 | MacDonald et al. |
| 8,658,853 B2 | 2/2014 | Macdonald et al. |
| 8,679,785 B2 | 3/2014 | Carter et al. |
| 8,697,940 B2 | 4/2014 | Macdonald et al. |
| 8,883,496 B2 | 11/2014 | MacDonald et al. |
| 8,912,385 B2 | 12/2014 | Meagher |
| 8,937,158 B2 | 1/2015 | Lazar et al. |
| 9,056,130 B2 | 6/2015 | Macdonald et al. |
| 9,089,599 B2 | 7/2015 | Macdonald et al. |
| 9,204,624 B2 | 12/2015 | McWhirter et al. |
| 9,221,894 B2 | 12/2015 | Macdonald et al. |
| 9,301,510 B2 | 4/2016 | McWhirter et al. |
| 9,334,334 B2 | 5/2016 | McWhirter et al. |
| 9,474,255 B2 | 10/2016 | Murphy et al. |
| 9,516,868 B2 | 12/2016 | Macdonald et al. |
| 9,546,384 B2 | 1/2017 | Frendewey et al. |
| 9,687,566 B2 | 6/2017 | Macdonald et al. |
| 9,738,877 B2 | 8/2017 | Schoenherr et al. |
| 9,930,871 B2 | 4/2018 | McWhirter et al. |
| 10,106,820 B2 | 10/2018 | Auerbach et al. |
| 10,251,377 B2 | 4/2019 | Clube |
| 2002/0088016 A1 | 7/2002 | Bruggemann |
| 2004/0154044 A1 | 8/2004 | Fraichard et al. |
| 2005/0054832 A1 | 3/2005 | Lazar et al. |
| 2006/0179501 A1 | 8/2006 | Chan et al. |
| 2006/0222653 A1 | 10/2006 | Abel et al. |
| 2006/0275282 A1 | 12/2006 | Moore et al. |
| 2006/0275283 A1 | 12/2006 | van Vlijmen et al. |
| 2007/0190063 A1 | 8/2007 | Bahjat et al. |
| 2008/0003225 A1 | 1/2008 | Vie et al. |
| 2008/0098490 A1 | 4/2008 | Jakobovits et al. |
| 2008/0125043 A1 | 5/2008 | Karmanenko et al. |
| 2008/0154025 A1 | 6/2008 | Lazar et al. |
| 2009/0042291 A1 | 2/2009 | Chu et al. |
| 2009/0053210 A1 | 2/2009 | Buelow |
| 2009/0098124 A1 | 4/2009 | Stavenhagen |
| 2010/0035280 A1 | 2/2010 | Kawai |
| 2011/0093963 A1 | 4/2011 | Buelow |
| 2011/0142857 A1 | 6/2011 | Melamed et al. |
| 2011/0154512 A1 | 6/2011 | Macdonald et al. |
| 2012/0073004 A1 | 3/2012 | MacDonald et al. |
| 2012/0167237 A1 | 6/2012 | Bradley et al. |
| 2012/0222140 A1 | 8/2012 | Kuroiwa et al. |
| 2013/0089541 A1 | 4/2013 | D'Angelo et al. |
| 2013/0096287 A1 | 4/2013 | Macdonald et al. |
| 2013/0108623 A1 | 5/2013 | D'Angelo et al. |
| 2013/0111616 A1 | 5/2013 | Macdonald et al. |
| 2013/0111617 A1 | 5/2013 | Macdonald et al. |
| 2013/0117873 A1 | 5/2013 | Wang et al. |
| 2013/0145484 A1 | 6/2013 | Logtenberg et al. |
| 2013/0185819 A1 | 7/2013 | Macdonald et al. |
| 2013/0185821 A1 | 7/2013 | Babb et al. |
| 2013/0195849 A1 | 8/2013 | Spreter Von Kreudenstein et al. |
| 2013/0198880 A1 | 8/2013 | Babb et al. |
| 2013/0247236 A1 | 9/2013 | McWhirter et al. |
| 2013/0326647 A1 | 12/2013 | Macdonald et al. |
| 2014/0013275 A1 | 1/2014 | Ochi et al. |
| 2014/0013456 A1 | 1/2014 | Mcwhirter et al. |
| 2014/0093908 A1 | 4/2014 | Ebi et al. |
| 2014/0134662 A1 | 5/2014 | Flavell et al. |
| 2014/0245466 A1 | 8/2014 | Macdonald et al. |
| 2014/0245467 A1 | 8/2014 | Macdonald et al. |
| 2014/0245468 A1 | 8/2014 | McWhirter et al. |
| 2014/0309487 A1 | 10/2014 | Lee et al. |
| 2015/0089678 A1 | 3/2015 | Murphy et al. |
| 2015/0143558 A1 | 5/2015 | McWhirter et al. |
| 2015/0282463 A1 | 10/2015 | Murphy et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0366174 A1 | 12/2015 | Burova et al. |
| 2016/0157469 A1 | 6/2016 | Burova et al. |
| 2016/0345549 A1 | 12/2016 | Gurer et al. |
| 2017/0086432 A1 | 3/2017 | Murphy et al. |
| 2017/0142943 A1 | 5/2017 | Mujica et al. |
| 2017/0164588 A1 | 6/2017 | Olson et al. |
| 2017/0332610 A1 | 11/2017 | Voronina et al. |
| 2018/0125043 A1 | 5/2018 | Guo et al. |
| 2018/0139940 A1 | 5/2018 | Macdonald et al. |
| 2019/0159436 A1 | 5/2019 | Mujica et al. |
| 2020/0154684 A1 | 5/2020 | Mujica et al. |

FOREIGN PATENT DOCUMENTS

| | | |
|---|---|---|
| EP | 3366125 A1 | 8/2018 |
| WO | WO-1995/028959 A1 | 11/1995 |
| WO | WO-9824893 A2 | 6/1998 |
| WO | WO-1999/000010 A2 | 1/1999 |
| WO | WO-02/06630 A1 | 1/2002 |
| WO | WO-2004060052 A2 | 7/2004 |
| WO | WO-2008/027986 A2 | 3/2008 |
| WO | WO-2008/028068 A2 | 3/2008 |
| WO | WO-2009076464 A2 | 6/2009 |
| WO | WO-2009/158696 A1 | 12/2009 |
| WO | WO-2011/072204 A1 | 6/2011 |
| WO | WO-2013/063346 A1 | 5/2013 |
| WO | WO-2013/144567 A1 | 10/2013 |
| WO | WO-2014/130690 A1 | 8/2014 |
| WO | WO-2015/157415 A1 | 10/2015 |
| WO | WO-2019/190990 A1 | 10/2019 |

OTHER PUBLICATIONS

Alevy, et al., "CD32A (FcgRIIA) mRNA expression and regulation in blood monocytes and cell lines," Mol Immunol, 29(11): 1289-1297 (1992).

Allen, et al., "Isolation and Expression of Functional High-Affinity Fc Receptor Complementary DNAs," Science, 243(4889): 378-381 (1989).

Amsbio: Fc receptor family proteins. Downloaded Sep. 2018.

Anderson, "Isolation of the receptor for IgG from a human monocyte cell line (U937) and from human peripheral blood monocytes," J Exp Med, 156(6): 1794-1805 (1982).

Anselmino, et al., "Human basophils selectively express the FcgRII (CDw32) subtype of IgG receptor," J Allergy Clin Immun, 84(6): 907-914 (1989).

Asaoka, et al., "The Binding of Soluble Recombinant Human FCY Receptor I for Human Immunoglobulin G is Conferred by Its First and Second Extracellular Domains," Mol Immunol, 29(11): 1407-1413 (1992).

Barnes, et al., "FcgRI-Deficient Mice Show Multiple Alterations to Inflammatory and Immune Responses," Immunity, 16(3): 379-389 (2002).

Bessa et al., "The immunogenicity of Antibody Aggregates in a Novel Transgenic Mouse Model," Pharmaceut Res 32(7):2344-2359 (2015).

Bi et al., "Development of a Human Antibody Tolerant Mouse Model to Assess the Immunogenicity Risk Due to Aggregated Biotherapeutics," J Pharmaceut Sci 102(10):3545-3555 (2013).

Binstadt et al., "IgG Fc Receptor Polymorphisms in human disease: Implications for Intravenous Immunoglobulin Therapy," J Allergy and Clinical Immun, 111(4): 697-703 (2003).

(56) References Cited

OTHER PUBLICATIONS

Bolland, "A Newly Discovered Fc Receptor that Explains IgG-lsotype Disparities in Effector Responses," Immunity, 23(1): 2-4 (2005).
Bonnerot, et al., "Role of B cell receptor Ig alpha and Ig beta subunits in MHC class II-restricted antigen presentation," Immunity, 3(3): 335-347 (1995).
Boros P. et al., "Fc Receptors" Encyclopedia of Life Sciences, pp. 1-8 (2008).
Breunis et al., "Copy Number Variation at the FCGR Locus Includes FCGR3A. FCGR2C and FCGR3B but not FCGR2A and FCGR2B," Human Mutation, 30(5):E640-650 (2009).
Brooks, et al., "Structure and expression of human IgG FcRII (CD32): Functional Heterogeneity Is Encoded by the Alternatively Spliced Products of Multiple Genes," J Exp Med, 170(4): 1369-1385 (1989).
Bruhns, "Properties of mouse and human IgG receptors and their contribution to disease models," Blood, 119(24): 5640-5649 (2012).
Cassatella, et al., "Fc gamma R (CD16) interaction with ligand induces Ca2+ mobilization and phosphoinositide turnover in human natural killer cells: Role of Ca2+ in FcgR(CD16)-induced transcription and expression of lymphokine genes," J Exp Med, 169(2): 549-567 (1989).
Chu et al., "Association of Fcgamma Receptor IIb Polymorphism with Susceptibility to Systemic Lupus Erythematosus in Chinese: A Common Susceptibility Gene in the Asian Populations," Tiger Antigens, 63(1): 21-27 (2004).
Coggeshall, "Inhibitory signaling by B cell Fc gamma RIIb," Curr Opini Immunol, 10(3): 308-312(1998).
Cohen-Solal, et al., "Fc gamma receptors," Immunol Lett, 92(3): 199-205 (2004).
Cowan et al., "Targeting gene expression to endothelium in transgenic animals: a comparision of the human ICAM-2, PECAM-1 and endoglin promoters," Xenotransplantation, 10: 223-231 (2003).
De Haas, "IgG-Fc receptors and the clinical relvance of their polymorphisms," Wiener Klinische Wochenschrift, 113(20-21): 825-831 (2001).
Deo, et al., "Clinical significance of IgG Fc receptors and Fc gamma R-directed immunotherapies," Immunol Today, 18(3): 127-135 (1997).
Deonarain, "Ligand-targeted receptor-mediated vectors for gene delivery," Expert Opin. Ther. Pat., 8:53-69 (1998).
Desjarlais, et al., "Optimizing engagement of the immune system by anti-tumor antibodies: an engineer's perspective," Drug Discov Today, 12(21-22): 898-910 (2007).
Desoize, "Antibodies in cancer treatment," Crit Rev Oncol Hematol, 62(1): 23-25 (2007).
Dombrowicz et al., "Anaphylaxis mediated through a humanized high affinity IgE receptor," J Immunol, 157:1645-1651 (1996).
Ebert et al., "A Moloney MLV-Rat Somatotropin Fusion Gene Produces Biologically Active Somatotropin in a Transgenic Pig," Mol. Endocrinology, 2: 277-283 (1988).
Edelstein et al., "Gene therapy clinical trials worldwide 1989-2004—an overview," J. Gene Med., 6: 597-602 (2004).
Extended European Search Report for EP Application No. 18154933 dated Jun. 29, 2018.
Extended European Search Report for EP Application No. 19154880.9 dated Mar. 21, 2019.
Fc Receptor, Wikipedia, retrieved Dec. 9, 2016, from <https://en.wikipedia.org/wiki/Fc_receptor>.
Filipe et al., "Immunogenicity of different stressed IgG monoclonal antibody formulations in immune tolerant transgenic mice," mAbs 4(6):740-752 (2012).
Fleit, et al., "Human neutrophil Fcg receptor distribution and structure," PNAS, 79(10): 3275-3279(1982).
Fung-Leung et al., "Transgenic Mice Expressing the Human High-Affinity Immunoglobulin (Ig) E Receptor ? Chain Respond to Human IgE in Mast Cell Degranulation and in Allergic Reactions," J Exp Med, 183:49-56 (1996).
Gessner, et al., "The IgG Fc receptor family," Annals Hematol, 76(6): 231-248 (1998).
Getahun, et al., "How antibodies act as natural adjuvants," Immunol Lett 104(1): 38-45 (2006).
Green et al., "Antibody engineering via genetic engineering of the mouse: XenoMouse strains are a vehicle for the facile generation of therapeutic human monoclonal antibodies," J Immunol Meth 231 (1-2):11-23 (1999).
Griggs, et al., "The state of the art: immune-mediated mechanisms of monoclonal antibodies in cancer therapy," Brit J Cancer, 101 (11): 1807-1812 (2009).
Guyre, et al., "Increased potency of Fc-receptor-targeted antigens," Cancer Immunol Immunother, 45(3-4): 146-148 (1997).
Haas, M., "IgG-Fc receptors and the clinical relvance of their polymorphisms," Wiener Klinische Wochenschrift, 113(20-21):825-831 (2001).
Hammer et al., "Spontaneous Inflammatory Disease in Transgenic Rats Expressing HLA-B27 and Human B2m: An Animal Model of HLA-B27-Associated Human Disorders," Cell, 63:1099-1112 (1990).
Harrison, et al., "High affinity IgG binding by Fc gamma RI (CD64) is modulated by two distinct IgSF domains and the transmembrane domain of the receptor," Protein Engineer, 11(3): 225-232(1998).
Hazenbos, et al., "Impaired IgG-Dependent Anaphylaxis and Arthus Reaction in FcgRIII (CD16) Deficient Mice," Immunity, 5(2): 181-188 (1996).
Heijnen, et al., "A Human FcgRI/CD64 Transgenic Model for In Vivo Analysis of (Bispecific) Antibody Therapeutics," J Hematother, 4(5): 351-356 (1995).
Heijnen, et al., "Antigen Targeting to Myeloid-specific Human FcgRI/CD64 Triggers Enhanced Antibody Responses in Transgenic Mice," J Clin Invest, 97(2): 331-338 (1996).
Heijnen, et al., "Human IgG Fc Receptors," Int Rev Immunol, 16(1-2): 29-55 (1996).
Heyman, "Regulation of Antibody Responses via Antibodies, Complement, and Fc Receptors," Ann Rev Immunol, 18(1): 709-737 (2000).
Hibbs, et al., "Molecular cloning of a human immunoglobulin G Fc receptor," PNAS, 85(7): 2240-2244(1988).
Hogarth, "Fc receptors are major mediators of antibody based inflammation in autoimmunity," Curr Opin Immunol, 14(6): 798-802 (2002).
Honeychurch, et al., "Therapeutic Efficacy of FcgRI/CD64-directed Bispecific Antibodies in B-cell Lymphoma," Blood, 96(10): 3544-3552 (2000).
Hulett, et al. "Molecular Basis of Fc Receptor Function," Adv Immunol, 57:1-127 (1994).
International Search Report for International Application No. PCT/US2010/060925 dated Mar. 14, 2011.
Jakobovits et al., "From XenoMouse technology to panitumumab, the first fully human antibody product from transgenic mice," Nat Biotech 25(10):1134-1143 (2007).
Jiskoot et al., "Mouse Models for Assessing Protein Immunogenicity: Lessons and Challenges," J Pharmaceut Sci 105(5):1567-1575 (2016).
Johnson-Saliba, "Gene Therapy: Optimising DNA Delivery to the Nucleus," Curr. Drug. Targets, 2:371-399 (2001).
Kellermann et al., "Developing the Xenomouse technology for evaluating immunogenicity," (from http://diagnosticscrc.org/publications/brochures/Antib0Z-2.pdf) (2004).
Kuster, et al., "Characterization and expression of the gene for the human Fc receptor g subunit," J Biol Chem, 265(11): 6448-6452 (1990).
Lanier, L. et al., "Membrane Anchoring of a Human IgG Fc Receptor (CD16) Determined by a Single Amino Acid," Science, 246: 1611-1613 (1989).
Lefranc, "Nomenclature of the Human Immunoglobulin Heavy (IGH) Genes," Exp Clin Immunogenet, 18: 100-116 (2001).
Leibson, "Signal transduction during natural killer cell activation: Inside the mind of a killer," Immunity, 6(6):655-661 (1997).
Letter from patentee to EPO for EP Application No. 10791039.0 dated Jul. 15, 2015.
Li, M. et al., "Reconstitution of Human FcgRIII Cell Type Specificity in Transgenic Mice," J Exp Med, 183: 1259-1263 (1996).
Liu, C. et al., "FcgRII on Human B Cells Can Mediate Enhanced Antigen Presentation," Cell Immunol, 167: 188-194 (1996).

(56) References Cited

OTHER PUBLICATIONS

Looney, et al., "Identification of a second class of IgG Fc receptors on human neutrophils," J Exp Med, 163(4): 826-836 (1986).
Looney, R. et al., "Human monocytes and U937 cells bear two dsitinct Fc receptors for IgG," J Immunol, 135(5): 1641-1647 (1987).
Louis, et al., "Association between polymorphism in IgG Fc receptor IIIA coding gene and biological response to infliximab in Crohn's disease," Aliment Pharm Ther 19(5): 511-519 (2004).
Luo et al., "Synthetic DNA delivery systems," Nature Biotechnol., 18: 33-37 (2000).
Macdonald et al., "Precise and in situ genetic humanization of 6 Mb of mouse immunoglobulin in gene," Proc Nat Acad Sci 111(14):5147-5152 (2014).
Malbec, et al., "Negative regulation of hematopoietic cell activation and proliferation by Fc gamma RIIb," Curr Top Microbiol, 244: 13-27 (1999).
Masuda, et al., "Association of all Three Types of FcgR (CD64, CD32, and CD16) with a g-Chain Homodimer in Cultured Human Monocytes," J Immunol, 151(12): 7188-7195 (1993).
Masuda, et al., "Enhanced binding affinity for FcgRIIIA of fucose-negative antibody is sufficient to induce maximal antibody-dependent cellular cytotoxicity," Mol Immunol, 44(12): 3122-3131 (2007).
McKenzie, "Humanized mouse models of FcR clearance in immune platelet disorders," Blood Reviews 16(1): 3-5 (2002).
McKenzie, et al., "The Role of the Human Fc Receptor FcgRIIA in the Immune Clearance of Platelets: A Transgenic Mouse Model," J Immunol, 162(7): 4311-4318 (1999).
Meyer, et al., "Bevacizumab immune complexes activate platelets and induce thrombosis in FCGR2A transgenic mice," J Thromb Haemost 7(1): 171-181 (2008).
Morgan, et al., "Analysis of Fcg receptor haplotypes in rheumatoid arthritis: FCGR3A remains a major susceptibility gene at this locus, with an additional contribution from FCGR3B," Arthritis Res Ther 8(1): 1 (2005).
Morgan, et al., "Association of FCGR2A and FCGR2A-FCGR3A haplotypes with susceptibility to giant cell arteritis," Arthritis Res Ther, 8(4): 1 (2006).
Muller, "Ten years of gene targeting: targeted mouse mutants, from vector design to phenotype analysis," Meeh Develop, 82(1): 3-21 (1999).
Mullins et al., "Expression of the DBA/2J Ren-2 gene in the adrenal gland of transgenic mice," EMBO, 8: 4065-4072 (1989).
Mullins et al., "Fulminant hypertension in transgenic rats harbouring the mouse Ren-2 gene," Nature, 344: 541-544 (1990).
Murphy et al., "Mice with megabase humanization of their immunoglobulin genes generate antibodies as efficiently as normal mice," Proc Nat Acad Sci 111(14):5153-5158 (2014).
Nimmerjahn, et al., "Divergent Immunoglobulin G Subclass Activity Through Selective Fc Receptor Binding," Science, 310(5753): 1510-1512 (2005).
Nimmerjahn, et al., "Fc gamma receptors as regulators of immune responses," Nat Rev, 8(1): 34-47 (2008).
Nimmerjahn, et al., "Fc gamma Receptors: Old Friends and New Family Members," Immunity, 24(1): 19-28 (2006).
Nimmerjahn, et al., "Fc gamma Riv: A Novel FcR with Distinct IgG Subclass Specificity," Immunity, 23(1): 41-51 (2005).
Nimmerjahn, et al., "Fc-Receptors as Regulators of Immunity," Adv Immunol, 96(Ch.5): 179-204 (2007).
Notice of Opposition for EP Application No. 10791039.0 dated Dec. 20, 2018.
Omi, et al., "Absence of Association between the Fcg Receptor IIIA-176F/V Polymorphism and the Severity of Malaria in Thai," Jap J Infect Dis, 55(5): 167-169 (2002).
Otten, et al., "Experimental Antibody Therapy of Liver Metastases Reveals Functional Redundancy between Fc gamma RI and Fc gamma RIV," J Immunol, 181(10): 6829-6836 (2008).

Ouma, et al., "Association of Fc gamma receptor IIa (CD32) polymorphism with malarial anemia and high-density parasitemia in infants and young children," Am J Trap Med Hyg, 74(4): 573-577 (2006).
Palu et al., "In pursuit of new developments for gene therapy of human diseases," J. Biotechnol., 68: 1-13(1999).
Pan, et al., "Genetic susceptibility and haplotype analysis between Fc gamma receptor IIB and IIIA gene with systemic lupus erythematosus in Chinese population," Lupus, 17(8): 733-738 (2008).
Park, et al., "Resistance of Fc Receptor-deficient Mice to Fatal Glomerulonephritis," J Clin Invest 102(6): 1229-1238 (1998).
Partial International Search Report and Written Opinion for International Application No. PCT/US2019/023899 dated Jun. 5, 2019.
Partial Search Report issued by the European Patent Office in corresponding Application No. EP 18154933.8, dated Mar. 22, 2018.
Peltz, et al., "Cloned and expressed human Fc receptor for IgG mediates anti-CD3-dependent lymphoproliferation," J Immunol, 141(6): 1891-1896 (1988).
Peltz, et al., "Human Fc gamma RIII: Cloning, expression, and identification of the chromosomal locus of two Fc receptors for IgG," PNAS, 86(3): 1013-1017 (1989).
Perussia, et al., "Murine natural killer cells express functional Fc gamma receptor II encoded by the Fc gamma Ra gene," J Exp Med, 170(1): 73-86 (1989).
Petkova et al., "Enhanced half-life of genetically engineered human IgG 1 antibodies in a humanized FcRn mouse model: potential application in humorally mediated autoimmune disease," Inter Immunol 18(12):1759-1769 (2006).
Pfeifer et al., "Gene Therapy: Promises and Problems," Annu. Rev. Genomics. Hum. Genet., 2:177-211 (2001).
Pietersz et al., "Inhibition of destructive autoimmune arthritis in Fc[gamma] RIIa transgenic mice by small chemical entities," Immun Cell Bio, 87(1): 3-12 (2008).
Poueymirou et al., "F0 generation mice fully derived from gene-targeted embryonic stem cells allowing immediate phenotypic analyses," Nature Biotech 25:91-99 (2007).
Proetzel et al., "Humanized RcRn Mouse Models for Evaluating Pharmacokinetics of human IgG Antibodies," Methods 65(1):148-153 (2014).
Raghavan, et al., "Fc receptors and their interactions with immunoglobulins," Ann Rev Cell Dev Biol, 12(1): 181-220 (1996).
Rappaport, et al., "A soluble form of the human Fc receptor Fc gamma RIIA: cloning, transcript analysis and detection," Exp Hematol, 21(5): 689-696 (1933).
Ravetch, et al., "Alternative membrane forms of Fc gamma RIII (CD 16) on human natural killer cells and neutrophils: Cell type-specific expression of two genes that differ in single nucleotide substitutions," J Exp Med, 170(2): 481-497 (1989).
Ravetch, et al., "Fc receptors," Ann Rev Immunol, 9(1): 457-492 (1991).
Ravetch, et al., "IgG Fc Receptors," Ann Rev Immunol, 19(1): 275-290 (2001).
Salmon, et al., "Human Receptors for Immunoglobulin G. Arthritis and Rheumatism," 44(4): 739-750 (2001).
Scallon, et al., "A human immunoglobulin G receptor exists in both polypeptide-anchored and phosphatidylinositol-glycan-anchored forms," PNAS, 86(13): 5079-5083 (1989).
Schmidt, et al., "Fc receptors and their interaction with complement in autoimmunity," Immunol Lett, 100(1): 56-67 (2005).
Selvaraj, et al., "Functional Regulation of Human Neutrophil Fc gamma Receptors," Immunol Res, 29(1-3): 219-229 (2004).
Sequence database: search result for SEQ ID No. 3 (2005).
Shoji et al., "Current Status of Delivery Systems to Improve Target Efficacy of Oligonucleotides," Current Pharmaceutical Design, 10: 785-796 (2004).
Siberil, et al., "Fc gamma R: The Key to Optimize Therapeutic Antibodies?" Crit Rev Oncol Hematol, 62(1): 26-33 (2007).
Simmons, et al., "The Fc gamma receptor of natural killer cells is a phospholipid-linked membrane protein," Nature, 333: 568-570 (1988).

(56) References Cited

OTHER PUBLICATIONS

Siriboonrit et al., "Association of Fcgamma Receptor IIb and IIIb Polymorphisms with Susceptibility to Systemic Lupus Erythematosus in Thais," Tissue Antigens, 61(5):2003-2005 (2003).
Smith, et al. "Mouse model recapitulating human Fc gamma receptor structural and functional diversity," PNAS, 109(16): 6181-6186 (2012).
Sondermann, et al., "Crystal structure of the soluble form of the human Fc gamma-receptor lib: a new member of the immunoglobulin superfamily at 1.7 a resolution," The EMBO Journal, 18(5): 1095-1103 (1999).
Song et al., "Modeling Disease in Human ESCs using an Efficient BAC-Based Homologous Recombination System," Cell Stem Cell, 6:80-89 (2010).
Sparwasser and Eberl, "BAC to Immunology—bacterial artificial chromosome-mediated transgenesis for targeting of immune cells," Immunology, 121:308-313 (2007).
Stacey et al., "Use of Double-Replacement Gene Targeting to Replace the Murine ?-Lactalbumin Gene with its Human Counterpart in embryonic Stem Cells and Mice," Molecular and Cellular Biology, 14(2):1009-1016 (1994).
Stavenhagen et al., "Fc Optimization of Therapeutic Antibodies Enhances Their Ability to Kill Tumor Cells in vitro and Controls Tumor Expansion in vivo via Low-Affinity activating fc gamma receptors," AACR, 67(18): 8882-8890 (2007).
Stuart, et al., "Isolation and expression of cDNA clones encoding a human receptor for IgG (Fc gamma RII)," J Exp Med, 166(6): 1668-1684 (1987).
Su, et al., "Genomic organization of classical human low-affinity Fc gamma receptor genes," Genes Immun, 3(Suppl 1): S51-S56 (2002).
Sullivan et al., "Targeted Replacement of the Mouse Apolipoprotein E Gene with the Common Human APOE3 Allele Enhances Dier-Induced Hypercholesterolemia and Atherosclerosis," J Biol Chem, 272(29):17971-17980 (1997).
Symons, et al., "Genomic Organisation and Sequence of the Extracellular Domain Exons of the Bovine Fc gamma RI Receptor, and Evidence for Restricted Binding of Ruminant IgG to U937 Cells," Mol Immunol, 29(11): 1407-1413 (1992).
Takai, "Fc Receptors and Their Role in Immune Regulation and Autoimmunity," J Clin Immunol, 25(1): 1-18 (2005).
Takai, "Roles of Fc Receptors in Autoimmunity," Nat Rev, 2(8): 580-592 (2002).
Takai, et al., "Augmented humoral and anaphylactic responses in Fc gamma RII-deficient mice," Nature, 379: 346-349 (1996).
Takai, et al., "FcR gamma Chain Deletion Results in Pleiotrophic Effector Cell Defects," Cell, 76(3): 519-529 (1994).
Taurog et al., "Cell Surface Expression and Recognition as an Alloantigen in the Absence of Human B2-Microglobulin," J. Immunol., 141(11): 4020-4023 (1988).
Trounstine, et al., "Reactivity of cloned, expressed human Fc gamma RII isoforms with monoclonal antibodies which distinguish cell-type-specific and allelic forms of Fc gamma RII," Int Immunol, 2(4): 303-310 (1990).
Tsuchiya, et al., "Role of Fc gamma receptor IIb polymorphism in the genetic background of systemic lupus eryhematosus: Insights from Asia," Autoimmunity, 38(5): 347-352 (2005).
Tsukahara, et al., "A polymorphism in the gene encoding the Fc gamma IIIA receptor is a possible genetic marker to predict the primary response to infliximab in Japanese patients with rheumatoid arthritis." Ann Rheum Dis, 67(12): 1791-1792 (2008).
Tuijnam, et al., "Human Low-Affinity IgG Receptor Fc gamma RIIa (CD32) Introduced Into Mouse Fibroblasts Mediates Phagocytosis of Sensitized Erythrocytes," Blood, 79(7): 1651-1656 (1992).
Valenzuela et al., "High-throughput engineering of the mouse genome coupled with high-resolution expression analysis," Nature Biotech, 21:652-659 (2003).
Van Vugt, et al., "FcR gamma-Chain is Essential for Both Surface Expression and Function of Human Fc gamma RI (CD64) In Vivo," Blood, 87(9): 3593-3599 (1996).

Van De Winkel, et al., "Biological functioning of human IgG Fc receptors," Res Immunol, 141(1): 64-67 (1990).
Van De Winkel, et al., "Biology of Human Immunoglobulin G Fc Receptors," J Leukocyte Biol, 49(5): 511-524 (1991).
Van De Winkel, et al., "Human IgG Fc receptor heterogeneity: molecular aspects and clinical implications," Immunol Today, 14(5): 215-221 (1993).
Van Den Herik-Oudijk, et al., "Functional Differences Between Two Fc Receptor ITAM Signaling Motifs," Blood, 86(9): 3302-3307 (1995).
Van Egmond et al., "Human Immunoglobulin A Receptor (Fc?RI, CD89) Function in Transgenic Mice Requires Both FcR ? Chain and CR3 (CD11b/CD18)," Blood, 93:4387-4394 (1999).
Vanvugt, M et al., "FcR g-Chain is Essential for Both Surface Expression and Function of Human FcgRI (CD64) In Vivo," Blood, 87(9):3593-3599 (1996).
Varriale et al., "An evolutionary conserved motif is responsible for Immunoglobulin heavy chain packing in the B cell membrane," Mol Phylogen Evol 57:1238-1244 (2010).
Verbeek, et al., "The role of FcR in immunity: lessons from gene targeting in mice," Res Immunol, 147(7): 466-474 (1997).
Verma et al., "Gene therapy—promises, problems and prospects," Nature, 389: 239-242 (1997).
Wall, "Transgenic Livestock: Progress and Prospects for the Future," Theriogenology, 45: 57-68 (1996).
Warmerdam, et al., "A single amino acid in the second Ig-like domain of the human Fc gamma receptor II is critical for human IgG2 binding," J Immunol, 147(4): 1338-1343 (1991).
Warmerdam, et al., "Interaction of a human Fc gamma RIIb1 (CD32) isoform with murine and human IgG subclasses," Int Immunol, 5(3): 239-247 (1993).
Weinshank, et al., "Function and regulation of a murine macrophage-specific IgG Fc receptor, Fc gamma R-a," J Exp Med, 167(6): 1909-1925 (1988).
Written Opinion for International Application No. PCT/US2010/060925 dated Mar. 14, 2011.
Yu et al., "Coordinate Regulation of RAG1 and RAG2 by Cell Type-Specific DNA Elements 5' of RAG2," Science, 285:1080-1084 (1999).
Zuniga, et al., "Low-Binding Alleles of Fc gamma Receptor Types IIA and IIIA Are Inherited Independently and Are Associated With Systemic Lupus Erythematosus in Hispanic Patients," Arthritis Rheum, 44(2): 361-367 (2001).
Brinks et al., "Immunogenicity of Therapeutic Proteins: The Use of Animal Models," Pharm Res 28:2379-2385 (2011).
Fischer et al., "Specific Immune Response to Phospholipase B-Like 2 Protein, a Host Cell Impurity in Lebrikizumab Clinical Material," APPS J 19(1):254-263 (2017).
Jawa et al., "Evaluating Immunogenicity Risk Due to Host Cell Protein Impurities in Antibody-Based Biotherapeutics," AAPS J 18(6):1439-1452 (2016).
Joubert et al., "Use of In Vitro Assays to Assess Immunogenicity Risk of Antibody-Based Biotherapeutics," PLOS One 11(8):1-22 (2016).
Moussa et al., "Immunogenicity of Therapeutic Protein Aggregates," J Pharma Sci 105:417-430 (2016).
Nicholson et al., "Antibody Repertoires of Four- and Five-Feature Translocus Mice Carrying Human Immunoglobulin Heavy Chain and ? and ? Light Chain Yeast Artificial Chromosomes," J Immunol 163:6898-6906 (1999).
Piccand et al., "Neonatal Immune Tolerance Induction to Allow Long-Term Studies With an Immunogenic Therapeutic Monoclonal Antibody in Mice," AAPS J 18(2):354-361 (2016).
Harari et al., "Bridging the Species Divide: Transgenic Mice Humanized for Type-I Interferon Response," Plos One, 9(1): e84259 (12 pages) (2014).
Abdiche et al., "The neonatal Fc receptor (FcRn) binds independently to both sites of the IgG homodimer with identical affinity," MABS, 7(2): 331-343 (2015).
Hong et al., "Antibody to Fc[epsilon]RI[alpha] Suppresses Immunoglobulin E Binding to High-Affinity Receptor I in Allergic Inflammation," Yonsei Medical Journal, 57(6): 1412-1419 (2016).

(56) References Cited

OTHER PUBLICATIONS

International Search Report and Written Opinion for International Application No. PCT/US2019/023899 dated Sep. 18, 2019.
Latvala et al., "Distribution of FcRn across species and tissues," Journal of Histochemistry & Cytochemistry, 65(6): 321-333 (2017).
Pang et al., Characterization of the Gene for the Human High Affinity IGE Receptor (FCEPSILONRI) Alpha-Chain, Journal of Immunology, 151(11): 6166-6174 (1993).
Proetzel et al., "Genetically Engineered Humanized Mouse Models for Preclinical Antibody Studies," BioDrugs, 28(2): 171-180 (2014).
Ra et al., "Complete Structure of the Mouse Mast Cell Receptor for IgE (FcεRI) and Surface Expression of Chimeric Receptors (Rat-Mouse-Human) on Transfected Cell," Journal of Biological Chemistry, 264(26): 15323-15327 (1989).

* cited by examiner

ND = Not Detected

GENETICALLY MODIFIED MOUSE WITH HUMANIZED IMMUNOGLOBULIN HEAVY CHAIN CONSTANT REGION GENES AND METHOD OF USING

RELATED APPLICATION

This application claims the benefit of priority to U.S. Provisional Patent Application Ser. No. 62/648,197, filed Mar. 26, 2018, and U.S. Provisional Patent Application Ser. No. 62/689,628, filed Jun. 25, 2018, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Mar. 20, 2019, is named RPB-01901_ (28744-01901)_SL.txt and is 11,590 bytes in size.

BACKGROUND

The safety, efficacy and pharmacokinetic properties of therapeutic agents are usually tested in animal models before such drugs are administered to humans. Use of larger animals, such as non-human primates, in such preclinical studies is expensive and suitable disease models are often not available which limits the usefulness of such animals in testing drug efficacy.

Due to their small size and well-characterized physiology rodents have long been used as animal models for the preclinical testing of therapeutic agents. Further, rodents are highly amenable to genetic modification using well-established techniques and thus, there are many disease models available in rodents that are not available in larger mammals. Complex therapeutic agents, however, such as antibodies and Fc fusion proteins, often behave differently in rodents than they do in humans. For example, such therapeutic agents often exhibit very different pharmacokinetic properties when administered to rodents compared to when they are administered to humans, limiting the usefulness of rodent models as predictors of the safety, efficacy and optimal dosing of complex therapeutic agents in humans. This in turn reduces the usefulness of such animal models in preclinical testing.

Thus, there is a great need for new animal models and methods that allow for precise pre-clinical testing of complex therapeutic agents in rodents that produce results that are more predictive of the properties of such therapeutic agents in human patients.

SUMMARY

Provided herein are methods and compositions related to the in vivo testing of therapeutic agents comprising a human Fc (e.g., the testing of the pharmacokinetic and/or pharmacodynamic properties of such therapeutic agents and dosing regimens) in genetically modified rodents (e.g., mice or rats).

In certain embodiments, provided herein are genetically modified rodents in which administration of human antibodies and/or human Fc fusion proteins induce a reduced anti-human Fc immune response (e.g., mouse anti-human antibody or MAHA response in mice). In some embodiments the genetically modified rodents (e.g., mice or rats) express antibodies comprising a human Fc (e.g., a human IgG1 Fc, a human IgG4 Fc). In some embodiments, the rodents express fully human antibodies (i.e., antibodies having human heavy chains and human light (γ or κ) chains).

In some embodiments, provided herein are rodents that express one or more humanized or partially-humanized Fc receptors that interact with Fc fusion proteins or antibodies in a way that mirrors how the Fc receptors of a human patient would interact with such Fc fusion proteins or antibodies. Thus, in certain embodiments the genetically modified rodents comprise one or more Fc receptors with a human extracellular domain (e.g., a Neonatal Fc Receptor (FcRn), a β-2-microglobulin polypeptide (β2M), a Fc receptor 1α (FcεR1α), a Fc γ receptor 1 alpha (FcγR1a), a Fc gamma receptor 2a (FcγR2a), a Fc gamma receptor 2b (FcγR2b), a Fc gamma receptor 3a (FcγR3a), a Fc gamma receptor 3b (FcγR3b), a Fc gamma receptor 2c (FcγR2c)). The transmembrane and cytoplasmic domain of such receptors can be human or non-human (e.g., rodent, such as rat or mouse).

In certain aspects provided herein are rodents (e.g., rats or mice) and rodent ES cells comprising in their genome a genetically modified immunoglobulin heavy chain (IgH) locus. In certain embodiments the IgH locus comprises: (i) an immunoglobulin heavy chain variable region comprising one or more $V_H$ gene segments, one or more $D_H$ gene segments and one or more $J_H$ gene segments (e.g., rat or mouse $V_H$ gene segments, $D_H$ gene segments and $J_H$ gene segments); and (ii) an immunoglobulin heavy chain constant region comprising one or more $C_H$ gene segments encoding an IgG constant domain comprising a human $C_H1$ domain, a human hinge region, a human $C_H2$ domain, a human $C_H3$ domain, a human or rodent IgG transmembrane domain and a human or rodent IgG cytoplasmic domain. In some embodiments all the $C_H$ gene segments in the immunoglobulin heavy chain constant region are human. In some embodiments the immunoglobulin heavy chain variable region is operably linked to the immunoglobulin heavy chain constant region such that the rodent produces IgG antibodies comprising variable domains derived from the $V_H$ gene segment, the $D_H$ gene segment and the $J_H$ gene segment and heavy chain constant domains derived from the $C_H$ gene segment. In certain embodiments the locus is positioned at the endogenous rodent immunoglobulin heavy chain locus. In some embodiments, human antibodies and Fc fusion proteins that are isotype matched to an Fc encoded by a human $C_H$ in the immunoglobulin heavy chain locus of the rodent elicit a reduced immune response when administered to such rodents. For example, in some embodiments, a human IgG1 antibody is administered to a rodent provided herein that expresses antibodies having human variable domains and human IgG1 constant domains. In some embodiments, a human IgG2 antibody is administered to a rodent provided herein that expresses antibodies having human variable domains and human IgG2 constant domains. In some embodiments, a human IgG3 antibody is administered to a rodent provided herein that expresses antibodies having human variable domains and human IgG3 constant domains. In some embodiments, a human IgG4 antibody is administered to a rodent provided herein that expresses antibodies having human variable domains and human IgG4 constant domains. In some embodiments, a human antibody having a κ light chain is administered to a rodent provided herein that expresses antibodies having a human κ light chain, e.g., expresses antibodies having a human κ constant domain, or expresses antibodies having human κ variable and constant domains. In some embodiments, a human antibody having a λ light chain is administered to a rodent provided herein that expresses antibodies having a human λ light chain, e.g., expresses antibodies having a human λ constant domain, or expresses antibodies having human λ variable and constant domains. In certain embodiments provided herein are animal models and methods for testing human antibodies and Fc-fusion proteins using such rodents.

In certain aspects provided herein are rodents (e.g., rats or mice) comprising in their genome a genetically modified immunoglobulin kappa (Igκ) chain locus. In some embodiments the Igκ locus comprises: (1) an immunoglobulin κ chain variable region comprising one or more human $V_\kappa$ gene segments and one or more human $J_\kappa$ gene segments; and (2) an immunoglobulin κ chain constant region comprising a human $C_\kappa$ gene segment. In some embodiments, the immunoglobulin κ chain variable region is operably linked to the immunoglobulin κ chain constant region such that the rodent produces antibodies comprising light chain variable domains derived from the human $V_\kappa$ gene segment and the human $J_\kappa$ gene segment and light chain constant domains derived from the $C_\kappa$ gene segment. In certain embodiments the locus is positioned at the endogenous rodent immunoglobulin κ chain locus. In some embodiments human antibodies that include a human κ chain elicit a reduced immune response when administered to such rodents. In certain embodiments provided herein are animal models and methods for testing human antibodies using such rodents.

In certain aspects provided herein are rodents (e.g., rats or mice) comprising in their genome a genetically modified immunoglobulin lambda (Igλ) chain locus. In certain embodiments the Igλ locus comprises one or more human $V_\lambda$ gene segments, one or more human $J_\lambda$ gene segments and one or more $C_\lambda$ gene segments. In some embodiments, the human $J_\lambda$ gene segments and the $C_\lambda$ gene segments are arranged as one or more $J_\lambda$-$C_\lambda$ clusters. In some embodiments, the human $J_\lambda$ gene segments and the $C_\lambda$ gene segments are arranged such that the human $J_\lambda$ gene segments are collectively positioned upstream of one or more $C_\lambda$ gene segments. In some embodiments, the human $J_\lambda$ gene segments and the $C_\lambda$ gene segments are arranged such that some of the human $J_\lambda$ gene segments and the $C_\lambda$ segments are arranged as one or more $J_\lambda$-$C_\lambda$ clusters, while other $J_\lambda$ gene segments are collectively positioned upstream of one or more $C_\lambda$ gene segments. In some embodiments, the human $V_\lambda$ gene segment and the human $J_\lambda$ gene segment are operably linked to the human $C_\lambda$ gene segment such that the rodent produces antibodies comprising light chain variable domains derived from the human $V_\lambda$ gene segment and the human $J_\lambda$ gene segment and light chain constant domains derived from the $C_\lambda$ gene segment. In certain embodiments the locus is positioned at the endogenous rodent immunoglobulin λ chain locus. In some embodiments human antibodies that include a human λ chain elicit a reduced immune response when administered to such rodents. In certain embodiments provided herein are animal models and methods for testing human antibodies using such rodents.

In certain aspects provided herein are rodents (e.g., rats or mice) comprising in their genome a genetically modified neonatal Fc receptor (FcRn) locus. In certain embodiment the FcRn locus comprises a nucleic acid sequence encoding an FcRn polypeptide comprising a human extracellular domain, a rodent or human transmembrane domain and rodent or human cytoplasmic domain. In certain embodiments the locus is positioned at the endogenous rodent FcRn locus. In some embodiments the rodents further comprise in their genome a β-2-microglobulin (β2M) locus comprising a nucleic acid sequence encoding a human β-2-microglobulin (β2M) polypeptide. In some embodiments the nucleic acid sequence encoding a human β2M polypeptide is positioned at an endogenous rodent β2M locus. In certain embodiments provided herein are animal models and methods for testing human antibodies and Fc fusion proteins using such rodents.

In certain aspects provided herein are rodents (e.g., rats or mice) comprising in their genome a genetically modified Fc epsilon receptor 1 alpha (FcεR1α) locus comprising a nucleic acid sequence encoding FcεR1α polypeptide comprising a human extracellular domain, a rodent or human transmembrane domain and a rodent or human cytoplasmic domain. In some embodiments the nucleic acid sequence encoding the FcεR1α polypeptide is positioned at an endogenous rodent FcεR1α locus. In certain embodiments provided herein are animal models and methods for testing human antibodies and Fc fusion proteins using such rodents.

In certain aspects provided herein are rodents (e.g., rats or mice) comprising in their genome a genetically modified Fc gamma receptor 1a (FcγR1a) α-chain locus comprising a nucleic acid sequence encoding FcγR1a α-chain polypeptide comprising a human extracellular domain, a rodent or human transmembrane domain and a rodent or human cytoplasmic domain. In some embodiments the nucleic acid sequence encoding the FcγR1a α-chain polypeptide is positioned at an endogenous rodent FcγR1a α-chain locus. In some embodiments the genetically modified rodents provided herein further comprise a functional FcR γ-chain. In certain embodiments the functional FcR γ-chain is a rodent FcR γ-chain (e.g., an FcR γ-chain endogenous to the genetically modified rodents). In certain embodiments provided herein are animal models and methods for testing human antibodies and Fc fusion proteins using such rodents.

In certain aspects provided herein are rodents (e.g., rats or mice) comprising in their genome a genetically modified Fc gamma receptor 2a α-chain (FcγR2a) locus comprising a nucleic acid sequence encoding a human FcγR2a α-chain polypeptide. In some embodiments the nucleic acid sequence encoding the FcγR2a α-chain polypeptide is positioned at an endogenous rodent low affinity FcγR α-chain locus. In certain embodiments provided herein are animal models and methods for testing human antibodies and Fc fusion proteins using such rodents.

In certain aspects provided herein are rodents (e.g., rats or mice) comprising in their genome a genetically modified Fc gamma receptor 2b (FcγR2b) α-chain locus comprising a nucleic acid sequence encoding a human FcγR2b α-chain polypeptide. In some embodiments the nucleic acid sequence encoding the FcγR2b α-chain polypeptide is positioned at an endogenous rodent low affinity FcγR α-chain locus. In certain embodiments provided herein are animal models and methods for testing human antibodies and Fc fusion proteins using such rodents.

In certain aspects provided herein are rodents (e.g., rats or mice) comprising in their genome a genetically modified Fc gamma receptor 3a (FcγR3a) α-chain locus comprising a nucleic acid sequence encoding a human FcγR3a α-chain polypeptide. In some embodiments the nucleic acid sequence encoding the FcγR3a α-chain polypeptide is positioned at an endogenous rodent low affinity FcγR α-chain locus. In some embodiments the genetically modified rodents provided herein further comprise a functional FcR γ-chain. In certain embodiments the functional FcR γ-chain is a rodent FcR γ-chain (e.g., an FcR γ-chain endogenous to the genetically modified rodents). In certain embodiments provided herein are animal models and methods for testing human antibodies and Fc fusion proteins using such rodents.

In certain aspects provided herein are rodents (e.g., rats or mice) comprising in their genome a genetically modified Fc gamma receptor 3b (FcγR3b) α-chain locus comprising a nucleic acid sequence encoding a human FcγR3b α-chain polypeptide. In some embodiments the nucleic acid sequence encoding the FcγR3b α-chain polypeptide is positioned at an endogenous rodent low affinity FcγR α-chain locus. In certain embodiments provided herein are animal models and methods for testing human antibodies and Fc fusion proteins using such rodents.

In certain aspects provided herein are rodents (e.g., rats or mice) comprising in their genome a genetically modified Fc gamma receptor 2c (FcγR2c) α-chain locus comprising a nucleic acid sequence encoding a human FcγR2c α-chain polypeptide. In some embodiments the nucleic acid sequence encoding the FcγR2c α-chain polypeptide is positioned at an endogenous rodent low affinity FcγR α-chain locus. In certain embodiments provided herein are animal models and methods for testing human antibodies and Fc fusion proteins using such rodents.

In certain aspects provided herein are rodents (e.g., rats or mice) comprising in their genome a combination of the genetically modified loci provided herein. For example, in some embodiments the rodents provided herein comprise one or more genetically modified loci selected from a genetically modified IgH locus provided herein, a genetically modified Igκ locus provided herein, a genetically modified Igλ locus provided herein, a genetically modified FcRn locus provided herein, a genetically modified β2M locus provided herein, a genetically modified FcεR1α locus provided herein, a genetically modified FcγR1a locus provided herein, a genetically modified FcγR2a locus provided herein, a genetically modified FcγR2b locus provided herein, a genetically modified FcγR2c locus provided herein, a genetically modified FcγR3a locus provided herein, and/or a genetically modified FcγR3b locus provided herein. In certain embodiments the rodents provided herein comprise a genetically modified IgH locus provided herein and/or a genetically modified Igκ locus provided herein. In some embodiments the rodents provided herein comprise a genetically modified IgH locus provided herein and/or a genetically modified Igλ locus provided herein. In some embodiments the rodents provided herein comprise a genetically modified IgH locus provided herein, a genetically modified Igκ and/or Igλ locus provided herein, a genetically modified FcRn locus provided herein and a genetically modified β2M locus provided herein. In some embodiments the rodents provided herein comprise a genetically modified IgH locus provided herein, a genetically modified FcRn locus provided herein, a genetically modified β2M locus provided herein, a genetically modified FcεR1α locus provided herein, a genetically modified FcγR1a locus provided herein, a genetically modified FcγR2a locus provided herein, a genetically modified FcγR2b locus provided herein, a genetically modified FcγR2c locus provided herein, a genetically modified FcγR3a locus provided herein, and/or a genetically modified FcγR3b locus provided herein.

In certain embodiments provided herein are methods of testing a therapeutic protein comprising a human Fc domain (e.g., a human antibody or an Fc fusion protein) comprising administering the therapeutic protein to a rodent (e.g., a mouse or rat) provided herein. In some embodiments the method further comprises measuring one or more pharmacokinetic properties of the administered therapeutic protein. In some embodiments the one or more pharmacokinetic parameters include, but are not limited to, area under the plasma concentration versus time (AUC), in vivo recovery (IVR), clearance rate (CL), mean residence time (MRT), agent half-life (t½), and volume of distribution at steady state (Vss). In some embodiments, the methods further comprise measuring the therapeutic efficacy of the administered therapeutic protein (e.g., the ability of an administered dose of the therapeutic protein to reduce or eliminate one or more disease symptoms in the animal model). In some embodiments, the methods further comprise measuring the safety of the administered therapeutic protein (e.g., the extent to which an administered dose of the therapeutic protein produces one or more adverse effects in the animal model). In certain embodiments, the method further comprises measuring the extent to which the therapeutic protein induces one or more Fc receptor mediated responses in the rodent (e.g., the extent to which the therapeutic protein induces antibody-dependent cell-mediated cytotoxicity (ADCC)). In some embodiments the method further comprises measuring the extent to which administration of the therapeutic protein induces an anti-human Fc immune response in the rodent. In some embodiments the method further comprises assessing the safety and/or efficacy of a dosing regimen of the therapeutic protein.

In certain embodiments provided herein are animal models for testing a therapeutic protein comprising a human Fc domain (e.g., a human antibody or a Fc fusion protein). In some embodiments the animal model comprises administering the therapeutic protein to a rodent (e.g., a mouse or rat) provided herein. In some embodiments the animal model further comprises measuring one or more pharmacokinetic properties of the administered therapeutic protein. In some embodiments the one or more pharmacokinetic parameters include, but are not limited to, area under the plasma concentration versus time (AUC), in vivo recovery (IVR), clearance rate (CL), mean residence time (MRT), agent half-life (t½), and volume of distribution at steady state (Vss). In some embodiments, the animal model further comprises measuring the therapeutic efficacy of the administered therapeutic protein (e.g., the ability of an administered dose of the therapeutic protein to reduce or eliminate one or more disease symptoms in the animal model). In some embodiments, the animal model further comprises measuring the safety of the administered therapeutic protein (e.g., the extent to which an administered dose of the therapeutic protein produces one or more adverse effects in the animal model). In certain embodiments, the animal model further comprises measuring the extent to which the therapeutic protein induces one or more Fc receptor mediated responses in the rodent (e.g., the extent to which the therapeutic protein induces antibody-dependent cell-mediated cytotoxicity (ADCC)). In some embodiments the animal model further comprises measuring the extent to which administration of the therapeutic protein induces an anti-human Fc immune response in the rodent. In some embodiments the animal model further comprises assessing the safety and/or efficacy of a dosing regimen of the therapeutic protein.

In some embodiments the administered therapeutic agent elicits a reduced immune response when administered to the rodent provided herein. In some embodiments the administered human antibody or Fc fusion protein has an isotype and/or allotype that matches the isotype and/or allotype of Fc domain encoded by a human $C_H$ in the genetically modified IgH locus of the rodent provided herein. In some embodiments, human antibodies and Fc fusion proteins that are isotype matched to an Fc encoded by a human $C_H$ in the immunoglobulin heavy chain locus of the rodent elicit a reduced immune response when administered to such rodents. For example, in some embodiments, a human IgG1 antibody is administered to a rodent provided herein that expresses antibodies having human variable domains and human IgG1 constant domains. In some embodiments, a human IgG2 antibody is administered to a rodent provided herein that expresses antibodies having human variable domains and human IgG2 constant domains. In some embodiments, a human IgG3 antibody is administered to a rodent provided herein that expresses antibodies having human variable domains and human IgG3 constant domains. In some embodiments, a human IgG4 antibody is administered to a rodent provided herein that expresses antibodies having human variable domains and human IgG4 constant domains. In some embodiments, a human antibody having a κ light chain is administered to a rodent provided herein that expresses antibodies having a human κ light chain, e.g., expresses antibodies having a human κ constant domain, or expresses antibodies having human κ variable and constant domains. In some embodiments, a human antibody having a λ light chain is administered to a rodent provided herein that expresses antibodies having a human λ light chain, e.g., expresses antibodies having a human λ constant domain, or expresses antibodies having human λ variable and constant domains. In some embodiments the agent is a human IgG1 antibody and the rodent comprises genetically modified IgH locus that comprises a $C_H$ gene segment encoding human IgG1 $CH_1$, hinge, $CH_2$ and $CH_3$ domains. In some embodiments the agent is a human IgG4 antibody and the rodent comprises genetically modified IgH locus that comprises a $C_H$ gene segment encoding human IgG4 $CH_1$, hinge, $CH_2$ and $CH_3$ domains. In some embodiments the therapeutic agent is a human antibody having an Igκ light chain and the rodent comprises a genetically modified Igκ locus provided herein. In some embodiments the therapeutic agent is a human antibody having an Igλ light chain and the rodent comprises a genetically modified Igλ locus provided herein.

In certain aspects, provided herein are rodent cells (e.g., ES cells, immune cells, endothelial cells, B cells, NK cells, macrophages, dendritic cells, Langerhans cells, eosinophils, mast cells and basophils) comprising one or more of the genetically modified loci provided herein. For example, in some embodiments the rodent cells (e.g., rodent ES cells) provided herein comprise a genetically modified IgH locus provided herein and/or a genetically modified Igκ locus provided herein. In some embodiments the rodent cells (e.g., rodent ES cells) provided herein comprise a genetically modified IgH locus provided herein and/or a genetically modified Igλ locus provided herein. In some embodiments the rodent cells (e.g., rodent ES cells) provided herein comprise a genetically modified IgH locus provided herein, a genetically modified Igκ and/or Igλ locus provided herein, a genetically modified FcRn locus provided herein and a genetically modified β2M locus provided herein. In some embodiments the rodent cells (e.g., rodent ES cells) provided herein comprise a genetically modified IgH locus provided herein, a genetically modified FcRn locus provided herein, a genetically modified β2M locus provided herein, a genetically modified FcεR1α locus provided herein, a genetically modified FcγR1a locus provided herein, a genetically modified FcγR2a locus provided herein, a genetically modified FcγR2b locus provided herein, a genetically modified FcγR2c locus provided herein, a genetically modified FcγR3a locus provided herein, and/or a genetically modified FcγR3b locus provided herein.

In some embodiments provided herein are methods of making the genetically modified rodents (e.g., rats or mice) and rodent ES cells (e.g., rat or mouse ES cells) provided herein. In certain embodiments the method comprises genetically modifying the genome of a rodent (e.g., a rat or a mouse) or a rodent ES cell (e.g., a rat or a mouse ES cell) such that it comprises one or more of the genetically modified locus provided herein.

DETAILED DESCRIPTION

General

Figure 1A:
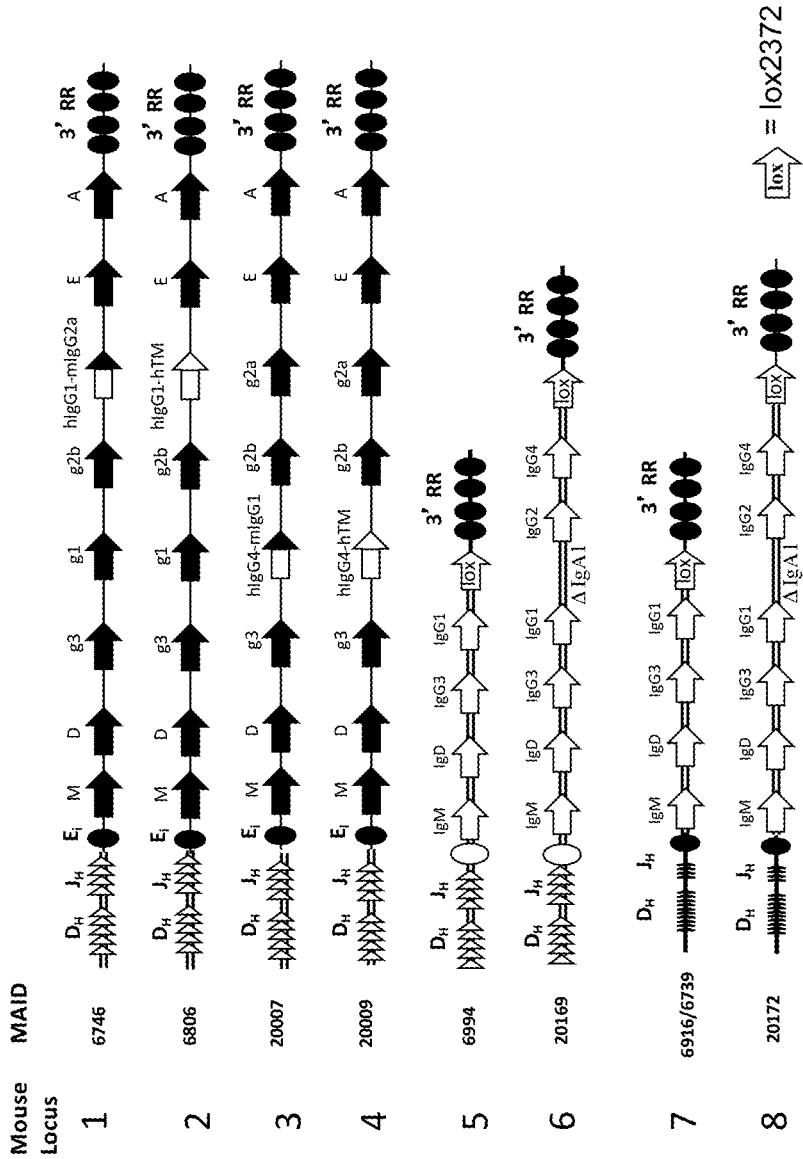
FIG. 1A shows schematic summaries, not to scale, of exemplary modified immunoglobulin heavy chain loci according to certain exemplary embodiments provided herein. As shown, exemplary mouse heavy chain locus 1 comprises, in 5' to 3' order, a human variable region (comprising human $V_H$, human $D_H$, and human $J_H$ gene segments, for simplicity, human $V_H$ gene segments are not shown; only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference), a mouse intronic enhancer, a mouse $C_\mu$ gene segment, a mouse $C_\delta$ gene segment, a mouse $C_{\gamma3}$ gene segment, a mouse $C_{\gamma1}$ gene segment, a mouse $C_{\gamma2b}$ gene segment, a hybrid $C_H$ gene segment encoding a human IgG1 extracellular domain and mouse IgG2a transmembrane and cytoplasmic domains, a mouse $C_\varepsilon$ gene segment, a mouse $C_\alpha$ gene segment, and a mouse 3' regulatory region. As shown, exemplary mouse heavy chain locus 2 comprises, in 5' to 3' order, a human variable region (comprising human $V_H$, human $D_H$, and human $J_H$ gene segments, for simplicity, human $V_H$ gene segments are not shown; only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference), a mouse intronic enhancer, a mouse $C_\mu$ gene segment, a mouse $C_\delta$ gene segment, a mouse $C_{\gamma3}$ gene segment, a mouse $C_{\gamma1}$ gene segment, a mouse $C_{\gamma2b}$ gene segment, a human $C_{\gamma1}$ gene segment (both IgG1 extracellular and transmembrane/cytoplasmic encoding sequences are human), a mouse $C_\varepsilon$ gene segment, a mouse $C_\alpha$ gene segment, and a mouse 3' regulatory region. As shown, exemplary mouse heavy chain locus 3 comprises, in 5' to 3' order, a human variable region (comprising human $V_H$, human $D_H$, and human $J_H$ gene segments, for simplicity, human $V_H$ gene segments are not shown; only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference), a mouse intronic enhancer, a mouse $C_\mu$ gene segment, a mouse $C_\delta$ gene segment, a mouse $C_{\gamma3}$ gene segment, a hybrid $C_H$ gene segment encoding a human IgG4 extracellular domain and mouse IgG1 transmembrane and cytoplasmic domains, a mouse $C_{\gamma2b}$ gene segment, a mouse $C_{\gamma2a}$ gene segment, a mouse $C_\varepsilon$ gene segment, a mouse $C_\alpha$ gene segment, and a mouse 3' regulatory region. As shown, exemplary mouse heavy chain locus 4 comprises, in 5' to 3' order, a human variable region (comprising human $V_H$, human $D_H$, and human $J_H$ gene segments, for simplicity, human $V_H$ gene segments are not shown; only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference), a mouse intronic enhancer, a mouse $C_\mu$ gene segment, a mouse $C_\delta$ gene segment, a mouse $C_{\gamma3}$ gene segment, a human $C_{\gamma4}$ gene segment (both IgG4 extracellular and transmembrane/cytoplasmic domain encoding sequences are human), a mouse $C_{\gamma2b}$ gene segment, a mouse $C_{\gamma2a}$ gene segment, a mouse $C_\epsilon$ gene segment, a mouse $C_\alpha$ gene segment, and a mouse 3' regulatory region. As shown, exemplary mouse heavy chain locus 5 comprises, in 5' to 3' order, a human variable region (comprising human $V_H$, human $D_H$, and human $J_H$ gene segments, for simplicity, human $V_H$ gene segments are not shown; only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference), a human intronic enhancer, a human $C_\mu$ gene segment, a human $C_\delta$ gene segment, a human $C_{\gamma3}$ gene segment, a human $C_{\gamma1}$ gene segment, and a mouse 3' regulatory region. As shown, exemplary mouse heavy chain locus 6 comprises, in 5' to 3' order, a human variable region (comprising human $V_H$, human $D_H$, and human $J_H$ gene segments, for simplicity, human $V_H$ gene segments are not shown; only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference), a human intronic enhancer, a human $C_\mu$ gene segment, a human $C_\delta$ gene segment, a human $C_{\gamma3}$ gene segment, a human $C_{\gamma1}$ gene segment, a human $C_{\gamma2}$ gene segment, a human $C_{\gamma4}$ gene segment, and a mouse 3' regulatory region. As shown, exemplary mouse heavy chain locus 7 comprises, in 5' to 3' order, a mouse variable region (comprising mouse $V_H$, mouse $D_H$, and mouse $J_H$ gene segments, for simplicity, mouse $V_H$ gene segments are not shown; only a small number of gene segments are represented schematically—for a full repertoire of possible present V, D, and J gene segments see imgt.org), a mouse intronic enhancer, a human $C_\mu$ gene segment, a human $C_\delta$ gene segment, a human $C_{\gamma3}$ gene segment, a human $C_{\gamma1}$ gene segment, and a mouse 3' regulatory region. As shown, exemplary mouse heavy chain locus 8 comprises, in 5' to 3' order, a mouse variable region (comprising mouse $V_H$, mouse $D_H$, and mouse $J_H$ gene segments, for simplicity, mouse $V_H$ gene segments are not shown; only a small number of gene segments are represented schematically—for a full repertoire of possible present V, D, and J gene segments see imgt.org), a mouse intronic enhancer, a human $C_\mu$ gene segment, a human $C_\delta$ gene segment, a human $C_{\gamma3}$ gene segment, a human $C_{\gamma1}$ gene segment, a human $C_{\gamma2}$ gene segment, a human $C_{\gamma4}$ gene segment, and a mouse 3' regulatory region. Although not shown, the loci in these embodiments comprise functional mouse Adam6 genes (e.g., Adam 6a and/or Adam6b). Unless otherwise indicated (e.g., for lox sites, etc.), empty shapes and double lines represent human sequences and filled shapes and single lines represent mouse sequences.

Provided herein are methods and compositions related to the in vivo testing of therapeutic agents comprising a human Fc in genetically modified rodents (e.g., the testing of the pharmacokinetic and/or pharmacodynamic properties and dosing regimens of such therapeutic agents in genetically modified rodents). In some embodiments the genetically modified rodents express antibodies comprising a human Fc (e.g., a human IgG1 Fc, a human IgG2 Fc, a human IgG3 Fc, a human IgG4 Fc) or human light chain constant regions. In some embodiments, the rodents express fully human antibodies (i.e., antibodies having human heavy chains and human light (γ or κ) chains). In certain embodiments the genetically modified rodents comprise one or more Fc receptors with a human extracellular domain (e.g., a Neonatal Fc Receptor (FcRn), a β-2-microglobulin polypeptide (β2M), a Fc ε receptor 1α (FcεR1α), a Fc γ receptor 1 alpha (FcγR1a), a Fc gamma receptor 2a (FcγR2a), a Fc gamma receptor 2b (FcγR2b), a Fc gamma receptor 3a (FcγR3a), a Fc gamma receptor 3b (FcγR3b), a Fc gamma receptor 2c (FcγR2c)). The transmembrane and cytoplasmic domain of such receptors can be human or non-human (e.g., rodent).

Therapeutic agents comprising a human Fc, such as therapeutic human antibodies and human Fc fusion proteins, are typically tested in non-human species before they are administered to humans. While such agents are often tested in non-human primates or other relatively large mammals, such testing is expensive and places a significant financial burden on drug developers. Moreover, non-human primates and other relatively large mammals are often not amenable to genetic modification, which limits the disease models available in such organisms.

In contrast, rodent species (e.g., rats and mice) are convenient animal models for testing therapeutic antibodies and Fc fusion proteins due to their small size, well-characterized physiology and amenability to genetic modification. Unfortunately, agents comprising a human Fc region often exhibit very different pharmacokinetic and pharmacodynamic properties when administered to prior art rodents compared to when administered to humans. For example, when therapeutic agents with human Fc regions are administered to conventional rodents, the human sequences in the Fc regions are often identified as foreign by the rodent (e.g., rat or mouse) immune system. As a consequence, the rodent may mount an immune response against the administered therapeutic agents (known as mouse anti-human response or MAHA), which affects the pharmacokinetic and pharmacodynamic properties of the administered agents. Moreover, the human Fc regions of the therapeutic agents may interact differently with the rodent (e.g., rat or mouse) Fc receptors in the rodents than they do with human Fc receptors in patients, which can also impact the pharmacokinetic and pharmacodynamic properties of the administered agents. Thus, conventional rodent (e.g., rat or mouse) models are often poor predictors of human therapeutic responses to therapeutic agents comprising a human Fc. Thus, mice having human immunoglobulin locus regions (e.g., see loci in FIGS. 1 and 2) are helpful in reducing or eliminating MAHA responses.

Having a molecule that can specifically bind a drug is extremely useful for research and diagnostic purposes. The creation of mice with mouse variables and human constants (e.g., mouse locus 8 in FIG. 1A) provides an improved method for generating anti-drug antibodies when the drug is a human monoclonal antibody. Any MAHA response generated by injecting the mice with a human antibody will be directed to the variable regions of the antibody. This eliminates the background response against the constant region of the antibody and makes generating drug specific antibodies more efficient.

Provided herein are in vivo systems for the development, screening and testing of human antibodies and Fc fusion proteins for therapeutic use. In certain embodiments, provided herein are genetically modified rodents with a reduced rodent-anti-human immune response following administration of a therapeutic agent comprising a human Fc. As demonstrated herein, this can be accomplished through the use of rodents that have been genetically modified such that they express a human Fc that matches the Fc present in the administered antibody or Fc fusion protein. Such mice can be made, for example, through the insertion of a nucleic acid sequence that encodes a human immunoglobulin heavy chain constant region, in whole or in part (e.g., IgG $C_H3$), in the place of a sequence that encodes the corresponding portions of an endogenous non-human immunoglobulin heavy chain constant region gene segment. Such animals recognize the human Fc as a "self" protein and are therefore less likely to develop an immune response against the administered human Fc-containing therapeutic.

In addition, in some embodiments provided herein are genetically modified rodents (e.g., mice or rats) expressing Fc receptors that are able interact with human Fc similarly to the Fc receptors expressed by a human patient. For example, in certain embodiments the genetically modified rodents provided herein express one or more Fc receptors having at least human extracellular domains (e.g., the transmembrane and cytoplasmic domains can be either human or rodent). Thus, in certain embodiments, the mice provided herein express a human or partially human FcRn, a human or partially human β2M, a human or partially human FcεR1α, a human or partially human FcγR1a, a human or partially human FcγR2a, a human or partially human FcγR2b, a human or partially human FcγR3a, a human or partially human FcγR3b, and/or a human or partially human FcγR2c. Such mice are therefore able to more accurately mimic the human Fc responses of human patients compared to rodents with fully non-human Fc receptors.

Thus, rodents (e.g., mice or rats) provided herein provide a novel in vivo system for the development, selection and testing of therapeutic human antibodies and Fc fusion proteins based not merely on specificity and/or affinity for antigen, but on the relevant whole biological function of the selected antibody through evaluation of effector functions within the internal milieu of an immune system. In this way, human therapeutic candidates can be developed and selected based on therapeutic potential evaluated on a whole molecule level with relevant biological responses (e.g., cellular responses) rather than predictions based solely on individual components evaluated separately. Thus, rodents provided herein specifically provide a system that is more suitable for the prediction of clinical human therapeutic antibody function in vivo.

Definitions

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

As used herein, the term "antibody" may refer to both an intact antibody and an antigen binding fragment thereof. Intact antibodies are glycoproteins that include at least two heavy (H) chains and two light (L) chains inter-connected by disulfide bonds. Each heavy chain includes a heavy chain variable domain and a heavy chain constant domain. Each light chain includes a light chain variable domain and a light chain constant domain. The heavy chain variable domains and light chain variable domains can be further subdivided into domains of hypervariability, termed complementarity determining regions (CDR), interspersed with regions that are more conserved, termed framework regions (FR). Each heavy chain variable domain and light chain variable domain is composed of three CDRs and four FRs, arranged from amino-terminus to carboxy-terminus in the following order: FR1, CDR1, FR2, CDR2, FR3, CDR3, FR4. The variable domains of the heavy and light chains contain a binding domain that interacts with an antigen.

The terms "antigen binding fragment" and "antigen-binding portion" of an antibody, as used herein, refers to one or more fragments of an antibody that retain the ability to bind to an antigen. Examples of binding fragments encompassed within the term "antigen-binding fragment" of an antibody include Fab, Fab', F(ab')$_2$, Fv, scFv, disulfide linked Fv, Fd, single-chain antibodies, isolated CDRH3, and other antibody fragments that retain at least a portion of the variable domain of an intact antibody. These antibody fragments can be obtained using conventional recombinant and/or enzymatic techniques and can be screened for antigen binding in the same manner as intact antibodies.

As used herein the term "area under the plasma concentration versus time curve" or "AUC" refers to the rate and extent of elimination of a therapeutic agent following administration. In some embodiments AUC is determined over a specified time period, such as 12, 18, 24, 36, 48, or 72 hours, or for infinity using extrapolation based on the slope of the curve. Unless otherwise specified herein, AUC is determined for infinity (AUC$_{INF}$). AUC may also be calculated on a per dose basis. As with many of the other PK parameters, the determination of AUC may be carried out in a single animal, or in a population of animals for which the average is calculated.

As used herein, the term "clearance rate" or "CL" refers to a measure of the body's ability to eliminate a drug, and is expressed as the volume of plasma cleared of drug over time.

The phrase "derived from" when used concerning a rearranged variable region gene "derived from" an unrearranged variable region and/or unrearranged variable region gene segments refers to the ability to trace the sequence of the rearranged variable region gene back to a set of unrearranged variable region gene segments that were rearranged to form a gene that expresses the variable domain (accounting for, where applicable, splice differences and somatic mutations). For example, a rearranged variable region gene that has undergone somatic mutation is still derived from the unrearranged variable region gene segments. In some embodiments, where the endogenous locus is replaced with a universal light chain or heavy chain locus, the term "derived from" indicates the ability to trace origin of the sequence to said rearranged locus even though the sequence may have undergone somatic mutations.

As used herein, the phrase "endogenous gene" or "endogenous gene segment" refers to a gene or gene segment found in a parent or reference organism prior to introduction of a disruption, deletion, replacement, alteration, or modification as described herein. In some embodiments, a reference organism is a wild-type organism. In some embodiments, a reference organism is an engineered organism. In some embodiments, a reference organism is a laboratory-bred organism (whether wild-type or engineered).

The term "in vivo recovery" or "IVR" refers to the incremental recovery (K-value), which is the observed peak activity minus predose level and then divided by the dose. IVR may also be calculated on a percentage basis. The mean IVR can be determined in an animal population, or the individual IVR can be determined in a single animal.

As used herein, the term "locus" refers to a location on a chromosome that contains a set of related genetic elements (e.g., genes, gene segments, regulatory elements). For example, an unrearranged immunoglobulin locus may include immunoglobulin variable region gene segments, one or more immunoglobulin constant region genes and associated regulatory elements (e.g., promoters, enhancers, switch elements, etc.) that direct V(D)J recombination and immunoglobulin expression. A locus can be endogenous or non-endogenous. The term "endogenous locus" refers to a location on a chromosome at which a particular genetic element is naturally found. In some embodiments, an endogenous locus has a sequence found in nature. In some embodiments, an endogenous locus is a wild-type locus. In some embodiments, an endogenous locus is an engineered locus. For example, an endogenous mouse immunoglobulin heavy chain locus refers to the location on mouse chromosome 12 that includes immunoglobulin heavy chain variable region gene segments and constant region genes in a wild-type mouse, an endogenous mouse immunoglobulin λ light chain locus refers to the location on mouse chromosome 16 that includes immunoglobulin λ light chain variable region gene segments and constant region genes in a wild-type mouse, while an endogenous mouse immunoglobulin κ light chain locus refers to the location on mouse chromosome 6 that includes immunoglobulin κ light chain variable region gene segments and constant region genes in a wild-type mouse.

Unrearranged variable region gene segments can be said to be "operably linked" to a contiguous constant region gene if the unrearranged variable region gene segments are capable of rearranging to form a rearranged variable region gene that is expressed in conjunction with the constant region gene as a polypeptide chain of an antigen binding protein.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The term "unrearranged" includes the state of an immunoglobulin variable region locus or variable region gene segments wherein V gene segments and J gene segments (for heavy variable regions, D gene segments as well) are maintained separately but are capable of being joined to form a rearranged V(D)J gene (a "variable region gene") that comprises a single V,(D),J of the V(D)J repertoire.

As used herein, the term "volume of distribution at steady state" or "Vss" refers to the apparent space (volume) into which a drug distributes. More particularly, Vss represents the amount of drug in an animal's body divided by the plasma concentration at steady state.

As used herein, the term "$C_H$ gene segment" (e.g., Cγ1 gene segment, $C_{γ2a}$ gene segment, $C_{γ2c}$ gene segment, Cμ gene segment, $C_{γ2b}$ gene segment, $C_{γ3}$ gene segment, $C_δ$ gene segment, Cε gene segment, $C_α$ gene segment, etc.) refers to a segment of DNA sequence that encodes the immunoglobulin heavy chain constant region and may be used interchangeably with $C_H$ gene (e.g., Cγ gene, $C_{γ2a}$ gene, $C_{γ2c}$ gene, $C_{γ3}$ gene, $C_{γ2b}$ gene, Cμ gene, $C_δ$ gene, Cε gene, $C_α$ gene, etc.). For example, Cγ1 gene segment or Cγ1 gene refers to a segment of DNA sequence that encodes the IgG1 constant region. The term "$C_H$ gene segment locus" refers to a location on a chromosome at which the $C_H$ gene segment or $C_H$ gene is naturally found.

Genetically Modified Loci

In certain aspects provided herein are genetically modified rodents (e.g., mice or rats) useful for the in vivo testing of therapeutic agents comprising a human Fc in genetically modified rodents (e.g., the testing of the pharmacokinetic and/or pharmacodynamic properties of such a therapeutic agent in genetically modified rodents). In some embodiments the genetically modified rodents comprise genetically modified loci that encode antibody heavy chains comprising a human Fc (e.g., a human IgG1 Fc, a human IgG4 Fc). In some embodiments, the rodents comprise genetically modified loci that encode fully or partially human light chains (e.g., that encode γ light chains or κ light chains). In certain embodiments, the genetically modified rodents comprise one or more loci that encode Fc receptors with a human extracellular domain (e.g., a Neonatal Fc Receptor (FcRn) α-chain, a β-2-microglobulin polypeptide (β2M), a Fc ε receptor 1α (FcεR1α) α-chain, a Fc γ receptor 1 alpha (FcγR1a) α-chain, a Fc gamma receptor 2a (FcγR2a) α-chain, a Fc gamma receptor 2b (FcγR2b) α-chain, a Fc gamma receptor 3a (FcγR3a) α-chain, a Fc gamma receptor 3b (FcγR3b) α-chain, a Fc gamma receptor 2c (FcγR2c) α-chain). In certain embodiments, the transmembrane and cytoplasmic domain encoded by such loci can be human or non-human (e.g., rodent).

Humanized Immunoglobulin Heavy Chain Loci

In certain aspects, provided herein are rodents (e.g., mice or rats) comprising genetically modified immunoglobulin (Ig) heavy chain loci. Such loci generally comprise a variable region and a constant region. The variable region includes Ig heavy chain variable region gene segments (e.g., at least a $V_H$ gene segment, a $D_H$ gene segment and a $J_H$ gene segment). The constant region locus includes one or more Ig heavy chain constant region gene segments ($C_H$). In certain embodiments the immunoglobulin heavy chain variable region is operably linked to the immunoglobulin heavy chain constant region such that the rodent produces antibodies comprising variable domains derived from the $V_H$ gene segment, the $D_H$ gene segment and the $J_H$ gene segment and heavy chain constant domains derived from the $C_H$ gene segment.

In some embodiments the variable region will be an unrearranged variable region and will contain unrearranged Ig variable region gene segments. In some embodiments, the variable region will be a rearranged variable region and will therefore contain a rearranged variable region gene. In certain embodiments, the Ig variable region gene segments are human variable region gene segments. In certain embodiments, the Ig variable region gene segments are rodent (e.g., rat or mouse) variable region gene segments (e.g., rat or mouse variable region gene segments). Thus, in certain embodiments, the Ig heavy chain variable region locus will contain human Ig variable region gene segments. Exemplary variable region loci comprising human variable region gene segments have been described in the art. For example, such loci are described in U.S. Pat. Nos. 5,770,429, 5,814,318, 6,114,598, 6,998,514, 8,232,449, 8,502,018 and 8,697,940, each of which is hereby incorporated by reference, and in U.S. Pat. Pub. Nos. 2008/0098490, 2012/0167237, 2013/0145484, 2013/0326647, 2014/013275 and 2014/093908, each of which is hereby incorporated by reference.

In certain embodiments, the Ig heavy chain variable region locus contains unrearranged human Ig heavy chain variable region gene segments. In some embodiments, the unrearranged human Ig variable region gene segments comprise one or more human $V_H$ segments, one or more human $D_H$ segments and one or more human $J_H$ segments. In some embodiments, the unrearranged human Ig variable region gene segments comprise at least 3 $V_H$ gene segments, at least 18 $V_H$ gene segments, at least 20 $V_H$ gene segments, at least 30 $V_H$ gene segments, at least 40 $V_H$ gene segments, at least 50 $V_H$ gene segments, at least 60 $V_H$ gene segments, at least 70 $V_H$ gene segments, or at least 80 $V_H$ gene segments. In some certain embodiments, an engineered IgH locus (or allele) comprises all or substantially all the functional human $V_H$ gene segments found between human $V_H$3-74 and human $V_H$6-1 gene segments, inclusive, of a human IgH locus that appears in nature. In some certain embodiments, an engineered IgH locus (or allele) comprises at least human $V_H$ gene segments $V_H$3-74, $V_H$3-73, $V_H$3-72, $V_H$2-70, $V_H$1-69, $V_H$3-66, $V_H$3-64, $V_H$4-61, $V_H$4-59, $V_H$1-58, $V_H$3-53, $V_H$5-51, $V_H$4-49, $V_H$3-48, $V_H$1-46, $V_H$1-45, $V_H$3-43, $V_H$2-39, $V_H$4-34, $V_H$3-33, $V_H$4-31, $V_H$3-30, $V_H$4-28, $V_H$2-26, $V_H$1-24, $V_H$3-23, $V_H$3-21, $V_H$3-20, $V_H$1-18, $V_H$3-13, $V_H$3-11, $V_H$3-9, $V_H$1-8, $V_H$3-7, $V_H$2-5, $V_H$7-4-1, $V_H$4-4, $V_H$1-3, $V_H$1-2 and $V_H$6-1. In some embodiments, the non-human animals provided herein have a restricted immunoglobulin heavy chain locus characterized by a single polymorphic human $V_H$ gene segment, a plurality of $D_H$ gene segments and a plurality of $J_H$ gene segments (e.g., as described in U.S. Pat. Pub. No. 2013/0096287, which is hereby incorporated by reference). In some embodiments the $V_H$ gene segment is $V_H$1-2 or $V_H$1-69. In some embodiments, the non-human animals provided herein have a rearranged heavy chain variable region (a universal heavy chain variable region or a common heavy chain encoding sequence, e.g., as described in U.S. Patent Pub. No. 20140245468 and U.S. Pat. Nos.: 9,204,624 and 9,930,871, each of which is hereby incorporated by reference herein in its entirety). In some embodiments, the non-human animals provided herein comprise human unrearranged immunoglobulin light chain, e.g., κ, gene segments operably linked to a heavy chain constant region gene at the immunoglobulin heavy chain locus (e.g., U.S. Pat. No. 9,516,868, incorporated herein by reference in its entirety).

In yet other embodiments, the non-human organism may comprise in its germline and/or genome a heavy chain immunoglobulin locus that includes insertions and/or replacements of histidine codons designed to introduce pH-dependent binding properties to the antibodies generated in such non-human organism. In some of such embodiments, the histidine codons are inserted and/or replaced in the nucleic acid sequences encoding CDR3. Various such heavy immunoglobulin loci are provided in U.S. Pat. Nos. 9,301,510, 9,334,334, U.S. Patent Application Publication Nos. 2013/0247236, 20140013456, incorporated herein by reference.

In some embodiments, an engineered IgH locus (or allele) comprises 5, 10, 15, 20, 25 or more (e.g., 26, 27, etc.) human $D_H$ gene segments. In some certain embodiments, an engineered IgH locus (or allele) comprises all or substantially all of the functional human $D_H$ gene segments found between a human $D_H$1-1 and human $D_H$7-27 gene segment, inclusive, of a human IgH locus that appears in nature. In some certain embodiments, an engineered IgH locus (or allele) comprises at least human $D_H$ gene segments $D_H$1-1, $D_H$2-2, $D_H$3-3, $D_H$4-4, $D_H$5-5, $D_H$6-6, $D_H$1-7, $D_H$2-8, $D_H$3-9, $D_H$3-10, $D_H$5-12, $D_H$6-13, $D_H$2-15, $D_H$3-16, $D_H$4-17, $D_H$6-19, $D_H$1-20, $D_H$2-21, $D_H$3-22, $D_H$6-25, $D_H$1-26 and $D_H$7-27. In some embodiments, the unrearranged human Ig gene segments include all of the human $D_H$ gene segments.

In some embodiments, an engineered IgH locus (or allele) comprises 1, 2, 3, 4, 5, 6 or more functional human $J_H$ gene segments. In some certain embodiments, an engineered IgH locus (or allele) comprises all or substantially all the functional human $J_H$ gene segments found between human $J_H$1 and human $J_H$6 gene segments, inclusive, of a human IgH locus that appears in nature. In some certain embodiments, an engineered IgH locus (or allele) comprises at least human $J_H$ gene segments $J_H$1, $J_H$2, $J_H$3, $J_H$4, $J_H$5 and $J_H$6. In some embodiments, the unrearranged human Ig gene segments include all of the human $J_H$ gene segments.

In some embodiments, an engineered IgH locus as described herein does not contain an endogenous Adam6 gene. In some embodiments, an engineered IgH locus as described herein does not contain an endogenous Adam6 gene (or Adam6-encoding sequence) in the same germline genomic position as found in a germline genome of a wild-type non-human animal of the same species. In some embodiments, an engineered IgH locus as described herein does not contain a human Adam6 pseudogene. In some embodiments, an engineered IgH locus as described herein comprises insertion of at least one nucleotide sequence that encodes one or more non-human (e.g., rodent) Adam6 polypeptides. Said insertion may be outside of an engineered immunoglobulin heavy chain locus as described herein (e.g., upstream of a 5' most $V_H$ gene segment), within an engineered IgH locus or elsewhere in the germline genome of a non-human animal (e.g., a randomly introduced non-human Adam6-encoding sequence), cell or tissue.

In some embodiments, an engineered endogenous immunoglobulin heavy chain locus lacks a functional endogenous rodent Adam6 gene. In some embodiments, a germline genome of a rodent comprising the engineered heavy chain locus includes one or more nucleotide sequences encoding one or more rodent ADAM6 polypeptides, functional orthologs, functional homologs, or functional fragments thereof. In some embodiments, one or more rodent ADAM6 polypeptides, functional orthologs, functional homologs, or functional fragments thereof are expressed (e.g., in a cell of the male reproductive system, e.g., a testes cell).

In some embodiments, one or more nucleotide sequences encoding one or more rodent ADAM6 polypeptides, functional orthologs, functional homologs, or functional fragments thereof are included on the same chromosome as the engineered endogenous immunoglobulin heavy chain locus. In some embodiments, one or more nucleotide sequences encoding one or more rodent ADAM6 polypeptides, functional orthologs, functional homologs, or functional fragments thereof are included in the engineered endogenous immunoglobulin heavy chain locus. In some embodiments, one or more nucleotide sequences encoding one or more rodent ADAM6 polypeptides, functional orthologs, functional homologs, or functional fragments thereof are between a first human $V_H$ gene segment and a second human $V_H$ gene segment. In some embodiments, a first human $V_H$ gene segment is $V_H1$-2 and a second human $V_H$ gene segment is $V_H6$-1. In some embodiments, one or more nucleotide sequences encoding one or more rodent ADAM6 polypeptides, functional orthologs, functional homologs, or functional fragments thereof are in place of a human Adam6 pseudogene. In some embodiments, one or more nucleotide sequences encoding one or more rodent ADAM6 polypeptides, functional orthologs, functional homologs, or functional fragments thereof replace a human Adam6 pseudogene. In some embodiments, one or more nucleotide sequences encoding one or more rodent ADAM6 polypeptides, functional orthologs, functional homologs, or functional fragments thereof are between a human $V_H$ gene segment and a human $D_H$ gene segment.

Exemplary Ig variable regions comprising Ig heavy chain gene segments are provided, for example, in Macdonald et al., *Proc. Natl. Acad. Sci. USA* 111:5147-52 and supplemental information, which is hereby incorporated by reference. Such mice are described, e.g., U.S. Pat. Nos. 8,642,835 and 8,697,940, incorporated herein by reference.

In some embodiments, the Ig heavy chain variable gene locus comprising unrearranged human Ig heavy chain variable region gene segments also includes human Ig heavy chain variable region intergenic sequences. In some embodiments, the Ig heavy chain variable gene locus includes non-human (e.g., rodent, rat, mouse) Ig heavy chain variable region intergenic sequences. In some embodiments, the IgH locus comprises non-human regulatory elements (e.g., non-human promoters and/or enhancers). In some embodiments, the non-human regulatory elements are rodent regulatory elements (e.g., rat or mouse promoters or enhancers). In some embodiments, the IgH locus comprises an IgM enhancer (Eμ). In some embodiments, the IgM enhancer is a non-human Eμ (e.g., a rodent Eμ, such as a mouse or rat Eμ).

In some embodiments, the Ig heavy chain variable region is a rearranged variable region comprising a Ig heavy chain variable region gene (a universal heavy chain variable region). In some embodiments, the rearranged Ig heavy chain variable region gene is a human rearranged Ig heavy chain variable region gene. Exemplary rearranged Ig heavy chain variable regions are provided in U.S. Patent Pub. No. 2014/0245468, which is hereby incorporated by reference.

In certain embodiments, the immunoglobulin constant region comprises a $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain. In some embodiments, the IgG transmembrane domain is a rodent IgG transmembrane domain (e.g., a mouse or rat transmembrane domain). In certain embodiments, transmembrane domain is a human IgG transmembrane domain. In some embodiments, the IgG cytoplasmic domain is a rodent IgG cytoplasmic domain (e.g., a mouse or rat cytoplasmic domain). In some embodiments, the IgG cytoplasmic domain is a human IgG cytoplasmic domain. In some embodiments, the IgG connecting region is a rodent IgG connecting region (e.g., a mouse or rat connecting domain). In certain embodiments, IgG connecting region is a human IgG connecting region.

In certain embodiments, the human $C_H1$ domain, the human hinge region, the human $C_H2$ domain and the human $C_H3$ domain are IgG1 domains. In some embodiments, such an IgG1 domain is encoded by an allele selected from IGHG1*01, IGHG1*02, IGHG1*03, IGHG1*04 and IGHG1*05.

In certain embodiments, the human $C_H1$ domain, the human hinge region, the human $C_H2$ domain and the human $C_H3$ domain are IgG2 domains. In some embodiments, such an IgG2 domain is encoded by an allele selected from IGHG2*01, IGHG2*02, IGHG2*03, IGHG2*04, IGHG2*05 and IGHG2*06.

In certain embodiments, the human $C_H1$ domain, the human hinge region, the human $C_H2$ domain and the human $C_H3$ domain are IgG3 domains. In some embodiments, such an IgG3 domain is encoded by an allele selected from IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19.

In certain embodiments, the human $C_H1$ domain, the human hinge region, the human $C_H2$ domain and the human $C_H3$ domain are IgG4 domains. In some embodiments, such an IgG4 domain is encoded by an allele selected from IGHG4*01, IGHG4*02, IGHG4*03 and IGHG4*04.

In some embodiments, the $C_H$ gene segment encodes variant human immunoglobulin heavy chain constant region sequence (i.e., a human immunoglobulin heavy chain constant region sequence that includes one or more additions, deletions, and/or substitutions relative to an appropriate reference human immunoglobulin heavy chain constant region sequence) that is characterized in that effector function and/or affinity for an FcR is enhanced or diminished relative to a reference human immunoglobulin heavy chain constant region.

In some embodiments, the $C_H$ gene segment encodes a human immunoglobulin heavy chain constant region characterized by an altered affinity for activating and/or inhibitory receptors. In some embodiments, the $C_H$ gene segment encodes a human immunoglobulin heavy chain constant region characterized by enhanced or diminished binding to an FcRn receptor, e.g., at acidic pH as compared to neutral pH. In some embodiments, the $C_H$ gene segment encodes a human immunoglobulin heavy chain constant region, in whole or in part, encodes a human immunoglobulin heavy chain constant region having one or more amino acid modifications. Exemplary amino acid modifications include, but are not limited to, a substitution at position 297 (e.g., N297A), position 250 (e.g., 250E or 250Q), position 252 (e.g., 252L, 252Y, 252F, 252W or 252T), position 254 (e.g., 254S or 254T), position 256 (e.g., 256S, 256R, 256Q, 256E, 256D, or 256T), position 307 (e.g., 307P or 307A), position 308 (e.g., 308F or 308V), position 428 (e.g., 428L or 428F), position 433 (e.g., 433H, 433Lm, 433R, 433S, 433P, 433Q or 433K), position 434 (e.g., 434A, 434W, 434H, 434F or 434Y), and combinations thereof. In some embodiments, the $C_H$ gene segment encodes a human immunoglobulin heavy chain constant region having one or more pairs or groups of amino acid modifications selected from the group consisting of 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

In some embodiments, the $C_H$ gene segment encodes a chimeric immunoglobulin heavy chain constant domain that includes segments or portions derived from (or that appear in) more than one human immunoglobulin isotypes. For example, such a chimeric $C_H$ region may comprise a $C_H2$ domain derived from a human IgG1, human IgG2 or human IgG4 molecule, combined with a $C_H3$ domain derived from a human IgG1, human IgG2 or human IgG4 molecule. In some certain embodiments, the chimeric $C_H$ region further comprises a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. In some certain embodiments, a chimeric hinge region comprises amino acid residues derived from a human IgG1 or a human IgG4 upper hinge and amino acid residues derived from a human IgG2 lower hinge.

In certain embodiments, the modified $C_H$ gene segment is located at an endogenous $C_H$ gene segment locus. In certain embodiments, the modified $C_H$ gene segment is located at an endogenous $C_{\gamma1}$ gene segment locus, an endogenous $C_{\gamma2a}$ gene segment locus, an endogenous $C_{\gamma2b}$ gene segment locus, an endogenous $C_{\gamma2c}$ gene segment locus or an endogenous $C_{\gamma3}$ gene segment locus.

The endogenous immunoglobulin heavy chain constant region gene structure can vary between rodents. For example, the Norwegian rat does not have a $C_{\gamma3}$ gene segment at the endogenous immunoglobulin heavy chain locus, whereas mouse strains generally do. Even for the same species, the immunoglobulin heavy chain constant region gene structure can vary from strain to strain. For example, while some mouse stains have a $C_{\gamma2a}$ gene segment at the endogenous immunoglobulin heavy chain locus, other mouse stains (e.g., mouse strains with the Igh1-b allele) have a $C_{\gamma2c}$ gene segment instead, and some mouse strains may have both $C_{\gamma2a}$ and $C_{\gamma2c}$ gene segments. The rodent $C_{\gamma1}$, $C_{\gamma2a}$, $C_{\gamma2b}$ and $C_{\gamma3}$ gene segments disclosed in the figures, examples, and/or descriptions herein are therefore exemplary rodent $C_H$ gene segments and one of skill in the art would appreciate that the specific constant region gene structure will vary from one rodent strain to another. Thus, for example, one of skill in the art would appreciate that the disclosure contemplates rodents comprising a rodent $C_{\gamma2c}$ gene segment in place of or in addition to any disclosed rodent $C_{\gamma2a}$ gene segment.

In some embodiments, the modified $C_H$ gene segment is a human $C_{\gamma1}$ gene segment (or at least the portion of the human $C_{\gamma1}$ gene segment encoding the $C_H1$ domain, the hinge region, the $C_H2$ domain and the $C_H3$ domain of the IgG1 constant domain) and it is positioned at an endogenous $C_{\gamma2a}$ gene segment locus. In some embodiments, the portion of the human $C_{\gamma1}$ gene segment encoding the $C_H1$ domain, the hinge region, the $C_H2$ domain and the $C_H3$ domain of the IgG1 constant domain is operably linked to the portion of the endogenous rodent $C_{\gamma2a}$ gene segment encoding the IgG2a transmembrane and/or cytoplasmic domain.

In some embodiments, the modified $C_H$ gene segment is a human $C_{\gamma1}$ gene segment (or at least the portion of the human $C_{\gamma1}$ gene segment encoding the $C_H1$ domain, the hinge region, the $C_H2$ domain and the $C_H3$ domain of the IgG1 constant domain) and it is positioned at an endogenous $C_{\gamma2c}$ gene segment locus. In some embodiments, the portion of the human $C_{\gamma1}$ gene segment encoding the $C_H1$ domain, the hinge region, the $C_H2$ domain and the $C_H3$ domain of the IgG1 constant domain is operably linked to the portion of the endogenous rodent $C_{\gamma2c}$ gene segment encoding the IgG2c transmembrane and/or cytoplasmic domain.

In some embodiments, the modified $C_H$ gene segment is a human $C_{\gamma4}$ gene segment (or at least the portion of the human $C_{\gamma4}$ gene segment encoding the $C_H1$ domain, the hinge region, the $C_H2$ domain and the $C_H3$ domain of the IgG4 constant domain) and it is positioned at an endogenous $C_{\gamma1}$ gene segment locus. In some embodiments, the portion of the human $C_{\gamma4}$ gene segment encoding the $C_H1$ domain, the hinge region, the $C_H2$ domain and the $C_H3$ domain of the IgG4 constant domain is operably linked to the portion of the endogenous rodent $C_{\gamma1}$ gene segment encoding the IgG1 transmembrane and/or cytoplasmic domain.

In certain embodiments, the modified $C_H$ gene segment replaces all or part of an endogenous $C_H$ gene segment. In certain embodiments, the modified $C_H$ gene segment replaces all or part of an endogenous $C_{\gamma1}$ gene segment, an endogenous $C_{\gamma2a}$ gene segment, an endogenous $C_{\gamma2b}$ gene segment, an endogenous $C_{\gamma2c}$ gene segment, or an endogenous $C_{\gamma3}$ gene segment.

In some embodiments, the modified $C_H$ gene segment is a human $C_{\gamma1}$ gene segment (or at least the portion of the human $C_{\gamma1}$ gene segment encoding the $C_H1$ domain, the hinge region, the $C_H2$ domain and the $C_H3$ domain of the IgG1 constant domain) and it replaces all or part of an endogenous $C_{\gamma2a}$ gene segment locus. In some embodiments, the portion of the human $C_{\gamma1}$ gene segment encoding the $C_H1$ domain, the hinge region, the $C_H2$ domain and the $C_H3$ domain of the IgG1 constant domain replaces the portion of the endogenous rodent $C_{\gamma 2a}$ gene segment encoding the $C_H1$ domain, the hinge region, the $C_H2$ domain and the $C_H3$ domain of the IgG2a constant domain such that the portion of the human $C_{\gamma 1}$ gene segment encoding the $C_H1$ domain, the hinge region, the $C_H2$ domain and the $C_H3$ domain of the IgG1 constant domain is operably linked to the portion of the endogenous rodent $C_{\gamma 2a}$ gene segment encoding the IgG2a transmembrane and/or cytoplasmic domain.

In some embodiments, the modified $C_H$ gene segment is a human $C_{\gamma 4}$ gene segment (or at least the portion of the human $C_{\gamma 4}$ gene segment encoding the $C_H1$ domain, the hinge region, the $C_H2$ domain and the $C_H3$ domain of the IgG4 constant domain) and it replaces all or part of an endogenous $C_{\gamma 1}$ gene segment locus. In some embodiments, the portion of the human $C_{\gamma 4}$ gene segment encoding the $C_H1$ domain, the hinge region, the $C_H2$ domain and the $C_H3$ domain of the IgG4 constant domain replaces the portion of the endogenous rodent $C_{\gamma 1}$ gene segment encoding the $C_H1$ domain, the hinge region, the $C_H2$ domain and the $C_H3$ domain of the IgG1 constant domain such that the portion of the human $C_{\gamma 4}$ gene segment encoding the $C_H1$ domain, the hinge region, the $C_H2$ domain and the $C_H3$ domain of the IgG4 constant domain is operably linked to the portion of the endogenous rodent $C_{\gamma 1}$ gene segment encoding the IgG1 transmembrane and/or cytoplasmic domain.

In certain embodiments the Ig heavy chain constant region includes one or more rodent (e.g., rat or mouse) $C_H$ gene segments. In some embodiments, the Ig constant region includes a rodent (e.g., rat or mouse) $C_\mu$ gene segment. In some embodiments, the Ig constant region includes a rodent (e.g., rat or mouse) $C_\delta$ gene segment. In some embodiments, the Ig constant region includes a rodent (e.g., rat or mouse) $C_{\gamma 1}$ gene segment. In some embodiments, the Ig constant region includes a rodent (e.g., rat or mouse) $C_{\gamma 2a}$ gene segment. In some embodiments, the Ig constant region includes a rodent (e.g., rat or mouse) $C_{\gamma 2b}$ gene segment. In some embodiments, the Ig constant region includes a rodent (e.g., rat or mouse) $C_{\gamma 2c}$ gene segment. In some embodiments, the Ig constant region includes a rodent (e.g., mouse) $C_{\gamma 3}$ gene segment. In some embodiments, the Ig constant region includes a rodent (e.g., rat or mouse) $C_\varepsilon$ gene segment. In some embodiments, the Ig constant region includes a rodent (e.g., rat or mouse) $C_\varepsilon$ gene segment. In some embodiments, the one or more rodent constant region gene segments are endogenous constant region gene segments. In some embodiments, the modified $C_H$ gene segment described above is the only modified $C_H$ gene segment in the Ig heavy chain constant region.

In some embodiments, the modified $C_H$ gene segment described above is one of a plurality of modified $C_H$ gene segments in the Ig heavy chain constant region (e.g., one of 2, 3, 4, 5, 6, 7 or 8 modified gene segments that are partially or fully humanized in the Ig heavy chain constant region). In some embodiments, the Ig heavy chain constant region includes a human or partially human $C_\mu$ gene segment. In some embodiments, the Ig heavy chain constant region includes a human or partially human $C_\delta$ gene segment. In some embodiments, the Ig heavy chain constant region includes a human or partially human $C_{\gamma 1}$ gene segment. In some embodiments, the Ig heavy chain constant region includes a human or partially human $C_{\gamma 2}$ gene segment. In some embodiments, the Ig heavy chain constant region includes a human or partially human $C_{\gamma 3}$ gene segment. In some embodiments, the Ig heavy chain constant region includes a human or partially human $C_{\gamma 4}$ gene segment. In some embodiments, the Ig heavy chain constant region includes a human or partially human $C_\varepsilon$ gene segment. In some embodiments, the Ig heavy chain constant region includes a human or partially human $C_\alpha$ gene segment. In some embodiments, the Ig heavy chain constant region comprises a human $C_\mu$ gene segment, a human $C_\delta$ gene segment, a human $C_{\gamma 1}$ gene segment and a human $C_{\gamma 3}$ gene segment. In some embodiments, the Ig heavy chain constant region further comprises a human $C_{\gamma 2}$ gene segment and a human $C_{\gamma 4}$ gene segment. In some embodiments, the Ig heavy chain constant region further comprises a human $C_\alpha$ gene segment. In some embodiments, the Ig heavy chain constant region further comprises a human $C_\varepsilon$ gene segment.

In some embodiments, the IgH locus comprises human or rodent (e.g., rat or mouse) regulatory elements. In some embodiments, the regulatory element is an endogenous regulatory element. In certain embodiments, the IgH locus comprises a rodent (e.g., rat or mouse) or human intronic enhancer ($E_i$). In some embodiments, the IgH locus comprises a rodent (e.g., rat or mouse) or human 3' regulatory region (3' RR).

In some embodiments, the modified immunoglobulin heavy chain locus is positioned at an endogenous immunoglobulin heavy chain locus. In some embodiments, the immunoglobulin heavy chain locus replaces all or part of the endogenous immunoglobulin heavy chain locus. In certain embodiments, the modified IgH locus is located on a transgene positioned outside of the endogenous locus. In some embodiments, the endogenous IgH locus is inactivated (e.g., through the deletion, relocation and/or inversion of all or part of the endogenous Ig heavy chain locus).

Thus, in some embodiments, one or more immunoglobulin heavy chain constant regions (or portion thereof) of an immunoglobulin heavy chain locus are not deleted (i.e., intact). In some embodiments, one or more $C_H$ gene segments of an immunoglobulin heavy chain locus are altered, disrupted, deleted or replaced with, among other things, an immunoglobulin heavy chain constant region sequence as described herein (e.g., a sequence encoding a human IgG $C_H1$-H-$C_H2$-$C_H3$ polypeptide) operably linked to a transmembrane and cytoplasmic encoding sequence(s) of a non-human immunoglobulin heavy chain IgG constant region gene (e.g., an M1 and/or M2 encoding sequence) and, in some embodiments, an immunoglobulin heavy chain constant region sequence (e.g., a sequence encoding a human IgE $C_H1$-$C_H2$-$C_H3$-$C_H4$ polypeptide) operably linked to a transmembrane and cytoplasmic encoding sequence(s) an IgE constant region gene. In some embodiments, all or substantially all of an immunoglobulin heavy chain constant region is replaced with a heterologous immunoglobulin heavy chain constant region. In some embodiments, a heterologous immunoglobulin heavy chain constant region sequence is operably linked to a transmembrane and cytoplasmic encoding sequence (e.g., M1 and M2 exons) of one or more IgG constant region gene. In some embodiments, a heterologous immunoglobulin heavy chain constant region sequence is operably linked to a transmembrane and cytoplasmic encoding sequence (e.g., M1 and M2 exons) of an IgE constant region gene. In some embodiments, a heterologous immunoglobulin heavy chain constant region sequence is operably linked to a transmembrane and cytoplasmic encoding sequence (e.g., an M exon[s]) of an IgA constant region gene. In some certain embodiments, one or more $C_H$ gene segments (e.g., $C_\mu$, $C_\delta$, etc.) are not deleted or replaced in an immunoglobulin heavy chain constant region that includes a heterologous immunoglobulin heavy chain constant region sequence operably linked to a transmembrane and cytoplasmic encoding sequence of one or more constant region genes as described herein. In some embodiments, a heterologous immunoglobulin heavy chain constant region sequence is a human immunoglobulin heavy chain constant region sequence. In some embodiments, an immunoglobulin heavy chain constant region that is altered, disrupted, deleted, replaced or engineered with one or more heterologous immunoglobulin heavy chain constant region sequences is a murine immunoglobulin heavy chain constant region. In some embodiments, a heterologous immunoglobulin heavy chain constant region sequence is inserted into one copy (i.e., allele) of an IgG constant region gene (e.g., $C_{\gamma 1}$, $C_{\gamma 2a}$, $C_{\gamma 2b}$, $C_{\gamma 2c}$ or $C_{\gamma 3}$) of the two copies of said IgG constant region gene of an immunoglobulin heavy chain constant region, giving rise to a non-human animal that is heterozygous with respect to the heterologous immunoglobulin heavy chain constant region sequence. In some embodiments, a non-human animal is provided that is homozygous for an immunoglobulin heavy chain constant region that includes a heterologous immunoglobulin heavy chain constant region sequence as described herein.

In some embodiments, an engineered immunoglobulin heavy chain constant region as described herein comprises one or more IgG encoding $C_H$ gene segments that each comprise a human extracellular domain encoding sequence (e.g., a human IgG $C_H1$-H-$C_H2$-$C_H3$) operably linked to a non-human transmembrane and cytoplasmic domain encoding sequence (e.g., a non-human IgG M1-M2) of the same or different IgG subclasses.

In some embodiments, an engineered immunoglobulin heavy chain constant region as described herein comprises one or more engineered IgG encoding $C_H$ gene segments as described herein and further comprises a wild-type (e.g., unmodified non-human such as rat or mouse) $C_\mu$ constant region gene.

In some embodiments, an engineered immunoglobulin heavy chain constant region as described herein comprises one or more engineered IgG encoding $C_H$ gene segments as described herein and further comprises wild-type (e.g., unmodified non-human such as rat or mouse) $C_\mu$ and $C_\delta$ constant region genes.

In various embodiments, an engineered IgG encoding $C_H$ gene segment comprising a human immunoglobulin heavy chain constant region sequence as described herein is an engineered IgG encoding $C_H$ gene segment of IgG subclass selected from $C_{\gamma 1}$, $C_{\gamma 2a}$, $C_{\gamma 2b}$, $C_{\gamma 2c}$, or $C_{\gamma 3}$.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$ in the place of $C_H1$-H-$C_H2$-$G_H3$ exons and operably linked to M1 and M2 exons of a non-human (e.g., rat or mouse) $C_{\gamma 2a}$ gene segment.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2a}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2c}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2c}$ gene segment.

In some certain embodiments, an engineered immunoglobulin heavy chain constant region as described herein comprises an engineered $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 1}$ gene segment.

In some certain embodiments, an engineered immunoglobulin heavy chain constant region as described herein comprises an engineered $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 1}$ gene segment.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2a}$ gene segment, and an engineered $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 1}$ gene segment.

In some certain embodiments, an engineered immunoglobulin heavy chain constant region as described herein comprises an engineered $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2a}$ gene segment, and an engineered $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 1}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 2c}$ gene segment, and an engineered $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1 and M2 exons of a non-human (e.g., rat or mouse) $C_{\gamma 1}$ gene segment.

In some certain embodiments, an engineered immunoglobulin heavy chain constant region as described herein comprises an engineered $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 2c}$ gene segment, and an engineered $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of a non-human (e.g., rat or mouse) $C_{\gamma 1}$ gene segment.

In various embodiments, an engineered immunoglobulin heavy chain constant region as described herein comprises one or more further modifications including rendering constant region genes (i.e., isotypes) other than one or more IgG constant regions that comprise a sequence encoding human IgG $C_H1$-H-$C_H2$-$C_H3$ or human IgG $C_H1$-H-$C_H2$-$C_H3$-M1-M2 (e.g., IgG1 and/or IgG2a) to be nonfunctional, e.g., via deletion in whole or in part, alteration in whole or in part, disruption in whole or in part, replacement in whole or in part of one or more immunoglobulin constant region genes encoding IgD, IgE, IgA and an IgG that does not itself contain a sequence encoding human IgG $C_H1$-H-$C_H2$-$C_H3$ or human IgG $C_H1$-H-$C_H2$-$C_H3$-M1-M2 as described herein (e.g., IgG2b and/or IgG3). Engineered non-human embryos, cells and targeting vectors for making such non-human animals, embryos and cells are also provided.

In some certain embodiments, an engineered immunoglobulin heavy chain constant region provided herein comprises a wild-type (e.g., unmodified non-human such as rat or mouse) $C_\mu$ gene segment, a $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1-M2 exons of said $C_{\gamma 1}$ gene segment, and a deletion of the $C_\delta$, $C_{\gamma 2a}$, $C_{\gamma 2c}$, $C_{\gamma 2b}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of said $C_{\gamma 1}$ gene segment, and a deletion of the $C_\delta$, $C_{\gamma 2a}$, $C_{\gamma 2c}$, $C_{\gamma 2b}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2a}$ gene segment, and a deletion of the $C_\delta$, $C_{\gamma 2b}$, $C_{\gamma 2c}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said a $C_{\gamma 2a}$ gene segment, and a deletion of the $C_\delta$, $C_{\gamma 1}$, $C_{\gamma 2b}$, $C_{\gamma 2c}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2c}$ gene segment, and a deletion of the $C_\delta$, $C_{\gamma 1}$, $C_{\gamma 2a}$, $C_{\gamma 2b}$, $C_{\gamma 3}$, $C_\varepsilon$ and $C_\alpha$ gene segments.

In some certain embodiments, an engineered immunoglobulin heavy chain constant region provided herein comprises a wild-type (e.g., unmodified non-human such as rat or mouse) $C_\mu$ gene segment, a $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said a $C_{\gamma 2c}$ gene segment, and a deletion of the $C_\delta$, $C_{\gamma 1}$, $C_{\gamma 2a}$, $C_{\gamma 2b}$, $C_{\gamma 3}$, $C_\varepsilon$ and $C_\alpha$ gene segments.

In various embodiments, an engineered immunoglobulin heavy chain constant region as described herein comprises one or more further modifications including engineering constant region genes (i.e., isotypes) other than one or more IgG constant regions that comprise a sequence encoding human IgG $C_H1$-H-$C_H2$-$C_H3$ or human IgG $C_H1$-H-$C_H2$-$C_H3$-M1-M2 (e.g., IgG1 and/or IgG2a) to be altered, modified, replaced, engineered, etc. via insertion of a human immunoglobulin heavy chain constant region sequence as described herein into one or more immunoglobulin constant region genes for IgD, IgE, IgA and an IgG that does not itself contain a sequence encoding human IgG $C_H1$-H-$C_H2$-$C_H3$ or human IgG $C_H1$-H-$C_H2$-$C_H3$-M1-M2 as described herein (e.g., IgG2b and/or IgG3).

Engineered non-human embryos, cells and targeting vectors for making non-human animals, embryos and cells comprising immunoglobulin loci with engineered constant regions described herein are also provided.

In some certain embodiments, an engineered immunoglobulin heavy chain constant region provided herein comprises a wild-type $C_\mu$ gene segment, a wild-type $C_\delta$ gene segment, a $C_{\gamma 3}$ gene segment comprising a sequence encoding human IgG3 $C_H1$-H-$C_H2$-$C_H3$ in the place of $C_H1$-H-$C_H2$-$C_H3$ exons and operably linked to M1-M2 exons of said $C_{\gamma 3}$ gene segment, a $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1-M2 exons of said $C_{\gamma 1}$ gene segment, a $C_{\gamma 2b}$ gene segment comprising a sequence encoding human IgG2 $C_H1$-H-$C_H2$-$C_H3$ in the place of $C_H1$-H-$C_H2$-$C_H3$ exons and operably linked to M1-M2 exons of said $C_{\gamma 2b}$ gene segment, a $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2a}$ gene segment (and/or a $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of said $C_{\gamma 2c}$ gene segment), a $C_\varepsilon$ gene segment comprising a sequence encoding human IgE $C_H1$-$C_H2$-$C_H3$-$C_H4$ in the place of $C_H1$-$C_H2$-$C_H3$-$C_H4$ exons and operably linked to M1-M2 exons of said an $C_\varepsilon$ gene segment, and a $C_\alpha$ gene segment comprising a sequence encoding human IgA1 or IgA2 $C_H1$-H-$C_H2$-$C_H3$ in the place of $C_H1$-H-$C_H2$-$C_H3$ exons and operably linked to M exon(s) of said $C_\alpha$ gene segment.

In some certain embodiments, an engineered immunoglobulin heavy chain constant region provided herein comprises a wild-type $C_\mu$ gene segment, a wild-type $C_\delta$ gene segment, a $C_{\gamma 3}$ gene segment comprising a sequence encoding human IgG3 $C_H1$-H-$C_H2$-$C_H3$-M1-M2 in the place of $C_H1$-H-$C_H2$-$C_H3$-M1-M2 exons and operably linked to the switch region of said $C_{\gamma 3}$ gene segment, a $C_{\gamma 1}$ gene segment comprising a sequence encoding human IgG4 $C_H1$-H-$C_H2$-$C_H3$-M1-M2 in the place of $C_H1$-H-$C_H2$-$C_H3$-M1-M2 exons and operably linked to the switch region of said a $C_{\gamma 1}$ gene segment, a $C_{\gamma 2b}$ gene segment comprising a sequence encoding human IgG2 $C_H1$-H-$C_H2$-$C_H3$-M1-M2 in the place of $C_H1$-H-$C_H2$-$C_H3$-M1-M2 exons and operably linked to the switch region of said $C_{\gamma 2b}$ gene segment, a $C_{\gamma 2a}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said $C_{\gamma 2a}$ gene segment (and/or a $C_{\gamma 2c}$ gene segment comprising a sequence encoding human IgG1 $C_H1$-H-$C_H2$-$C_H3$-M1-M2 in the place of $C_H1$-H-$C_H2$-$C_H3$-M1-M2 exons and operably linked to the switch region of said $C_{\gamma 2c}$ gene segment), a $C_\varepsilon$ gene segment comprising a sequence encoding human IgE $C_H1$-$C_H2$-$C_H3$-$C_H4$ in the place of $C_H1$-$C_H2$-$C_H3$-$C_H4$ exons and operably linked to M1-M2 exons of said an $C_\varepsilon$ gene segment, and a $C_\alpha$ gene segment comprising a sequence encoding human IgA1 or IgA2 $C_H1$-H-$C_H2$-$C_H3$ in the place of $C_H1$-H-$C_H2$-$C_H3$ exons and operably linked to M exon(s) of said $C_\alpha$ gene segment.

In various embodiments provided herein are genetically engineered heavy chain immunoglobulin loci depicted in FIG. 1, as well as genetically modified rodents (e.g., rats or mice), ES and other cells, and tissues comprising such loci. Thus, in one embodiment, provided here is a genetically engineered heavy chain immunoglobulin locus comprising human heavy chain variable gene segments (human heavy chain V, D, and J gene segments), rodent (e.g., rat or mouse) Ei enhancer, rodent (e.g., rat or mouse) $C_\mu$, $C_\delta$, $C_{\gamma 3}$, $C_{\gamma 1}$, $C_{\gamma 2b}$ gene segments, a chimeric $C_{\gamma 2a}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of a rodent (e.g., rat or mouse) $C_{\gamma 2a}$ gene segment (for example such that exons encoding the extracellular domain of human IgG1 operably linked to exons encoding transmembrane and cytoplasmic domains of rodent, e.g., rat or mouse, IgG2a) (and/or a chimeric $C_{\gamma 2c}$ gene segment comprising a sequence encoding human IgG1 $C_H1$-H-$C_H2$-$C_H3$ in the place of $C_H1$-H-$C_H2$-$C_H3$ exons and operably linked to M1-M2 exons of a rodent (e.g., rat or mouse) $C_{\gamma 2c}$ gene segment (for example such that exons encoding the extracellular domain of human IgG1 operably linked to exons encoding transmembrane and cytoplasmic domains of rodent, e.g., rat or mouse, IgG2c), rodent (e.g., rat or mouse) $C_\varepsilon$ and $C_\alpha$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 1. In some embodiments, the genetically modified locus comprises a functional Adam6 gene as described herein and in U.S. Pat. Nos. 8,642,835 and 8,697,940, each of which is incorporated herein by reference in its entirety. Genetically modified non-human animals, ES cells and other cells, and tissues, comprising such genetically engineered loci, are also provided.

In one embodiment, provided here is a genetically engineered heavy chain immunoglobulin locus comprising human heavy chain variable gene segments (human heavy chain V, D, and J gene segments), rodent (e.g., rat or mouse) Ei enhancer, rodent (e.g., rat or mouse) $C_\mu$, $C_\delta$, $C_{\gamma 3}$, $C_{\gamma 1}$, $C_{\gamma 2b}$ gene segments, a human $C_{\gamma 1}$ gene segment comprising a sequence encoding human IgG1 $C_H1$-H-$C_H2$-$C_H3$-M1-M2 such that both IgG1 extracellular and transmembrane/cytoplasmic encoding sequences are human, rodent (e.g., rat or mouse) $C_\varepsilon$ and $C_\alpha$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 2. In some embodiments, the genetically modified locus comprises a functional Adam6 gene as described herein and in U.S. Pat. Nos. 8,642,835 and 8,697,940, each of which is incorporated herein by reference in its entirety. Genetically modified non-human animals, ES cells and other cells, and tissues, comprising such genetically engineered loci, are also provided.

In one embodiment, provided here is a genetically engineered heavy chain immunoglobulin locus comprising human heavy chain variable gene segments (human heavy chain V, D, and J gene segments), rodent (e.g., rat or mouse) Ei enhancer, rodent (e.g., rat or mouse) $C_\mu$, $C_\delta$, $C_{\gamma 3}$ gene segments, a chimeric $C_{\gamma 1}$ gene segment comprising a sequence encoding human IgG4 $C_H1$-H-$C_H2$-$C_H3$ in the place of $C_H1$-H-$C_H2$-$C_H3$ exons and operably linked to M1-M2 exons of a rodent (e.g., rat or mouse) $C_{\gamma 1}$ gene segment (for example such that exons encoding the extracellular domain of human IgG4 operably linked to exons encoding transmembrane and cytoplasmic domains of rodent, e.g., rat or mouse, IgG1), rodent (e.g., rat or mouse) $C_{\gamma 2b}$, $C_{\gamma 2a}$ (and/or $C_{\gamma 2c}$), $C_\varepsilon$, $C_\alpha$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 3. In some embodiments, the genetically modified locus comprises a functional Adam6 gene as described here and in U.S. Pat. Nos. 8,642,835 and 8,697,940, each of which is incorporated herein by reference in its entirety. Genetically modified non-human animals, ES cells and other cells, and tissues, comprising such genetically engineered loci, are also provided.

In one embodiment, provided here is a genetically engineered heavy chain immunoglobulin locus comprising human heavy chain variable gene segments (human heavy chain V, D, and J gene segments), rodent (e.g., rat or mouse) Ei enhancer, rodent (e.g., rat or mouse) $C_\mu$, $C_\delta$, $C_{\gamma 3}$ gene segments, a human $C_{\gamma 4}$ gene segment comprising a sequence encoding human IgG4 $C_H1$-H-$C_H2$-$C_H3$-M1-M2 such that both IgG4 extracellular and transmembrane/cytoplasmic encoding sequences are human, rodent (e.g., rat or mouse) $C_{\gamma 2b}$, $C_{\gamma 2a}$ (and/or $C_{\gamma 2c}$) gene segments, rodent (e.g., rat or mouse) $C_\varepsilon$ and $C_\alpha$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 4. In some embodiments, the genetically modified locus comprises a functional Adam6 gene as described here and in U.S. Pat. Nos. 8,642,835 and 8,697,940, each of which is incorporated herein by reference in its entirety. Genetically modified non-human animals, ES cells and other cells, and tissues, comprising such genetically engineered loci, are also provided.

In one embodiment, provided here is a genetically engineered heavy chain immunoglobulin locus comprising human heavy chain variable gene segments (human heavy chain V, D, and J gene segments), human Ei enhancer, human $C_\mu$, $C_\delta$, $C_{\gamma 3}$ and $C_{\gamma 1}$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 5. In some embodiments, the genetically modified locus comprises a functional Adam6 gene as described here and in U.S. Pat. Nos. 8,642,835 and 8,697,940, each of which is incorporated herein by reference in its entirety. Genetically modified non-human animals, ES cells and other cells, and tissues, comprising such genetically engineered loci, are also provided.

In one embodiment, provided here is a genetically engineered heavy chain immunoglobulin locus comprising human heavy chain variable gene segments (human heavy chain V, D, and J gene segments), human Ei enhancer, human $C_\mu$, $C_\delta$, $C_{\gamma 3}$, $C_{\gamma 1}$, $C_{\gamma 2}$ and $C_{\gamma 4}$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 6. In some embodiments, the genetically modified locus comprises a functional Adam6 gene as described here and in U.S. Pat. Nos. 8,642,835 and 8,697,940, each of which is incorporated herein by reference in its entirety. Genetically modified non-human animals, ES cells and other cells, and tissues, comprising such genetically engineered loci, are also provided.

In one embodiment, provided here is a genetically engineered heavy chain immunoglobulin locus comprising rodent (e.g., rat or mouse) heavy chain variable gene segments (rodent (e.g., rat or mouse) heavy chain V, D, and J gene segments), rodent (e.g., rat or mouse) Ei enhancer, human $C_\mu$, $C_\delta$, $C_{\gamma 3}$, and $C_{\gamma 1}$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 7. In some embodiments, the genetically modified locus comprises a functional Adam6 gene. Genetically modified non-human animals, ES cells and other cells, and tissues, comprising such genetically engineered loci, are also provided.

In one embodiment, provided here is a genetically engineered heavy chain immunoglobulin locus comprising rodent (e.g., rat or mouse) heavy chain variable gene segments (rodent (e.g., rat or mouse) heavy chain V, D, and J gene segments), rodent (e.g., rat or mouse) Ei enhancer, human $C_\mu$, $C_\delta$, $C_{\gamma 3}$, $C_{\gamma 1}$, $C_{\gamma 2}$ and $C_{\gamma 4}$ gene segments, and rodent (e.g., rat or mouse) 3' regulatory region comprising rodent (e.g., rat or mouse) 3' enhancers. An exemplary genetically modified heavy chain locus is provided in FIG. 1 as mouse locus 8. In some embodiments, the genetically modified locus comprises a functional Adam6 gene. Genetically modified non-human animals, ES cells and other cells, and tissues, comprising such genetically engineered loci, are also provided.

Also provided herein are methods for making engineered immunoglobulin heavy chain loci. In some embodiments, methods for making engineered immunoglobulin heavy chain loci described herein include inserting about 1.6 kb of DNA that includes a human IgG1 $C_H1$-H-$C_H2$-$C_H3$ nucleotide sequence encoding an immunoglobulin heavy chain constant domain polypeptide in the place of a $C_H1$-H-$C_H2$-$C_H3$ exons of a $C_{\gamma 2a}$ gene segment so that said human IgG1 $C_H1$-H-$C_H2$-$C_H3$ nucleotide sequence is operably linked to M1 and M2 exons of said $C_{\gamma 2a}$ gene segment.

In some embodiments, methods for making engineered immunoglobulin heavy chain loci described herein include inserting about 6.8 kb of DNA that includes a human IgG1 $C_H1$-H-$C_H2$-$C_H3$-M1-M2 nucleotide sequence encoding an immunoglobulin heavy chain constant domain polypeptide in the place of a $C_H1$-H-$C_H2$-$C_H3$-M1-M2 exons of a $C_{\gamma 2a}$ gene segment so that said human IgG1 $C_H1$-H-$C_H2$-$C_H3$-M1-M2 nucleotide sequence is operably linked to the switch region of said $C_{\gamma 2a}$ gene segment.

Also provided herein are methods for making engineered immunoglobulin heavy chain loci. In some embodiments, methods for making engineered immunoglobulin heavy chain loci described herein include inserting about 1.6 kb of DNA that includes a human IgG1 $C_H1$-H-$C_H2$-$C_H3$ nucleotide sequence encoding an immunoglobulin heavy chain constant domain polypeptide in the place of a $C_H1$-H-$C_H2$-$C_H3$ exons of a $C_{\gamma 2c}$ gene segment so that said human IgG1 $C_H1$-H-$C_H2$-$C_H3$ nucleotide sequence is operably linked to M1 and M2 exons of said $C_{\gamma 2c}$ gene segment.

In some embodiments, methods for making engineered immunoglobulin heavy chain loci described herein include inserting about 6.8 kb of DNA that includes a human IgG1 $C_H1$-H-$C_H2$-$C_H3$-M1-M2 nucleotide sequence encoding an immunoglobulin heavy chain constant domain polypeptide in the place of a $C_H1$-H-$C_H2$-$C_H3$-M1-M2 exons of a $C_{\gamma 2c}$ gene segment so that said human IgG1 $C_H1$-H-$C_H2$-$C_H3$-M1-M2 nucleotide sequence is operably linked to the switch region of said $C_{\gamma 2c}$ gene segment.

In some embodiments, methods for making engineered immunoglobulin heavy chain loci described herein include inserting about 1.5 kb of DNA that includes a human IgG4 $C_H1$-H-$C_H2$-$C_H3$ nucleotide sequence encoding an immunoglobulin heavy chain constant domain polypeptide in the place of a $C_H1$-H-$C_H2$-$C_H3$ exons of a $C_{\gamma 1}$ gene segment so that said human IgG4 $C_H1$-H-$C_H2$-$C_H3$ nucleotide sequence is operably linked to M1 and M2 exons of said $C_{\gamma 1}$ gene segment.

In some embodiments, methods for making engineered immunoglobulin heavy chain loci described herein include inserting about 5.8 kb of DNA that includes a human IgG4 $C_H1$-H-$C_H2$-$C_H3$-M1-M2 nucleotide sequence encoding an immunoglobulin heavy chain constant domain polypeptide in the place of a $C_H1$-H-$C_H2$-$C_H3$-M1-M2 exons of a $C_{\gamma 1}$ gene segment so that said human IgG4 $C_H1$-H-$C_H2$-$C_H3$-M1-M2 nucleotide sequence is operably linked to the switch region of said $C_{\gamma 1}$ gene segment.

In some embodiments, methods for making engineered immunoglobulin heavy chain loci described herein include inserting about 130 kb of DNA comprising human $C_\mu$, $C_\delta$, $C_{\gamma 3}$, $C_{\gamma 1}$ sequences. In other embodiments, the methods further comprise inserting additional about 43 kb of DNA comprising human $C_{\gamma 2}$ and $C_{\gamma 4}$ sequences.

In various methods for making engineered immunoglobulin heavy chain loci described above, the DNA can be introduced into either endogenous rodent (e.g., rat or mouse) immunoglobulin heavy chain locus comprising endogenous rodent (e.g., rat or mouse) heavy chain variable gene segments, or immunoglobulin heavy chain locus comprising human heavy chain variable gene segments. The DNA can be introduced either via homologous recombination or via other methods known in the art or described herein.

In some embodiments, the rodent (e.g., rat or mouse) is heterozygous for the modified immunoglobulin heavy chain locus described herein. In certain embodiments, the rodent (e.g., rat or mouse) is homozygous for the modified immunoglobulin heavy chain locus described herein.

Humanized Immunoglobulin Kappa Loci

In certain aspects, provided herein are rodents (e.g., mice or rats) comprising genetically modified Igκ chain loci. Such loci comprise a κ variable region and a κ constant region. The κ variable region includes Igκ chain variable region gene segments (i.e., at least a $V_\kappa$ gene segment and a $J_\kappa$ gene segment). The constant region includes an Igκ chain constant region ($C_\kappa$) gene segment. In certain embodiments, the immunoglobulin κ chain variable region such as human Igκ variable region is operably linked to the immunoglobulin κ chain constant region such that the rodent (e.g., rat or mouse) produces antibodies comprising light chain variable domains derived from the human $V_\kappa$ gene segment and the human $J_\kappa$ gene segment and light chain constant domains derived from the $C_\kappa$ gene segment. In some embodiments the Igκ variable region will be an unrearranged Igκ variable region and will therefore contain unrearranged Igκ variable region gene segments. In some embodiments, the Igκ variable region will be a rearranged Igκ variable region and will therefore contain a rearranged Igκ variable region gene. In certain embodiments, the Igκ variable region gene segments are human Igκ variable region gene segments. In certain embodiments, the Igκ variable region gene segments are rodent Igκ variable region gene segments (e.g., rat or mouse variable region gene segments). In some embodiments, the Igκ constant region locus comprises an Igκ constant region gene segment that is partially or completely human. In some embodiments, the Igκ chain loci described herein are located at an endogenous Igκ chain locus.

In certain embodiments, the Igκ variable region contains unrearranged human Igκ variable region gene segments. In some certain embodiments, an engineered Igκ light chain locus (or allele) comprises at least human $V_\kappa$ gene segments that appear in the distal variable cluster (or distal arm, or distal duplication) of a human Igκ light chain locus that appears in nature. In some certain embodiments, an engineered Igκ light chain locus (or allele) comprises at least human $V_\kappa$ gene segments that appear in the proximal variable cluster (or proximal arm, or proximal duplication) of a human Igκ light chain locus that appears in nature. In some certain embodiments, an engineered Igκ light chain locus (or allele) comprises human $V_\kappa$ gene segments that appear in the distal and proximal variable clusters of a human Igκ light chain locus that appears in nature. In some certain embodiments, an engineered Igκ light chain locus (or allele) comprises all or substantially all the functional human $V_\kappa$ gene segments found between human $V_\kappa$ 2-40 (or $V_\kappa$ 3D-7) and human $V_\kappa$ 4-1 gene segments, inclusive, of a human Igκ light chain locus that appears in nature.

In some embodiments, the unrearranged human immunoglobulin variable region gene segments comprise a plurality of human $V_\kappa$ segments and one or more human $J_\kappa$ segments. In some embodiments, the immunoglobulin variable region gene segments comprise four functional $V_\kappa$ segments and all human $J_\kappa$ segments. In some embodiments, the immunoglobulin variable region gene segments comprise 16 functional $V_\kappa$ segments and all human $J_\kappa$ segments. In some embodiments, the unrearranged human immunoglobulin variable region gene segments comprise all of the human $V_\kappa$ segments and all human $J_\kappa$ segments.

In some certain embodiments, an engineered Igκ light chain locus (or allele) comprises 1, 2, 3, 4, 5, 6, 7, 8, 9, 10, 15, 20, 25, 30, 35 or more (e.g., 36, 37, 38, 39, 40 etc.) human $V_\kappa$ gene segments. In some certain embodiments, an engineered Igκ light chain locus (or allele) comprises human $V_\kappa$ gene segments $V_\kappa$ 3D-7, $V_\kappa$ 1D-8, $V_\kappa$ 1D-43, $V_\kappa$ 3D-11, $V_\kappa$ 1D-12, $V_\kappa$ 1D-13, $V_\kappa$ 3D-15, $V_\kappa$ 1D-16, $V_\kappa$ 1D-17, $V_\kappa$ 3D-20, $V_\kappa$ 6D-21, $V_\kappa$ 2D-26, $V_\kappa$ 2D-28, $V_\kappa$ 2D-29, $V_\kappa$ 2D-30, $V_\kappa$ 1D-33, $V_\kappa$ 1D-39, $V_\kappa$ 2D-40, $V_\kappa$ 2-40, $V_\kappa$ 1-39, $V_\kappa$ 1-33, $V_\kappa$ 2-30, $V_\kappa$ 2-28, $V_\kappa$ 1-27, $V_\kappa$ 2-24, $V_\kappa$ 6-21, $V_\kappa$ 3-20, $V_\kappa$ 1-17, $V_\kappa$ 1-16, $V_\kappa$ 3-15, $V_\kappa$ 1-12, $V_\kappa$ 3-11, $V_\kappa$ 1-9, $V_\kappa$ 1-8, $V_\kappa$ 1-6, $V_\kappa$ 1-5, $V_\kappa$ 5-2 and $V_\kappa$ 4-1. In some certain embodiments, an engineered Igκ light chain locus (or allele) comprises at least human $V_\kappa$ gene segments $V_\kappa$ 3D-7, $V_\kappa$ 1D-8, $V_\kappa$ 1D-43, $V_\kappa$ 3D-11, $V_\kappa$ 1D-12, $V_\kappa$ 1D-13, $V_\kappa$ 3D-15, $V_\kappa$ 1D-16, $V_\kappa$ 1D-17, $V_\kappa$ 3D-20, $V_\kappa$ 6D-21, $V_\kappa$ 2D-26, $V_\kappa$ 2D-28, $V_\kappa$ 2D-29, $V_\kappa$ 2D-30, $V_\kappa$ 1D-33, $V_\kappa$ 1D-39 and $V_\kappa$ 2D-40. In some certain embodiments, an engineered Igκ light chain locus (or allele) comprises at least human $V_\kappa$ gene segments $V_\kappa$ 2-40, $V_\kappa$ 1-39, $V_\kappa$ 1-33, $V_\kappa$ 2-30, $V_\kappa$ 2-28, $V_\kappa$ 1-27, $V_\kappa$ 2-24, $V_\kappa$ 6-21, $V_\kappa$ 3-20, $V_\kappa$ 1-17, $V_\kappa$ 1-16, $V_\kappa$ 3-15, $V_\kappa$ 1-12, $V_\kappa$ 3-11, $V_\kappa$ 1-9, $V_\kappa$ 1-8, $V_\kappa$ 1-6, $V_\kappa$ 1-5, $V_\kappa$ 5-2 and $V_\kappa$ 4-1.

In some embodiments, the non-human animals provided herein have a restricted immunoglobulin light chain locus characterized by no more than two human $V_L$ gene segments and a plurality of $J_L$ gene segments (e.g., dual light chain mice, or DLC, as described in U.S. Pat. Pub. No. 2013/0198880, which is hereby incorporated by reference).

In some embodiments the $V_L$ gene segments are $V_\kappa$ gene segments. In some embodiments the $V_L$ gene segments are $V_\lambda$ gene segments. In some embodiments the $V_\kappa$ gene segments are $V_\kappa$ 3-20 and $V_\kappa$ 1-39.

In some embodiments, an engineered Igκ light chain locus (or allele) comprises 1, 2, 3, 4, 5 or more functional human $J_\kappa$ gene segments. In some certain embodiments, an engineered Igκ light chain locus (or allele) comprises all or substantially all the functional human $J_\kappa$ gene segments found between human $J_\kappa$1 and human $J_\kappa$5 gene segments, inclusive, of a human Igκ light chain locus that appears in nature. In some certain embodiments, an engineered Igκ light chain locus (or allele) comprises at least human $J_\kappa$ gene segments $J_\kappa$1, $J_\kappa$2, $J_\kappa$3, $J_\kappa$4 and $J_\kappa$5.

In yet other embodiments, the non-human organism may comprise in its germline and/or genome a light chain immunoglobulin locus that includes insertions and/or replacements of histidine codons designed to introduce pH-dependent binding properties to the antibodies generated in such non-human organism. In some of such embodiments, the histidine codons are inserted and/or replaced in the nucleic acid sequences encoding CDR3. Various such light chain immunoglobulin loci are provided in U.S. Pat. Nos. 9,301,510, 9,334,334, U.S. Patent Application Publication Nos. 2013/0247236, 20140013456, incorporated herein by reference.

Exemplary variable regions comprising Igκ gene segments are provided, for example, in Macdonald et al., Proc. Natl. Acad. Sci. USA 111:5147-52 and supplemental information, which is hereby incorporated by reference. In some embodiments, the unrearranged human immunoglobulin variable region gene segments comprise all of the human $J_\kappa$ segments.

In some embodiments, the Igκ variable gene locus containing unrearranged human Igκ variable region gene segments also includes human Igκ variable region intergenic sequences. In some embodiments, the Igκ variable gene locus includes non-human (e.g., rodent, rat, mouse) Igκ variable region intergenic sequences. In some embodiments, the Igκ gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the Igκ variable region locus is a rearranged variable region locus comprising a Igκ variable region gene (a universal light chain variable region). In some embodiments, the rearranged Igκ variable region gene is a human rearranged Igκ variable region gene. Use of universal light chain variable regions facilitate the generation of bispecific antibodies. Exemplary rearranged Ig light chain variable regions are provided in U.S. Patent Pub. No. 2013/0185821, which is hereby incorporated by reference.

In some embodiments, the Igκ chain locus comprises human or rodent (e.g., rat or mouse) regulatory elements. In some embodiments, the regulatory element is an endogenous regulatory element. In certain embodiments, the Igκ chain locus comprises a rodent (e.g., rat or mouse) or human intronic κ enhancer ($E_{\kappa i}$). In some embodiments, the IgH locus comprises a rodent (e.g., rat or mouse) or human 3' κ enhancer ($E_{\kappa 3'}$).

In some embodiments, the modified immunoglobulin κ chain locus is positioned at an endogenous immunoglobulin κ chain locus. In some embodiments, the immunoglobulin κ chain locus replaces all or part of the endogenous immunoglobulin κ chain locus. In certain embodiments, the modified Igκ chain locus is located on a transgene positioned outside of the endogenous locus. In some embodiments, the endogenous Igκ chain locus is inactivated (e.g., through the deletion, relocation and/or inversion of all or part of the endogenous Igκ chain locus).

In some embodiments, methods for making engineered immunoglobulin κ light chain loci described herein include inserting about 0.5 kb of DNA that includes a human Igκ constant nucleotide sequence encoding an immunoglobulin κ light chain constant domain polypeptide in the place of a Igκ constant exon of an Igκ constant region gene so that said human Igκ constant nucleotide sequence is operably linked to the enhancer and/or regulatory regions of said Igκ constant region gene.

In some embodiments, the rodent (e.g., rat or mouse) is heterozygous for the modified immunoglobulin κ chain locus described herein. In certain embodiments, the rodent (e.g., rat or mouse) is homozygous for modified the immunoglobulin κ chain locus described herein.

Humanized Immunoglobulin Lambda Loci

In certain aspects, provided herein are rodents (e.g., mice or rats) comprising genetically modified Igλ chain loci. Such loci comprise Igλ chain variable region gene segments (i.e., at least a $V_\lambda$ gene segment and a h gene segment). The modified λ locus further includes at least one Igλ chain constant region ($C_\lambda$) gene segment. In certain embodiments, the $V_\lambda$ gene segment and $J_\lambda$ gene segment such as human $V_\lambda$ gene segment and human $J_\lambda$ gene segment are operably linked to the $C_\lambda$ such that the rodent (e.g., rat or mouse) produces antibodies comprising light chain variable domains derived from the human $V_\lambda$ gene segment and the human $J_\lambda$ gene segment and light chain constant domains derived from the $C_\lambda$ gene segment. In some embodiments the $V_\lambda$ gene segment and $J_\lambda$ gene segment will be unrearranged $V_\lambda$ and $J_\lambda$ gene segments. In some embodiments, the $V_\lambda$ gene segment and $J_\lambda$ gene segment will be a rearranged $V_\lambda$ and $J_\lambda$ gene segments and will therefore be in the form of a rearranged variable region gene. In certain embodiments, the $Ig_\lambda$ variable region gene segments are human variable region gene segments. In certain embodiments, the $Ig_\lambda$ variable region gene segments are rodent variable region gene segments (e.g., rat or mouse variable region gene segments). In some embodiments, the $Ig_\lambda$ constant region locus comprises a λ constant region gene segment that is partially or completely human. In some embodiments, the Igλ chain loci described herein are located at an endogenous Igλ chain locus. Exemplary variable regions comprising Igλ gene segments are provided, for example, U.S. Pat. Pub. Nos. 2012/0073004 and 2002/0088016, and U.S. patent application Ser. No. 15/803,513 (filed Nov. 3, 2017; published as US2018/0125043), each of which is hereby incorporated by reference.

In some embodiments, the Igλ variable gene locus containing unrearranged human Igκ variable region gene segments also includes human Igλ variable region intergenic sequences. In some embodiments, the Igλ variable gene locus includes non-human (e.g., rodent, rat, mouse) Igλ variable region intergenic sequences. In some embodiments, the Igλ gene locus comprises non-human regulatory elements (e.g., non-human promoters and/or enhancers). In some embodiments, the non-human regulatory elements are rodent regulatory elements (e.g., rat or mouse promoters or enhancers).

A human Igλ light chain locus, in some embodiments, comprises genetic material from a human Igλ light chain locus. In some embodiments, a human Igλ light chain locus as described herein comprises at least one human $V_\lambda$ gene segment at least one human $J_\lambda$ gene segment, at least one human $C_\lambda$ gene segment, and one or more sequences necessary to promote rearrangement (e.g., recombination signal sequence[s]) of said at least one human $V_\lambda$ gene segment with said at least one human $J_\lambda$ gene segment to form a functional rearranged human $V_\lambda$-$J_\lambda$ sequence that encodes a human $V_\lambda$ domain. In many embodiments, a human Igλ light chain sequence comprises a plurality of human $V_\lambda$ gene segments and one or more sequences necessary to promote rearrangement of said human $V_\lambda$ gene segments with at least one human $J_\lambda$ gene segment. In some embodiments, a human Igλ light chain sequence as described herein is a genomic sequence of a human Igλ light chain locus (e.g., isolated and/or cloned from a bacterial artificial chromosome) and contains a plurality of human $V_\lambda$ gene segments in germline configuration. In some embodiments, a human Igλ light chain sequence comprises human $V_\lambda$, $J_\lambda$ and $C_\lambda$ sequences in germline configuration (i.e., as said human $V_\lambda$, $J_\lambda$ and $C_\lambda$ sequences appear in an Igλ light chain locus in a human cell, in other words, $J_\lambda$ and $C_\lambda$ sequences appear as $J_\lambda$ $C_\lambda$ clusters). In some embodiments, a human Igλ light chain sequence encodes an Igλ light chain polypeptide, in whole or in part, which Igλ light chain polypeptide appears in an immunoglobulin, in particular, an immunoglobulin that is expressed by a human B cell. Non-human animals, embryos, cells and targeting constructs for making non-human animals, non-human embryos, and cells containing said human Igλ light chain sequence in the place of a corresponding non-human Igλ light chain sequence (e.g., an endogenous rodent Igλ light chain locus) are also provided.

In some embodiments, a human Igλ light chain sequence is inserted in the place of a corresponding non-human Igλ light chain sequence within the germline genome of a non-human animal. In some embodiments, a human Igλ light chain sequence is inserted upstream of a non-human Igλ light chain sequence (e.g., a non-human Igλ light chain constant region sequence). In some embodiments, a human Igλ light chain sequence is inserted in the midst of one or more non-human Igλ light chain sequences so that said human Igλ light chain sequence is juxtaposed by non-human Igλ light chain sequences.

Figure 2A:
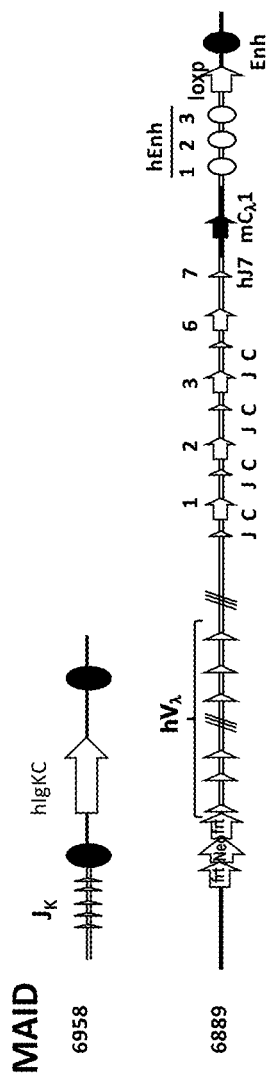
FIG. 2A shows schematic summaries, not to scale, of exemplary modified immunoglobulin light chain loci according to certain exemplary embodiments provided herein. The top exemplary schematic depicts an Igκ locus comprising a human variable region, a mouse intronic enhancer, a human $C_\kappa$ constant region gene segment, and a mouse 3' enhancer. The bottom exemplary schematic depicts an Igλ locus comprising $V_\lambda$ gene segments, human $J_\lambda$-$C_\lambda$ tandem pairs, a human $J_{\lambda7}$ and a mouse $C_{\lambda1}$ gene segment, human enhancers 1, 2, and 3, and a mouse 3' enhancer. Unless otherwise indicated (e.g., for loxp site, etc.), empty shapes and double lines represent human sequences and filled shapes and single lines represent mouse sequences.

In certain embodiments, the Igλ chain locus comprises at least 2, 3, 4, 5, 6, 7, 8, 10, 20, 30 or 40 functional $V_\lambda$ gene segments. In some embodiments, the locus comprises human $V_\lambda$ gene segments $V_\lambda$3-10, $V_\lambda$2-8, $V_\lambda$4-3 and $V_\lambda$3-1. In some embodiments, the locus comprises $V_\lambda$2-11, $V_\lambda$3-12, $V_\lambda$2-14, $V_\lambda$3-16, $V_\lambda$3-19, $V_\lambda$3-21, $V_\lambda$3-22, $V_\lambda$2-23, $V_\lambda$3-25 and $V_\lambda$3-27. In some embodiments, the locus comprises $V_\lambda$3-27, $V_\lambda$1-36, $V_\lambda$5-37, $V_\lambda$5-39, $V_\lambda$1-40, $V_\lambda$1-44, $V_\lambda$5-45, $V_\lambda$1-47, $V_\lambda$9-49, $V_\lambda$1-51 and $V_\lambda$5-52. In certain embodiments, the locus comprises $V_\lambda$10-54, $V_\lambda$6-57, $V_\lambda$4-60, $V_\lambda$8-61 and $V_\lambda$4-69. In some embodiments, the Igλ chain locus comprises one or more human $J_\lambda$-$C_\lambda$ pairs. For example, in certain embodiments, the Igλ chain locus comprises human $J_\lambda$1-$C_\lambda$1, $J_\lambda$2-$C_\lambda$2, $J_\lambda$3-$C_\lambda$3, $J_\lambda$6-$C_\lambda$6 and/or $J_\lambda$7-$C_\lambda$7 downstream of the human $V_\lambda$ gene segments. In some embodiments, the $Ig_\lambda$ chain locus comprises human $J_\lambda$1-$C_\lambda$1, $J_\lambda$2-$C_\lambda$2, $J_\lambda$3-$C_\lambda$3, $J_\lambda$6-$C_\lambda$6, human $J_\lambda$7 and mouse $C_\lambda$1 downstream of the human $V_\lambda$ gene segments, as depicted in FIG. 2A.

In some embodiments, the Igλ locus is a rearranged locus comprising a Igλ variable region gene (a universal light chain variable region). In some embodiments, the rearranged Igλ variable region gene is a human rearranged Igλ variable region gene. Use of universal light chain variable regions facilitate the generation of bispecific antibodies in which at least one antigen-binding domain has binding. Exemplary rearranged Ig light chain variable regions are provided in U.S. Patent Pub. No. 2013/0185821, which is hereby incorporated by reference.

In some embodiments, the Igλ chain locus comprises human or rodent (e.g., rat or mouse) regulatory elements. In some embodiments, the regulatory element is an endogenous regulatory element. In certain embodiments, the Igλ chain locus comprises a rodent (e.g., rat or mouse) λ enhancer 2.4. In some embodiments, the Igλ chain locus comprises a human or rodent (e.g., rat or mouse) 3' λ enhancer. In some embodiments, the Igλ chain locus comprises a rodent (e.g., rat or mouse) λ enhancer 3.1.

In some embodiments, the modified immunoglobulin λ chain locus is positioned at an endogenous immunoglobulin λ chain locus. In some embodiments, the immunoglobulin λ chain locus replaces all or part of the endogenous immunoglobulin λ chain locus. In certain embodiments, the modified Igλ chain locus is located on a transgene positioned outside of the endogenous locus. In some embodiments, the endogenous Igλ chain locus is inactivated (e.g., through the deletion, relocation and/or inversion of all or part of the endogenous Igλ chain locus).

In some embodiments, the rodent (e.g., rat or mouse) is heterozygous for the modified immunoglobulin λ chain locus. In certain embodiments, the rodent (e.g., rat or mouse) is homozygous for modified the immunoglobulin λ chain locus.

In some embodiments, the non-human organism comprises in its germline and/or genome a light chain immunoglobulin locus comprising a limited repertoire of light chain variable gene segments (e.g., a dual light chain variable region comprising two light chain variable gene segments). In some embodiments, the light chain variable gene segments in the limited repertoire of light chain gene segments are a human light chain gene segments. Exemplary dual light chain variable regions are provided in U.S. Patent Pub. No. 2013/0198880, which is hereby incorporated by reference. In some embodiments, the non-human organism comprising a dual light chain variable region is used to produce bispecific antibodies.

Humanized CD79a and CD79b Loci

In some embodiments, rodents (e.g., mice or rats) described herein comprise human or humanized B-cell antigen receptor complex-associated protein alpha chain (CD79a or Igα) and/or B-cell antigen receptor complex-associated protein beta chain (CD79b or Igβ) loci. Rodents that contain human or humanized CD79a and CD79b genes express human or humanized CD79a and CD79b polypeptides as heterodimers on the surface of B cells, which associate with membrane-expressed immunoglobulins in a noncovalent manner to form the B cell receptor (BCR). The BCR associates with antigen and functions in signal transduction and internalization after engagement with antigen. In some embodiments, rodents described herein comprise human or humanized CD79a and CD79b genes. In some certain embodiments, rodents as described herein further comprise a CD79a gene that comprises a rodent CD79a portion and a human CD79a portion, and a CD79b gene that comprises a rodent CD79b portion and a human CD79b portion, wherein the human CD79a portion encodes substantially all of the extracellular domain of a human CD79a polypeptide (e.g., amino acids corresponding to residues 33-143 of a human CD79a polypeptide) and the human CD79b portion encodes substantially all of the extracellular domain of a human CD79b polypeptide (e.g., amino acids corresponding to residues 29-159 of a human CD79b polypeptide). In some embodiments, rodent CD79a and CD79b portions each encode at least the intracellular domain of endogenous CD79a and CD79b polypeptides, respectively; in some certain embodiments the transmembrane and intracellular domains of endogenous CD79a and CD79b polypeptides, respectively. In some embodiments, human and endogenous portions are operably linked to endogenous CD79a or CD79b promoters, respectively.

In some embodiments, rodents as described herein further comprise a chimeric CD79a gene that comprises a rodent CD79a portion and a human CD79a portion, wherein the human CD79a portion encodes the sequence comprising amino acids corresponding to residues 33-116 of a human CD79a polypeptide, in one embodiment it encodes the sequence comprising amino acids 33-119 of a human CD79a polypeptide, in one embodiment it encodes the sequence comprising amino acids 33-143 of a human CD79a polypeptide, in one embodiment, it encodes the sequence comprising amino acids 33-165 of a human CD79a polypeptide. In some embodiments, the chimeric CD79a polypeptide comprises a human Ig C2-like domain; in some embodiments, the chimeric CD79a polypeptide also comprises a human stalk region; in some embodiment, the chimeric CD79a polypeptide also comprises a human transmembrane domain; and in some embodiments, the chimeric CD79a polypeptide further comprises a rodent (e.g., mouse) cytoplasmic domain. In some embodiments, the rodent comprises a chimeric CD79a gene comprising a human region portion described herein and a sequence encoding a human or rodent (e.g., mouse) CD79a signal peptide; in one embodiment, the sequence encoding the signal peptide is a mouse CD79a sequence encoding amino acids 1-28 of the mouse CD79a.

In some embodiments, rodents as described herein further comprise a chimeric CD79b gene that comprises a rodent CD79b portion and a human CD79b portion, wherein the human CD79b portion encodes the sequence comprising amino acids corresponding to residues 29-135 of a human CD79b polypeptide, in one embodiment it encodes the sequence comprising amino acids 29-159 of a human CD79b polypeptide, in one embodiment it encodes the sequence comprising amino acids 29-184 of a human CD79b polypeptide. In some embodiments, the chimeric CD79b polypeptide comprises a human Ig V-like domain; in some embodiments, the chimeric CD79b polypeptide also comprises a human stalk region; in some embodiment, the chimeric CD79b polypeptide also comprises a human transmembrane domain; and in some embodiments, the chimeric CD79b polypeptide further comprises a rodent (e.g., mouse) cytoplasmic domain. In some embodiments, the rodent comprises a chimeric CD79b gene comprising a human region portion described herein and a sequence encoding a human or rodent (e.g., mouse) CD79b signal peptide; in one embodiment, the sequence encoding the signal peptide is a mouse CD79b sequence encoding amino acids 1-25 of the mouse CD79b.

GenBank accession nos. NP_001774.1, NM_001783.3, NP_067612.1 and NM_021601.3, and UniProt ID P11912 provide representative source sequences of a human CD79A gene and human CD79A polypeptide from which a desired human portion may be obtained. GenBank accession nos. NP_000617.1, NM_000626.2, NP_001035022.1, NM_001039933.1, NP_067613.1 and NM_021602.2, and UniProt ID P40259 provide representative source sequences of a human CD79B gene and human CD79B polypeptide from which a desired human portion may be obtained.

In some embodiments, the rodents (e.g., mice or rats) provided herein further comprise one or more human CD79A and CD79B genes as described in U.S. Patent Application Publication Nos. 2011-0093963 A1 and 2009-0053210 A1; International Patent Application Publication No. WO 2008/027986; and European Patent No. 2 064 325 B1, each of which is hereby incorporated by reference. In some certain embodiments, the rodents provided herein comprise a humanized CD79a gene that comprises an endogenous CD79a portion and a human CD79a portion, and a humanized CD79b gene that comprises an endogenous CD79b portion and a human CD79b portion, wherein the human CD79a portion encodes substantially all of the extracellular domain of a human CD79a polypeptide (e.g., amino acids corresponding to residues 33-143 of a human CD79a polypeptide) and the human CD79b portion encodes substantially all of the extracellular domain of a human CD79b polypeptide (e.g., amino acids corresponding to residues 29-159 of a human CD79b polypeptide). In some embodiments, the rodents provided herein comprise a humanized CD79a gene that comprises an endogenous CD79a portion and a human CD79a portion, and a humanized CD79b gene that comprises an endogenous CD79b portion and a human CD79b portion, wherein the human CD79a portion encodes the sequence comprising amino acids 33-116 (e.g., the sequence comprising amino acids 33-119, the sequence comprising amino acids 33-143, or the sequence comprising amino acids 33-165 of a human CD79a polypeptide), and wherein the human CD79b portion encodes the sequence comprising amino acids 29-135 (e.g., the sequence comprising amino acids 29-159, or the sequence comprising amino acids 29-184 of a human CD79a polypeptide) In some embodiments, endogenous CD79a and CD79b portions each encode at least the intracellular domain of endogenous CD79a and CD79b polypeptides, respectively; in some certain embodiments the transmembrane and intracellular domains of endogenous CD79a and CD79b polypeptides, respectively.

Humanized Neonatal Fc Receptor Loci

In some embodiments the rodents (e.g., mice or rats) provided herein express and/or comprise in their genome a humanized or human neonatal Fc receptor (FcRn) locus. FcRn, also known as the Brambell receptor, is a protein that is expressed by endothelial cells and associates with beta-2-microglobulin (β2M) and binds to both the Fc domains of IgG antibodies and serum albumin FcRn extends the half-life of IgG and serum albumin Specifically, by binding IgG and serum albumin in a pH dependent manner, FcRn is able to rescue these serum proteins from lysosomal degradation by endothelial cells, thereby increasing the serum half-life of such proteins.

In some embodiments, the FcRn locus comprises a nucleic acid sequence encoding an FcRn polypeptide comprising a human extracellular domain, a rodent (e.g., mouse or rat) transmembrane domain and a rodent (e.g., mouse or rat) cytoplasmic domain. In some embodiments, the FcRn locus comprises a nucleic acid sequence encoding an FcRn polypeptide comprising a human extracellular domain, a human (e.g., mouse or rat) transmembrane domain and a rodent (e.g., mouse or rat) cytoplasmic domain. In some embodiments, the FcRn locus comprises a nucleic acid sequence encoding an FcRn polypeptide comprising a human extracellular domain, a human (e.g., mouse or rat) transmembrane domain and a human (e.g., mouse or rat) cytoplasmic domain.

In some embodiments the nucleic acid sequence encoding the FcRn polypeptide is positioned at an endogenous rodent FcRn locus. In certain embodiments the nucleic acid sequence encoding the FcRn polypeptide replaces all or part of an endogenous rodent FcRn gene. For example, in some embodiments, the nucleic acid sequence encoding the extracellular domain in an endogenous FcRn locus is replaced with a nucleic acid sequence encoding the extracellular domain of a human FcRn such that a rodent comprising such a locus expresses an FcRn with a human extracellular domain and a rodent (e.g., rat or mouse) transmembrane and cytoplasmic domain. In some embodiments, the rodent does not express a rodent FcRn, or does not express a functional rodent FcRn. In some embodiments, the FcRn gene locus comprises non-human regulatory elements (e.g., non-human promoters and/or enhancers). In some embodiments, the non-human regulatory elements are rodent regulatory elements (e.g., rat or mouse promoters or enhancers).

Figure 4:
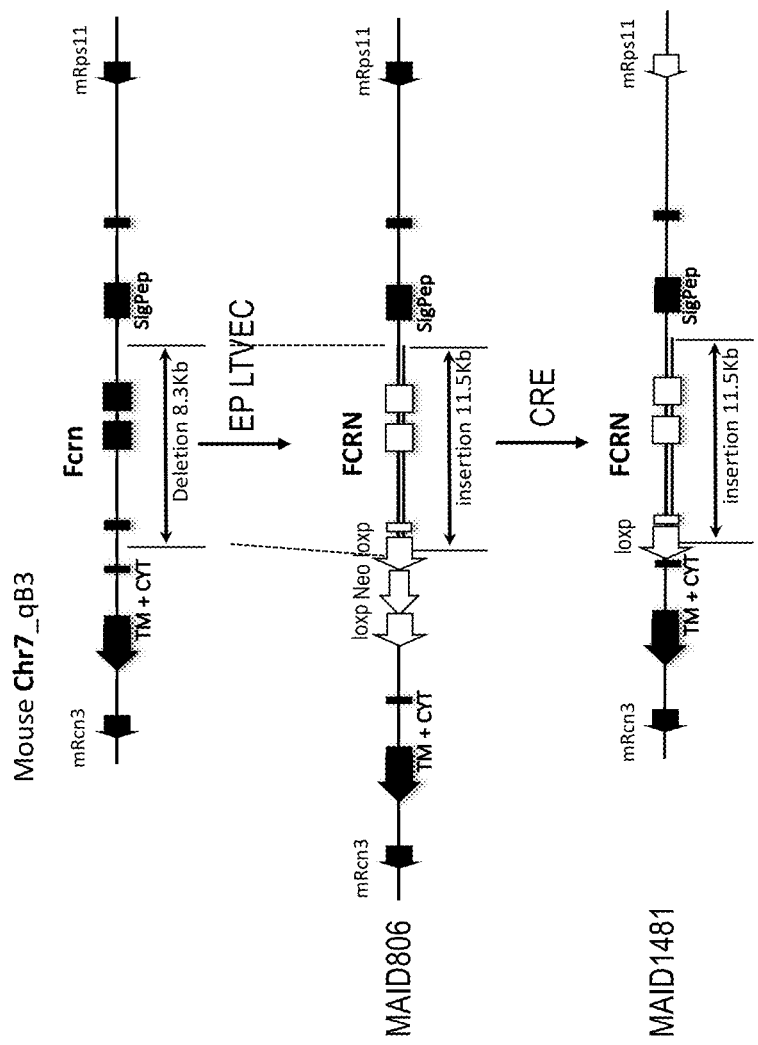
FIG. 4 shows a schematic summary, not to scale, of an exemplary method for the creation of an exemplary modified FcRn locus as described in Example 3. Unless otherwise indicated (e.g., for loxp sites, etc.), empty shapes and double lines represent human sequences and filled shapes and single lines represent mouse sequences.

In certain embodiments, the mouse exons encoding alpha 1, alpha 2, and alpha 3 domains (exons 3, 4, and 5, which are the first three coding exons) of the mouse FcRn gene are replaced with human exons encoding alpha 1, alpha 2, and alpha 3 domains (exons 3, 4, and 5) of the human FcRn gene (see FIG. 4). In some embodiments, the FcRn gene comprises mouse exon 1 (non-coding exon), mouse exon 2 (comprising nucleic acid sequence encoding the signal peptide), and human exons 3-6, mouse exons 6 and 7 (encoding transmembrane and cytoplasmic domains). In some embodiments the amino acid sequence of the humanized FcRn encoded by the locus is SEQ ID NO: 16.

GenBank accession nos. NC_000019.10 (49512279-49526428), NM_001136019.1, and NP_001129491.1 provide representative source sequences of a human FcRn gene, cDNA and polypeptide from which a desired human portion may be obtained. GenBank accession nos. NC_000073.6 (45092992-45103846), NM_010189.1, and NP_034319.1 provide representative source sequences of a mouse FcRn gene, cDNA and polypeptide from which a desired mouse portion may be obtained and/or which can be used in the design of targeting vector homology arms.

In some embodiments, the rodent is heterozygous for the genetically modified FcRn locus. In some embodiments, the rodent is homozygous for the genetically modified FcRn locus.

Humanized β-2-Microglobulin

In some embodiments, the genetically modified rodents (e.g., rats or mice) and ES cells described herein express and/or comprise in their genome a locus encoding humanized β-2-microglobulin (β2M) polypeptide. β2M is a polypeptide that lacks a transmembrane region and that associates with the FcRn and MHC class I molecules.

In some embodiments, the β2M locus comprises a nucleic acid sequence encoding a human β2M polypeptide. In some embodiments the nucleic acid sequence encoding the human β2M polypeptide is positioned at an endogenous rodent β2M locus. In certain embodiments the nucleic acid sequence encoding the β2M polypeptide replaces all or part of an endogenous rodent β2M gene. In some embodiments, the rodent does not express a rodent β2M, or does not express a functional rodent β2M polypeptide. In some embodiments, the β2M gene locus comprises non-human regulatory elements (e.g., non-human promoters and/or enhancers). In some embodiments, the non-human regulatory elements are rodent regulatory elements (e.g., rat or mouse promoters or enhancers).

Figure 5:
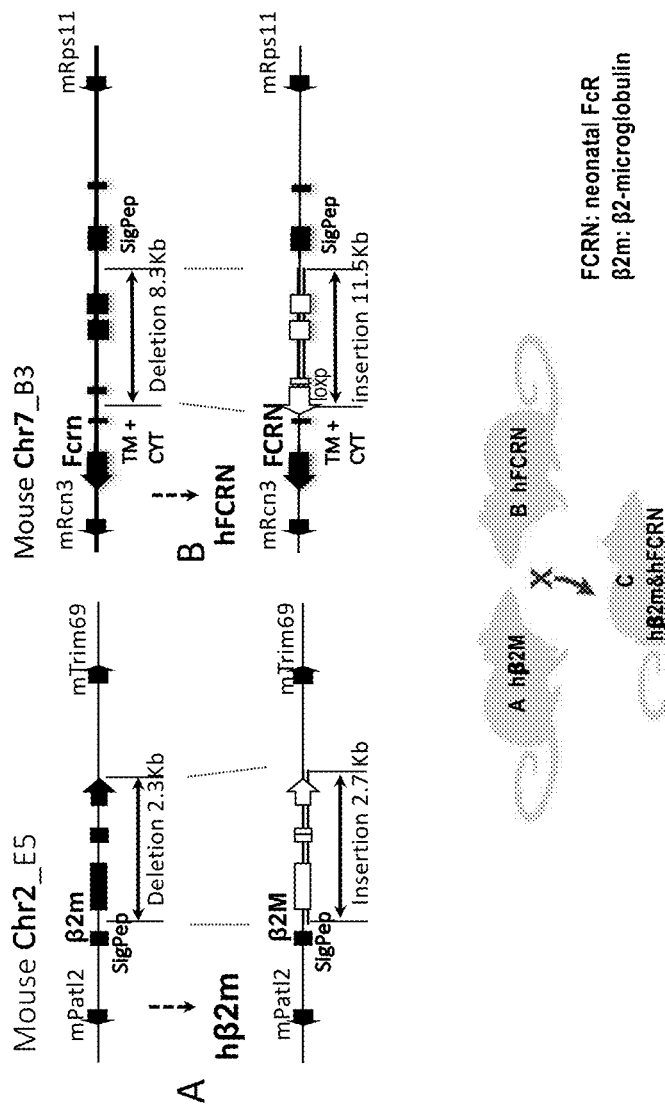
FIG. 5 shows a schematic summary, not to scale, of an exemplary method for the creation of mice comprising exemplary modified FcRn and β2M loci as described in Example 3. Unless otherwise indicated (e.g., for loxp sites, etc.), empty shapes and double lines represent human sequences and filled shapes and single lines represent mouse sequences.

Humanized β2M polypeptides, loci encoding humanized β2M polypeptides and non-human animals expressing humanized β2M polypeptides are described in U.S. Pat. Pub. Nos. 2013/0111617 and 2013/0185819, each of which is incorporated by reference herein. Thus, as described in U.S. Pat. Pub. Nos. 2013/0111617 and 2013/0185819, in some embodiments, non-human animals (e.g., mice) comprise a humanized β2M gene, wherein the gene comprises exons 2, 3, and 4 of the human β2M gene, and in some embodiments, the humanized β2M gene comprises exon 1 of the non-human (e.g., mouse) β2M gene. The humanized β2M locus is depicted schematically in FIG. 5. In some embodiments, the rodent is heterozygous for the genetically modified β2M locus. In some embodiments, the rodent is homozygous for the genetically modified β2M locus.

Humanized Fc Epsilon Receptor 1 Alpha

In some embodiments the rodents (e.g., mice or rats) provided herein express and/or comprise in their genome a humanized or human Fc epsilon receptor 1 alpha (FcεR1α) locus. FcεR1α associates with FcεR1β and FcεR1γ to form FcεR1, a high-affinity receptor for IgE that is expressed on epidermal Langerhans cells, eosinophils, mast cells and basophils. The IgE binding site of FcεR1 is found in the FcεR1α subunit.

Figure 9:
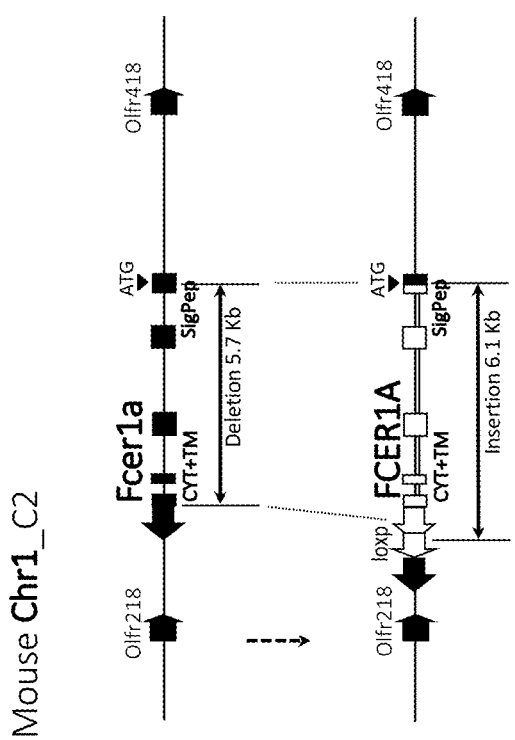
FIG. 9 shows a schematic summary, not to scale, of an exemplary method for the creation of mice comprising an exemplary modified FcεR1α locus as described in Example 5. Unless otherwise indicated (e.g., for loxp site, etc.), empty shapes and double lines represent human sequences and filled shapes and single lines represent mouse sequences.

In some embodiments, the FcεR1α locus comprises a nucleic acid sequence encoding an FcεR1α polypeptide comprising a human extracellular domain, a rodent (e.g., mouse or rat) transmembrane domain and a rodent (e.g., mouse or rat) cytoplasmic domain. In some embodiments, the FcεR1α locus comprises a nucleic acid sequence encoding an FcεR1α polypeptide comprising a human extracellular domain, a human transmembrane domain and a rodent (e.g., mouse or rat) cytoplasmic domain. In some embodiments, the FcεR1α locus comprises a nucleic acid sequence encoding an FcεR1α polypeptide comprising a human extracellular domain, a human transmembrane domain and a human cytoplasmic domain. An exemplary embodiment of an engineered FcεR1α locus is depicted in FIG. 9.

In some embodiments the nucleic acid sequence encoding the FcεR1α polypeptide is positioned at an endogenous rodent FcεR1α locus. In certain embodiments the nucleic acid sequence encoding the FcεR1α polypeptide replaces all or part of an endogenous rodent FcεR1α gene. For example, in some embodiments, the nucleic acid sequence encoding the extracellular domain in an endogenous FcεR1α locus is replaced with a nucleic acid sequence encoding the extracellular domain of a human FcεR1α such that a rodent comprising such a locus expresses a FcεR1α with a human extracellular domain and a rodent (e.g., rat or mouse) transmembrane and cytoplasmic domain. In some embodiments the nucleic acid sequence encoding a FcεR1α polypeptide comprising a human extracellular domain, a human transmembrane domain, and a human cytoplasmic domain is positioned at an endogenous rodent FcεR1α locus. In some embodiments the nucleic acid sequence encoding a FcεR1α polypeptide comprising a human extracellular domain, a human transmembrane domain, and a human cytoplasmic domain replaces all or part of an endogenous rodent FcεR1α gene. In some embodiments, the rodent does not express a rodent FcεR1α, or does not express a functional rodent FcεR1α. In some embodiments, the FcεR1α gene locus comprises non-human regulatory elements (e.g., non-human promoters and/or enhancers). In some embodiments, the non-human regulatory elements are rodent regulatory elements (e.g., rat or mouse promoters or enhancers).

In certain embodiments, part of mouse coding exon 1, coding exon 2, coding exon 3, coding exon 4, and coding exon 5 of the mouse FcεR1α are replaced by part of human coding exon 1, coding exon 2, coding exon 3, coding exon 4, and coding exon 5 of the human FcεR1α gene. In some embodiments, the FcεR1α gene comprised chimeric mouse/human exon 1 (comprising mouse promoter and 5' UTR), human coding exons 2-5 through the stop codon, human 3'UTR and polyA, followed by the mouse 3'UTR and polyA. In some embodiments, chimeric gene exons 1 (partial) and 2 encode the signal peptide, exon 3 and 4 encode the two Ig-like domains of FcεR1α that are believed to interact with IgE, and exon 5 encodes the cytoplasmic and transmembrane domains of the protein (see FIG. 9).

GenBank accession nos. NC_000001.11 (159283888-159308224), NM_002001.3, and NP_001992.1 provide representative source sequences of a human FcεR1α gene, cDNA and polypeptide from which a desired human portion may be obtained. GenBank accession nos. NC_000067.6 (173221269-173227232), NM_010184.1, and NP_034314.1 provide representative source sequences of a mouse FcεR1α gene, cDNA and polypeptide from which a desired mouse portion may be obtained and/or which can be used in the design of targeting vector homology arms.

In some embodiments, the rodent is heterozygous for the genetically modified FcεR1α locus. In some embodiments, the rodent is homozygous for the genetically modified FcεR1α locus.

Humanized Fc Gamma Receptor 1a

In some embodiments the rodents (e.g., mice or rats) provided herein express and/or comprise in their genome a humanized or human Fc gamma receptor 1a (FcεR1a, often labeled FcγR1 in the Figures) locus. FcγR1a is a high affinity FcγR protein expressed on monocytes that binds to the Fc portion of IgG and causes activation of the host cell.

In some embodiments, the FcγR1a locus comprises a nucleic acid sequence encoding a FcγR1a polypeptide comprising a human extracellular domain, a rodent (e.g., mouse or rat) transmembrane domain and a rodent (e.g., mouse or rat) cytoplasmic domain. In some embodiments, the FcγR1a locus comprises a nucleic acid sequence encoding a FcγR1a polypeptide comprising a human extracellular domain, a human (e.g., mouse or rat) transmembrane domain and a rodent (e.g., mouse or rat) cytoplasmic domain. In some embodiments, the FcγR1a locus comprises a nucleic acid sequence encoding a FcγR1a polypeptide comprising a human extracellular domain, a human (e.g., mouse or rat) transmembrane domain and a human (e.g., mouse or rat) cytoplasmic domain.

In some embodiments the nucleic acid sequence encoding the FcεR1α polypeptide is positioned at an endogenous rodent FcγR1a locus. In certain embodiments the nucleic acid sequence encoding the FcγR1a polypeptide replaces all or part of an endogenous rodent FcγR1a gene. For example, in some embodiments, the nucleic acid sequence encoding the extracellular domain in an endogenous FcγR1a locus is replaced with a nucleic acid sequence encoding the extracellular domain of a human FcεR1α such that a rodent comprising such a locus expresses a FcγR1a with a human extracellular domain and a rodent (e.g., rat or mouse) transmembrane and cytoplasmic domain. In some embodiments, the rodent does not express a rodent FcεR1a, or does not express a functional rodent FcγR1a. In some embodiments, the FcγR1a gene locus comprises non-human regulatory elements (e.g., non-human promoters and/or enhancers). In some embodiments, the non-human regulatory elements are rodent regulatory elements (e.g., rat or mouse promoters or enhancers).

Humanized FcγR1a polypeptides, loci encoding humanized FcγR1a polypeptides and non-human animals expressing humanized FcγR1a polypeptides are described in U.S. Pat. No. 9,474,255 and U.S. Pat. Pub. No. 2017/0086432, each of which is incorporated by reference herein.

In some embodiments, the rodent is heterozygous for the genetically modified FcγR1a locus. In some embodiments, the rodent is homozygous for the genetically modified FcγR1a locus.

Humanized Low Affinity Fc Gamma Receptors

In some embodiments, the genetically modified rodents (e.g., rats or mice) and ES cells described herein express and/or comprise in their genome a locus encoding human low affinity Fc gamma receptor (FcγR) polypeptide (e.g., a human FcγRIIa, FcγRIIb, FcγRIIc, FcγRIIIa or FcγRIIIb polypeptide).

In some embodiments, the low affinity FcγR locus comprises a nucleic acid sequence encoding a human FcγRIIa polypeptide. In some embodiments the nucleic acid sequence encoding the human FcγRIIa polypeptide is positioned at an endogenous rodent low affinity FcγR locus. In certain embodiments the nucleic acid sequence encoding the FcγRIIa polypeptide replaces all or part of an endogenous rodent low affinity FcγR locus. In a specific embodiment, the human FcγRIIa gene comprises a polymorphism, wherein the polymorphism is selected from a 131 His low responder polymorphism and a 131Arg high responder polymorphism. In a specific embodiment, the FcγRIIa polymorphism is the 131His low responder polymorphism. In some embodiments, the rodent does not express a rodent low affinity FcγR polypeptide (e.g., does not express a rodent FcγRIIb, FcγRIV and/or FcγRIII polypeptide, or does not express functional rodent FcγRIIb, FcγRIV and/or FcγRIII polypeptide). In some embodiments, the FcγRIIa gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIb polypeptide. In some embodiments the nucleic acid sequence encoding the human FcγRIIb polypeptide is positioned at an endogenous rodent low affinity FcγR locus. In certain embodiments the nucleic acid sequence encoding the FcγRIIb polypeptide replaces all or part of an endogenous rodent low affinity FcγR locus. In a specific embodiment, the human FcγRIIb gene comprises an amino acid substitution, wherein the substitution is selected from an 187Ile or a 187Thr substitution. In some embodiments, the rodent does not express a rodent low affinity FcγR polypeptide (e.g., does not express a rodent FcγRIIb, FcγRIV and/or FcγRIII polypeptide, or does not express functional rodent FcγRIIb, FcγRIV and/or FcγRIII polypeptide). In some embodiments, the FcγRIIb gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIc polypeptide. In some embodiments the nucleic acid sequence encoding the human FcγRIIc polypeptide is positioned at an endogenous rodent low affinity FcγR locus. In certain embodiments the nucleic acid sequence encoding the FcγRIIc polypeptide replaces all or part of an endogenous rodent low affinity FcγR locus. In one embodiment, the FcγRIIc gene is a specific allelic variant, wherein the allelic variant is selected from a 57Stop variant and a 57Q variant. In some embodiments, the rodent does not express a rodent low affinity FcγR polypeptide (e.g., does not express a rodent FcγRIIB, FcγRIV and/or FcγRIII polypeptide). In some embodiments, the FcγRIIc gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIIa polypeptide. In some embodiments the nucleic acid sequence encoding the human FcγRIIIa polypeptide is positioned at an endogenous rodent low affinity FcγR locus. In certain embodiments the nucleic acid sequence encoding the FcγRIIIa polypeptide replaces all or part of an endogenous rodent low affinity FcγR locus. In some embodiments, the rodent does not express a rodent low affinity FcγR polypeptide (e.g., does not express a rodent FcγRIIb, FcγRIV and/or FcγRIII polypeptide, or does not express functional rodent FcγRIIb, FcγRIV and/or FcγRIII polypeptide). In one embodiment, the FcγRIIIa gene is a specific allelic variant, wherein the allelic variant is selected from a 176Val variant and a 176Phe variant. In a specific embodiment, the FcγRIIIa allelic variant is the 176Val variant. In some embodiments, the FcγRIIIa gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, the low affinity FcγR locus comprises a nucleic acid sequence encoding a human FcγRIIIb polypeptide. In some embodiments the nucleic acid sequence encoding the human FcγRIIIb polypeptide is positioned at an endogenous rodent low affinity FcγR locus. In certain embodiments the nucleic acid sequence encoding the FcγRIIIb polypeptide replaces all or part of an endogenous rodent low affinity FcγR locus. In a specific embodiment, the FcγRIIIb gene is a specific allelic variant, wherein the allelic variant is selected from a NA1 variant and a NA2 variant. In another specific embodiment, the FcγRIIIb allelic variant is a NA2 variant. In some embodiments, the rodent does not express a rodent low affinity FcγR polypeptide (e.g., does not express a rodent FcγRIIb, FcγRIV and/or FcγRIII polypeptide, or does not express functional rodent FcγRIIb, FcγRIV and/or FcγRIII polypeptide). In some embodiments, the FcγRIIIb gene locus comprises non-human regulatory elements (e.g., non-human promoters and/or enhancers). In some embodiments, the non-human regulatory elements are rodent regulatory elements (e.g., rat or mouse promoters or enhancers).

In some embodiments, a rodent (e.g., rat or mouse) provided herein comprises one or more human low affinity FcγR genes as described in U.S. Pat. Nos. 9,221,894, 9,056,130, 9,089,599, 8,658,154, 8,883,496 or 8,658,853. In some embodiments, a rodent (e.g., rat or mouse) provided herein comprises at least two low affinity human FcγR genes and an endogenous rodent (e.g., rat or mouse) Fc γ-chain gene, wherein the low affinity human FcγR genes are selected from the group consisting of human FcγRIIa, FcγRIIb, FcγRIIc, FcγRIIIa and FcγRIIIb. In some certain embodiments, a rodent (e.g., rat or mouse) provided herein comprises a human FcγRIIa and FcγRIIIb, and an endogenous rodent (e.g., rat or mouse) Fc γ-chain gene. In some certain embodiments, a rodent (e.g., rat or mouse) provided herein comprises FcγRIIa, FcγRIIIa, FcγRIIb, FcγRIIc and FcγRIIId genes, and an endogenous rodent (e.g., rat or mouse) Fc γ-chain gene. In various embodiments, a rodent (e.g., rat or mouse) comprising one or more human FcγRs further comprises a homozygous disruption in endogenous rodent (e.g., rat or mouse) FcγRIIB, FcγRIV and FcγRIII genes (i.e., endogenous rodent FcγRIIb, FcγRIV and FcγRIII α-chain encoding sequences). In various embodiments, a rodent (e.g., rat or mouse) comprising one or more human low affinity FcγRs as described herein does not detectably express an endogenous rodent low affinity FcγR polypeptide (e.g., an endogenous low affinity FcγR α-chain polypeptide).

In some embodiments, the rodent is heterozygous for the genetically modified low affinity FcγR locus. In some embodiments, the rodent is homozygous for the genetically modified low affinity FcγR locus.

Genetically Modified Non-Human Animals and ES Cells

In certain aspects, provided herein are genetically modified non-human animals (e.g., rodents, such as rats or mice) comprising one or more of the humanized loci disclosed herein as well as genetically modified non-human animal ES cells useful in the making of such non-human animals.

In certain aspects, provided herein are genetically modified non-human animals and non-human animal ES cells comprising in their germline and/or genome one or more of the engineered loci described herein. For example, in some embodiments the non-human animal or ES cell comprises in its germline and/or genome an IgH locus provided herein. In certain embodiments, the non-human animal or ES cell further comprises an Igκ and/or an Igλ locus provided herein. In some embodiments the non-human animal or ES cell comprises in their germline and/or genome a CD79a and/or a CD79b locus provided herein. In certain embodiments, the non-human animal or ES cell comprises in their germline and/or genome a FcRn locus provided herein. In certain embodiments, the non-human animal or ES cell comprises in their germline and/or genome a β2M locus provided herein. In certain embodiments, the non-human animal or ES cell comprises in their germline and/or genome a FcεR1α locus provided herein. In certain embodiments, the non-human animal or ES cell comprises in their germline and/or genome a FcγR1a locus provided herein. In certain embodiments, the non-human animal or ES cell comprises in their germline and/or genome a FcγR2a locus provided herein. In certain embodiments, the non-human animal or ES cell comprises in their germline and/or genome a FcγR2b locus provided herein. In certain embodiments, the non-human animal or ES cell comprises in their germline and/or genome a FcγR3a locus provided herein. In certain embodiments, the non-human animal or ES cell comprises in their germline and/or genome a FcγR3b locus provided herein. In certain embodiments, the non-human animal or ES cell comprises in their germline and/or genome a FcγR2c locus provided herein. In some embodiments, the non-human animal or ES cell is heterozygous for one or more of the loci, e.g., genetically engineered loci, provided herein. In some embodiments, the non-human animal or ES cell is homozygous for one or more of the loci, e.g., genetically engineered loci, provided herein.

In some embodiments, the non-human animal can be any non-human animal. In some embodiments, the non-human animal is a vertebrate. In some embodiments, the non-human animal is a mammal. In some embodiments, the genetically modified non-human animal described herein may be selected from a group consisting of a mouse, rat, rabbit, pig, bovine (e.g., cow, bull, buffalo), deer, sheep, goat, llama, chicken, cat, dog, ferret, primate (e.g., marmoset, rhesus monkey). For non-human animals where suitable genetically modifiable ES cells are not readily available, other methods can be employed to make a non-human animal comprising the genetic modifications described herein. Such methods include, for example, modifying a non-ES cell genome (e.g., a fibroblast or an induced pluripotent cell) and employing nuclear transfer to transfer the modified genome to a suitable cell, such as an oocyte, and gestating the modified cell (e.g., the modified oocyte) in a non-human animal under suitable conditions to form an embryo.

In various embodiments, provided herein are non-human animals, e.g., rodents (e.g., rats or mice) comprising genetically engineered immunoglobulin heavy chain locus. Exemplary embodiments of such genetically engineered loci are depicted schematically in FIG. 1 and described in detail herein. In some embodiments, a non-human animal described herein includes an Adam6 gene in its genome (e.g., its germline genome), which encodes an ADAM6 polypeptide, functional ortholog, functional homolog, or functional fragment thereof (see, e.g., U.S. Pat. Nos. 8,642,835 and 8,697,940, each of which is incorporated herein by reference in its entirety). In some embodiments, an ADAM6 polypeptide, functional ortholog, functional homolog, or functional fragment thereof is expressed from an Adam6 gene. In some embodiments, an Adam6 gene does not originate from the non-human animal that includes an Adam6 gene (e.g., a mouse that includes a rat Adam6 gene or a mouse Adam6 gene obtained from another strain of mouse). In some embodiments, a non-human animal described herein includes an ectopic Adam6 gene. An "ectopic" Adam6 gene, as used herein, refers to an Adam6 gene that is in a different context than the Adam6 gene appears in a wild-type non-human animal. For example, the Adam6 gene could be located on a different chromosome, located at a different locus, or positioned adjacent to different sequences. An exemplary ectopic Adam6 gene is a mouse Adam6 gene located within human immunoglobulin sequences (e.g., human heavy chain variable region gene segments). In some embodiments, a non-human animal described herein includes an inserted or integrated Adam6 gene.

In some embodiments, a non-human animal described herein includes an insertion of one or more nucleotide sequences encoding one or more non-human Adam6 polypeptides, functional orthologs, functional homologs, or functional fragments thereof in its genome (e.g., its germline genome).

In some embodiments, a non-human animal described herein includes one or more nucleotide sequences encoding one or more non-human ADAM6 polypeptides, functional orthologs, functional homologs, or functional fragments thereof in its genome (e.g., its germline genome). In some embodiments, a non-human animal described herein includes a mouse Adam6a gene and/or a mouse Adam6b gene in its genome (e.g. its germline genome). In some embodiments, a non-human animal described herein includes one or more nucleotide sequences encoding a mouse ADAM6a, functional ortholog, functional homolog, or functional fragment thereof, and/or a mouse ADAM6b, functional ortholog, functional homolog, or functional fragment thereof.

In some embodiments, one or more nucleotide sequences encoding one or more non-human ADAM6 polypeptides, functional orthologs, functional homologs, or functional fragments thereof are inserted and/or are located on the same chromosome as the endogenous immunoglobulin heavy chain locus. In some embodiments, one or more nucleotide sequences encoding one or more non-human ADAM6 polypeptides, functional orthologs, functional homologs, or functional fragments thereof are inserted and/or are located in a position so that the one or more nucleotide sequences encoding one or more non-human ADAM6 polypeptides, functional orthologs, functional homologs, or functional fragments thereof are contiguous with human immunoglobulin heavy chain variable region gene segments. In some embodiments, one or more nucleotide sequences encoding one or more non-human ADAM6 polypeptides, functional orthologs, functional homologs, or functional fragments thereof are inserted and/or are located in a position so that the one or more nucleotide sequences encoding one or more non-human ADAM6 polypeptides, functional orthologs, functional homologs, or functional fragments thereof are adjacent to human immunoglobulin heavy chain variable region gene segments. In some embodiments, one or more nucleotide sequences encoding one or more non-human ADAM6 polypeptides, functional orthologs, functional homologs, or functional fragments thereof are inserted and/or are located in a position so that the one or more nucleotide sequences encoding one or more non-human ADAM6 polypeptides, functional orthologs, functional homologs, or functional fragments thereof are located in between human immunoglobulin heavy chain variable region gene segments. In some embodiments, one or more nucleotide sequences encoding one or more non-human ADAM6 polypeptides, functional orthologs, functional homologs, or functional fragments thereof are inserted and/or are located between a first and a second human $V_H$ gene segment. In some embodiments, a first human $V_H$ gene segment is human $V_H$1-2 and a second human $V_H$ gene segment is human $V_H$6-1. In some embodiments, one or more nucleotide sequences encoding one or more non-human ADAM6 polypeptides, functional orthologs, functional homologs, or functional fragments thereof are inserted and/or are located in the place of a human Adam6 pseudogene. In some embodiments, one or more nucleotide sequences encoding one or more non-human ADAM6 polypeptides, functional orthologs, functional homologs, or functional fragments thereof are inserted between a human $V_H$ gene segment and a human $D_H$ gene segment.

In some embodiments, a non-human animal described herein includes an Adam6 gene that restores or enhances ADAM6 activity. In some embodiments, the Adam6 gene restores ADAM6 activity to the level of a comparable non-human animal that includes a functional, endogenous Adam6 gene. In some embodiments, the Adam6 gene enhances ADAM6 activity to a level that is at least 2 times, at least 3 times, at least 4 times, at least 5 times, at least 6 times, at least 7 times, at least 8 times, at least 9 times, or at least 10 times the ADAM6 activity of a comparable non-human animal that does not include a functional Adam6 gene.

In some embodiments, a non-human animal described herein includes an Adam6 gene that restores or enhances fertility in a male non-human animal. In some embodiments, the Adam6 gene restores fertility in a male non-human animal to a level of a comparable non-human animal that includes a functional, endogenous Adam6 gene. In some embodiments, the Adam6 gene restores fertility in a male non-human animal so that the number of pups produced by mating the male non-human animal is at least 70%, at least 80%, at least 90%, at least 95% the number of pups produced from a comparable mating of a comparable, male non-human animal that does not include a functional Adam6 gene. In some embodiments, the Adam6 gene enhances fertility in a male non-human animal so that number of pups produced by the mating of the male non-human animal include at least 2 times, at least 3 times, at least 4 times, at least 5 times, at least 6 times, at least 7 times, at least 8 times, at least 9 times, or at least 10 times the number of pups produced from a comparable mating of a comparable, male non-human animal that does not include a functional Adam6 gene.

In some embodiments, a non-human immunoglobulin heavy chain locus as described herein lacks at least one endogenous non-human Adam6 gene. In some embodiments, the lack of the at least one endogenous non-human Adam6 gene reduces ADAM6 activity and/or fertility in a male mouse that lacks an endogenous non-human Adam6 gene. In some embodiments, a non-human immunoglobulin heavy chain locus as described herein includes a disruption of at least one endogenous non-human Adam6 gene. In some embodiments, the disruption of at least one endogenous non-human Adam6 gene reduces ADAM6 activity and/or fertility in a male mouse that lacks an endogenous non-human Adam6 gene.

In some embodiments, the non-human animal is a mammal. In some embodiments, the non-human animal is a small mammal, e.g., of the superfamily Dipodoidea or Muroidea. In some embodiments, the non-human animal is a rodent. In certain embodiments, the rodent is a mouse, a rat or a hamster. In some embodiments, the rodent is selected from the superfamily Muroidea. In some embodiments, the non-human animal is from a family selected from Calomyscidae (e.g., mouse-like hamsters), Cricetidae (e.g., hamster, New World rats and mice, voles), Muridae (e.g., true mice and rats, gerbils, spiny mice, crested rats), Nesomyidae (e.g., climbing mice, rock mice, white-tailed rats, Malagasy rats and mice), Platacanthomyidae (e.g., spiny dormice), and Spalacidae (e.g., mole rats, bamboo rats, and zokors). In some embodiments, the rodent is selected from a true mouse or rat (family Muridae), a gerbil, a spiny mouse, and a crested rat. In some embodiments, the mouse is from a member of the family Muridae. In some embodiments, the non-human animal is a rodent. In some embodiments, the rodent is selected from a mouse and a rat. In some embodiments, the non-human animal is a mouse.

In some embodiments, the non-human animal is a mouse of a C57BL strain. In some embodiments, the C57BL strain is selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the non-human animal is a mouse of a 129 strain. In some embodiments, the 129 strain is selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. In some embodiments, the genetically modified mouse is a mix of a 129 strain and a C57BL strain. In some embodiments, the mouse is a mix of 129 strains and/or a mix of C57BL/6 strains. In some embodiments, the 129 strain of the mix is a 129S6 (129/SvEvTac) strain. In some embodiments, the mouse is a BALB strain (e.g., BALB/c). In some embodiments, the mouse is a mix of a BALB strain and another strain (e.g., a C57BL strain and/or a 129 strain). In some embodiments, the non-human animals provided herein can be a mouse derived from any combination of the aforementioned strains.

In some embodiments, the non-human animal provided herein is a rat. In some embodiments, the rat is selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

In certain embodiments, the genetically modified non-human animals or ES cells comprise in their genome and/or germline multiple loci provided herein, such as multiple genetically engineered loci provided herein. For example, in some embodiments the non-human animal or ES cell comprises in its germline and/or genome an IgH locus provided herein and an Igκ and/or an Igλ locus provided herein. In some embodiments the non-human animal or ES cell comprises in its germline and/or genome an IgH locus provided herein, an Igκ and/or an Igλ locus provided herein and, optionally, a CD79a and/or a CD79b locus provided herein. In some embodiments the non-human animal or ES cell comprises in its germline and/or genome an IgH locus provided herein, an Igκ and/or an Igλ locus provided herein, a FcRn locus provided herein and a β2M locus provided herein. In some embodiments the non-human animal or ES cell comprises in its germline and/or genome an IgH locus provided herein, an Igκ and/or an Igλ locus provided herein, a FcRn locus provided herein, a β2M locus provided herein, a FcεR1α locus provided herein, a FcγR1a locus provided herein, a FcγR2a locus provided herein, a FcγR2b locus provided herein, a FcγR3a locus provided herein, a FcγR3b locus provided herein, and/or a FcγR2c locus provided herein, and any combinations thereof.

In certain aspects, the genetically modified non-human animal expresses one or more of the humanized polypeptides encoded by the humanized loci provided herein. For example, in some embodiments the non-human animal expresses a humanized Ig heavy chain polypeptide. In certain embodiments, the non-human animal expresses a humanized Igκ polypeptide and/or a humanized Igλ polypeptide. In some embodiments the non-human animal expresses a humanized CD79a polypeptide and/or a humanized CD79b polypeptide. In certain embodiments, the non-human animal expresses a humanized FcRn polypeptide. In certain embodiments, the non-human animal expresses a humanized β2M polypeptide. In certain embodiments, the non-human animal expresses a humanized FcεR1α polypeptide. In certain embodiments, the non-human animal expresses a humanized FcγR1a polypeptide. In certain embodiments, the non-human animal or ES cell the non-human animal expresses a humanized FcγR2a polypeptide. In certain embodiments, the non-human animal expresses a humanized FcγR2b locus polypeptide. In certain embodiments, the non-human animal expresses a humanized FcγR3a polypeptide. In certain embodiments, the non-human animal expresses a humanized FcγR3b polypeptide. In certain embodiments, the non-human animal expresses a humanized FcγR2c polypeptide.

The genetically modified non-human animals and ES cells can be generated using any appropriate method known in the art. For example, such genetically modified non-human animal ES cells can be generated using VELOCIGENE® technology, which is described in U.S. Pat. Nos. 6,586,251, 6,596,541, 7,105,348, and Valenzuela et al. (2003) "High-throughput engineering of the mouse genome coupled with high-resolution expression analysis" *Nat. Biotech.* 21(6): 652-659, each of which is hereby incorporated by reference. Modifications can also be made using a genome targeted nuclease system, such as a CRISPR/Cas system, a transcription activator-like effector nuclease (TALEN) system or a zinc finger nuclease (ZFN) system. In some embodiments, modifications are made using a CRISPR/Cas system, as described, for example, in U.S. patent application Ser. Nos. 14/314,866, 14/515,503, 14/747,461 and 14/731,914, each of which is incorporated by reference. Exemplary methods of making such genetically modified non-human animals and ES cells are also provided herein in Examples 1 and 3-5.

ES cells described herein can then be used to generate a non-human animal using methods known in the art. For example, the mouse non-human animal ES cells described herein can be used to generate genetically modified mice using the VELOCIMOUSE® method, as described in U.S. Pat. No. 7,294,754 and Poueymirou et al., *Nature Biotech* 25:91-99 (2007), each of which is hereby incorporated by reference. Resulting mice can be bread to homozygosity.

Methods of Testing Human Fc-Containing Therapeutics

In certain aspects provided herein are methods of testing a therapeutic protein comprising a human Fc domain (e.g., a human antibody or a Fc fusion protein) comprising administering the therapeutic protein to a rodent provided herein (e.g., a mouse or rat provided herein). In certain embodiments, provided herein are animal models for performing such methods.

In some embodiments the administered human antibody or Fc fusion protein has an isotype and/or allotype that matches the isotype and/or allotype of Fc domain encoded by a human $C_H$ in the genetically modified IgH locus of the rodent provided herein. For example, in some embodiments the agent is a human IgG1 antibody and the rodent comprises genetically modified IgH locus that comprises a $C_H$ gene segment encoding human IgG1 $CH_1$, hinge, $CH_2$ and $CH_3$ domains. In some embodiments the agent is a human IgG4 antibody and the rodent comprises genetically modified IgH locus that comprises a $C_H$ gene segment encoding human IgG4 $CH_1$, hinge, $CH_2$ and $CH_3$ domains. In some embodiments the agent is a human IgG1 antibody and the rodent comprises genetically modified IgH locus that comprises a $C_H$ gene segment encoding human IgG1 $CH_1$, hinge, $CH_2$, $CH_3$, M1 and M2 domains. In some embodiments the agent is a human IgG2 antibody and the rodent comprises genetically modified IgH locus that comprises a $C_H$ gene segment encoding human IgG2 $CH_1$, hinge, $CH_2$, $CH_3$, M1 and M2 domains. In some embodiments the agent is a human IgG3 antibody and the rodent comprises genetically modified IgH locus that comprises a $C_H$ gene segment encoding human IgG3 $CH_1$, hinge, $CH_2$, $CH_3$, M1 and M2 domains. In some embodiments the agent is a human IgG4 antibody and the rodent comprises genetically modified IgH locus that comprises a $C_H$ gene segment encoding human IgG4 $CH_1$, hinge, $CH_2$, $CH_3$, M1 and M2 domains. In some embodiments the agent is a human IgM antibody and the rodent comprises genetically modified IgH locus that comprises a $C_H$ gene segment encoding human IgM $CH_1$, $CH_2$, $CH_3$ and $CH_4$ domains. In some embodiments the agent is a human IgD antibody and the rodent comprises genetically modified IgH locus that comprises a $C_H$ gene segment encoding human IgD $CH_1$, H1, H2, $CH_2$, $CH_3$, M1 and M2 domains. In some embodiments the therapeutic agent is a human antibody having an Igκ light chain and the rodent comprises a genetically modified Igκ locus provided herein. In some embodiments the therapeutic agent is a human antibody having an Igλ light chain and the rodent comprises a genetically modified Igλ locus provided herein.

In some embodiments the method comprises measuring one or more pharmacokinetic properties of the administered therapeutic protein. In certain embodiments the animal model used to determine the pharmacokinetic properties of the administered human antibody or fusion protein is a genetically modified rodent provided herein comprising a modified IgH locus provide herein. In certain embodiments the animal model used to determine the pharmacokinetic properties of the administered human antibody or fusion protein is a genetically modified rodent provided herein comprising a modified IgH locus provide herein and a modified Igκ locus and/or a modified Igλ locus provided herein. In some embodiments the administered human antibody or Fc fusion protein has an isotype and/or allotype that matches the isotype and/or allotype of the constant domain encoded by a humanized $C_H$ in the genetically modified IgH locus. In some embodiments the rodent further comprises a modified FcRn locus provided herein. In some embodiments, the rodent further comprises a modified β2M provided herein.

In some embodiments the one or more pharmacokinetic parameters include, but are not limited to, area under the plasma concentration versus time (AUC), in vivo recovery (IVR), clearance rate (CL), mean residence time (MRT), agent half-life (t½), and volume of distribution at steady state (Vss). In general, the pharmacokinetic properties of the administered therapeutic agent is determined by administering a selected dose of the therapeutic agent (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more) and then determining how the plasma concentration of the therapeutic agent changes over time (e.g., 0 hr, 6 hr, 1 day, 2 days, 3 days, 4 days, 5 days, 6 days, 7 days, 8 days, 9 days, 10 days, 11 days, or up to 30 or more days).

In some embodiments, the methods further comprise measuring the therapeutic efficacy of the administered therapeutic protein (e.g., the ability of an administered dose of the therapeutic protein to reduce or eliminate one or more disease symptoms in the animal model). In some embodiments the animal model is a cancer model and disease symptoms can include, for example, tumor size, tumor metastasis and/or animal survival. In certain embodiments the animal model is an autoimmune or inflammation model and the disease symptoms can include, for example, levels of cytokine expression, proliferation of immune cells, tissue damage and/or animal survival. In some embodiments the animal model is an infectious disease model and the disease symptoms can include, for example, levels of the infectious agent, tissue damage and/or animal survival.

In some embodiments, the methods further comprise measuring the safety and dosing of the administered therapeutic protein (e.g., the extent to which an administered dose of the therapeutic protein produces one or more adverse effects in the animal model). Adverse effects include, but are not limited to, allergic reactions, alopecia, anaphylaxis, anemia, lack of appetite, loss of balance, bleeding, blood clots, difficulty breathing, bronchitis, bruising, low white blood cell count, low red blood cell count, low platelet count, cardiotoxicity, conjunctivitis, constipation, coughing, dehydration, diarrhea, electrolyte imbalance, loss of fertility, fever, hair loss, heart failure, infection, injection site reactions, iron deficiency, kidney failure, leukopenia, liver dysfunction, pneumonia, rapid heartbeat, rectal bleeding, seizures, weight loss and weight gain. For example, in certain embodiments provided herein is a method of measuring allergic reactions induced by a therapeutic agent using passive cutaneous anaphylaxis (PCA) and/or passive systemic anaphylaxis (PSA) models.

In certain embodiments, the method further comprises measuring the extent to which the therapeutic protein induces one or more Fc receptor mediated responses in the rodent (e.g., the extent to which the therapeutic protein induces antibody-dependent cell-mediated cytotoxicity (ADCC)). For example, in certain embodiments provided herein is a method of screening a therapeutic agent comprising a human Fc region of a human antibody comprising: (a) administering an agent comprising an Fc region of a human antibody to a rodent provided herein, wherein the agent binds to a target cell in the rodent; (b) measuring antibody-dependent cell-mediated cytotoxicity (ADCC) of natural killer (NK) cells against the target cell; and (c) comparing the amount of ADCC in step (b) to a control, wherein increased target cell killing indicates the agent has increased ability to mediate ADCC.

In some embodiments the method further comprises measuring the extent to which administration of the therapeutic protein induces an anti-human Fc immune response in the rodent.

In some embodiments the administered therapeutic agent elicits a reduced immune response when administered to the rodent provided herein. In some embodiments the administered human antibody or Fc fusion protein has an isotype and/or allotype that matches the isotype and/or allotype of Fc domain encoded by a human $C_H$ in the genetically modified IgH locus of the rodent provided herein. For example, in some embodiments the agent is a human IgG1 antibody and the rodent comprises genetically modified IgH locus that comprises a $C_H$ gene segment encoding human IgG1 $CH_1$, hinge, $CH_2$ and $CH_3$ domains. In some embodiments the agent is a human IgG4 antibody and the rodent comprises genetically modified IgH locus that comprises a $C_H$ gene segment encoding human IgG4 $CH_1$, hinge, $CH_2$ and $CH_3$ domains. In some embodiments the agent is a human IgG1 antibody and the rodent comprises genetically modified IgH locus that comprises a $C_H$ gene segment encoding human IgG1 $CH_1$, hinge, $CH_2$, $CH_3$, M1 and M2 domains. In some embodiments the agent is a human IgG2 antibody and the rodent comprises genetically modified IgH locus that comprises a $C_H$ gene segment encoding human IgG2 $CH_1$, hinge, $CH_2$, $CH_3$, M1 and M2 domains. In some embodiments the agent is a human IgG3 antibody and the rodent comprises genetically modified IgH locus that comprises a $C_H$ gene segment encoding human IgG3 $CH_1$, hinge, $CH_2$, $CH_3$, M1 and M2 domains. In some embodiments the agent is a human IgG4 antibody and the rodent comprises genetically modified IgH locus that comprises a $C_H$ gene segment encoding human IgG4 $CH_1$, hinge, $CH_2$, $CH_3$, M1 and M2 domains. In some embodiments the agent is a human IgM antibody and the rodent comprises genetically modified IgH locus that comprises a $C_H$ gene segment encoding human IgM $CH_1$, $CH_2$, $CH_3$ and $CH_4$ domains. In some embodiments the agent is a human IgD antibody and the rodent comprises genetically modified IgH locus that comprises a $C_H$ gene segment encoding human IgD $CH_1$, H1, H2, $CH_2$, $CH_3$, M1 and M2 domains. In some embodiments the therapeutic agent is a human antibody having an Igκ light chain and the rodent comprises a genetically modified Igκ locus provided herein. In some embodiments the therapeutic agent is a human antibody having an Igλ light chain and the rodent comprises a genetically modified Igλ locus provided herein.

In certain embodiments, the methods provided herein include the testing of therapeutic antibodies comprising a human Fc. In some embodiments, the antibodies tested comprise human heavy chain variable domains. In some embodiments, the antibodies comprise human heavy chain constant domains. In some embodiments, the antibodies provided herein comprise a IgG1, IgG2, IgG3, IgG4, IgA, IgE, IgM or IgD constant domain. The sequences of human heavy chain constant domains are known in the art (see e.g., Kabat, E. A., et al. (1991) Sequences of Proteins of Immunological Interest, Fifth Edition, U.S. Department of Health and Human Services, NIH Publication No. 91-3242 and the IMGT database available at www.imgt.org).

In some embodiments, the antibodies tested comprise a modified Fc domain (e.g., a mutation that alters the interaction between the Fc and a Fc receptor). For example, in some embodiments, the antibodies provided herein comprise modification to their Fc domain at position 235, 236, 237, 239, 265, 267, 268, 269, 270, 298, 326, 327, 330, 332, 350, 351, 366, 392, 394, 405 and/or 407 (using the EU numbering system). In some embodiments, the modification is selected from the group consisting of L235A, G236E, G237F, S239E, S239D, D265E, D265S, S267E, S267D, S267G, H268E, H268D, E269L, D270N, D270E, S298A, K326A, K326D, A327H, A327V, A327L, A330I, A330S, I332E, T350V, L351Y, T366L, K392M, K392L, T394W, F405A and/or Y407V (using the EU numbering system). In some embodiments, the antibodies comprise multiple modifications to their Fc domain. In some embodiments, the multiple modifications are selected from the group consisting of D270N/K326D, S239E/S298A/K326A/A327H, L235A/ S239E/D265E/A327H, G236E/G237F/S239E, G237F/ S239E/D265E, G237F/S239E/H268D, G236E/D270N/ A327V/I332E, G237F/S239E/A327H, G237F/A327L/ A330I, S239D/D265S/S298A/I332E, S239E/D265S/ H268D/I332E, S239E/D265S/I332E, S239E/S267E/ H268D, S239E/A327L/A330I, D265E/S267D/A330S, S267G/H268E/D270E, H268D/E269L/S298A/K326A/ A327H, H268D//K326A/A327H. Additional Fc modifications and combinations of Fc modifications are provided in U.S. Pat. Nos. 5,624,821, 5,648,260, 6,528,624, 6,737,056, 7,122,637, 7,183,387, 7,297,775, 7,317,091, 7,332,581, 7,632,497, 7,662,925, 7,695,936, 8,093,359, 8,216,805, 8,218,805, 8,388,955 and 8,937,158, and U.S. Patent Publication Nos. 2005/0054832, 2006/0222653, 2006/0275282, 2006/0275283, 2007/0190063, 2008/0154025, 2009/ 0042291 2013/0108623 and 2013/0089541, each of which is hereby incorporated by reference.

In some embodiments, the antibody tested is a bi-specific antibody. In some embodiments, the two antigen binding domains of the bi-specific antibody have distinct heavy chain variable domains but have identical light chain variable domains. In some embodiments, the Fc domains of the heavy chains comprise modifications to facilitate heavy chain heterodimer formation and/or to inhibit heavy chain homodimer formation. Such modifications are provided, for example, in U.S. Pat. Nos. 5,731,168, 5,807,706, 5,821,333, 7,642,228 and 8,679,785 and in U.S. Pat. Pub. No. 2013/ 0195849, each of which is hereby incorporated by reference.

In some embodiments, the antibodies tested in the methods provided herein have human light chain variable domains. In some embodiments, the light chain variable domains are λ light chain variable domains. In some embodiments, the light chain variable domains are κ light chain variable domains. In some embodiments, the antibodies have human light chain constant domains. In some embodiments, the light chain constant domains are λ light chain constant domains. In some embodiments, the light chain constant domains are κ light chain constant domains. The sequences of human light chain constant domains are known in the art (see e.g., Kabat, E. A., et al. (1991) Sequences of Proteins of Immunological Interest, Fifth Edition, U.S. Department of Health and Human Services, NIH Publication No. 91-3242 and the IMGT database available at www.imgt.org)

In certain embodiments, the therapeutic agent is administered to a rodent provided herein as part of a pharmaceutical composition e.g., a pharmaceutical composition, containing a human antibody or Fc fusion protein formulated together with a pharmaceutically acceptable carrier.

The pharmaceutical compositions provided herein may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Pharmaceutical compositions suitable for parenteral administration comprise a human antibody or Fc fusion protein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, the compositions comprise a human antibody or Fc fusion protein in a concentration resulting in a w/v appropriate for a desired dose. The antibody may be present in the composition at a concentration of at least 1 mg/mL, at least 5 mg/mL, at least 10 mg/mL, at least 15 mg/mL, at least 20 mg/mL, at least 25 mg/mL, at least 30 mg/mL, at least 35 mg/mL, at least 40 mg/mL, at least 45 mg/mL, at least 50 mg/mL, at least 55 mg/mL, at least 60 mg/mL, at least 65 mg/mL, at least 70 mg/mL, at least 75 mg/mL, at least 80 mg/mL, at least 85 mg/mL, at least 90 mg/mL, at least 95 mg/mL, at least 100 mg/mL, at least 105 mg/mL, at least 110 mg/mL, at least 115 mg/mL, at least 120 mg/mL, at least 125 mg/mL, at least 130 mg/mL, at least 135 mg/mL, at least 140 mg/mL, at least 150 mg/mL, at least 200 mg/mL, at least 250 mg/mL, or at least 300 mg/mL.

In some embodiments, compositions are prepared by mixing a human antibody or Fc fusion protein with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, 12th edition, L. Brunton, et al. and Remington's Pharmaceutical Sciences, 16th edition, Osol, A. Ed. (1999)), in the form of lyophilized compositions or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS® or polyethylene glycol (PEG).

In some embodiments, the buffering agent is histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, MgCl2, or CaCl2.

In some embodiments, the composition comprises a buffering or pH adjusting agent to provide improved pH control. Such a composition may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, such a composition has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a composition has a pH of about 6.0. One of skill in the art understands that the pH of a composition generally should not be equal to the isoelectric point of a human antibody or Fc fusion protein to be used in the composition. Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the composition as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13th ed., O'Neil et al. ed. (Merck & Co., 2001).

In certain embodiments, the composition comprises histidine as a buffering agent. In certain embodiments the histidine is present in the composition at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a composition comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the composition comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a composition may comprise about 10 mM, about 25 mM, or no histidine.

In some embodiments, the composition comprises a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

In some embodiments, the composition comprises a carbohydrate excipient. Carbohydrate excipients suitable for use in the compositions include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In certain embodiments, the carbohydrate excipients for use in the compositions provided herein are chosen from sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In some embodiments, the composition comprises trehalose. In certain embodiments, a composition comprises at least about 1%, at least about 2%, at least about 4%, at least about 8%, at least about 20%, at least about 30%, or at least about 40% trehalose. In another embodiment, a composition comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a composition comprises about 1%, about 2%, about 4%, about 6%, about 8%, about 15%, about 20%, about 30%, or about 40% trehalose. In a specific embodiment, a composition comprises about 4%, about 6% or about 15% trehalose.

In certain embodiments, the composition comprises an excipient. In a specific embodiment, a composition comprises at least one excipient chosen from: sugar, salt, surfactant, amino acid, polyol, chelating agent, emulsifier and preservative. In certain embodiments, a composition comprises a salt, e.g., a salt selected from: NaCl, KCl, CaCl2, and MgCl2. In a specific embodiment, the composition comprises NaCl.

In some embodiments, the composition comprises an amino acid, e.g., lysine, arginine, glycine, histidine or an amino acid salt. The composition may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the composition may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a composition comprises about 1 mM, 1.6 mM, 25 mM, about 50 mM, about 100 mM, about 150 mM, about 200 mM, about 250 mM, about 300 mM, about 350 mM, or about 400 mM of an amino acid.

In some embodiments, the composition comprises a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA® series (Mona Industries, Inc., Paterson, N.J.), polyethyl glycol, polypropyl glycol, and copolymers of ethylene and propylene glycol (e.g., PLURONICS® PF68, etc.), can optionally be added to the compositions to reduce aggregation. In certain embodiments, a composition comprises Polysorbate 20, Polysorbate 40, Polysorbate 60, or Polysorbate 80. Surfactants are particularly useful if a pump or plastic container is used to administer the composition.

The presence of a pharmaceutically acceptable surfactant mitigates the propensity for the protein to aggregate. The compositions may comprise a polysorbate which is at a concentration ranging from between about 0.001% to about 1%, or about 0.001% to about 0.1%, or about 0.01% to about 0.1%. In other specific embodiments, the compositions comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

In some embodiments, the composition comprises other excipients and/or additives including, but not limited to, diluents, binders, stabilizers, lipophilic solvents, preservatives, adjuvants, or the like. Pharmaceutically acceptable excipients and/or additives may be used in the compositions provided herein. Commonly used excipients/additives, such as pharmaceutically acceptable chelators (for example, but not limited to, EDTA, DTPA or EGTA) can optionally be added to the compositions to reduce aggregation. These additives are particularly useful if a pump or plastic container is used to administer the composition.

In some embodiments, the composition comprises a preservative. Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the compositions at any suitable concentration such as between about 0.001% to about 5%, or any range or value therein. The concentration of preservative used in the compositions is a concentration sufficient to yield a microbial effect. Such concentrations are dependent on the preservative selected and are readily determined by the skilled artisan.

In some embodiments, the composition is isotonic with human blood, wherein the compositions have essentially the same osmotic pressure as human blood. Such isotonic compositions will generally have an osmotic pressure from about 250 mOSm to about 350 mOSm. Isotonicity can be measured by, for example, using a vapor pressure or ice-freezing type osmometer. Tonicity of a composition is adjusted by the use of tonicity modifiers. "Tonicity modifiers" are those pharmaceutically acceptable inert substances that can be added to the composition to provide an isotonity of the composition. Tonicity modifiers suitable for the compositions provided herein include, but are not limited to, saccharides, salts and amino acids.

In certain embodiments, the composition is a pyrogen-free composition which is substantially free of endotoxins and/or related pyrogenic substances. Endotoxins include toxins that are confined inside a microorganism and are released only when the microorganisms are broken down or die. Pyrogenic substances also include fever-inducing, thermostable substances from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In some embodiments, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the composition described herein should be sterile. The composition may be sterilized by various sterilization methods, including sterile filtration, radiation, etc. In certain embodiments, composition is filter-sterilized with a presterilized 0.22-micron filter. Sterile compositions for injection can be formulated according to conventional pharmaceutical practice as described in "Remington: The Science & Practice of Pharmacy", 21st ed., Lippincott Williams & Wilkins, (2005). Compositions comprising proteins of interest (e.g., antibodies) such as those disclosed herein, ordinarily will be stored in lyophilized form or in solution. It is contemplated that sterile compositions comprising proteins of interest (e.g., antibody) are placed into a container having a sterile access port, for example, an intravenous solution bag or vial having an adapter that allows retrieval of the composition, such as a stopper pierceable by a hypodermic injection needle. In certain embodiments, a composition is provided as a pre-filled syringe.

In certain embodiments, the composition is a lyophilized formulation. The term "lyophilized" or "freeze-dried" includes a state of a substance that has been subjected to a drying procedure such as lyophilization, where at least 50% of moisture has been removed.

Regardless of the route of administration selected, agents provided herein, which may be used in a suitable hydrated form, and/or the pharmaceutical compositions of the provided herein, are formulated into pharmaceutically-acceptable dosage forms by conventional methods known to those of skill in the art.

In the methods provided herein the human antibody, Fc fusion protein and/or pharmaceutical compositions may be delivered by any suitable route of administration, including orally, nasally, as by, for example, a spray, rectally, intravaginally, parenterally, intracisternally and topically, as by powders, ointments or drops, including buccally and sublingually. In certain embodiments the pharmaceutical compositions are delivered generally (e.g., via oral or parenteral administration).

In certain embodiments, actual dosage levels of the active ingredients in the pharmaceutical compositions described herein may be varied so as to determine an amount of the active ingredient which is effective to achieve the desired therapeutic response in the animal model, composition, and mode of administration, without being toxic in the animal model.

For example, in certain embodiments, non-human animals described herein are used to determine the pharmacokinetic profiles of one or more human antibody candidates. In various embodiments, one or more non-human animals as described herein and one or more control or reference non-human animals are each exposed to one or more human antibody candidates at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals as described herein are used to measure the therapeutic effect of blocking or modulating the activity of a polypeptide of interest and the effect on gene expression as a result of cellular changes or, in the context of a receptor polypeptide, the density of a receptor polypeptide on the surface of cells in the non-human animals. In various embodiments, a non-human animal as described herein or cells isolated therefrom are exposed to a candidate therapeutic that binds a polypeptide of interest and, after a subsequent period of time, analyzed for effects on specific cellular processes that are associated with said polypeptide of interest, for example, ligand-receptor interactions or signal transduction.

Non-human animals as described herein provide an improved in vivo system for development and selection of human antibodies for use in oncology and/or infectious diseases. In various embodiments, non-human animals as described herein and control non-human animals (e.g., having a genetic modification that is different than as described herein or no genetic modification, i.e., wild-type) may be implanted with a tumor (or tumor cells) or infected with a virus (e.g., influenza, HIV, HCV, HPV, etc.). Following implantation of infection, non-human animals may be administered a candidate therapeutic. The tumor or virus may be allowed sufficient time to be established in one or more locations within the non-human animals prior to administration of a candidate therapeutic. Alternatively and/or additionally, the immune response may be monitored in such non-human animals so as to characterize and select potential human antibodies that may be developed as a therapeutic.

Methods of Making Human Antibodies

In certain aspects, provided herein are method of making a human antibody using a rodent (e.g., a mouse or a rat) that comprises a humanized heavy chain locus provided herein and a human light chain locus provided herein (e.g. a humanized κ and/or λ light chain locus provided herein). In some embodiments, the rodent further comprises a humanized CD79a locus provided herein and/or a humanized CD79b locus provided herein. In some embodiments, the rodent further comprises a humanized FcRn locus provided herein and/or a humanized β2M locus provided herein. In certain embodiments, the rodent further comprises a humanized FcγR1a locus provided herein. In some embodiments, the rodent further comprises a humanized FcεR1α locus provided herein. In some embodiments, the rodent further comprises a humanized FcγR2b locus provided herein, a humanized FcγR2c locus provided herein, a humanized FcγR3a locus provided herein, and/or a humanized FcγR3b locus provided herein.

Rodents provided herein may be employed for making an antibody (e.g., a human antibody) using standard methods known in the art. For example, in some embodiments a rodent provided herein is immunized with an antigen of interest under conditions and for a time sufficient that the rodent develops an immune response to said antigen of interest. In some embodiments, the antigen of interest is a human antibody (e.g., a human therapeutic antibody) or Fc-fusion protein (e.g., a therapeutic Fc-fusion protein). Antibodies are isolated from the rodent (or one or more cells, for example, one or more B cells) and characterized using various assays measuring, for example, affinity, specificity, epitope mapping, ability for blocking ligand-receptor interaction, inhibition receptor activation, etc.

In some embodiments, a method of producing an antibody in rodent (e.g., a mouse or a rat) is provided, the method comprising the steps of (a) immunizing a rodent that produced human antibodies as described herein with an antigen of interest, (b) maintaining the rodent under conditions sufficient that the rodent produces an immune response to the antigen of interest, and (c) recovering an antibody from the rodent, or a rodent cell, that binds the antigen of interest. In some embodiments the method further comprises breaking immunological tolerance to the antigen in the rodent or otherwise deleting the antigen of interest, for example, employing CRISPR/Cas9 systems using multiple guide RNAs to reduce or eliminate the expression of a self-antigen homologous to or sharing an epitope of interest with the antigen of interest with which the rodent is immunized (e.g., as described in U.S. Pat. Pub. No. 2017/0332610, which is hereby incorporated by reference).

In some embodiments, a method of producing a nucleic acid encoding a human heavy and/or light chain in a rodent is provided, the method comprising the steps of (a) immunizing a rodent expressing human antibodies as described herein with an antigen of interest, (b) maintaining the rodent under conditions sufficient that the rodent produces an immune response to the antigen of interest, and (c) recovering a nucleic acid encoding a human heavy and/or light chain from the rodent, or a rodent cell.

In some embodiments, rodents provided herein may be employed for making anti-drug antibodies (e.g., anti-idiotype antibodies). For example, in some embodiments a rodent provided herein is immunized with a human therapeutic antibody under conditions and for a time sufficient that the rodent develops an immune response to said human therapeutic antibody. In some embodiments, the human therapeutic antibody has the same heavy chain constant domains as the heavy chain constant domains encoded by the humanized immunoglobulin heavy chain locus of the rodent provided herein. In some embodiments, the human therapeutic antibody has the same light chain constant domain as the light chain constant domain encoded by the humanized immunoglobulin light chain locus (e.g. the humanized κ and/or λ light chain locus) of the rodent provided herein. In some embodiments the rodent does not comprise in its genome one or more of the human variable region gene segments from which the therapeutic antibody is derived (e.g., one or more immunoglobulin loci in the rodent comprises rodent variable regions or portions thereof). Anti-drug antibodies (e.g., anti-idiotype antibodies) are isolated from the rodent (or one or more cells, for example, one or more B cells) and characterized using various assays measuring, for example, affinity, specificity, epitope mapping, ability for blocking antigen-therapeutic antibody interaction, etc. The generated anti-drug antibodies (e.g., anti-idiotype antibodies) may be used for pharmacokinetic (PK) analysis of the human therapeutic antibody, or used to analyze the immunogenicity of the human therapeutic antibody during preclinical analysis, or used to localize human therapeutic antibody.

In some embodiments, a method of producing an anti-drug antibody (e.g., an anti-idiotype antibody) in rodent (e.g., a mouse or a rat) is provided, the method comprising the steps of (a) immunizing a rodent that produces antibodies comprising human constant region(s) as described herein with a human therapeutic antibody that is isotype-matched to the human constant region present in the rodent, (b) maintaining the rodent under conditions sufficient that the rodent produces an immune response to the human therapeutic antibody, and (c) recovering an antibody from the rodent, or a rodent cell, that binds the human therapeutic antibody.

Methods of Making Genetically Modified Non-Human Animals and ES Cells

In certain aspects, provided herein are methods of making non-human animals (e.g., a mouse or a rat) and ES cells that comprise one or more of the genetically modified loci provided here. For example, in some embodiments provided herein are methods of making non-human animals (e.g., a mouse or a rat) and ES cells that comprise a humanized heavy chain locus provided herein and/or a human light chain locus provided herein (e.g. a humanized κ and/or λ light chain locus provided herein). In some embodiments, provided herein are methods of making non-human animals (e.g., a mouse or a rat) and ES cells that further comprises a humanized CD79a locus provided herein and/or a humanized CD79b locus provided herein. In some embodiments, provided herein are methods of making non-human animals (e.g., a mouse or a rat) and ES cells that further comprises a humanized FcRn locus provided herein and/or a humanized β2M locus provided herein. In some embodiments, provided herein are methods of making non-human animals (e.g., a mouse or a rat) and ES cells that further comprises a humanized FcεR1α locus provided herein. In certain embodiments, provided herein are methods of making non-human animals (e.g., a mouse or a rat) and ES cells that further comprises a humanized FcγR1a locus provided herein. In some embodiments, provided herein are methods of making non-human animals (e.g., a mouse or a rat) and ES cells that further comprises a humanized FcεR1α locus provided herein. In some embodiments, provided herein are methods of making non-human animals (e.g., a mouse or a rat) and ES cells that further comprises a humanized FcγR2a locus provided herein, a humanized FcγR2b locus provided herein, a humanized FcγR2c locus provided herein, a humanized FcγR3a locus provided herein, and/or a humanized FcγR3b locus provided herein. In certain embodiments, provided herein are methods of making non-human animals (e.g., a mouse or a rat) and ES cells that comprises a humanized FcRn locus provided herein and/or a humanized β2M locus provided herein. In certain embodiments, provided herein are methods of making non-human animals (e.g., a mouse or a rat) and ES cells that comprises a humanized FcεR1α locus provided herein. The exemplary methods of making genetically modified non-human animals and ES cells provided herein are described in the description, examples, and/or figures herein.

Kits

Provided herein a pack or kit comprising one or more containers filled with at least one non-human animal, non-human cell, DNA fragment and/or targeting vector as described in the description, examples, and/or figures herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, (c) a contract that governs the transfer of materials and/or biological products (e.g., a non-human animal or non-human cell as described herein) between two or more entities and combinations thereof.

Additional Exemplary Embodiments

In exemplary embodiment 1, provided herein is a rodent comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain, wherein the immunoglobulin heavy chain variable region is operably linked to the immunoglobulin heavy chain constant region such that the rodent produces IgG antibodies comprising variable domains derived from the $V_H$ gene segment, the $D_H$ gene segment and the $J_H$ gene segment and heavy chain constant domains derived from the $C_H$ gene segment.

In exemplary embodiment 2, provided herein is the rodent of embodiment 1, wherein the IgG transmembrane domain is a rodent IgG transmembrane domain.

In exemplary embodiment 3, provided herein is the rodent of embodiment 1, wherein the IgG transmembrane domain is a human IgG transmembrane domain.

In exemplary embodiment 4, provided herein is the rodent of any one of embodiments 1 to 3, wherein the IgG cytoplasmic domain is a rodent IgG cytoplasmic domain.

In exemplary embodiment 5, provided herein is the rodent of any one of embodiments 1 to 3, wherein the IgG cytoplasmic domain is a human IgG cytoplasmic domain.

In exemplary embodiment 6, provided herein is the rodent of any one of embodiments 1 to 5, wherein the human $C_H1$ domain, the human hinge region, the human $C_H2$ domain and the human $C_H3$ domain are IgG1 domains.

In exemplary embodiment 7, provided herein is the rodent of embodiment 6, wherein the IgG1 domain is encoded by an allele selected from IGHG1*01, IGHG1*02, IGHG1*03, IGHG1*04 and IGHG1*05.

In exemplary embodiment 8, provided herein is the rodent of any one of embodiments 1 to 5, wherein the human $C_H1$ domain, the human hinge region, the human $C_H2$ domain and the human $C_H3$ domain are IgG2 domains.

In exemplary embodiment 9, provided herein is the rodent of embodiment 8, wherein the IgG2 domain is encoded by an allele selected from IGHG2*01, IGHG2*02, IGHG2*03, IGHG2*04, IGHG2*05 and IGHG2*06.

In exemplary embodiment 10, provided herein is the rodent of any one of embodiments 1 to 5, wherein the human $C_H1$ domain, the human hinge region, the human $C_H2$ domain and the human $C_H3$ domain are IgG3 domains.

In exemplary embodiment 11, provided herein is the rodent of embodiment 10, wherein the IgG3 domain is encoded by an allele selected from IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19.

In exemplary embodiment 12, provided herein is the rodent of any one of embodiments 1 to 5, wherein the human $C_H1$ domain, the human hinge region, the human $C_H2$ domain and the human $C_H3$ domain are IgG4 domains.

In exemplary embodiment 13, provided herein is the rodent of embodiment 12, wherein the IgG4 domain is encoded by an allele selected from IGHG4*01, IGHG4*02, IGHG4*03 and IGHG4*04.

In exemplary embodiment 14, provided herein is the rodent of any one of embodiments 6 to 13, wherein the $C_H$ gene segment encoding the human $C_H1$ domain, the human hinge region, the human $C_H2$ domain and the human $CH_3$ domain is located at an endogenous $C_{\gamma 2a}$ or $C_{\gamma 2c}$ gene segment locus.

In exemplary embodiment 15, provided herein is the rodent of embodiment 14, wherein the $C_H$ gene segment encoding the human $C_H1$ domain, the human hinge region, the human $C_H2$ domain and the human $C_H3$ domain replaces an endogenous $C_{\gamma 2a}$ or $C_{\gamma 2b}$ gene segment.

In exemplary embodiment 16, provided herein is the rodent of any one of embodiments 6 to 13, wherein the $C_H$ gene segment encoding the human $C_H1$ domain, the human hinge region, the human $C_H2$ domain and the human $C_H3$ domain is located at an endogenous $C_{\gamma 1}$ gene segment locus.

In exemplary embodiment 17, provided herein is the rodent of embodiment 16, wherein the $C_H$ gene segment encoding the human $C_H1$ domain, the human hinge region, the human $C_H2$ domain and the human $C_H3$ domain replaces an endogenous $C_{\gamma 1}$ gene segment.

In exemplary embodiment 18, provided herein is the rodent of any one of embodiments 6 to 13, wherein the $C_H$ gene segment encoding the human $C_H1$ domain, the human hinge region, the human $C_H2$ domain and the human $C_H3$ domain is located at an endogenous $C_{\gamma 2b}$ gene segment locus.

In exemplary embodiment 19, provided herein is the rodent of embodiment 18, wherein the $C_H$ gene segment encoding the human $C_H1$ domain, the human hinge region, the human $C_H2$ domain and the human $C_H3$ domain replaces an endogenous $C_{\gamma 2b}$ gene segment.

In exemplary embodiment 20, provided herein is the rodent of any one of embodiments 6 to 13, wherein the $C_H$ gene segment the human $C_H1$ domain, the human hinge region, the human $C_H2$ domain and the human $C_H3$ domain is located at an endogenous $C_{\gamma 3}$ gene segment locus.

In exemplary embodiment 21, provided herein is the rodent of embodiment 20, wherein the $C_H$ gene segment encoding the human $C_H1$ domain, the human hinge region, the human $C_H2$ domain and the human $C_H3$ domain replaces an endogenous $C_{\gamma 3}$ gene segment.

In exemplary embodiment 22, provided herein is the rodent of any one of embodiments 1 to 21, wherein the immunoglobulin heavy chain constant region further comprises a rodent $C_\mu$ gene segment.

In exemplary embodiment 23, provided herein is the rodent of any one of embodiments 1 to 21, wherein the immunoglobulin heavy chain constant region further comprises a human $C_\mu$ gene segment.

In exemplary embodiment 24, provided herein is the rodent of any one of embodiments 1 to 23, wherein the immunoglobulin heavy chain constant region further comprises a rodent $C_\delta$ gene segment.

In exemplary embodiment 25, provided herein is the rodent of any one of embodiments 1 to 23, wherein the immunoglobulin heavy chain constant region further comprises a human $C_\delta$ gene segment.

In exemplary embodiment 26, provided herein is the rodent of any one of embodiments 1 to 25, wherein the immunoglobulin heavy chain constant region further comprises a rodent $C_{\gamma1}$ gene segment.

In exemplary embodiment 27, provided herein is the rodent of any one of embodiments 1 to 26, wherein the immunoglobulin heavy chain constant region further comprises a rodent $C_{\gamma2a}$ and/or $C_{\gamma2c}$ gene segment.

In exemplary embodiment 28, provided herein is the rodent of any one of embodiments 1 to 27, wherein the immunoglobulin heavy chain constant region further comprises a rodent $C_{\gamma2b}$ gene segment.

In exemplary embodiment 29, provided herein is the rodent of any one of embodiments 1 to 28, wherein the immunoglobulin heavy chain constant region further comprises a rodent $C_{\gamma3}$ gene segment.

In exemplary embodiment 30, provided herein is the rodent of any one of embodiments 1 to 29, wherein the immunoglobulin heavy chain constant region further comprises a rodent $C_\varepsilon$ gene segment.

In exemplary embodiment 31, provided herein is the rodent of any one of embodiments 1 to 29, wherein the immunoglobulin heavy chain constant region further comprises a human $C_\varepsilon$ gene segment.

In exemplary embodiment 32, provided herein is the rodent of any one of embodiments 1 to 31, wherein the immunoglobulin heavy chain constant region further comprises a rodent $C_\alpha$ gene segment.

In exemplary embodiment 33, provided herein is the rodent of any one of embodiments 1 to 31, wherein the immunoglobulin heavy chain constant region further comprises a human $C_\alpha$ gene segment.

In exemplary embodiment 34, provided herein is the rodent of any one of embodiments 1 to 21, wherein the immunoglobulin heavy chain constant region comprises a human $C_\mu$ gene segment, a human $C_\delta$ gene segment, a human $C_{\gamma3}$ gene segment and a human $C_{\gamma1}$ gene segment.

In exemplary embodiment 35, provided herein is the rodent of embodiment 34, wherein the immunoglobulin heavy chain constant region further comprises a human $C_{\gamma2}$ gene segment and a human $C_{\gamma4}$ gene segment.

In exemplary embodiment 36, provided herein is the rodent of embodiment 34 or embodiment 35, wherein the immunoglobulin heavy chain constant region further comprises a human $C_\alpha$ gene segment.

In exemplary embodiment 37, provided herein is the rodent of any one of embodiments 34 to 36, wherein the immunoglobulin heavy chain constant region further comprises a human $C_\varepsilon$ gene segment.

In exemplary embodiment 38, provided herein is a rodent comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgM constant domain comprising a human $C_H1$ domain, a human $C_H2$ domain, a human $C_H3$ domain, a human $C_H4$ domain, a human IgM transmembrane domain and a human IgM cytoplasmic domain, wherein the immunoglobulin heavy chain variable region is operably linked to the immunoglobulin heavy chain constant region such that the rodent produces IgM antibodies comprising variable domains derived from the $V_H$ gene segment, the $D_H$ gene segment and the $J_H$ gene segment and heavy chain constant domains derived from the $C_H$ gene segment.

In exemplary embodiment 39, provided herein is the rodent of embodiment 38, wherein the immunoglobulin heavy chain constant region further comprises a human $C_\delta$ gene segment.

In exemplary embodiment 40, provided herein is the rodent of embodiments 38 or 39, wherein the immunoglobulin heavy chain constant region further comprises a human $C_{\gamma3}$ gene segment.

In exemplary embodiment 41, provided herein is the rodent of any one of embodiments 38 to 40, wherein the immunoglobulin heavy chain constant region further comprises a human $C_{\gamma1}$ gene segment.

In exemplary embodiment 42, provided herein is the rodent of any one of embodiments 38 to 41, wherein the immunoglobulin heavy chain constant region further comprises a human $C_{\gamma2}$ gene segment.

In exemplary embodiment 43, provided herein is the rodent of any one of embodiments 38 to 42, wherein the immunoglobulin heavy chain constant region further comprises a human $C_{\gamma4}$ gene segment.

In exemplary embodiment 44, provided herein is the rodent of any one of embodiments 38 to 43, wherein the immunoglobulin heavy chain constant region comprises a human $C_\mu$ gene segment, a human $C_\delta$ gene segment, a human $C_{\gamma3}$ gene segment and a human $C_{\gamma1}$ gene segment.

In exemplary embodiment 45, provided herein is the rodent of embodiment 44, wherein the immunoglobulin heavy chain constant region further comprises a human $C_{\gamma2}$ gene segment and a human $C_{\gamma4}$ gene segment.

In exemplary embodiment 46, provided herein is the rodent of embodiment 44 or embodiment 45, wherein the immunoglobulin heavy chain constant region further comprises a human $C_\varepsilon$ gene segment.

In exemplary embodiment 47, provided herein is the rodent of any one of embodiments 44 to 46, wherein the immunoglobulin heavy chain constant region further comprises a human $C_\varepsilon$ gene segment.

In exemplary embodiment 48, provided herein is a rodent comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgD constant domain comprising a human $C_H1$ domain, a human hinge H1 domain, a human hinge H2 domain, a human $C_H2$ domain, a human $C_H3$ domain, a human IgD transmembrane domain and a human IgD cytoplasmic domain, wherein the immunoglobulin heavy chain variable region is operably linked to the immunoglobulin heavy chain constant region such that the rodent produces IgD antibodies comprising variable domains derived from the $V_H$ gene segment, the $D_H$ gene segment and the $J_H$ gene segment and heavy chain constant domains derived from the $C_H$ gene segment.

In exemplary embodiment 49, provided herein is the rodent of embodiment 48, wherein the immunoglobulin heavy chain constant region further comprises a human $C_\mu$ gene segment.

In exemplary embodiment 50, provided herein is the rodent of embodiments 48 or 49, wherein the immunoglobulin heavy chain constant region further comprises a human $C_{\gamma 3}$ gene segment.

In exemplary embodiment 51, provided herein is the rodent of any one of embodiments 48 to 50, wherein the immunoglobulin heavy chain constant region further comprises a human $C_{\gamma 1}$ gene segment.

In exemplary embodiment 52, provided herein is the rodent of any one of embodiments 48 to 51, wherein the immunoglobulin heavy chain constant region further comprises a human $C_{\gamma 2}$ gene segment.

In exemplary embodiment 53, provided herein is the rodent of any one of embodiments 48 to 52, wherein the immunoglobulin heavy chain constant region further comprises a human $C_{\gamma 4}$ gene segment.

In exemplary embodiment 54, provided herein is the rodent of any one of embodiments 48 to 53, wherein the immunoglobulin heavy chain constant region comprises a human $C_\mu$ gene segment, a human $C_\delta$ gene segment, a human $C_{\gamma 3}$ gene segment and a human $C_{\gamma 1}$ gene segment.

In exemplary embodiment 55, provided herein is the rodent of embodiment 54, wherein the immunoglobulin heavy chain constant region further comprises a human $C_{\gamma 2}$ gene segment and a human $C_{\gamma 4}$ gene segment.

In exemplary embodiment 56, provided herein is the rodent of embodiment 54 or embodiment 55, wherein the immunoglobulin heavy chain constant region further comprises a human $C_\alpha$ gene segment.

In exemplary embodiment 57, provided herein is the rodent of any one of embodiments 54 to 56, wherein the immunoglobulin heavy chain constant region further comprises a human $C_\varepsilon$ gene segment.

In exemplary embodiment 58, provided herein is the rodent of any one of embodiments 1 to 57, wherein the engineered immunoglobulin heavy chain locus further comprises a rodent intronic enhancer ($E_i$).

In exemplary embodiment 59, provided herein is the rodent of any one of embodiments 1 to 57, wherein the engineered immunoglobulin heavy chain locus further comprises a human intronic enhancer ($E_i$).

In exemplary embodiment 60, provided herein is the rodent of any one of embodiments 1 to 59, wherein the engineered immunoglobulin heavy chain locus further comprises a rodent 3' regulatory region (3' RR).

In exemplary embodiment 61, provided herein is the rodent of any one of embodiments 1 to 5, wherein the engineered immunoglobulin heavy chain locus further comprises a human 3' regulatory region (3' RR).

In exemplary embodiment 62, provided herein is the rodent of any one of embodiments 1 to 61, wherein the engineered immunoglobulin heavy chain locus further comprises a rodent $S_\mu$ switch site.

In exemplary embodiment 63, provided herein is the rodent of any one of embodiments 1 to 62, wherein the engineered immunoglobulin heavy chain locus further comprises a rodent $S_{\gamma 3}$ switch site.

In exemplary embodiment 64, provided herein is the rodent of any one of embodiments 1 to 63, wherein the engineered immunoglobulin heavy chain locus further comprises a rodent $S_{\gamma 1}$ switch site.

In exemplary embodiment 65, provided herein is the rodent of any one of embodiments 1 to 64, wherein the engineered immunoglobulin heavy chain locus further comprises a rodent $S_{\gamma 2b}$ switch site.

In exemplary embodiment 66, provided herein is the rodent of any one of embodiments 1 to 65, wherein the engineered immunoglobulin heavy chain locus further comprises a rodent $S_{\gamma 2a}$ and/or $S_{\gamma 2b}$ switch site.

In exemplary embodiment 67, provided herein is the rodent of any one of embodiments 1 to 66, wherein the engineered immunoglobulin heavy chain locus further comprises a rodent $S_\varepsilon$ switch site.

In exemplary embodiment 68, provided herein is the rodent of any one of embodiments 1 to 67, wherein the engineered immunoglobulin heavy chain locus further comprises a rodent $S_\alpha$ switch site.

In exemplary embodiment 69, provided herein is the rodent of any one of embodiments 1 to 61, wherein the engineered immunoglobulin heavy chain locus further comprises a human $S_\mu$ switch site.

In exemplary embodiment 70, provided herein is the rodent of any one of embodiments 1 to 61 and 69, wherein the engineered immunoglobulin heavy chain locus further comprises a human $S_{\gamma 3}$ switch site.

In exemplary embodiment 71, provided herein is the rodent of any one of embodiments 1 to 61 and 69-70, wherein the engineered immunoglobulin heavy chain locus further comprises a human $S_{\gamma 1}$ switch site.

In exemplary embodiment 72, provided herein is the rodent of any one of embodiments 1 to 61 and 69-71, wherein the engineered immunoglobulin heavy chain locus further comprises a human $S_{\gamma 2}$ switch site.

In exemplary embodiment 73, provided herein is the rodent of any one of embodiments 1 to 61 and 69-72, wherein the engineered immunoglobulin heavy chain locus further comprises a human $S_{\gamma 4}$ switch site.

In exemplary embodiment 74, provided herein is the rodent of any one of embodiments 1 to 61 and 69-73, wherein the engineered immunoglobulin heavy chain locus further comprises a human $S_\varepsilon$ switch site.

In exemplary embodiment 75, provided herein is the rodent of any one of embodiments 1 to 61 and 69-74, wherein the engineered immunoglobulin heavy chain locus further comprises a human $S_\alpha$ switch site.

In exemplary embodiment 76, provided herein is the rodent of any one of embodiments 1 to 75, wherein the $V_H$ gene segment is a rodent $V_H$ gene segment, the $D_H$ gene segment is a rodent $D_H$ gene segment and the $J_H$ gene segment is a rodent $J_H$ gene segment.

In exemplary embodiment 77, provided herein is the rodent of embodiment 76, wherein the rodent $V_H$ gene segment, the rodent $D_H$ gene segment and the rodent $J_H$ gene segment are endogenous rodent gene segments.

In exemplary embodiment 78, provided herein is the rodent of any one of embodiments 1 to 75, wherein the $V_H$ gene segment is a human $V_H$ gene segment, the $D_H$ gene segment is a human $D_H$ gene segment and the $J_H$ gene segment is a human $J_H$ gene segment.

In exemplary embodiment 79, provided herein is the rodent of embodiment 78, wherein the immunoglobulin heavy chain variable region comprises at least 3 human $V_H$ gene segments.

In exemplary embodiment 80, provided herein is the rodent of embodiment 78 or embodiment 79, wherein the immunoglobulin heavy chain variable region comprises all of the human $D_H$ gene segments.

In exemplary embodiment 81, provided herein is the rodent of any one of embodiments 78 to 80, wherein the immunoglobulin heavy chain variable region comprises all of the human $J_H$ gene segments.

In exemplary embodiment 82, provided herein is the rodent of any one of embodiments 78 to 81, wherein the immunoglobulin heavy chain variable region lacks a functional endogenous rodent Adam6 gene.

In exemplary embodiment 83, provided herein is the rodent of any one of embodiments 78 to 82, wherein the germline genome further comprises a nucleotide sequence encoding a functional rodent Adam6 polypeptide, a functional ortholog, a functional homolog, or a functional fragment thereof.

In exemplary embodiment 84, provided herein is the rodent of embodiment 83, wherein the functional rodent Adam6 polypeptide, the functional ortholog, the functional homolog, or the functional fragment thereof is expressed.

In exemplary embodiment 85, provided herein is the rodent of embodiment 83 or embodiment 84, wherein the nucleotide sequence encoding the rodent ADAM6 polypeptide, the functional ortholog, the functional homolog, or the functional fragment thereof is included on the same chromosome as the immunoglobulin heavy chain variable region.

In exemplary embodiment 86, provided herein is the rodent of any one of embodiments 83 to 85, wherein the nucleotide sequence encoding the rodent ADAM6 polypeptide, the functional ortholog, the functional homolog, or the functional fragment thereof is included in the engineered immunoglobulin heavy chain locus.

In exemplary embodiment 87, provided herein is the rodent of any one of embodiments 83 to 86, wherein the nucleotide sequence encoding the rodent ADAM6 polypeptides, the functional ortholog, the functional homolog, or the functional fragment thereof is in place of a human Adam6 pseudogene.

In exemplary embodiment 88, provided herein is the rodent of any one of embodiments 83 to 87, wherein the nucleotide sequence encoding the rodent ADAM6 polypeptide, the functional ortholog, the functional homolog, or the functional fragment thereof replaces a human Adam6 pseudogene.

In exemplary embodiment 89, provided herein is the rodent of any one of embodiments 83 to 88, wherein the nucleotide sequence encoding the rodent ADAM6 polypeptide, the functional ortholog, the functional homolog, or the functional fragment thereof is between a first human $V_H$ gene segment and a second human $V_H$ gene segment.

In exemplary embodiment 90, provided herein is the rodent of embodiment 89, wherein the first human $V_H$ gene segment is $V_H1$-2 and the second human $V_H$ gene segment is $V_H6$-1.

In exemplary embodiment 91, provided herein is the rodent of any one of embodiments 83 to 86, wherein the nucleotide sequence encoding the rodent ADAM6 polypeptides, the functional ortholog, the functional homolog, or the functional fragment thereof is between a human $V_H$ gene segment and a human $D_H$ gene segment.

In exemplary embodiment 92, provided herein is the rodent of any one of embodiments 1 to 91, wherein the engineered immunoglobulin heavy chain locus is positioned at an endogenous immunoglobulin heavy chain locus.

In exemplary embodiment 93, provided herein is the rodent of embodiment 92, wherein the engineered immunoglobulin heavy chain locus replaces all or part of the endogenous immunoglobulin heavy chain locus.

In exemplary embodiment 94, provided herein is the rodent of any one of embodiments 1 to 93, wherein the rodent is heterozygous for the engineered immunoglobulin heavy chain locus.

In exemplary embodiment 95, provided herein is the rodent of any one of embodiments 1 to 93, wherein the rodent is homozygous for the engineered immunoglobulin heavy chain locus.

In exemplary embodiment 96, provided herein is a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a rodent $C_{\gamma 1}$ gene segment; (e) a rodent $C_{\gamma 2b}$ gene segment; (f) a modified $C_H$ gene segment encoding a human IgG1 $C_H1$ domain, a human IgG1 hinge region, a human IgG1 $C_H2$ domain, a human IgG1 $C_H3$ domain, a rodent IgG2a transmembrane domain, and a rodent IgG2a cytoplasmic domain;(g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 97, provided herein is a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a rodent $C_{\gamma 1}$ gene segment; (e) a rodent $C_{\gamma 2b}$ gene segment; (f) a modified $C_H$ gene segment encoding a human IgG1 $C_H1$ domain, a human IgG1 hinge region, a human IgG1 $C_H2$ domain, a human IgG1 $C_H3$ domain, a human IgG1 transmembrane domain, and a human IgG1 cytoplasmic domain; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 98, provided herein is a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a rodent IgG1 transmembrane domain, and a rodent IgG1 cytoplasmic domain; (e) a rodent $C_{\gamma 2b}$ gene segment; (f) a rodent $C_{\gamma 2a}$ and/or $C_{\gamma 2c}$ gene segment; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 99, provided herein is a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a human IgG4 transmembrane domain, and a human IgG4 cytoplasmic domain; (e) a rodent $C_{\gamma2b}$ gene segment; (f) a rodent $C_{\gamma2a}$ and/or $C_{\gamma2c}$ gene segment; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 100, provided herein is a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma3}$ gene segment; (d) a human $C_{\gamma1}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a fully human heavy chain.

In exemplary embodiment 101, provided herein is a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma3}$ gene segment; (d) a human $C_{\gamma1}$ gene segment; (c) a human $C_{\gamma2}$ gene segment; (d) a human $C_{\gamma4}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a fully human heavy chain.

In exemplary embodiment 102, provided herein is a rodent comprising in its genome: an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a human $C_\delta$ gene segment; (c) a human $C_{\gamma3}$ gene segment; (d) a human $C_{\gamma1}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a heavy chain comprising a rodent variable domain and a human constant domain.

In exemplary embodiment 103, provided herein is a rodent comprising in its genome: an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a human $C_\delta$ gene segment; (c) a human $C_{\gamma3}$ gene segment; (d) a human $C_{\gamma1}$ gene segment; (c) a human $C_2$ gene segment; (d) a human $C_{\gamma4}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a heavy chain comprising a rodent variable domain and a human constant domain.

In exemplary embodiment 104, provided herein is the rodent of any one of embodiments 96 to 103, wherein the engineered immunoglobulin heavy chain locus is positioned at an endogenous immunoglobulin heavy chain locus.

In exemplary embodiment 105, provided herein is the rodent of embodiment 104, wherein the engineered immunoglobulin heavy chain locus replaces all or part of the endogenous immunoglobulin heavy chain locus.

In exemplary embodiment 106, provided herein is the rodent of any one of embodiments 96 to 105, wherein the rodent is heterozygous for the engineered immunoglobulin heavy chain locus.

In exemplary embodiment 107, provided herein is the rodent of any one of embodiments 96 to 105, wherein the rodent is homozygous for the engineered immunoglobulin heavy chain locus.

In exemplary embodiment 108, provided herein is the rodent of any one of embodiments 1 to 107 further comprising in its genome: an engineered immunoglobulin kappa (κ) chain locus that comprises: (1) an immunoglobulin κ chain variable region comprising a human $V_\kappa$ gene segment and a human $J_\kappa$ gene segment; and (2) an immunoglobulin κ chain constant region comprising a human $C_\kappa$ gene segment, wherein the immunoglobulin κ chain variable region is operably linked to the immunoglobulin κ chain constant region such that the rodent produces antibodies comprising light chain variable domains derived from the human $V_\kappa$ gene segment and the human $J_\kappa$ gene segment and light chain constant domains derived from the human $C_\kappa$ gene segment.

In exemplary embodiment 109, provided herein is the rodent of embodiment 108, wherein the engineered immunoglobulin κ chain locus further comprises a rodent intronic κ enhancer ($E_{\kappa i}$).

In exemplary embodiment 110, provided herein is the rodent of embodiment 108, wherein the engineered immunoglobulin κ chain locus further comprises a human intronic κ enhancer ($E_{\kappa i}$).

In exemplary embodiment 111, provided herein is the rodent of any one of embodiments 108 to 110, wherein the engineered immunoglobulin κ chain locus further comprises a rodent 3' κ enhancer ($E_{\kappa 3'}$).

In exemplary embodiment 112, provided herein is the rodent of any one of embodiments 108 to 110, wherein the engineered immunoglobulin κ chain locus further comprises a human 3' κ enhancer ($E_{\kappa 3'}$).

In exemplary embodiment 113, provided herein is the rodent of any one of embodiments 108 to 112, wherein the immunoglobulin κ chain variable region comprises at least 6 human $V_\kappa$ gene segments.

In exemplary embodiment 114, provided herein is the rodent of any one of embodiments 108 to 113, wherein the immunoglobulin κ chain variable region comprises all of the human $J_\kappa$ gene segments.

In exemplary embodiment 115, provided herein is the rodent of any one of embodiments 108 to 114, wherein the engineered immunoglobulin κ chain locus is positioned at an endogenous immunoglobulin κ chain locus.

In exemplary embodiment 116, provided herein is the rodent of embodiment 115, wherein the engineered immunoglobulin κ chain locus replaces all or part of the endogenous immunoglobulin κ chain locus.

In exemplary embodiment 117, provided herein is the rodent of any one of embodiments 108 to 116, wherein the rodent is heterozygous for the engineered immunoglobulin κ chain locus.

In exemplary embodiment 118, provided herein is the rodent of any one of embodiments 108 to 116, wherein the rodent is homozygous for the engineered immunoglobulin κ chain locus.

In exemplary embodiment 119, provided herein is the rodent of any one of embodiments 1 to 118 further comprising in its genome: an engineered immunoglobulin lambda (λ) chain locus that comprises: a human $V_\lambda$ gene segment, a human $J_\lambda$ gene segment and a human $C_\lambda$ gene segment, wherein the human $V_\lambda$ gene segment and the human $J_\lambda$ gene segment are operably linked to the human $C_\lambda$ gene segment such that the rodent produces antibodies comprising light chain variable domains derived from the human $V_\lambda$ gene segment and the human $J_\lambda$ gene segment and light chain constant domains derived from the human $C_\lambda$ gene segment.

In exemplary embodiment 120, provided herein is the rodent of embodiment 119, wherein the human $C_\lambda$ gene segment is a human $C_{\lambda 1}$ gene segment.

In exemplary embodiment 121, provided herein is the rodent of embodiment 120, wherein the human $J_\lambda$ gene segment is a human $J_{\lambda 1}$ gene segment.

In exemplary embodiment 122, provided herein is the rodent of embodiment 119, wherein the human $C_\lambda$ gene segment is a human $C_{\lambda 2}$ gene segment.

In exemplary embodiment 123, provided herein is the rodent of embodiment 122, wherein the human $J_\lambda$ gene segment is a human $J_{\lambda 2}$ gene segment.

In exemplary embodiment 124, provided herein is the rodent of embodiment 119, wherein the human $C_\lambda$ gene segment is a human $C_{\lambda 3}$ gene segment.

In exemplary embodiment 125, provided herein is the rodent of embodiment 124, wherein the human $J_\lambda$ gene segment is a human $J_{\lambda 3}$ gene segment.

In exemplary embodiment 126, provided herein is the rodent of embodiment 119, wherein the human $C_\lambda$ gene segment is a human $C_{\lambda 6}$ gene segment.

In exemplary embodiment 127, provided herein is the rodent of embodiment 126, wherein the human $J_\lambda$ gene segment is a human $J_{\lambda 6}$ gene segment.

In exemplary embodiment 128, provided herein is the rodent of embodiment 119, wherein the human $J_\lambda$ gene segment is a human $J_{\lambda 7}$ gene segment.

In exemplary embodiment 129, provided herein is the rodent of any one of embodiments 119 to 128, wherein the engineered immunoglobulin λ chain locus comprises a human $C_{\lambda 1}$ gene segment, a human $C_{\lambda 2}$ gene segment, a human $C_{\lambda 3}$ gene segment, a human $C_{\lambda 6}$ gene segment and a rodent $C_{\lambda 1}$ gene segment.

In exemplary embodiment 130, provided herein is the rodent of embodiment 129, wherein the engineered immunoglobulin λ chain locus comprises a human $J_{\lambda 1}$ gene segment, a human $J_{\lambda 2}$ gene segment, a human $J_{\lambda 3}$ gene segment, a human $J_{\lambda 6}$ gene segment and a human $J_{\lambda 7}$ gene segment.

In exemplary embodiment 131, provided herein is the rodent ES cell of embodiment 130, wherein the engineered immunoglobulin λ chain locus comprises a human $J_{\lambda 1}$-$C_{\lambda 1}$ gene segment cluster, a human $J_{\lambda 2}$-$C_{\lambda 2}$ gene segment cluster, a human $J_{\lambda 3}$-$C_{\lambda 3}$ gene segment cluster, a human $J_{\lambda 6}$-$C_{\lambda 6}$ gene segment cluster and a human $J_{\lambda 7}$-rodent $C_{\lambda 1}$ gene segment cluster.

In exemplary embodiment 132, provided herein is the rodent of any one of embodiments 119 to 131, wherein the engineered immunoglobulin λ chain locus comprises at least 7 human $V_\lambda$ gene segments.

In exemplary embodiment 133, provided herein is the rodent of any one of embodiments 119 to 132, wherein the engineered immunoglobulin λ chain locus further comprises a rodent λ enhancer 2.4.

In exemplary embodiment 134, provided herein is the rodent of any one of embodiments 119 to 133, wherein the engineered immunoglobulin λ chain locus further comprises a rodent 3'λ enhancer.

In exemplary embodiment 135, provided herein is the rodent of any one of embodiments 119 to 134, wherein the engineered immunoglobulin λ chain locus further comprises a rodent λ enhancer 3.1.

In exemplary embodiment 136, provided herein is the rodent of any one of embodiments 119 to 135, wherein the engineered immunoglobulin λ chain locus further comprises a human 3'λ enhancer.

In exemplary embodiment 137, provided herein is the rodent of any one of embodiments 119 to 136, wherein the engineered immunoglobulin λ chain locus is positioned at an endogenous immunoglobulin λ chain locus.

In exemplary embodiment 138, provided herein is the rodent of embodiment 137, wherein the engineered immunoglobulin λ chain locus replaces all or part of the endogenous immunoglobulin λ chain locus.

In exemplary embodiment 139, provided herein is the rodent of any one of embodiments 119 to 138, wherein the rodent is heterozygous for the engineered immunoglobulin λ chain locus.

In exemplary embodiment 140, provided herein is the rodent of any one of embodiments 119 to 138, wherein the rodent is homozygous for the engineered immunoglobulin λ chain locus.

In exemplary embodiment 141, provided herein is the rodent of any one of embodiments 1 to 140, further comprising in its genome an engineered neonatal Fc receptor (FcRn) locus comprising a nucleic acid sequence encoding an FcRn polypeptide comprising a human extracellular domain.

In exemplary embodiment 142, provided herein is the rodent of embodiment 141, wherein the FcRn polypeptide further comprises a rodent transmembrane domain.

In exemplary embodiment 143, provided herein is the rodent of embodiment 141, wherein the FcRn polypeptide further comprises a human transmembrane domain.

In exemplary embodiment 144, provided herein is the rodent of any one of embodiments 141 to 143, wherein the FcRn polypeptide further comprises a rodent cytoplasmic domain.

In exemplary embodiment 145, provided herein is the rodent of any one of embodiments 141 to 143, wherein the FcRn polypeptide further comprises a human cytoplasmic domain.

In exemplary embodiment 146, provided herein is the rodent of any one of embodiment 141 to 145, wherein the nucleic acid sequence encoding the FcRn polypeptide is positioned at an endogenous rodent FcRn locus.

In exemplary embodiment 147, provided herein is the rodent of embodiment 146, wherein the nucleic acid sequence encoding the FcRn polypeptide replaces all or part of an endogenous rodent FcRn gene.

In exemplary embodiment 148, provided herein is the rodent of embodiment 141, wherein the nucleic acid sequence encoding the FcRn extracellular domain replaces an endogenous nucleic acid sequence encoding a rodent FcRn extracellular domain.

In exemplary embodiment 149, provided herein is the rodent of any one of embodiments 141 to 148, wherein the rodent does not express a rodent FcRn.

In exemplary embodiment 150, provided herein is the rodent of any one of embodiments 141 to 149, wherein the rodent is heterozygous for the engineered FcRn locus.

In exemplary embodiment 151, provided herein is the rodent of any one of embodiments 141 to 149, wherein the rodent is homozygous for the engineered FcRn locus.

In exemplary embodiment 152, provided herein is the rodent of any one of embodiments 141 to 151, further comprising in its genome an engineered β-2-microglobulin (β2M) locus comprising a nucleic acid sequence encoding a human or humanized β-2-microglobulin (β2M) polypeptide.

In exemplary embodiment 153, provided herein is the rodent of embodiment 152, wherein the nucleic acid sequence encoding a human or humanized β2M polypeptide is positioned at an endogenous rodent β2M locus.

In exemplary embodiment 154, provided herein is the rodent of embodiment 153, wherein the nucleic acid sequence encoding a human or humanized β2M polypeptide replaces all or part of the endogenous rodent β2M gene.

In exemplary embodiment 155, provided herein is the rodent of any one of embodiments 152 to 154, wherein the nucleic acid sequence comprises exons 2-4 of a human β2M gene.

In exemplary embodiment 156, provided herein is the rodent of any one of embodiments 152 to 155, wherein the rodent does not express a rodent β2M polypeptide.

In exemplary embodiment 157, provided herein is the rodent of any one of embodiments 152 to 156, wherein the rodent is heterozygous for the engineered β2M locus.

In exemplary embodiment 158, provided herein is the rodent of any one of embodiments 152 to 156, wherein the rodent is homozygous for the engineered β2M locus.

In exemplary embodiment 159, provided herein is the rodent of any one of embodiments 1 to 158, further comprising in its genome an engineered Fc epsilon receptor 1 alpha (FcεR1α) locus comprising a nucleic acid sequence encoding an FcεR1α polypeptide comprising a human extracellular domain.

In exemplary embodiment 160, provided herein is the rodent of embodiment 159, wherein the FcεR1α polypeptide further comprises a rodent transmembrane domain.

In exemplary embodiment 161, provided herein is the rodent of embodiment 159, wherein the FcεR1α polypeptide further comprises a human transmembrane domain.

In exemplary embodiment 162, provided herein is the rodent of any one of embodiments 159 to 161, wherein the FcεR1α polypeptide further comprises a rodent cytoplasmic domain.

In exemplary embodiment 163, provided herein is the rodent of any one of embodiments 159 to 161, wherein the FcεR1α polypeptide further comprises a human cytoplasmic domain.

In exemplary embodiment 164, provided herein is the rodent of any one of embodiment 159 to 163, wherein the nucleic acid sequence encoding the FcεR1α polypeptide is positioned at an endogenous rodent FcεR1α locus.

In exemplary embodiment 165, provided herein is the rodent of embodiment 164, wherein the nucleic acid sequence encoding the FcεR1α polypeptide replaces all or part of an endogenous rodent FcεR1α gene.

In exemplary embodiment 166, provided herein is the rodent of embodiment 165, wherein the FcεR1α polypeptide comprises a human extracellular domain, a human transmembrane domain and a human cytoplasmic domain.

In exemplary embodiment 167, provided herein is the rodent of embodiment 159, wherein the nucleic acid sequence encoding the human FcεR1α extracellular domain replaces an endogenous nucleic acid sequence encoding a rodent FcεR1α extracellular domain.

In exemplary embodiment 168, provided herein is the rodent of any one of embodiments 159 to 167, wherein the rodent does not express a rodent FcεR1α.

In exemplary embodiment 169, provided herein is the rodent of any one of embodiments 159 to 168, wherein the rodent is heterozygous for the engineered FcεR1α locus.

In exemplary embodiment 170, provided herein is the rodent of any one of embodiments 159 to 168, wherein the rodent is homozygous for the engineered FcεR1α locus.

In exemplary embodiment 171, provided herein is the rodent of any one of embodiments 1 to 170, further comprising in its genome an engineered Fc gamma receptor 1a (FcγR1a) locus comprising a nucleic acid sequence encoding an FcγR1a polypeptide comprising a human extracellular domain.

In exemplary embodiment 172, provided herein is the rodent of embodiment 171, wherein the FcγR1a polypeptide further comprises a rodent transmembrane domain.

In exemplary embodiment 173, provided herein is the rodent of embodiment 171, wherein the FcγR1a polypeptide further comprises a human transmembrane domain.

In exemplary embodiment 174, provided herein is the rodent of any one of embodiments 171 to 173, wherein the FcγR1a polypeptide further comprises a rodent cytoplasmic domain.

In exemplary embodiment 175, provided herein is the rodent of any one of embodiments 171 to 173, wherein the FcγR1a polypeptide further comprises a human cytoplasmic domain.

In exemplary embodiment 176, provided herein is the rodent of any one of embodiment 171 to 175, wherein the nucleic acid sequence encoding the FcγR1a polypeptide is positioned at an endogenous rodent FcγR1a locus.

In exemplary embodiment 177, provided herein is the rodent of embodiment 176, wherein the nucleic acid sequence encoding the FcγR1a polypeptide replaces all or part of an endogenous rodent FcγR1a gene.

In exemplary embodiment 178, provided herein is the rodent of embodiment 171, wherein the nucleic acid sequence encoding the human FcγR1a extracellular domain replaces an endogenous nucleic acid sequence encoding a rodent FcγR1a extracellular domain.

In exemplary embodiment 179, provided herein is the rodent of any one of embodiments 171 to 178, wherein the rodent does not express a rodent FcγR1a.

In exemplary embodiment 180, provided herein is the rodent of any one of embodiments 171 to 179, wherein the rodent is heterozygous for the engineered FcγR1a locus.

In exemplary embodiment 181, provided herein is the rodent of any one of embodiments 171 to 179, wherein the rodent is homozygous for the engineered FcγR1a locus.

In exemplary embodiment 182, provided herein is the rodent of any one of embodiments 1 to 181, further comprising in its genome an engineered Fc gamma receptor 2a (FcγR2a) locus comprising a nucleic acid sequence encoding a human FcγR2a polypeptide.

In exemplary embodiment 183, provided herein is the rodent embodiment 182, wherein the nucleic acid sequence encoding the FcγR2a polypeptide is positioned at an endogenous rodent low affinity FcγR locus.

In exemplary embodiment 184, provided herein is the rodent of embodiment 183, wherein the nucleic acid sequence encoding the human FcγR2a polypeptide replaces all or part of an endogenous rodent low affinity FcγR gene.

In exemplary embodiment 185, provided herein is the rodent of any one of embodiments 182 to 184, wherein the rodent is heterozygous for the engineered FcγR2a locus.

In exemplary embodiment 186, provided herein is the rodent of any one of embodiments 182 to 184, wherein the rodent is homozygous for the engineered FcγR2a locus.

In exemplary embodiment 187, provided herein is the rodent of any one of embodiments 1 to 186, further comprising in its genome an engineered Fc gamma receptor 2b (FcγR2b) locus comprising a nucleic acid sequence encoding a human FcγR2b polypeptide.

In exemplary embodiment 188, provided herein is the rodent embodiment 187, wherein the nucleic acid sequence encoding the FcγR2b polypeptide is positioned at an endogenous rodent low affinity FcγR locus.

In exemplary embodiment 189, provided herein is the rodent of embodiment 188, wherein the nucleic acid sequence encoding the human FcγR2b polypeptide replaces all or part of endogenous rodent low affinity FcγR gene.

In exemplary embodiment 190, provided herein is the rodent of any one of embodiments 187 to 189, wherein the rodent is heterozygous for the engineered FcγR2b locus.

In exemplary embodiment 191, provided herein is the rodent of any one of embodiments 187 to 189, wherein the rodent is homozygous for the engineered FcγR2b locus.

In exemplary embodiment 192, provided herein is the rodent of any one of embodiments 1 to 191, further comprising in its genome an engineered Fc gamma receptor 3a (FcγR3a) locus comprising a nucleic acid sequence encoding a human FcγR3a polypeptide.

In exemplary embodiment 193, provided herein is the rodent embodiment 192, wherein the nucleic acid sequence encoding the FcγR3a polypeptide is positioned at an endogenous rodent low affinity FcγR locus.

In exemplary embodiment 194, provided herein is the rodent of embodiment 193, wherein the nucleic acid sequence encoding the human FcγR3a polypeptide replaces all or part of endogenous rodent low affinity FcγR gene.

In exemplary embodiment 195, provided herein is the rodent of any one of embodiments 192 to 194, wherein the rodent is heterozygous for the engineered FcγR3a locus.

In exemplary embodiment 196, provided herein is the rodent of any one of embodiments 192 to 194, wherein the rodent is homozygous for the engineered FcγR3a locus.

In exemplary embodiment 197, provided herein is the rodent of any one of embodiments 1 to 196, further comprising in its genome an engineered Fc gamma receptor 3b (FcγR3b) locus comprising a nucleic acid sequence encoding a human FcγR3b polypeptide.

In exemplary embodiment 198, provided herein is the rodent of embodiment 197, wherein the nucleic acid sequence encoding the FcγR3b polypeptide is positioned at an endogenous rodent low affinity FcγR locus.

In exemplary embodiment 199, provided herein is the rodent of embodiment 197, wherein the nucleic acid sequence encoding the human FcγR3b polypeptide replaces all or part of endogenous rodent low affinity FcγR gene.

In exemplary embodiment 200, provided herein is the rodent of any one of embodiments 197 to 199, wherein the rodent is heterozygous for the engineered FcγR3b locus.

In exemplary embodiment 201, provided herein is the rodent of any one of embodiments 197 to 199, wherein the rodent is homozygous for the engineered FcγR3b locus.

In exemplary embodiment 202, provided herein is the rodent of any one of embodiments 1 to 201, further comprising in its genome an engineered Fc gamma receptor 2c (FcγR2c) locus comprising a nucleic acid sequence encoding a human FcγR2c polypeptide.

In exemplary embodiment 203, provided herein is the rodent of embodiment 202, wherein the nucleic acid sequence encoding the FcγR2c polypeptide is positioned at an endogenous rodent low affinity FcγR locus.

In exemplary embodiment 204, provided herein is the rodent of embodiment 203, wherein the nucleic acid sequence encoding the human FcγR2c polypeptide replaces all or part of endogenous rodent low affinity FcγR gene.

In exemplary embodiment 205, provided herein is the rodent of any one of embodiments 202 to 204, wherein the rodent does not express a rodent FcγR2c.

In exemplary embodiment 206, provided herein is the rodent of any one of embodiments 202 to 205, wherein the rodent is heterozygous for the engineered FcγR2c locus.

In exemplary embodiment 207, provided herein is the rodent of any one of embodiments 202 to 205, wherein the rodent is homozygous for the engineered FcγR2c locus.

In exemplary embodiment 208, provided herein is a rodent comprising in its genome an engineered neonatal Fc receptor (FcRn) locus comprising a nucleic acid sequence encoding a FcRn polypeptide comprising a human extracellular domain.

In exemplary embodiment 209, provided herein is the rodent of embodiment 208, wherein the FcRn polypeptide further comprises a rodent transmembrane domain.

In exemplary embodiment 210, provided herein is the rodent of embodiment 208, wherein the FcRn polypeptide further comprises a human transmembrane domain.

In exemplary embodiment 211, provided herein is the rodent of any one of embodiments 208 to 210, wherein the FcRn polypeptide further comprises a rodent cytoplasmic domain.

In exemplary embodiment 212, provided herein is the rodent of any one of embodiments 208 to 210, wherein the FcRn polypeptide further comprises a human cytoplasmic domain.

In exemplary embodiment 213, provided herein is the rodent of any one of embodiment 208 to 212, wherein the nucleic acid sequence encoding the FcRn polypeptide is positioned at an endogenous rodent FcRn locus.

In exemplary embodiment 214, provided herein is the rodent of embodiment 213, wherein the nucleic acid sequence encoding the FcRn polypeptide replaces all or part of an endogenous rodent FcRn gene.

In exemplary embodiment 215, provided herein is the rodent of embodiment 208, wherein the nucleic acid sequence encoding the human FcRn extracellular domain replaces an endogenous nucleic acid sequence encoding a rodent FcRn extracellular domain.

In exemplary embodiment 216, provided herein is the rodent of any one of embodiments 208 to 215, wherein the rodent does not express a rodent FcRn.

In exemplary embodiment 217, provided herein is the rodent of any one of embodiments 208 to 216, wherein the rodent is heterozygous for the engineered FcRn locus.

In exemplary embodiment 218, provided herein is the rodent of any one of embodiments 208 to 216, wherein the rodent is homozygous for the engineered FcRn locus.

In exemplary embodiment 219, provided herein is the rodent of any one of embodiments 208 to 218, further comprising in its genome β-2-microglobulin (β2M) locus comprising a nucleic acid sequence encoding a human or humanized β-2-microglobulin (β2M) polypeptide.

In exemplary embodiment 220, provided herein is the rodent of embodiment 219, wherein the nucleic acid sequence encoding a human or humanized β2M polypeptide is positioned at an endogenous rodent β2M locus.

In exemplary embodiment 221, provided herein is the rodent of embodiment 220, wherein the nucleic acid sequence encoding a human or humanized β2M polypeptide replaces all or part of the endogenous rodent β2M gene.

In exemplary embodiment 222, provided herein is the rodent of any one of embodiments 219 to 221, wherein the nucleic acid sequence comprises exons 2-4 of a human β2M gene.

In exemplary embodiment 223, provided herein is the rodent of any one of embodiments 219 to 222, wherein the rodent does not express a rodent β2M polypeptide.

In exemplary embodiment 224, provided herein is the rodent of any one of embodiments 219 to 223, wherein the rodent is heterozygous for the engineered β2M locus.

In exemplary embodiment 225, provided herein is the rodent of any one of embodiments 219 to 223, wherein the rodent is homozygous for the engineered β2M locus.

In exemplary embodiment 226, provided herein is a rodent comprising in its genome an engineered Fc epsilon receptor 1 alpha (FcεR1α) locus comprising a nucleic acid sequence encoding an FcεR1α polypeptide comprising a human extracellular domain.

In exemplary embodiment 227, provided herein is the rodent of embodiment 226, wherein the FcεR1α polypeptide further comprises a rodent transmembrane domain.

In exemplary embodiment 228, provided herein is the rodent of embodiment 226, wherein the FcεR1α polypeptide further comprises a human transmembrane domain.

In exemplary embodiment 229, provided herein is the rodent of any one of embodiments 226 to 228 wherein the FcεR1α polypeptide further comprises a rodent cytoplasmic domain.

In exemplary embodiment 230, provided herein is the rodent of any one of embodiments 226 to 228, wherein the FcεR1α polypeptide further comprises a human cytoplasmic domain.

In exemplary embodiment 231, provided herein is the rodent of any one of embodiment 226 to 230, wherein the nucleic acid sequence encoding the FcεR1α polypeptide is positioned at an endogenous rodent FcεR1α locus.

In exemplary embodiment 232, provided herein is the rodent of embodiment 231, wherein the nucleic acid sequence encoding the FcεR1α polypeptide replaces all or part of an endogenous rodent FcεR1α gene.

In exemplary embodiment 233, provided herein is the rodent of embodiment 232, wherein the FcεR1α polypeptide comprises a human extracellular domain, a human transmembrane domain and a human cytoplasmic domain.

In exemplary embodiment 234, provided herein is the rodent of embodiment 226, wherein the nucleic acid sequence encoding the human FcεR1α extracellular domain replaces an endogenous nucleic acid sequence encoding a rodent FcεR1α extracellular domain.

In exemplary embodiment 235, provided herein is the rodent of any one of embodiments 226 to 234, wherein the rodent does not express a rodent FcεR1α.

In exemplary embodiment 236, provided herein is the rodent of any one of embodiments 226 to 235, wherein the rodent is heterozygous for the engineered FcεR1α locus.

In exemplary embodiment 237, provided herein is the rodent of any one of embodiments 226 to 235, wherein the rodent is homozygous for the engineered FcεR1α locus.

In exemplary embodiment 238, provided herein is the rodent of any one of embodiments 1 to 237, wherein the rodent is a mouse.

In exemplary embodiment 239, provided herein is the rodent of any one of embodiments 1 to 237, wherein the rodent is a rat.

In exemplary embodiment 240, provided herein is a method of testing a therapeutic protein comprising a human Fc domain, the method comprising administering the therapeutic protein to a rodent of any one of embodiments 1 to 207 and measuring one or more pharmacokinetic properties of the administered therapeutic protein.

In exemplary embodiment 241, provided herein is the method of embodiment 240, wherein the one or more pharmacokinetic properties are selected from one or more of area under the plasma concentration versus time (AUC), in vivo recovery (IVR), clearance rate (CL), mean residence time (MRT), agent half-life (t½), and volume of distribution at steady state (Vss).

In exemplary embodiment 242, provided herein is a method of testing the therapeutic efficacy of a therapeutic protein comprising a human Fc domain, the method comprising administering the therapeutic protein to a rodent of any one of embodiments 1 to 207 and measuring the therapeutic efficacy of the administered therapeutic protein.

In exemplary embodiment 243, provided herein is a method of determining a therapeutically effective dose of a therapeutic protein comprising a human Fc domain, the method comprising administering a plurality of doses of the therapeutic protein to a rodent of any one of embodiments 1 to 207 and determining a therapeutic efficacy of each dose of the therapeutic protein.

In exemplary embodiment 244, provided herein is a method of determining a safe dose of a therapeutic protein comprising a human Fc domain, the method comprising administering a plurality of doses of the therapeutic protein to a rodent of any one of embodiments 1 to 207 and determining the safety of each dose of the therapeutic protein.

In exemplary embodiment 245, provided herein is a method of determining a tolerable dose of a therapeutic protein comprising a human Fc domain, the method comprising administering a plurality of doses of the therapeutic protein to a rodent of any one of embodiments 1 to 207 and determining the tolerability of each dose of the therapeutic protein.

In exemplary embodiment 246, provided herein is a method of testing a therapeutic protein comprising a human Fc domain, the method comprising administering the therapeutic protein to a rodent of any one of embodiments 148 to 239 and measuring one or more Fc receptor mediated responses in the rodent.

In exemplary embodiment 247, provided herein is the method of embodiment 246, wherein the one or more Fc receptor mediated responses comprise an ADCC response.

In exemplary embodiment 248, provided herein is a method of screening a therapeutic agent comprising a human Fc region of a human antibody comprising: (a) administering an agent comprising an Fc region of a human antibody to a rodent of any one of embodiments 148 to 239, wherein the agent binds to a target cell in the mouse; (b) measuring antibody-dependent cell-mediated cytotoxicity (ADCC) of natural killer (NK) cells against the target cell; and (c) comparing the amount of ADCC in step (b) to a control, wherein increased target cell killing indicates the agent has increased ability to mediate ADCC.

In exemplary embodiment 249, provided herein is a method of measuring an immune response generated by a rodent against a therapeutic protein comprising a human Fc domain, the method comprising administering the therapeutic protein to a rodent of any one of embodiments 1 to 207 and measuring the immune response generated by a rodent against a therapeutic protein.

In exemplary embodiment 250, provided herein is the method of any one of embodiments 240 to 249, wherein the therapeutic protein is a human antibody.

In exemplary embodiment 251, provided herein is the method of any one of embodiments 240 to 249, wherein the therapeutic protein is an Fc fusion protein.

In exemplary embodiment 252, provided herein is the method of any one of embodiments 240 to 251, wherein the human Fc domain is a human IgG1 Fc domain.

In exemplary embodiment 253, provided herein is the method embodiment 252, wherein the therapeutic protein is a human IgG1 antibody.

In exemplary embodiment 254, provided herein is the method of embodiment 252, wherein the therapeutic protein is an Fc fusion protein comprising a human IgG1 Fc domain.

In exemplary embodiment 255, provided herein is the method of any one of embodiments 252 to 254, wherein the $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain is a $C_{\gamma 1}$ gene segment.

In exemplary embodiment 256, provided herein is the method of any one of embodiments 240 to 251, wherein the human Fc domain is a human IgG2 Fc domain.

In exemplary embodiment 257, provided herein is the method embodiment 256, wherein the therapeutic protein is a human IgG2 antibody.

In exemplary embodiment 258, provided herein is the method of embodiment 256, wherein the therapeutic protein is an Fc fusion protein comprising a human IgG2 Fc domain.

In exemplary embodiment 259, provided herein is the method of any one of embodiments 256 to 258, wherein the $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain is a $C_{\gamma 2}$ gene segment.

In exemplary embodiment 260, provided herein is the method of any one of embodiments 240 to 251, wherein the human Fc domain is a human IgG3 Fc domain.

In exemplary embodiment 261, provided herein is the method embodiment 260, wherein the therapeutic protein is a human IgG3 antibody.

In exemplary embodiment 262, provided herein is the method of embodiment 260, wherein the therapeutic protein is an Fc fusion protein comprising a human IgG3 Fc domain.

In exemplary embodiment 263, provided herein is the method of any one of embodiments 260 to 262, wherein the $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain is a $C_{\gamma 3}$ gene segment.

In exemplary embodiment 264, provided herein is the method of any one of embodiments 240 to 251, wherein the human Fc domain is a human IgG4 Fc domain.

In exemplary embodiment 265, provided herein is the method embodiment 264, wherein the therapeutic protein is a human IgG4 antibody.

In exemplary embodiment 266, provided herein is the method of embodiment 264, wherein the therapeutic protein is an Fc fusion protein comprising a human IgG4 Fc domain.

In exemplary embodiment 267, provided herein is the method of any one of embodiments 264 to 266, wherein the $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain is a $C_{\gamma 4}$ gene segment.

In exemplary embodiment 268, provided herein is the method of any one of embodiments 250, 252, 253, 255-257, 259-261, 263-265, and 267, wherein the therapeutic protein is a human antibody with a κ light chain and the rodent expresses antibodies comprising human κ light chains.

In exemplary embodiment 269, provided herein is the method of any one of embodiments 250, 252, 253, 255-257, 259-261, 263-265, and 267, wherein the therapeutic protein is a human antibody with a λ light chain and the rodent expresses antibodies comprising human λ light chains.

In exemplary embodiment 270, provided herein is the method of any one of embodiments 240 to 269, wherein the rodent is a mouse.

In exemplary embodiment 271, provided herein is the method of any one of embodiments 240 to 269, wherein the rodent is a rat.

In exemplary embodiment 272, provided herein is an animal model for testing a therapeutic protein comprising a human Fc domain, wherein the model comprises administering the therapeutic protein to a rodent of any one of embodiments 1 to 207 and measuring one or more pharmacokinetic properties of the administered therapeutic protein.

In exemplary embodiment 273, provided herein is the animal model of embodiment 272, wherein the one or more pharmacokinetic properties are selected from one or more of area under the plasma concentration versus time (AUC), in vivo recovery (IVR), clearance rate (CL), mean residence time (MRT), agent half-life (t½), and volume of distribution at steady state (Vss).

In exemplary embodiment 274, provided herein is an animal model for testing the therapeutic efficacy of a therapeutic protein comprising a human Fc domain, the animal model comprising administering the therapeutic protein to a rodent of any one of embodiments 1 to 207 and measuring the therapeutic efficacy of the administered therapeutic protein.

In exemplary embodiment 275, provided herein is an animal model for determining a therapeutically effective dose of a therapeutic protein comprising a human Fc domain, the animal model comprising administering a plurality of doses of the therapeutic protein to a rodent of any one of embodiments 1 to 207 and determining a therapeutic efficacy of each dose of the therapeutic protein.

In exemplary embodiment 276, provided herein is an animal model for determining a safe dose of a therapeutic protein comprising a human Fc domain, the animal model comprising administering a plurality of doses of the therapeutic protein to a rodent of any one of embodiments 1 to 207 and determining the safety of each dose the therapeutic protein.

In exemplary embodiment 277, provided herein is an animal model for determining a tolerable dose of a therapeutic protein comprising a human Fc domain, the animal model comprising administering a plurality of doses of the therapeutic protein to a rodent of any one of embodiments 1 to 207 and determining the tolerability of each dose the therapeutic protein.

In exemplary embodiment 278, provided herein is an animal model for testing a therapeutic protein comprising a human Fc domain, the animal model comprising administering the therapeutic protein to a rodent of any one of embodiments 148 to 239 and measuring one or more Fc receptor mediated responses in the rodent.

In exemplary embodiment 279, provided herein is the animal model of embodiment 278, wherein the one or more Fc receptor mediated responses comprise an ADCC response.

In exemplary embodiment 280, provided herein is an animal model for screening a therapeutic agent comprising a human Fc region of a human antibody, the animal model comprising: (a) administering an agent comprising an Fc region of a human antibody to a rodent of any one of embodiments 148 to 239, wherein the agent binds to a target cell in the mouse; (b) measuring antibody-dependent cell-mediated cytotoxicity (ADCC) of natural killer (NK) cells against the target cell; and (c) comparing the amount of ADCC in step (b) to a control, wherein increased target cell killing indicates the agent has increased ability to mediate ADCC.

In exemplary embodiment 281, provided herein is an animal model for measuring an immune response generated by a rodent against a therapeutic protein comprising a human Fc domain, the animal model comprising administering the therapeutic protein to a rodent of any one of embodiments 1 to 207 and measuring the immune response generated by a rodent against a therapeutic protein.

In exemplary embodiment 282, provided herein is the animal model of any one of embodiments 272 to 281, wherein the therapeutic protein is a human antibody.

In exemplary embodiment 283, provided herein is the animal model of any one of embodiments 272 to 281 wherein the therapeutic protein is an Fc fusion protein.

In exemplary embodiment 284, provided herein is the animal model of any one of embodiments 272 to 283, wherein the human Fc domain is a human IgG1 Fc domain.

In exemplary embodiment 285, provided herein is the animal model of embodiment 284, wherein the therapeutic protein is a human IgG1 antibody.

In exemplary embodiment 286, provided herein is the animal model of embodiment 284, wherein the therapeutic protein is an Fc fusion protein comprising a human IgG1 Fc domain.

In exemplary embodiment 287, provided herein is the animal model of any one of embodiments 272 to 286, wherein the $C_H$ gene segment encoding an IgG constant domain comprising a human $C_H 1$ domain, a human hinge region, a human $C_H 2$ domain, a human $C_H 3$ domain, an IgG transmembrane domain and an IgG cytoplasmic domain is a $C_{\gamma 1}$ gene segment.

In exemplary embodiment 288, provided herein is the animal model of any one of embodiments 272 to 283, wherein the human Fc domain is a human IgG2 Fc domain.

In exemplary embodiment 289, provided herein is the animal model of embodiment 288, wherein the therapeutic protein is a human IgG2 antibody.

In exemplary embodiment 290, provided herein is the animal model of embodiment 288, wherein the therapeutic protein is an Fc fusion protein comprising a human IgG2 Fc domain.

In exemplary embodiment 291, provided herein is the animal model of any one of embodiments 288 to 290, wherein the $C_H$ gene segment encoding an IgG constant domain comprising a human $C_H 1$ domain, a human hinge region, a human $C_H 2$ domain, a human $C_H 3$ domain, an IgG transmembrane domain and an IgG cytoplasmic domain is a $C_{\gamma 2}$ gene segment.

In exemplary embodiment 292, provided herein is the animal model of any one of embodiments 272 to 283, wherein the human Fc domain is a human IgG3 Fc domain.

In exemplary embodiment 293, provided herein is the animal model embodiment 292, wherein the therapeutic protein is a human IgG3 antibody.

In exemplary embodiment 294, provided herein is the animal model of embodiment 292, wherein the therapeutic protein is an Fc fusion protein comprising a human IgG3 Fc domain.

In exemplary embodiment 295, provided herein is the animal model of any one of embodiments 292 to 294, wherein the $C_H$ gene segment encoding an IgG constant domain comprising a human $C_H 1$ domain, a human hinge region, a human $C_H 2$ domain, a human $C_H 3$ domain, an IgG transmembrane domain and an IgG cytoplasmic domain is a $C_{\gamma 3}$ gene segment.

In exemplary embodiment 296, provided herein is the animal model of any one of embodiments 272 to 283, wherein the human Fc domain is a human IgG4 Fc domain.

In exemplary embodiment 297, provided herein is the animal model of embodiment 296, wherein the therapeutic protein is a human IgG4 antibody.

In exemplary embodiment 298, provided herein is the animal model of embodiment 296, wherein the therapeutic protein is an Fc fusion protein comprising a human IgG4 Fc domain.

In exemplary embodiment 299, provided herein is the animal model of any one of embodiments 296 to 298, wherein the $C_H$ gene segment encoding an IgG constant domain comprising a human $C_H 1$ domain, a human hinge region, a human $C_H 2$ domain, a human $C_H 3$ domain, an IgG transmembrane domain and an IgG cytoplasmic domain is a $C_{\gamma 4}$ gene segment.

In exemplary embodiment 300, provided herein is the animal model of any one of embodiments 282, 284, 285, 287-289, 291-293, 295-297, and 299, wherein the therapeutic protein is a human antibody with a κ light chain and the rodent expresses antibodies comprising human κ light chains.

In exemplary embodiment 301, provided herein is the animal model of any one of embodiments 282, 284, 285, 287-289, 291-293, 295-297, and 299, wherein the therapeutic protein is a human antibody with a λ light chain and the rodent expresses antibodies comprising human λ light chains.

In exemplary embodiment 302, provided herein is the animal model of any one of embodiments 272 to 301, wherein the rodent is a mouse.

In exemplary embodiment 303, provided herein is the animal model of any one of embodiments 272 to 301, wherein the rodent is a rat.

In exemplary embodiment 304, provided herein is a rodent embryonic stem (ES) cell comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain, wherein the immunoglobulin heavy chain variable region is operably linked to the immunoglobulin heavy chain constant region.

In exemplary embodiment 305, provided herein is the rodent ES cell of embodiment 304, wherein the IgG transmembrane domain is a rodent IgG transmembrane domain.

In exemplary embodiment 306, provided herein is the rodent ES cell of embodiment 304, wherein the IgG transmembrane domain is a human IgG transmembrane domain.

In exemplary embodiment 307, provided herein is the rodent ES cell of any one of embodiments 304 to 306, wherein the IgG cytoplasmic domain is a rodent IgG cytoplasmic domain.

In exemplary embodiment 308, provided herein is the rodent ES cell of any one of embodiments 304 to 306, wherein the IgG cytoplasmic domain is a human IgG cytoplasmic domain.

In exemplary embodiment 309, provided herein is the rodent ES cell of any one of embodiments 304 to 308, wherein the human $C_H1$ domain, the human hinge region, the human $C_H2$ domain and the human $C_H3$ domain are IgG1 domains.

In exemplary embodiment 310, provided herein is the rodent ES cell of embodiment 309, wherein the IgG1 domain is encoded by an allele selected from IGHG1*01, IGHG1*02, IGHG1*03, IGHG1*04 and IGHG1*05.

In exemplary embodiment 311, provided herein is the rodent ES cell of any one of embodiments 304 to 308, wherein the human $C_H1$ domain, the human hinge region, the human $C_H2$ domain and the human $C_H3$ domain are IgG2 domains.

In exemplary embodiment 312, provided herein is the rodent ES cell of embodiment 311, wherein the IgG2 domain is encoded by an allele selected from IGHG2*01, IGHG2*02, IGHG2*03, IGHG2*04, IGHG2*05 and IGHG2*06.

In exemplary embodiment 313, provided herein is the rodent ES cell of any one of embodiments 304 to 308, wherein the human $C_H1$ domain, the human hinge region, the human $C_H2$ domain and the human $C_H3$ domain are IgG3 domains.

In exemplary embodiment 314, provided herein is the rodent ES cell of embodiment 313, wherein the IgG3 domain is encoded by an allele selected from IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19.

In exemplary embodiment 315, provided herein is the rodent ES cell of any one of embodiments 304 to 308, wherein the human $C_H1$ domain, the human hinge region, the human $C_H2$ domain and the human $C_H3$ domain are IgG4 domains.

In exemplary embodiment 316, provided herein is the rodent ES cell of embodiment 315, wherein the IgG4 domain is encoded by an allele selected from IGHG4*01, IGHG4*02, IGHG4*03 and IGHG4*04.

In exemplary embodiment 317, provided herein is the rodent ES cell of any one of embodiments 309 to 316, wherein the $C_H$ gene segment encoding the human $C_H1$ domain, the human hinge region, the human $C_H2$ domain and the human $C_H3$ domain is located at an endogenous $C_{\gamma 2a}$ or $C_{\gamma 2c}$ gene segment locus.

In exemplary embodiment 318, provided herein is the rodent ES cell of embodiment 317, wherein the $C_H$ gene segment encoding the human $C_H1$ domain, the human hinge region, the human $C_H2$ domain and the human $C_H3$ domain replaces an endogenous $C_{\gamma 2a}$ or $C_{\gamma 2c}$ gene segment.

In exemplary embodiment 319, provided herein is the rodent ES cell of any one of embodiments 309 to 316, wherein the $C_H$ gene segment encoding the human $C_H1$ domain, the human hinge region, the human $C_H2$ domain and the human $C_H3$ domain is located at an endogenous $C_{\gamma 1}$ gene segment locus.

In exemplary embodiment 320, provided herein is the rodent ES cell of embodiment 319, wherein the $C_H$ gene segment encoding the human $C_H1$ domain, the human hinge region, the human $C_H2$ domain and the human $C_H3$ domain replaces an endogenous $C_{\gamma 1}$ gene segment.

In exemplary embodiment 321, provided herein is the rodent ES cell of any one of embodiments 309 to 316, wherein the $C_H$ gene segment encoding the human $C_H1$ domain, the human hinge region, the human $C_H2$ domain and the human $C_H3$ domain is located at an endogenous $C_{\gamma 2b}$ gene segment locus.

In exemplary embodiment 322, provided herein is the rodent ES cell of embodiment 321, wherein the $C_H$ gene segment encoding the human $C_H1$ domain, the human hinge region, the human $C_H2$ domain and the human $C_H3$ domain replaces an endogenous $C_{\gamma 2b}$ gene segment.

In exemplary embodiment 323, provided herein is the rodent ES cell of any one of embodiments 309 to 316, wherein the $C_H$ gene segment the human $C_H1$ domain, the human hinge region, the human $C_H2$ domain and the human $C_H3$ domain is located at an endogenous $C_{\gamma 3}$ gene segment locus.

In exemplary embodiment 324, provided herein is the rodent ES cell of embodiment 323, wherein the $C_H$ gene segment encoding the human $C_H1$ domain, the human hinge region, the human $C_H2$ domain and the human $C_H3$ domain replaces an endogenous $C_{\gamma 3}$ gene segment.

In exemplary embodiment 325, provided herein is the rodent ES cell of any one of embodiments 304 to 324, wherein the immunoglobulin heavy chain constant region further comprises a rodent $C_\mu$ gene segment.

In exemplary embodiment 326, provided herein is the rodent ES cell of any one of embodiments 304 to 324, wherein the immunoglobulin heavy chain constant region further comprises a human $C_\mu$ gene segment.

In exemplary embodiment 327, provided herein is the rodent ES cell of any one of embodiments 304 to 326, wherein the immunoglobulin heavy chain constant region further comprises a rodent $C_\delta$ gene segment.

In exemplary embodiment 328, provided herein is the rodent ES cell of any one of embodiments 304 to 326, wherein the immunoglobulin heavy chain constant region further comprises a human $C_\delta$ gene segment.

In exemplary embodiment 329, provided herein is the rodent ES cell of any one of embodiments 304 to 328, wherein the immunoglobulin heavy chain constant region further comprises a rodent $C_{\gamma 1}$ gene segment.

In exemplary embodiment 330, provided herein is the rodent ES cell of any one of embodiments 304 to 329, wherein the immunoglobulin heavy chain constant region further comprises a rodent $C_{\gamma 2a}$ and/or $C_{\gamma 2c}$ gene segment.

In exemplary embodiment 331, provided herein is the rodent ES cell of any one of embodiments 304 to 330, wherein the immunoglobulin heavy chain constant region further comprises a rodent $C_{\gamma 2b}$ gene segment.

In exemplary embodiment 332, provided herein is the rodent ES cell of any one of embodiments 304 to 331, wherein the immunoglobulin heavy chain constant region further comprises a rodent $C_{\gamma 3}$ gene segment.

In exemplary embodiment 333, provided herein is the rodent ES cell of any one of embodiments 304 to 332, wherein the immunoglobulin heavy chain constant region further comprises a rodent $C_\varepsilon$ gene segment.

In exemplary embodiment 334, provided herein is the rodent ES cell of any one of embodiments 304 to 332, wherein the immunoglobulin heavy chain constant region further comprises a human $C_\varepsilon$ gene segment.

In exemplary embodiment 335, provided herein is the rodent ES cell of any one of embodiments 304 to 334, wherein the immunoglobulin heavy chain constant region further comprises a rodent $C_\alpha$ gene segment.

In exemplary embodiment 336, provided herein is the rodent ES cell of any one of embodiments 304 to 334, wherein the immunoglobulin heavy chain constant region further comprises a human $C_\alpha$ gene segment.

In exemplary embodiment 337, provided herein is the rodent ES cell of any one of embodiments 304 to 324, wherein the immunoglobulin heavy chain constant region comprises a human $C_\mu$ gene segment, a human $C_\delta$ gene segment, a human $C_{\gamma 3}$ gene segment and a human $C_{\gamma 1}$ gene segment.

In exemplary embodiment 338, provided herein is the rodent ES cell of embodiment 337, wherein the immunoglobulin heavy chain constant region further comprises a human $C_{\gamma 2}$ gene segment and a human $C_{\gamma 4}$ gene segment.

In exemplary embodiment 339, provided herein is the rodent ES cell of embodiment 337 or embodiment 338, wherein the immunoglobulin heavy chain constant region further comprises a human $C_\alpha$ gene segment.

In exemplary embodiment 340, provided herein is the rodent ES cell of any one of embodiments 337 to 339, wherein the immunoglobulin heavy chain constant region further comprises a human $C_\varepsilon$ gene segment.

In exemplary embodiment 341, provided herein is the rodent ES cell of any one of embodiments 304 to 340, wherein the engineered immunoglobulin heavy chain locus further comprises a rodent intronic enhancer ($E_i$).

In exemplary embodiment 342, provided herein is the rodent ES cell of any one of embodiments 304 to 340, wherein the engineered immunoglobulin heavy chain locus further comprises a human intronic enhancer ($E_i$).

In exemplary embodiment 343, provided herein is the rodent ES cell of any one of embodiments 304 to 342, wherein the engineered immunoglobulin heavy chain locus further comprises a rodent 3' regulatory region (3' RR).

In exemplary embodiment 344, provided herein is the rodent ES cell of any one of embodiments 304 to 342, wherein the engineered immunoglobulin heavy chain locus further comprises a human 3' regulatory region (3' RR).

In exemplary embodiment 345, provided herein is the rodent ES cell of any one of embodiments 304 to 344 wherein the engineered immunoglobulin heavy chain locus further comprises a rodent $S_\mu$ switch site.

In exemplary embodiment 346, provided herein is the rodent ES cell of any one of embodiments 304 to 345, wherein the engineered immunoglobulin heavy chain locus further comprises a rodent $S_{\gamma 3}$ switch site.

In exemplary embodiment 347, provided herein is the rodent ES cell of any one of embodiments 304 to 346, wherein the engineered immunoglobulin heavy chain locus further comprises a rodent $S_{\gamma 1}$ switch site.

In exemplary embodiment 348, provided herein is the rodent ES cell of any one of embodiments 304 to 347, wherein the engineered immunoglobulin heavy chain locus further comprises a rodent $S_{\gamma 2b}$ switch site.

In exemplary embodiment 349, provided herein is the rodent ES cell of any one of embodiments 304 to 348, wherein the engineered immunoglobulin heavy chain locus further comprises a rodent $S_{\gamma 2a}$ and/or $S_{\gamma 2c}$ switch site.

In exemplary embodiment 350, provided herein is the rodent ES cell of any one of embodiments 304 to 349, wherein the engineered immunoglobulin heavy chain locus further comprises a rodent $S_\varepsilon$ switch site.

In exemplary embodiment 351, provided herein is the rodent ES cell of any one of embodiments 304 to 350, wherein the engineered immunoglobulin heavy chain locus further comprises a rodent $S_\alpha$ switch site.

In exemplary embodiment 352, provided herein is the rodent of any one of embodiments 304 to 344, wherein the engineered immunoglobulin heavy chain locus further comprises a human $S_\mu$ switch site.

In exemplary embodiment 353, provided herein is the rodent of any one of embodiments 304 to 344 and 352, wherein the engineered immunoglobulin heavy chain locus further comprises a human $S_{\gamma 3}$ switch site.

In exemplary embodiment 354, provided herein is the rodent of any one of embodiments 304 to 344 and 352-353, wherein the engineered immunoglobulin heavy chain locus further comprises a human $S_{\gamma 1}$ switch site.

In exemplary embodiment 355, provided herein is the rodent of any one of embodiments 304 to 344 and 352-354, wherein the engineered immunoglobulin heavy chain locus further comprises a human $S_{\gamma 2}$ switch site.

In exemplary embodiment 356, provided herein is the rodent of any one of embodiments 304 to 344 and 352-355, wherein the engineered immunoglobulin heavy chain locus further comprises a human $S_{\gamma 4}$ switch site.

In exemplary embodiment 357, provided herein is the rodent of any one of embodiments 304 to 344 and 352-356, wherein the engineered immunoglobulin heavy chain locus further comprises a human $S_\varepsilon$ switch site.

In exemplary embodiment 358 provided herein is the rodent of any one of embodiments 304 to 344 and 352-357, wherein the engineered immunoglobulin heavy chain locus further comprises a human $S_\alpha$ switch site.

In exemplary embodiment 359, provided herein is the rodent ES cell of any one of embodiments 304 to 358, wherein the $V_H$ gene segment is a rodent $V_H$ gene segment, the $D_H$ gene segment is a rodent $D_H$ gene segment and the $J_H$ gene segment is a rodent $J_H$ gene segment.

In exemplary embodiment 360, provided herein is the rodent ES cell of embodiment 359, wherein the rodent $V_H$ gene segment, the rodent $D_H$ gene segment and the rodent $J_H$ gene segment are endogenous rodent gene segments.

In exemplary embodiment 361, provided herein is the rodent ES cell of any one of embodiments 304 to 358, wherein the $V_H$ gene segment is a human $V_H$ gene segment, the $D_H$ gene segment is a human $D_H$ gene segment and the $J_H$ gene segment is a human $J_H$ gene segment.

In exemplary embodiment 362, provided herein is the rodent ES cell of embodiment 361, wherein the immunoglobulin heavy chain variable region comprises at least 3 human $V_H$ gene segments.

In exemplary embodiment 363, provided herein is the rodent ES cell of embodiment 361 or embodiment 362, wherein the immunoglobulin heavy chain variable region comprises all of the human $D_H$ gene segments.

In exemplary embodiment 364, provided herein is the rodent ES cell of any one of embodiments 361 to 363, wherein the immunoglobulin heavy chain variable region comprises all of the human $J_H$ gene segments.

In exemplary embodiment 365, provided herein is the rodent ES cell of any one of embodiments 361 to 364, wherein the immunoglobulin heavy chain variable region lacks a functional endogenous rodent Adam6 gene.

In exemplary embodiment 366, provided herein is the rodent ES cell of any one of embodiments 361 to 365, wherein the germline genome further comprises a nucleotide sequence encoding a functional rodent Adam6 polypeptide, a functional ortholog, a functional homolog, or a functional fragment thereof.

In exemplary embodiment 367, provided herein is the rodent ES cell of embodiment 366, wherein the functional rodent Adam6 polypeptide, the functional ortholog, the functional homolog, or the functional fragment thereof is expressed.

In exemplary embodiment 368, provided herein is the rodent ES cell of embodiment 366 or embodiment 367, wherein the nucleotide sequence encoding the rodent ADAM6 polypeptide, the functional ortholog, the functional homolog, or the functional fragment thereof is included on the same chromosome as the immunoglobulin heavy chain variable region.

In exemplary embodiment 369, provided herein is the rodent ES cell of any one of embodiments 366 to 368, wherein the nucleotide sequence encoding the rodent ADAM6 polypeptide, the functional ortholog, the functional homolog, or the functional fragment thereof is included in the engineered immunoglobulin heavy chain locus.

In exemplary embodiment 370, provided herein is the rodent ES cell of any one of embodiments 366 to 369, wherein the nucleotide sequence encoding the rodent ADAM6 polypeptides, the functional ortholog, the functional homolog, or the functional fragment thereof is in place of a human Adam6 pseudogene.

In exemplary embodiment 371, provided herein is the rodent ES cell of any one of embodiments 366 to 370, wherein the nucleotide sequence encoding the rodent ADAM6 polypeptide, the functional ortholog, the functional homolog, or the functional fragment thereof replaces a human Adam6 pseudogene.

In exemplary embodiment 372, provided herein is the rodent ES cell of any one of embodiments 366 to 371, wherein the nucleotide sequence encoding the rodent ADAM6 polypeptide, the functional ortholog, the functional homolog, or the functional fragment thereof is between a first human $V_H$ gene segment and a second human $V_H$ gene segment.

In exemplary embodiment 373, provided herein is the rodent ES cell of embodiment 372, wherein the first human $V_H$ gene segment is $V_H1$-2 and the second human $V_H$ gene segment is $V_H6$-1.

In exemplary embodiment 374, provided herein is the rodent ES cell of any one of embodiments 366 to 369, wherein the nucleotide sequence encoding the rodent ADAM6 polypeptides, the functional ortholog, the functional homolog, or the functional fragment thereof is between a human $V_H$ gene segment and a human $D_H$ gene segment.

In exemplary embodiment 375, provided herein is the rodent ES cell of any one of embodiments 304 to 374, wherein the engineered immunoglobulin heavy chain locus is positioned at an endogenous immunoglobulin heavy chain locus.

In exemplary embodiment 376, provided herein is the rodent ES cell of embodiment 375, wherein the engineered immunoglobulin heavy chain locus replaces all or part of the endogenous immunoglobulin heavy chain locus.

In exemplary embodiment 377, provided herein is the rodent ES cell of any one of embodiments 304 to 376, wherein the rodent is heterozygous for the engineered immunoglobulin heavy chain locus.

In exemplary embodiment 378, provided herein is the rodent ES cell of any one of embodiments 304 to 376, wherein the rodent is homozygous for the engineered immunoglobulin heavy chain locus.

In exemplary embodiment 379, provided herein is a rodent ES cell comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma3}$ gene segment; (d) a rodent $C_{\gamma1}$ gene segment; (e) a rodent $C_{\gamma2b}$ gene segment; (f) a modified $C_H$ gene segment encoding a human IgG1 $C_H1$ domain, a human IgG1 hinge region, a human IgG1 $C_H2$ domain, a human IgG1 $C_H3$ domain, a rodent IgG2a transmembrane domain, and a rodent IgG2a cytoplasmic domain; (g) a rodent $C_\epsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region.

In exemplary embodiment 380, provided herein is a rodent ES cell comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma3}$ gene segment; (d) a rodent $C_{\gamma1}$ gene segment; (e) a rodent $C_{\gamma2b}$ gene segment; (f) a modified $C_H$ gene segment encoding a human IgG1 $C_H1$ domain, a human IgG1 hinge region, a human IgG1 $C_H2$ domain, a human IgG1 $C_H3$ domain, a human IgG1 transmembrane domain, and a human IgG1 cytoplasmic domain; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region.

In exemplary embodiment 381, provided herein is a rodent ES cell comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a rodent IgG1 transmembrane domain, and a rodent IgG1 cytoplasmic domain; (e) a rodent $C_{\gamma2b}$ gene segment; (f) a rodent $C_{\gamma2a}$ and/or $C_{\gamma2c}$ gene segment; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region.

In exemplary embodiment 382, provided herein is a rodent ES cell comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a human IgG4 transmembrane domain, and a human IgG4 cytoplasmic domain; (e) a rodent $C_{\gamma2b}$ gene segment; (f) a rodent $C_{\gamma2a}$ and/or $C_{\gamma2c}$ gene segment; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region.

In exemplary embodiment 383, provided herein is a rodent ES cell comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma3}$ gene segment; (d) a human $C_{\gamma1}$ gene segment; and (iv) a rodent 3' regulatory region (3' RR), wherein the immunoglobulin heavy chain variable region is operably linked to the immunoglobulin heavy chain constant region.

In exemplary embodiment 384, provided herein is a rodent ES cell comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ segment; (b) a human $C_\delta$ gene segment; (c) a human $C_{\gamma3}$ gene segment; (d) a human $C_{\gamma1}$ gene segment; (c) a human $C_{\gamma2}$ gene segment; (d) a human $C_{\gamma4}$ gene segment; and (iv) a rodent 3' regulatory region (3' RR), wherein the immunoglobulin heavy chain variable region is operably linked to the immunoglobulin heavy chain constant region.

In exemplary embodiment 385, provided herein is a rodent ES cell comprising in its genome: an endogenous immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a r human $C_\delta$ gene segment; (c) a human $C_{\gamma3}$ gene segment; (d) a human $C_{\gamma1}$ gene segment; and (iv) a rodent 3' regulatory region (3' RR), wherein the immunoglobulin heavy chain variable region is operably linked to the immunoglobulin heavy chain constant region.

In exemplary embodiment 386, provided herein is a rodent ES cell comprising in its genome: an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a human $C_\delta$ gene segment; (c) a human $C_{\gamma3}$ gene segment; (d) a human $C_{\gamma1}$ gene segment; (c) a human $C_{\gamma2}$ gene segment; (d) a human $C_{\gamma4}$ gene segment; and (iv) a rodent 3' regulatory region (3' RR), wherein the immunoglobulin heavy chain variable region is operably linked to the immunoglobulin heavy chain constant region.

In exemplary embodiment 387, provided herein is the rodent ES cell of any one of embodiments 304 to 386 further comprising in its genome: an engineered immunoglobulin kappa (κ) chain locus that comprises: (1) an immunoglobulin κ chain variable region comprising a human $V_\kappa$ gene segment and a human $J_\kappa$ gene segment; and (2) an immunoglobulin κ chain constant region comprising a human $C_\kappa$ gene segment, wherein the immunoglobulin κ chain variable region is operably linked to the immunoglobulin κ chain constant region.

In exemplary embodiment 388, provided herein is the rodent ES cell of embodiment 387, wherein the engineered immunoglobulin κ chain locus further comprises a rodent intronic κ enhancer ($E_{\kappa i}$).

In exemplary embodiment 389, provided herein is the rodent ES cell of embodiment 387, wherein the engineered immunoglobulin κ chain locus further comprises a human intronic κ enhancer ($E_{\kappa i}$).

In exemplary embodiment 390, provided herein is the rodent ES cell of any one of embodiments 387 to 389, wherein the engineered immunoglobulin κ chain locus further comprises a rodent 3' κ enhancer ($E_{\kappa 3'}$).

In exemplary embodiment 391, provided herein is the rodent ES cell of any one of embodiments 387 to 389, wherein the engineered immunoglobulin κ chain locus further comprises a human 3' κ enhancer ($E_{\kappa 6'}$).

In exemplary embodiment 392, provided herein is the rodent ES cell of any one of embodiments 387 to 391, wherein the engineered immunoglobulin κ chain variable region comprises at least 6 human $V_\kappa$ gene segments.

In exemplary embodiment 393, provided herein is the rodent ES cell of embodiment 387 or embodiment 392, wherein the engineered immunoglobulin κ chain variable region comprises all of the human $J_\kappa$ gene segments.

In exemplary embodiment 394, provided herein is the rodent ES cell of any one of embodiments 387 to 393, wherein engineered the immunoglobulin κ chain locus is positioned at an endogenous immunoglobulin κ chain locus.

In exemplary embodiment 395, provided herein is the rodent ES cell of embodiment 394, wherein the engineered immunoglobulin κ chain locus replaces all or part of the endogenous immunoglobulin κ chain locus.

In exemplary embodiment 396, provided herein is the rodent ES cell of any one of embodiments 387 to 395, wherein the rodent is heterozygous for the engineered immunoglobulin κ chain locus.

In exemplary embodiment 397, provided herein is the rodent ES cell of any one of embodiments 387 to 395, wherein the rodent is homozygous for the engineered immunoglobulin κ chain locus.

In exemplary embodiment 398, provided herein is the rodent ES cell of any one of embodiments 304 to 397 further comprising in its genome: an engineered immunoglobulin lambda (λ) chain locus that comprises: a human $V_\lambda$ gene segment, a human $J_\lambda$ gene segment and a human $C_\lambda$ gene segment, wherein the human $V_\lambda$ gene segment and the human $J_\lambda$ gene segment are operably linked to the human $C_\lambda$ gene segment.

In exemplary embodiment 399, provided herein is the rodent ES cell of embodiment 398, wherein the human $C_\lambda$ gene segment is a human $C_{\lambda 1}$ gene segment.

In exemplary embodiment 400, provided herein is the rodent ES cell of embodiment 399, wherein the human $J_\lambda$ gene segment is a human $J_{\lambda 1}$ gene segment.

In exemplary embodiment 401, provided herein is the rodent ES cell of embodiment 398, wherein the human $C_\lambda$ gene segment is a human $C_{\lambda 2}$ gene segment.

In exemplary embodiment 402, provided herein is the rodent ES cell of embodiment 401, wherein the human $J_\lambda$ gene segment is a human $J_{\lambda 2}$ gene segment.

In exemplary embodiment 403, provided herein is the rodent ES cell of embodiment 398, wherein the human $C_\lambda$ gene segment is a human $C_{\lambda 3}$ gene segment.

In exemplary embodiment 404, provided herein is the rodent ES cell of embodiment 403, wherein the human $J_\lambda$ gene segment is a human $J_{\lambda 3}$ gene segment.

In exemplary embodiment 405, provided herein is the rodent ES cell of embodiment 398, wherein the human $C_\lambda$ gene segment is a human $C_{\lambda 6}$ gene segment.

In exemplary embodiment 406, provided herein is the rodent ES cell of embodiment 405, wherein the human $J_\lambda$ gene segment is a human $J_{\lambda 6}$ gene segment.

In exemplary embodiment 407, provided herein is the rodent ES cell of embodiment 398, wherein the human $J_\lambda$ gene segment is a human $J_{\lambda 7}$ gene segment.

In exemplary embodiment 408, provided herein is the rodent ES cell of any one of embodiments 398 to 407, wherein the engineered immunoglobulin λ chain locus comprises a human $C_{\lambda 1}$ gene segment, a human $C_{\lambda 2}$ gene segment, a human $C_{\lambda 3}$ gene segment, a human $C_{\lambda 6}$ gene segment and a rodent $C_{\lambda 1}$ gene segment.

In exemplary embodiment 409, provided herein is the rodent ES cell of embodiment 408, wherein the engineered immunoglobulin λ chain locus comprises a human $J_{\lambda 1}$ gene segment, a human $J_{\lambda 2}$ gene segment, a human $J_{\lambda 3}$ gene segment, a human $J_{\lambda 6}$ gene segment and a human $J_{\lambda 7}$ gene segment.

In exemplary embodiment 410, provided herein is the rodent ES cell of embodiment 409, wherein the engineered immunoglobulin λ chain locus comprises a human $J_{\lambda 1}$-$C_{\lambda 1}$ gene segment cluster, a human $J_{\lambda 2}$-$C_{\lambda 2}$ gene segment cluster, a human $J_{\lambda 3}$-$C_{\lambda 3}$ gene segment cluster, a human $J_{\lambda 6}$-$C_{\lambda 6}$ gene segment cluster and a human $J_{\lambda 7}$-rodent $C_{\lambda 1}$ gene segment cluster.

In exemplary embodiment 411, provided herein is the rodent ES cell of any one of embodiments 398 to 410, wherein the engineered immunoglobulin λ chain locus comprises at least 7 human $V_\lambda$ gene segments.

In exemplary embodiment 412, provided herein is the rodent ES cell of any one of embodiments 398 to 411, wherein the engineered immunoglobulin λ chain locus further comprises a rodent λ enhancer 2.4.

In exemplary embodiment 413, provided herein is the rodent ES cell of any one of embodiments 398 to 412, wherein the engineered immunoglobulin λ chain locus further comprises a rodent 3' λ enhancer.

In exemplary embodiment 414, provided herein is the rodent ES cell of any one of embodiments 398 to 413, wherein the engineered immunoglobulin λ chain locus further comprises a rodent λ enhancer 3.1.

In exemplary embodiment 415, provided herein is the rodent ES cell of any one of embodiments 398 to 414, wherein the engineered immunoglobulin λ chain locus further comprises a human 3' λ enhancer.

In exemplary embodiment 416, provided herein is the rodent ES cell of any one of embodiments 398 to 415, wherein the engineered immunoglobulin λ chain locus is positioned at an endogenous immunoglobulin λ chain locus.

In exemplary embodiment 417, provided herein is the rodent ES cell of embodiment 416, wherein the engineered immunoglobulin λ chain locus replaces all or part of the endogenous immunoglobulin λ chain locus.

In exemplary embodiment 418, provided herein is the rodent ES cell of any one of embodiments 398 to 417, wherein the rodent is heterozygous for the engineered immunoglobulin λ chain locus.

In exemplary embodiment 419, provided herein is the rodent ES cell of any one of embodiments 398 to 417, wherein the rodent is homozygous for the engineered immunoglobulin λ chain locus.

In exemplary embodiment 420, provided herein is the rodent ES cell of any one of embodiments 304 to 419, further comprising in its genome a neonatal Fc receptor (FcRn) locus comprising a nucleic acid sequence encoding an engineered FcRn polypeptide comprising a human extracellular domain.

In exemplary embodiment 421, provided herein is the rodent ES cell of embodiment 420, wherein the FcRn polypeptide further comprises a rodent transmembrane domain.

In exemplary embodiment 422, provided herein is the rodent ES cell of embodiment 420, wherein the FcRn polypeptide further comprises a human transmembrane domain.

In exemplary embodiment 423, provided herein is the rodent ES cell of any one of embodiments 420 to 422, wherein the FcRn polypeptide further comprises a rodent cytoplasmic domain.

In exemplary embodiment 424, provided herein is the rodent ES cell of any one of embodiments 420 to 422, wherein the FcRn polypeptide further comprises a human cytoplasmic domain.

In exemplary embodiment 425, provided herein is the rodent ES cell of any one of embodiment 420 to 424, wherein the nucleic acid sequence encoding the FcRn polypeptide is positioned at an endogenous rodent FcRn locus.

In exemplary embodiment 426, provided herein is the rodent ES cell of embodiment 425, wherein the nucleic acid sequence encoding the FcRn polypeptide replaces all or part of an endogenous rodent FcRn gene.

In exemplary embodiment 427, provided herein is the rodent ES cell of embodiment 420, wherein the nucleic acid sequence encoding the FcRn extracellular domain replaces an endogenous nucleic acid sequence encoding a rodent FcRn extracellular domain.

In exemplary embodiment 428, provided herein is the rodent ES cell of any one of embodiments 420 to 427, wherein the rodent does not express a rodent FcRn.

In exemplary embodiment 429, provided herein is the rodent ES cell of any one of embodiments 420 to 428, wherein the rodent is heterozygous for the engineered FcRn locus.

In exemplary embodiment 430, provided herein is the rodent ES cell of any one of embodiments 420 to 428, wherein the rodent is homozygous for the engineered FcRn locus.

In exemplary embodiment 431, provided herein is the rodent ES cell of any one of embodiments 420 to 430, further comprising in its genome an engineered β-2-microglobulin (β2M) locus comprising a nucleic acid sequence encoding a human or humanized β-2-microglobulin (β2M) polypeptide.

In exemplary embodiment 432, provided herein is the rodent ES cell of embodiment 431, wherein the nucleic acid sequence encoding a human or humanized β2M polypeptide is positioned at an endogenous rodent β2M locus.

In exemplary embodiment 433, provided herein is the rodent ES cell of embodiment 432, wherein the nucleic acid sequence encoding a human or humanized β2M polypeptide replaces all or part of the endogenous rodent β2M gene.

In exemplary embodiment 434, provided herein is the rodent of any one of embodiments 431 to 433, wherein the nucleic acid sequence comprises exons 2-4 of a human β2M gene.

In exemplary embodiment 435, provided herein is the rodent ES cell of any one of embodiments 431 to 434, wherein the rodent does not express a rodent β2M polypeptide.

In exemplary embodiment 436, provided herein is the rodent ES cell of any one of embodiments 431 to 435, wherein the rodent is heterozygous for the engineered β2M locus.

In exemplary embodiment 437, provided herein is the rodent ES cell of any one of embodiments 431 to 435, wherein the rodent is homozygous for the engineered β2M locus.

In exemplary embodiment 438, provided herein is the rodent ES cell of any one of embodiments 304 to 437, further comprising in its genome an engineered Fc epsilon receptor 1 alpha (FcεR1α) locus comprising a nucleic acid sequence encoding an FcεR1α polypeptide comprising a human extracellular domain.

In exemplary embodiment 439, provided herein is the rodent ES cell of embodiment 438, wherein the FcεR1α polypeptide further comprises a rodent transmembrane domain.

In exemplary embodiment 440, provided herein is the rodent ES cell of embodiment 438, wherein the FcεR1α polypeptide further comprises a human transmembrane domain.

In exemplary embodiment 441, provided herein is the rodent ES cell of any one of embodiments 438 to 440, wherein the FcεR1α polypeptide further comprises a rodent cytoplasmic domain.

In exemplary embodiment 442, provided herein is the rodent ES cell of any one of embodiments 438 to 440, wherein the FcεR1α polypeptide further comprises a human cytoplasmic domain.

In exemplary embodiment 443, provided herein is the rodent ES cell of any one of embodiment 438 to 442, wherein the nucleic acid sequence encoding the FcεR1α polypeptide is positioned at an endogenous rodent FcεR1α locus.

In exemplary embodiment 444, provided herein is the rodent ES cell of embodiment 443, wherein the nucleic acid sequence encoding the FcεR1α polypeptide replaces all or part of an endogenous rodent FcεR1α gene.

In exemplary embodiment 445, provided herein is the rodent ES cell of embodiment 444, wherein the FcεR1α polypeptide comprises a human extracellular domain, a human transmembrane domain and a human cytoplasmic domain In exemplary embodiment 446, provided herein is the rodent ES cell of embodiment 438, wherein the nucleic acid sequence encoding the human FcεR1α extracellular domain replaces an endogenous nucleic acid sequence encoding a rodent FcεR1α extracellular domain.

In exemplary embodiment 447, provided herein is the rodent ES cell of any one of embodiments 438 to 446, wherein the rodent does not express a rodent FcεR1α.

In exemplary embodiment 448, provided herein is the rodent ES cell of any one of embodiments 438 to 447, wherein the rodent is heterozygous for the engineered FcεR1α locus.

In exemplary embodiment 449, provided herein is the rodent ES cell of any one of embodiments 438 to 447, wherein the rodent is homozygous for the engineered FcεR1α locus.

In exemplary embodiment 450, provided herein is the rodent ES cell of any one of embodiments 304 to 449, further comprising in its genome an engineered Fc gamma receptor 1a (FcγR1a) locus comprising a nucleic acid sequence encoding an FcγR1a polypeptide comprising a human extracellular domain.

In exemplary embodiment 451, provided herein is the rodent ES cell of embodiment 450, wherein the FcγR1a polypeptide further comprises a rodent transmembrane domain.

In exemplary embodiment 452, provided herein is the rodent ES cell of embodiment 450, wherein the FcγR1a polypeptide further comprises a human transmembrane domain.

In exemplary embodiment 453, provided herein is the rodent ES cell of any one of embodiments 450 to 452, wherein the FcγR1a polypeptide further comprises a rodent cytoplasmic domain.

In exemplary embodiment 454, provided herein is the rodent ES cell of any one of embodiments 450 to 452, wherein the FcγR1a polypeptide further comprises a human cytoplasmic domain.

In exemplary embodiment 455, provided herein is the rodent ES cell of any one of embodiment 450 to 454, wherein the nucleic acid sequence encoding the FcγR1a polypeptide is positioned at an endogenous rodent FcγR1a locus.

In exemplary embodiment 456, provided herein is the rodent ES cell of embodiment 455, wherein the nucleic acid sequence encoding the FcγR1a polypeptide replaces all or part of an endogenous rodent FcγR1a gene.

In exemplary embodiment 457, provided herein is the rodent ES cell of embodiment 450, wherein the nucleic acid sequence encoding the human FcγR1a extracellular domain replaces an endogenous nucleic acid sequence encoding a rodent FcγR1a extracellular domain.

In exemplary embodiment 458, provided herein is the rodent ES cell of any one of embodiments 450 to 457, wherein the rodent does not express a rodent FcγR1a.

In exemplary embodiment 459, provided herein is the rodent ES cell of any one of embodiments 450 to 458, wherein the rodent is heterozygous for the engineered FcγR1a locus.

In exemplary embodiment 460, provided herein is the rodent ES cell of any one of embodiments 450 to 458, wherein the rodent is homozygous for the engineered FcγR1a locus.

In exemplary embodiment 461, provided herein is the rodent ES cell of any one of embodiments 304 to 460, further comprising in its genome an engineered Fc gamma receptor 2a (FcγR2a) locus comprising a nucleic acid sequence encoding a human FcγR2a polypeptide.

In exemplary embodiment 462, provided herein is the rodent ES cell embodiment 461, wherein the nucleic acid sequence encoding the FcγR2a polypeptide is positioned at an endogenous rodent low affinity FcγR locus.

In exemplary embodiment 463, provided herein is the rodent ES cell of embodiment 462, wherein the nucleic acid sequence encoding the human FcγR2a polypeptide replaces all or part of an endogenous rodent low affinity FcγR gene.

In exemplary embodiment 464, provided herein is the rodent ES cell of any one of embodiments 461 to 463, wherein the rodent is heterozygous for the engineered FcγR2a locus.

In exemplary embodiment 465, provided herein is the rodent ES cell of any one of embodiments 461 to 463, wherein the rodent is homozygous for the engineered FcγR2a locus.

In exemplary embodiment 466, provided herein is the rodent ES cell of any one of embodiments 304 to 465, further comprising in its genome an engineered Fc gamma receptor 2b (FcγR2b) locus comprising a nucleic acid sequence encoding a human FcγR2b polypeptide.

In exemplary embodiment 467, provided herein is the rodent ES cell embodiment 466, wherein the nucleic acid sequence encoding the FcγR2b polypeptide is positioned at an endogenous rodent low affinity FcγR locus.

In exemplary embodiment 468, provided herein is the rodent ES cell of embodiment 467, wherein the nucleic acid sequence encoding the human FcγR2b polypeptide replaces all or part of endogenous rodent low affinity FcγR gene.

In exemplary embodiment 469, provided herein is the rodent ES cell of any one of embodiments 466 to 468, wherein the rodent is heterozygous for the engineered FcγR2b locus.

In exemplary embodiment 470, provided herein is the rodent ES cell of any one of embodiments 466 to 468, wherein the rodent is homozygous for the engineered FcγR2b locus.

In exemplary embodiment 471, provided herein is the rodent ES cell of any one of embodiments 304 to 470, further comprising in its genome an engineered Fc gamma receptor 3a (FcγR3a) locus comprising a nucleic acid sequence encoding a human FcγR3a polypeptide.

In exemplary embodiment 472, provided herein is the rodent ES cell embodiment 471, wherein the nucleic acid sequence encoding the FcγR3a polypeptide is positioned at an endogenous rodent low affinity FcγR locus.

In exemplary embodiment 473, provided herein is the rodent ES cell of embodiment 472, wherein the nucleic acid sequence encoding the human FcγR3a polypeptide replaces all or part of endogenous rodent low affinity FcγR gene.

In exemplary embodiment 474, provided herein is the rodent ES cell of any one of embodiments 471 to 473, wherein the rodent is heterozygous for the engineered FcγR3a locus.

In exemplary embodiment 475, provided herein is the rodent ES cell of any one of embodiments 471 to 473, wherein the rodent is homozygous for the engineered FcγR3a locus.

In exemplary embodiment 476, provided herein is the rodent ES cell of any one of embodiments 304 to 475, further comprising in its genome an engineered Fc gamma receptor 3b (FcγR3b) locus comprising a nucleic acid sequence encoding a human FcγR3b polypeptide.

In exemplary embodiment 477, provided herein is the rodent ES cell of embodiment 476, wherein the nucleic acid sequence encoding the FcγR3b polypeptide is positioned at an endogenous rodent low affinity FcγR locus.

In exemplary embodiment 478, provided herein is the rodent ES cell of embodiment 477, wherein the nucleic acid sequence encoding the human FcγR3b polypeptide replaces all or part of endogenous rodent low affinity FcγR gene.

In exemplary embodiment 479, provided herein is the rodent ES cell of any one of embodiments 476 to 478, wherein the rodent is heterozygous for the engineered FcγR3b locus.

In exemplary embodiment 480, provided herein is the rodent ES cell of any one of embodiments 476 to 478, wherein the rodent is homozygous for the engineered FcγR3b locus.

In exemplary embodiment 481, provided herein is the rodent ES cell of any one of embodiments 304 to 480, further comprising in its genome an engineered Fc gamma receptor 2c (FcγR2c) locus comprising a nucleic acid sequence encoding a human FcγR2c polypeptide.

In exemplary embodiment 482, provided herein is the rodent ES cell of embodiment 481, wherein the nucleic acid sequence encoding the FcγR2c polypeptide is positioned at an endogenous rodent low affinity FcγR locus.

In exemplary embodiment 483, provided herein is the rodent ES cell of embodiment 482, wherein the nucleic acid sequence encoding the human FcγR2c polypeptide replaces all or part of endogenous rodent low affinity FcγR gene.

In exemplary embodiment 484, provided herein is the rodent ES cell of any one of embodiments 481 to 483, wherein the rodent does not express a rodent FcγR2c.

In exemplary embodiment 485, provided herein is the rodent ES cell of any one of embodiments 481 to 484, wherein the rodent is heterozygous for the engineered FcγR2c locus.

In exemplary embodiment 486, provided herein is the rodent ES cell of any one of embodiments 481 to 484, wherein the rodent is homozygous for the engineered FcγR2c locus.

In exemplary embodiment 487, provided herein is a rodent ES cell comprising in its genome an engineered neonatal Fc receptor (FcRn) locus comprising a nucleic acid sequence encoding a FcRn polypeptide comprising a human extracellular domain.

In exemplary embodiment 488, provided herein is the rodent ES cell of embodiment 487, wherein the FcRn polypeptide further comprises a rodent transmembrane domain.

In exemplary embodiment 489, provided herein is the rodent ES cell of embodiment 487, wherein the FcRn polypeptide further comprises a human transmembrane domain.

In exemplary embodiment 490, provided herein is the rodent ES cell of any one of embodiments 487 to 489, wherein the FcRn polypeptide further comprises a rodent cytoplasmic domain.

In exemplary embodiment 491, provided herein is the rodent ES cell of any one of embodiments 487 to 489, wherein the FcRn polypeptide further comprises a human cytoplasmic domain.

In exemplary embodiment 492, provided herein is the rodent ES cell of any one of embodiment 487 to 491, wherein the nucleic acid sequence encoding the FcRn polypeptide is positioned at an endogenous rodent FcRn locus.

In exemplary embodiment 493, provided herein is the rodent ES cell of embodiment 492, wherein the nucleic acid sequence encoding the FcRn polypeptide replaces all or part of an endogenous rodent FcRn gene.

In exemplary embodiment 494, provided herein is the rodent ES cell of embodiment 493, wherein the nucleic acid sequence encoding the human FcRn extracellular domain replaces an endogenous nucleic acid sequence encoding a rodent FcRn extracellular domain.

In exemplary embodiment 495, provided herein is the rodent ES cell of any one of embodiments 487 to 494, wherein the rodent does not express a rodent FcRn.

In exemplary embodiment 496, provided herein is the rodent ES cell of any one of embodiments 487 to 495, wherein the rodent is heterozygous for the engineered FcRn locus.

In exemplary embodiment 497, provided herein is the rodent ES cell of any one of embodiments 487 to 495, wherein the rodent is homozygous for the engineered FcRn locus.

In exemplary embodiment 498, provided herein is the rodent ES cell of any one of embodiments 487 to 497, further comprising in its genome an engineered β-2-microglobulin (β2M) locus comprising a nucleic acid sequence encoding a human or humanized β-2-microglobulin (β2M) polypeptide.

In exemplary embodiment 499, provided herein is the rodent ES cell of embodiment 498, wherein the nucleic acid sequence encoding a human or humanized β2M polypeptide is positioned at an endogenous rodent β2M locus.

In exemplary embodiment 500, provided herein is the rodent ES cell of embodiment 499, wherein the nucleic acid sequence encoding a human or humanized β2M polypeptide replaces all or part of the endogenous rodent β2M gene.

In exemplary embodiment 501, provided herein is the rodent of any one of embodiments 498 to 500, wherein the nucleic acid sequence comprises exons 2-4 of a human β2M gene.

In exemplary embodiment 502, provided herein is the rodent ES cell of any one of embodiments 498 to 501, wherein the rodent does not express a rodent PM polypeptide.

In exemplary embodiment 503, provided herein is the rodent ES cell of any one of embodiments 498 to 502, wherein the rodent is heterozygous for the engineered β2M locus.

In exemplary embodiment 504, provided herein is the rodent ES cell of any one of embodiments 498 to 502, wherein the rodent is homozygous for the engineered β2M locus.

In exemplary embodiment 505, provided herein is a rodent ES cell comprising in its genome an engineered Fc epsilon receptor 1 alpha (FcεR1α) locus comprising a nucleic acid sequence encoding an FcεR1α polypeptide comprising a human extracellular domain.

In exemplary embodiment 506, provided herein is the rodent ES cell of embodiment 505, wherein the FcεR1α polypeptide further comprises a rodent transmembrane domain.

In exemplary embodiment 507, provided herein is the rodent ES cell of embodiment 505, wherein the FcεR1α polypeptide further comprises a human transmembrane domain.

In exemplary embodiment 508, provided herein is the rodent ES cell of any one of embodiments 505 to 507 wherein the FcεR1α polypeptide further comprises a rodent cytoplasmic domain.

In exemplary embodiment 509, provided herein is the rodent ES cell of any one of embodiments 505 to 507, wherein the FcεR1α polypeptide further comprises a human cytoplasmic domain.

In exemplary embodiment 510, provided herein is the rodent ES cell of any one of embodiment 505 to 509, wherein the nucleic acid sequence encoding the FcεR1α polypeptide is positioned at an endogenous rodent FcεR1α locus.

In exemplary embodiment 511, provided herein is the rodent ES cell of embodiment 510, wherein the nucleic acid sequence encoding the FcεR1α polypeptide replaces all or part of an endogenous rodent FcεR1α gene.

In exemplary embodiment 512, provided herein is the rodent ES cell of embodiment 511, wherein the FcεR1α polypeptide comprises a human extracellular domain, a human transmembrane domain and a human cytoplasmic domain In exemplary embodiment 513, provided herein is the rodent ES cell of embodiment 505, wherein the nucleic acid sequence encoding the human FcεR1α extracellular domain replaces an endogenous nucleic acid sequence encoding a rodent FcεR1α extracellular domain.

In exemplary embodiment 514, provided herein is the rodent ES cell of any one of embodiments 505 to 513, wherein the rodent does not express a rodent FcεR1α.

In exemplary embodiment 515, provided herein is the rodent ES cell of any one of embodiments 505 to 514, wherein the rodent is heterozygous for the engineered FcεR1α locus.

In exemplary embodiment 516, provided herein is the rodent ES cell of any one of embodiments 505 to 514, wherein the rodent is homozygous for the engineered FcεR1α locus.

In exemplary embodiment 517, provided herein is the rodent ES cell of any one of embodiments 304 to 516, wherein the rodent is a mouse.

In exemplary embodiment 518, provided herein is the rodent ES cell of any one of embodiments 304 to 516, wherein the rodent is a rat.

In exemplary embodiment 519, provided herein is a method of making a rodent comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain, the method comprising modifying the genome of a rodent so that it comprises an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgG constant domain comprising a human $C_H1$ domain, a human hinge region, a human $C_H2$ domain, a human $C_H3$ domain, an IgG transmembrane domain and an IgG cytoplasmic domain, wherein the immunoglobulin heavy chain variable region is operably linked to the immunoglobulin heavy chain constant region such that the rodent produces IgG antibodies comprising variable domains derived from the $V_H$ gene segment, the $D_H$ gene segment and the $J_H$ gene segment and heavy chain constant domains derived from the $C_H$ gene segment.

In exemplary embodiment 520, provided herein is the method of embodiment 519, wherein the IgG transmembrane domain is a rodent IgG transmembrane domain.

In exemplary embodiment 521, provided herein is the method of embodiment 519, wherein the IgG transmembrane domain is a human IgG transmembrane domain.

In exemplary embodiment 522, provided herein is the method of any one of embodiments 519 to 521, wherein the IgG cytoplasmic domain is a rodent IgG cytoplasmic domain.

In exemplary embodiment 523, provided herein is the method of any one of embodiments 519 to 521, wherein the IgG cytoplasmic domain is a human IgG cytoplasmic domain.

In exemplary embodiment 524, provided herein is the method of any one of embodiments 519 to 523, wherein the human $C_H1$ domain, the human hinge region, the human $C_H2$ domain and the human $C_H3$ domain are IgG1 domains.

In exemplary embodiment 525, provided herein is the method of embodiment 524, wherein the IgG1 domain is encoded by an allele selected from IGHG1*01, IGHG1*02, IGHG1*03, IGHG1*04 and IGHG1*05.

In exemplary embodiment 526, provided herein is the method of any one of embodiments 519 to 523, wherein the human $C_H1$ domain, the human hinge region, the human $C_H2$ domain and the human $C_H3$ domain are IgG2 domains.

In exemplary embodiment 527, provided herein is the method of embodiment 526, wherein the IgG2 domain is encoded by an allele selected from IGHG2*01, IGHG2*02, IGHG2*03, IGHG2*04, IGHG2*05 and IGHG2*06.

In exemplary embodiment 528, provided herein is the method of any one of embodiments 519 to 523, wherein the human $C_H1$ domain, the human hinge region, the human $C_H2$ domain and the human $C_H3$ domain are IgG3 domains.

In exemplary embodiment 529, provided herein is the method of embodiment 528, wherein the IgG3 domain is encoded by an allele selected from IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19.

In exemplary embodiment 530, provided herein is the method of any one of embodiments 519 to 523, wherein the human $C_H1$ domain, the human hinge region, the human $C_H2$ domain and the human $C_H3$ domain are IgG4 domains.

In exemplary embodiment 531, provided herein is the method of embodiment 530, wherein the IgG4 domain is encoded by an allele selected from IGHG4*01, IGHG4*02, IGHG4*03 and IGHG4*04.

In exemplary embodiment 532, provided herein is the method of any one of embodiments 524 to 531, wherein the $C_H$ gene segment encoding the human $C_H1$ domain, the human hinge region, the human $C_H2$ domain and the human $C_H3$ domain is located at an endogenous $C_{\gamma 2a}$ or $C_{\gamma 2c}$ gene segment locus.

In exemplary embodiment 533, provided herein is the method of embodiment 532, wherein the $C_H$ gene segment encoding the human $C_H1$ domain, the human hinge region, the human $C_H2$ domain and the human $C_H3$ domain replaces an endogenous $C_{\gamma 2a}$ or $C_{\gamma 2c}$ gene segment.

In exemplary embodiment 534, provided herein is the method of any one of embodiments 524 to 531, wherein the $C_H$ gene segment encoding the human $C_H1$ domain, the human hinge region, the human $C_H2$ domain and the human $C_H3$ domain is located at an endogenous $C_{\gamma 1}$ gene segment locus.

In exemplary embodiment 535, provided herein is the method of embodiment 534, wherein the $C_H$ gene segment encoding the human $C_H1$ domain, the human hinge region, the human $C_H2$ domain and the human $C_H3$ domain replaces an endogenous $C_{\gamma 1}$ gene segment.

In exemplary embodiment 536, provided herein is the method of any one of embodiments 524 to 531, wherein the $C_H$ gene segment encoding the human $C_H1$ domain, the human hinge region, the human $C_H2$ domain and the human $C_H3$ domain is located at an endogenous $C_{\gamma 2b}$ gene segment locus.

In exemplary embodiment 537, provided herein is the method of embodiment 536, wherein the $C_H$ gene segment encoding the human $C_H1$ domain, the human hinge region, the human $C_H2$ domain and the human $C_H3$ domain replaces an endogenous $C_{\gamma 2b}$ gene segment.

In exemplary embodiment 538, provided herein is the method of any one of embodiments 524 to 531, wherein the $C_H$ gene segment the human $C_H1$ domain, the human hinge region, the human $C_H2$ domain and the human $C_H3$ domain is located at an endogenous $C_{\gamma 3}$ gene segment locus.

In exemplary embodiment 539, provided herein is the method of embodiment 538, wherein the $C_H$ gene segment encoding the human $C_H1$ domain, the human hinge region, the human $C_H2$ domain and the human $C_H3$ domain replaces an endogenous $C_{\gamma 3}$ gene segment.

In exemplary embodiment 540, provided herein is the method of any one of embodiments 519 to 539, wherein the immunoglobulin heavy chain constant region further comprises a rodent $C_\mu$ gene segment.

In exemplary embodiment 541, provided herein is the method of any one of embodiments 519 to 539, wherein the immunoglobulin heavy chain constant region further comprises a human $C_\mu$ gene segment.

In exemplary embodiment 542, provided herein is the method of any one of embodiments 519 to 541, wherein the immunoglobulin heavy chain constant region further comprises a rodent $C_\delta$ gene segment.

In exemplary embodiment 543, provided herein is the method of any one of embodiments 519 to 541, wherein the immunoglobulin heavy chain constant region further comprises a human $C_\delta$ gene segment.

In exemplary embodiment 544, provided herein is the method of any one of embodiments 519 to 543, wherein the immunoglobulin heavy chain constant region further comprises a rodent $C_{\gamma 1}$ gene segment.

In exemplary embodiment 545, provided herein is the method of any one of embodiments 519 to 544, wherein the immunoglobulin heavy chain constant region further comprises a rodent $C_{\gamma 2a}$ and/or $C_{\gamma 2c}$ gene segment.

In exemplary embodiment 546, provided herein is the method of any one of embodiments 519 to 545, wherein the immunoglobulin heavy chain constant region further comprises a rodent $C_{\gamma 2b}$ gene segment.

In exemplary embodiment 547 provided herein is the method of any one of embodiments 519 to 546, wherein the immunoglobulin heavy chain constant region further comprises a rodent $C_{\gamma 3}$ gene segment.

In exemplary embodiment 548, provided herein is the method of any one of embodiments 519 to 547, wherein the immunoglobulin heavy chain constant region further comprises a rodent $C_\varepsilon$ gene segment.

In exemplary embodiment 549, provided herein is the method of any one of embodiments 519 to 548, wherein the immunoglobulin heavy chain constant region further comprises a human $C_\varepsilon$ gene segment.

In exemplary embodiment 550, provided herein is the method of any one of embodiments 519 to 549, wherein the immunoglobulin heavy chain constant region further comprises a rodent $C_\alpha$ gene segment.

In exemplary embodiment 551, provided herein is the method of any one of embodiments 519 to 549, wherein the immunoglobulin heavy chain constant region further comprises a human $C_\alpha$ gene segment.

In exemplary embodiment 552, provided herein is the method of any one of embodiments 519 to 539, wherein the immunoglobulin heavy chain constant region comprises a human $C_\mu$ gene segment, a human $C_\delta$ gene segment, a human $C_{\gamma 3}$ gene segment and a human $C_{\gamma 1}$ gene segment.

In exemplary embodiment 553, provided herein is the method of embodiment 552, wherein the immunoglobulin heavy chain constant region further comprises a human $C_{\gamma 2}$ gene segment and a human $C_{\gamma 4}$ gene segment.

In exemplary embodiment 554, provided herein is the method of embodiment 552 or embodiment 553, wherein the immunoglobulin heavy chain constant region further comprises a human $C_\alpha$ gene segment.

In exemplary embodiment 555, provided herein is the method of any one of embodiments 552 to 554, wherein the immunoglobulin heavy chain constant region further comprises a human $C_\varepsilon$ gene segment.

In exemplary embodiment 556, provided herein is a method of making a rodent comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgM constant domain comprising a human $C_H1$ domain, a human $C_H2$ domain, a human $C_H3$ domain, a human $C_H4$ domain, a human IgM transmembrane domain and a human IgM cytoplasmic domain, the method comprising modifying the genome of a rodent so that it comprises an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgM constant domain comprising a human $C_H1$ domain, a human $C_H2$ domain, a human $C_H3$ domain, a human $C_H4$ domain, a human IgM transmembrane domain and a human IgM cytoplasmic domain, wherein the immunoglobulin heavy chain variable region is operably linked to the immunoglobulin heavy chain constant region such that the rodent produces IgM antibodies comprising variable domains derived from the $V_H$ gene segment, the $D_H$ gene segment and the $J_H$ gene segment and heavy chain constant domains derived from the $C_H$ gene segment.

In exemplary embodiment 557, provided herein is the method of embodiment 556, wherein the immunoglobulin heavy chain constant region further comprises a human $C_\delta$ gene segment.

In exemplary embodiment 558, provided herein is the method of embodiments 556 or 557, wherein the immunoglobulin heavy chain constant region further comprises a human $C_{\gamma 3}$ gene segment.

In exemplary embodiment 559, provided herein is the method of any one of embodiments 556 to 558, wherein the immunoglobulin heavy chain constant region further comprises a human $C_{\gamma 1}$ gene segment.

In exemplary embodiment 560, provided herein is the method of any one of embodiments 556 to 559, wherein the immunoglobulin heavy chain constant region further comprises a human $C_{\gamma 2}$ gene segment.

In exemplary embodiment 561, provided herein is the method of any one of embodiments 556 to 560, wherein the immunoglobulin heavy chain constant region further comprises a human $C_{\gamma 4}$ gene segment.

In exemplary embodiment 562, provided herein is the method of any one of embodiments 556 to 561, wherein the immunoglobulin heavy chain constant region comprises a human $C_\mu$ gene segment, a human $C_\delta$ gene segment, a human $C_{\gamma 3}$ gene segment and a human $C_{\gamma 1}$ gene segment.

In exemplary embodiment 563, provided herein is the method of embodiment 562, wherein the immunoglobulin heavy chain constant region further comprises a human $C_{\gamma 2}$ gene segment and a human $C_{\gamma 4}$ gene segment.

In exemplary embodiment 564, provided herein is the method of embodiment 562 or embodiment 563, wherein the immunoglobulin heavy chain constant region further comprises a human $C_\alpha$ gene segment.

In exemplary embodiment 565, provided herein is the method of any one of embodiments 562 to 564, wherein the immunoglobulin heavy chain constant region further comprises a human $C_\varepsilon$ gene segment.

In exemplary embodiment 566, provided herein is a method of making a rodent comprising in its genome: an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgD constant domain comprising a human $C_H1$ domain, a human hinge H1 domain, a human hinge H2 domain, a human $C_H2$ domain, a human $C_H3$ domain, a human IgD transmembrane domain and a human IgD cytoplasmic domain, the method comprising modifying the genome of a rodent so that it comprises an engineered immunoglobulin heavy chain locus that comprises: (i) an immunoglobulin heavy chain variable region comprising a $V_H$ gene segment, a $D_H$ gene segment and a $J_H$ gene segment; and (ii) an immunoglobulin heavy chain constant region comprising a $C_H$ gene segment encoding an IgD constant domain comprising a human $C_H1$ domain, a human hinge H1 domain, a human hinge H2 domain, a human $C_H2$ domain, a human $C_H3$ domain, a human IgD transmembrane domain and a human IgD cytoplasmic domain, wherein the immunoglobulin heavy chain variable region is operably linked to the immunoglobulin heavy chain constant region such that the rodent produces IgD antibodies comprising variable domains derived from the $V_H$ gene segment, the $D_H$ gene segment and the $J_H$ gene segment and heavy chain constant domains derived from the $C_H$ gene segment.

In exemplary embodiment 567, provided herein is the method of embodiment 566, wherein the immunoglobulin heavy chain constant region further comprises a human $C_\mu$ gene segment.

In exemplary embodiment 568, provided herein is the method of embodiments 566 or 567, wherein the immunoglobulin heavy chain constant region further comprises a human $C_{\gamma 3}$ gene segment.

In exemplary embodiment 569, provided herein is the method of any one of embodiments 566 to 568, wherein the immunoglobulin heavy chain constant region further comprises a human $C_{\gamma 1}$ gene segment.

In exemplary embodiment 570, provided herein is the method of any one of embodiments 566 to 569, wherein the immunoglobulin heavy chain constant region further comprises a human $C_{\gamma 2}$ gene segment.

In exemplary embodiment 571, provided herein is the method of any one of embodiments 566 to 570, wherein the immunoglobulin heavy chain constant region further comprises a human $C_{\gamma 4}$ gene segment.

In exemplary embodiment 572, provided herein is the method of any one of embodiments 566 to 571, wherein the immunoglobulin heavy chain constant region comprises a human $C_\mu$ gene segment, a human $C_\delta$ gene segment, a human $C_{\gamma 3}$ gene segment and a human $C_{\gamma 1}$ gene segment.

In exemplary embodiment 573, provided herein is the method of embodiment 572, wherein the immunoglobulin heavy chain constant region further comprises a human $C_{\gamma 2}$ gene segment and a human $C_{\gamma 4}$ gene segment.

In exemplary embodiment 574, provided herein is the method of embodiment 572 or embodiment 573, wherein the immunoglobulin heavy chain constant region further comprises a human $C_\alpha$ gene segment.

In exemplary embodiment 575, provided herein is the method of any one of embodiments 572 to 574, wherein the immunoglobulin heavy chain constant region further comprises a human $C_\epsilon$ gene segment.

In exemplary embodiment 576, provided herein is the method of any one of embodiments 519 to 575, wherein the engineered immunoglobulin heavy chain locus further comprises a rodent intronic enhancer ($E_i$).

In exemplary embodiment 577, provided herein is the method of any one of embodiments 519 to 575, wherein the engineered immunoglobulin heavy chain locus further comprises a human intronic enhancer ($E_i$).

In exemplary embodiment 578, provided herein is the method of any one of embodiments 519 to 577, wherein the engineered immunoglobulin heavy chain locus further comprises a rodent 3' regulatory region (3' RR).

In exemplary embodiment 579, provided herein is the method of any one of embodiments 519 to 577, wherein the engineered immunoglobulin heavy chain locus further comprises a human 3' regulatory region (3' RR).

In exemplary embodiment 580, provided herein is the method of any one of embodiments 519 to 579, wherein the engineered immunoglobulin heavy chain locus further comprises a rodent $S_\mu$ switch site.

In exemplary embodiment 581, provided herein is the method of any one of embodiments 519 to 580, wherein the engineered immunoglobulin heavy chain locus further comprises a rodent $S_{\gamma 3}$ switch site.

In exemplary embodiment 582, provided herein is the method of any one of embodiments 519 to 581, wherein the engineered immunoglobulin heavy chain locus further comprises a rodent $S_{\gamma 1}$ switch site.

In exemplary embodiment 583, provided herein is the method of any one of embodiments 519 to 582, wherein the engineered immunoglobulin heavy chain locus further comprises a rodent $S_{\gamma 2b}$ switch site.

In exemplary embodiment 584, provided herein is the method of any one of embodiments 519 to 583, wherein the engineered immunoglobulin heavy chain locus further comprises a rodent $S_{\gamma 2a}$ and/or $S_{\gamma 2c}$ switch site.

In exemplary embodiment 585, provided herein is the method of any one of embodiments 519 to 584, wherein the engineered immunoglobulin heavy chain locus further comprises a rodent $S_\epsilon$ switch site.

In exemplary embodiment 586, provided herein is the method of any one of embodiments 519 to 585, wherein the engineered immunoglobulin heavy chain locus further comprises a rodent $S_\alpha$ switch site.

In exemplary embodiment 587, provided herein is the rodent of any one of embodiments 519 to 579, wherein the engineered immunoglobulin heavy chain locus further comprises a human $S_\mu$ switch site.

In exemplary embodiment 588, provided herein is the rodent of any one of embodiments 519 to 579 and 587, wherein the engineered immunoglobulin heavy chain locus further comprises a human $S_{\gamma 3}$ switch site.

In exemplary embodiment 589, provided herein is the rodent of any one of embodiments 519 to 579 and 587-588, wherein the engineered immunoglobulin heavy chain locus further comprises a human $S_{\gamma 1}$ switch site.

In exemplary embodiment 590, provided herein is the rodent of any one of embodiments 519 to 579 and 587-589, wherein the engineered immunoglobulin heavy chain locus further comprises a human $S_{\gamma 2}$ switch site.

In exemplary embodiment 591, provided herein is the rodent of any one of embodiments 519 to 579 and 587-590, wherein the engineered immunoglobulin heavy chain locus further comprises a human $S_{\gamma 4}$ switch site.

In exemplary embodiment 592, provided herein is the rodent of any one of embodiments 519 to 579 and 587-591, wherein the engineered immunoglobulin heavy chain locus further comprises a human $S_\epsilon$ switch site.

In exemplary embodiment 593, provided herein is the rodent of any one of embodiments 519 to 579 and 587-592, wherein the engineered immunoglobulin heavy chain locus further comprises a human $S_\alpha$ switch site.

In exemplary embodiment 594, provided herein is the method of any one of embodiments 519 to 593, wherein the $V_H$ gene segment is a rodent $V_H$ gene segment, the $D_H$ gene segment is a rodent $D_H$ gene segment and the $J_H$ gene segment is a rodent $J_H$ gene segment.

In exemplary embodiment 595, provided herein is the method of embodiment 594, wherein the rodent $V_H$ gene segment, the rodent $D_H$ gene segment and the rodent $J_H$ gene segment are endogenous rodent gene segments.

In exemplary embodiment 596, provided herein is the method of any one of embodiments 519 to 593, wherein the $V_H$ gene segment is a human $V_H$ gene segment, the $D_H$ gene segment is a human $D_H$ gene segment and the $J_H$ gene segment is a human $J_H$ gene segment.

In exemplary embodiment 597, provided herein is the method of embodiment 596, wherein the immunoglobulin heavy chain variable region comprises at least 3 human $V_H$ gene segments.

In exemplary embodiment 598, provided herein is the method of embodiment 596 or embodiment 597, wherein the immunoglobulin heavy chain variable region comprises all of the human $D_H$ gene segments.

In exemplary embodiment 599, provided herein is the method of any one of embodiments 596 to 598, wherein the immunoglobulin heavy chain variable region comprises all of the human $J_H$ gene segments.

In exemplary embodiment 600, provided herein is the method of any one of embodiments 596 to 599, wherein the immunoglobulin heavy chain variable region lacks a functional endogenous rodent Adam6 gene.

In exemplary embodiment 601, provided herein is the method of any one of embodiments 596 to 600, wherein the germline genome further comprises a nucleotide sequence encoding a functional rodent Adam6 polypeptide, a functional ortholog, a functional homolog, or a functional fragment thereof.

In exemplary embodiment 602, provided herein is the method of embodiment 601, wherein the functional rodent Adam6 polypeptide, the functional ortholog, the functional homolog, or the functional fragment thereof is expressed.

In exemplary embodiment 603, provided herein is the method of embodiment 601 or embodiment 602, wherein the nucleotide sequence encoding the rodent ADAM6 polypeptide, the functional ortholog, the functional homolog, or the functional fragment thereof is included on the same chromosome as the immunoglobulin heavy chain variable region.

In exemplary embodiment 604, provided herein is the method of any one of embodiments 601 to 603, wherein the nucleotide sequence encoding the rodent ADAM6 polypeptide, the functional ortholog, the functional homolog, or the functional fragment thereof is included in the engineered immunoglobulin heavy chain locus.

In exemplary embodiment 605, provided herein is the method of any one of embodiments 601 to 604, wherein the nucleotide sequence encoding the rodent ADAM6 polypeptides, the functional ortholog, the functional homolog, or the functional fragment thereof is in place of a human Adam6 pseudogene.

In exemplary embodiment 606, provided herein is the method of any one of embodiments 601 to 605, wherein the nucleotide sequence encoding the rodent ADAM6 polypeptide, the functional ortholog, the functional homolog, or the functional fragment thereof replaces a human Adam6 pseudogene.

In exemplary embodiment 607, provided herein is the method of any one of embodiments 601 to 606, wherein the nucleotide sequence encoding the rodent ADAM6 polypeptide, the functional ortholog, the functional homolog, or the functional fragment thereof is between a first human $V_H$ gene segment and a second human $V_H$ gene segment.

In exemplary embodiment 608, provided herein is the rodent of embodiment 607, wherein the first human $V_H$ gene segment is $V_H 1$-2 and the second human $V_H$ gene segment is $V_H 6$-1.

In exemplary embodiment 609, provided herein is the method of any one of embodiments 601 to 604, wherein the nucleotide sequence encoding the rodent ADAM6 polypeptides, the functional ortholog, the functional homolog, or the functional fragment thereof is between a human $V_H$ gene segment and a human $D_H$ gene segment.

In exemplary embodiment 610, provided herein is the method of any one of embodiments 519 to 609, wherein the engineered immunoglobulin heavy chain locus is positioned at an endogenous immunoglobulin heavy chain locus.

In exemplary embodiment 611, provided herein is the method of embodiment 610, wherein the engineered immunoglobulin heavy chain locus replaces all or part of the endogenous immunoglobulin heavy chain locus.

In exemplary embodiment 612, provided herein is the method of any one of embodiments 519 to 611, wherein the rodent is heterozygous for the engineered immunoglobulin heavy chain locus.

In exemplary embodiment 613, provided herein is the method of any one of embodiments 519 to 611, wherein the rodent is homozygous for the engineered immunoglobulin heavy chain locus.

In exemplary embodiment 614, provided herein is a method of making a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a rodent $C_{\gamma 1}$ gene segment; (e) a rodent $C_{\gamma 2b}$ gene segment; (f) a modified $C_H$ gene segment encoding a human IgG1 $C_H 1$ domain, a human IgG1 hinge region, a human IgG1 CH2 domain, a human IgG1 $CH_3$ domain, a rodent IgG2a transmembrane domain, and a rodent IgG2a cytoplasmic domain; (g) a rodent $C_\varepsilon$ gene segment; and (h) a rodent $C_\alpha$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a rodent $C_{\gamma 1}$ gene segment; (e) a rodent $C_{\gamma 2b}$ gene segment; (f) a modified $C_H$ gene segment encoding a human IgG1 $C_H 1$ domain, a human IgG1 hinge region, a human IgG1 $C_H 2$ domain, a human IgG1 $C_H 3$ domain, a rodent IgG2a transmembrane domain, and a rodent IgG2a cytoplasmic domain; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 615, provided herein is a method of making a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a rodent $C_{\gamma 1}$ gene segment; (e) a rodent $C_{\gamma 2b}$ gene segment; (f) a modified $C_H$ gene segment encoding a human IgG1 $C_H 1$ domain, a human IgG1 hinge region, a human IgG1 $C_H 2$ domain, a human IgG1 $C_H 3$ domain, a human IgG1 transmembrane domain, and a human IgG1 cytoplasmic domain; (g) a rodent $C_\varepsilon$ gene segment; and (h) a rodent $C_\alpha$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a rodent $C_{\gamma 1}$ gene segment; (e) a rodent $C_{\gamma 2b}$ gene segment; (f) a modified $C_H$ gene segment encoding a human IgG1 $C_H1$ domain, a human IgG1 hinge region, a human IgG1 $C_H2$ domain, a human IgG1 $C_H3$ domain, a human IgG1 transmembrane domain, and a human IgG1 cytoplasmic domain; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 616, provided herein is a method of making a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a rodent IgG1 transmembrane domain, and a rodent IgG1 cytoplasmic domain; (e) a rodent $C_{\gamma 2b}$ gene segment; (f) a rodent $C_{\gamma 2a}$ and/or $C_{\gamma 2c}$ gene segment; (g) a rodent $C_\varepsilon$ gene segment; and (h) a rodent $C_\alpha$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a rodent IgG1 transmembrane domain, and a rodent IgG1 cytoplasmic domain; (e) a rodent $C_{\gamma 2b}$ gene segment; (f) a rodent $C_{\gamma 2a}$ and/or $C_{\gamma 2c}$ gene segment; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 617, provided herein is a method of making a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a human IgG4 transmembrane domain, and a human IgG4 cytoplasmic domain; (e) a rodent $C_{\gamma 2b}$ gene segment; (f) a rodent $C_{\gamma 2a}$ and/or $C_{\gamma 2c}$ gene segment; (g) a rodent $C_\varepsilon$ gene segment; and (h) a rodent $C_\alpha$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a human $V_H$ gene segment, a human $D_H$ gene segment and a human $J_H$ gene segment; (ii) a rodent intronic enhancer ($E_i$); (iii) an immunoglobulin heavy chain constant region comprising: (a) a rodent $C_\mu$ gene segment; (b) a rodent $C_\delta$ gene segment; (c) a rodent $C_{\gamma 3}$ gene segment; (d) a modified $C_H$ gene segment encoding a human IgG4 $C_H1$ domain, a human IgG4 hinge region, a human IgG4 $C_H2$ domain, a human IgG4 $C_H3$ domain, a human IgG4 transmembrane domain, and a human IgG4 cytoplasmic domain; (e) a rodent $C_{\gamma 2b}$ gene segment; (f) a rodent $C_{\gamma 2a}$ and/or $C_{\gamma 2c}$ gene segment; (g) a rodent $C_\varepsilon$ gene segment; and (h) a rodent $C_\alpha$ gene segment; and (iv) a rodent 3' regulatory region (3' RR), wherein the immunoglobulin heavy chain variable region is operably linked to the immunoglobulin heavy chain constant region such that the rodent produces IgG antibodies comprising variable domains derived from the human $V_H$ gene segment, the human $D_H$ gene segment and the human $J_H$ gene segment and heavy chain constant domains derived from the modified $C_H$ gene segment.

In exemplary embodiment 618, provided herein is a method of making a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma 3}$ gene segment; (d) a human $C_{\gamma 1}$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma 3}$ gene segment; (d) a human $C_{\gamma 1}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a fully human heavy chain.

In exemplary embodiment 619, provided herein is a method of making a rodent comprising in its genome: an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma 3}$ gene segment; (d) a human $C_{\gamma 1}$ gene segment; (c) a human $C_{\gamma 2}$ gene segment; (d) a human $C_{\gamma 4}$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a human $V_H$ gene segment, a human $D_H$ gene segment and a human $J_H$ gene segment; (ii) a human intronic enhancer ($E_i$); (iii) an immunoglobulin heavy chain constant region comprising: (a) a human $C_\mu$ gene segment; (b) a human $C_\delta$ gene segment; (c) a human $C_{\gamma 3}$ gene segment; (d) a human $C_{\gamma 1}$ gene segment; (c) a human $C_{\gamma 2}$ gene segment; (d) a human $C_{\gamma 4}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a fully human heavy chain.

In exemplary embodiment 620, provided herein is a method of making a rodent comprising in its genome: an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a r human $C_\delta$ gene segment; (c) a human $C_{\gamma 3}$ gene segment; (d) a human $C_{\gamma 1}$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a r human $C_\delta$ gene segment; (c) a human $C_{\gamma 3}$ gene segment; (d) a human $C_{\gamma 1}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a heavy chain comprising a rodent variable domain and a human constant domain.

In exemplary embodiment 621, provided herein is a method of making a rodent comprising in its genome: an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a human $C_\delta$ gene segment; (c) a human $C_{\gamma 3}$ gene segment; (d) a human $C_{\gamma 1}$ gene segment; (c) a human $C_{\gamma 2}$ gene segment; (d) a human $C_{\gamma 4}$ gene segment; and (iv) a rodent 3' regulatory region (3' RR), the method comprising modifying the genome of a rodent so that it comprises an engineered immunoglobulin heavy chain locus that comprises: (i) an immunoglobulin heavy chain variable region comprising a rodent $V_H$ gene segment, a rodent $D_H$ gene segment and a rodent $J_H$ gene segment; (ii) a rodent intronic enhancer ($E_i$); (iii) an immunoglobulin heavy chain constant region comprising: (a) a human $C_\mu$ gene segment; (b) a human $C_\delta$ gene segment; (c) a human $C_{\gamma 3}$ gene segment; (d) a human $C_{\gamma 1}$ gene segment; (c) a human $C_{\gamma 2}$ gene segment; (d) a human $C_{\gamma 4}$ gene segment; and (iv) a rodent 3' regulatory region (3' RR), wherein the immunoglobulin heavy chain variable region is operably linked to the immunoglobulin heavy chain constant region such that the rodent produces IgG antibodies comprising a heavy chain comprising a rodent variable domain and a human constant domain.

In exemplary embodiment 622, provided herein is the method of any one of embodiments 614 to 621, wherein the engineered immunoglobulin heavy chain locus is positioned at an endogenous immunoglobulin heavy chain locus.

In exemplary embodiment 623, provided herein is the method of embodiment 622, wherein the engineered immunoglobulin heavy chain locus replaces all or part of the endogenous immunoglobulin heavy chain locus.

In exemplary embodiment 624, provided herein is the method of any one of embodiments 614 to 623, wherein the rodent is heterozygous for the engineered immunoglobulin heavy chain locus.

In exemplary embodiment 625, provided herein is the method of any one of embodiments 614 to 623, wherein the rodent is homozygous for the engineered immunoglobulin heavy chain locus.

In exemplary embodiment 626, provided herein is the method of any one of embodiments 519 to 625 further comprising modifying the genome of the rodent so that it further comprises in its genome: an engineered immunoglobulin kappa (κ) chain locus that comprises: (1) an immunoglobulin κ chain variable region comprising a human $V_\kappa$ gene segment and a human $J_\kappa$ gene segment; and (2) an immunoglobulin κ chain constant region comprising a human $C_\kappa$ gene segment, wherein the immunoglobulin κ chain variable region is operably linked to the immunoglobulin κ chain constant region such that the rodent produces antibodies comprising light chain variable domains derived from the human $V_\kappa$ gene segment and the human $J_\kappa$ gene segment and light chain constant domains derived from the human $C_\kappa$ gene segment.

In exemplary embodiment 627, provided herein is the method of embodiment 626, wherein the engineered immunoglobulin κ chain locus further comprises a rodent intronic κ enhancer ($E_{\kappa i}$).

In exemplary embodiment 628, provided herein is the method of embodiment 626, wherein the engineered immunoglobulin κ chain locus further comprises a human intronic κ enhancer ($E_{\kappa i}$).

In exemplary embodiment 629, provided herein is the method of any one of embodiments 626 to 628, wherein the engineered immunoglobulin κ chain locus further comprises a rodent 3' κ enhancer ($E_{\kappa 3'}$).

In exemplary embodiment 630, provided herein is the method of any one of embodiments 626 to 628, wherein the engineered immunoglobulin κ chain locus further comprises a human 3' κ enhancer ($E_{\kappa 3'}$).

In exemplary embodiment 631, provided herein is the method of any one of embodiments 626 to 630, wherein the immunoglobulin κ chain variable region comprises at least 6 human $V_\kappa$ gene segments.

In exemplary embodiment 632, provided herein is the method of any one of embodiments 626 to 631, wherein the immunoglobulin κ chain variable region comprises all of the human $J_\kappa$ gene segments.

In exemplary embodiment 633, provided herein is the method of any one of embodiments 626 to 632, wherein the engineered immunoglobulin κ chain locus is positioned at an endogenous immunoglobulin κ chain locus.

In exemplary embodiment 634, provided herein is the method of embodiment 633, wherein the engineered immunoglobulin κ chain locus replaces all or part of the endogenous immunoglobulin κ chain locus.

In exemplary embodiment 635, provided herein is the method of any one of embodiments 626 to 634, wherein the rodent is heterozygous for the engineered immunoglobulin κ chain locus.

In exemplary embodiment 636, provided herein is the method of any one of embodiments 626 to 634, wherein the rodent is homozygous for the engineered immunoglobulin κ chain locus.

In exemplary embodiment 637, provided herein is the method of any one of embodiments 519 to 636 further comprising in its genome: an engineered immunoglobulin lambda (λ) chain locus that comprises: a human $V_\lambda$ gene segment, a human $J_\lambda$ gene segment and a human $C_\lambda$ segment, wherein the human $V_\lambda$ gene segment and the human $J_\lambda$ segment are operably linked to the human $C_\lambda$ segment such that the rodent produces antibodies comprising light chain variable domains derived from the human $V_\lambda$ gene segment and the human $J_\lambda$ gene segment and light chain constant domains derived from the human $C_\lambda$ gene segment.

In exemplary embodiment 638, provided herein is the method of embodiment 637, wherein the human $C_\lambda$ gene segment is a human $C_{\lambda 1}$ gene segment.

In exemplary embodiment 639, provided herein is the method of embodiment 638, wherein the human $J_\lambda$ gene segment is a human $J_{\lambda 1}$ gene segment.

In exemplary embodiment 640, provided herein is the method of embodiment 637, wherein the human $C_\lambda$ gene segment is a human $C_{\lambda 2}$ gene segment.

In exemplary embodiment 641, provided herein is the method of embodiment 640, wherein the human $J_\lambda$ gene segment is a human $J_{\lambda 2}$ gene segment.

In exemplary embodiment 642, provided herein is the method of embodiment 637, wherein the human $C_\lambda$ gene segment is a human $C_{\lambda 3}$ gene segment.

In exemplary embodiment 643, provided herein is the method of embodiment 642, wherein the human $J_\lambda$ gene segment is a human $J_{\lambda 3}$ gene segment.

In exemplary embodiment 644, provided herein is the method of embodiment 637, wherein the human $C_\lambda$ gene segment is a human $C_{\lambda 6}$ gene segment.

In exemplary embodiment 645, provided herein is the method of embodiment 644, wherein the human $J_\lambda$ gene segment is a human $J_{\lambda 6}$ gene segment.

In exemplary embodiment 646, provided herein is the method of embodiment 637, wherein the human $J_\lambda$ gene segment is a human $J_{\lambda 7}$ gene segment.

In exemplary embodiment 647, provided herein is the method of any one of embodiments 637 to 646, wherein the engineered immunoglobulin λ chain locus comprises a human $C_{\lambda 1}$ gene segment, a human $C_{\lambda 2}$ gene segment, a human $C_{\lambda 3}$ gene segment, a human $C_{\lambda 6}$ gene segment and a rodent $C_{\lambda 1}$ gene segment.

In exemplary embodiment 648, provided herein is the method of embodiment 647, wherein the engineered immunoglobulin λ chain locus comprises a human $J_{\lambda 1}$ gene segment, a human $J_{\lambda 2}$ gene segment, a human $J_{\lambda 3}$ gene segment, a human $J_{\lambda 6}$ gene segment and a human $J_{\lambda 7}$ gene segment.

In exemplary embodiment 649, provided herein is the rodent ES cell of embodiment 648, wherein the engineered immunoglobulin λ chain locus comprises a human $J_{\lambda 1}$-$C_{\lambda 1}$ gene segment cluster, a human $J_{\lambda 2}$-$C_{\lambda 2}$ gene segment cluster, a human $J_{\lambda 3}$-$C_{\lambda 3}$ gene segment cluster, a human $J_{\lambda 6}$-$C_{\lambda 6}$ gene segment cluster and a human $J_{\lambda 7}$-rodent $C_{\lambda 1}$ gene segment cluster.

In exemplary embodiment 650, provided herein is the method of any one of embodiments 637 to 649, wherein the engineered immunoglobulin λ chain locus comprises at least 7 human $V_\lambda$ gene segments.

In exemplary embodiment 651, provided herein is the method of any one of embodiments 637 to 650, wherein the engineered immunoglobulin λ chain locus further comprises a rodent λ enhancer 2.4.

In exemplary embodiment 652, provided herein is the method of any one of embodiments 637 to 651, wherein the engineered immunoglobulin λ chain locus further comprises a rodent 3' λ enhancer.

In exemplary embodiment 653, provided herein is the method of any one of embodiments 637 to 652, wherein the engineered immunoglobulin λ chain locus further comprises a rodent λ enhancer 3.1.

In exemplary embodiment 654, provided herein is the method of any one of embodiments 637 to 653, wherein the engineered immunoglobulin λ chain locus further comprises a human 3' λ enhancer.

In exemplary embodiment 655, provided herein is the of any one of embodiments 637 to 654, wherein the engineered immunoglobulin λ chain locus is positioned at an endogenous immunoglobulin λ chain locus.

In exemplary embodiment 656, provided herein is the method of embodiment 655, wherein the engineered immunoglobulin λ chain locus replaces all or part of the endogenous immunoglobulin λ chain locus.

In exemplary embodiment 657, provided herein is the method of any one of embodiments 637 to 656, wherein the rodent is heterozygous for the engineered immunoglobulin λ chain locus.

In exemplary embodiment 658, provided herein is the method of any one of embodiments 637 to 656, wherein the rodent is homozygous for the engineered immunoglobulin λ chain locus.

In exemplary embodiment 659, provided herein is the method of any one of embodiments 519 to 658, further comprising in its genome an engineered neonatal Fc receptor (FcRn) locus comprising a nucleic acid sequence encoding a FcRn polypeptide comprising a human extracellular domain.

In exemplary embodiment 660, provided herein is the method of embodiment 659, wherein the FcRn polypeptide further comprises a rodent transmembrane domain.

In exemplary embodiment 661, provided herein is the method of embodiment 659, wherein the FcRn polypeptide further comprises a human transmembrane domain.

In exemplary embodiment 662, provided herein is the method of any one of embodiments 659 to 661, wherein the FcRn polypeptide further comprises a rodent cytoplasmic domain.

In exemplary embodiment 663, provided herein is the method of any one of embodiments 659 to 661, wherein the FcRn polypeptide further comprises a human cytoplasmic domain.

In exemplary embodiment 664, provided herein is the method of any one of embodiment 659 to 663, wherein the nucleic acid sequence encoding the FcRn polypeptide is positioned at an endogenous rodent FcRn locus.

In exemplary embodiment 665, provided herein is the method of embodiment 664, wherein the nucleic acid sequence encoding the FcRn polypeptide replaces all or part of an endogenous rodent FcRn gene.

In exemplary embodiment 666, provided herein is the method of embodiment 665, wherein the nucleic acid sequence encoding the FcRn extracellular domain replaces an endogenous nucleic acid sequence encoding a rodent FcRn extracellular domain.

In exemplary embodiment 667, provided herein is the method of any one of embodiments 659 to 666, wherein the rodent does not express a rodent FcRn.

In exemplary embodiment 668, provided herein is the method of any one of embodiments 659 to 667, wherein the rodent is heterozygous for the engineered FcRn locus.

In exemplary embodiment 669, provided herein is the method of any one of embodiments 659 to 667, wherein the rodent is homozygous for the engineered FcRn locus.

In exemplary embodiment 670, provided herein is the method of any one of embodiments 659 to 669, further comprising in its genome an engineered β-2-microglobulin (β2M) locus comprising a nucleic acid sequence encoding a human or humanized β-2-microglobulin (β2M) polypeptide.

In exemplary embodiment 671, provided herein is the method of embodiment 670, wherein the nucleic acid sequence encoding a human or humanized β2M polypeptide is positioned at an endogenous rodent β2M locus.

In exemplary embodiment 672, provided herein is the method of embodiment 671, wherein the nucleic acid sequence encoding a human or humanized β2M polypeptide replaces all or part of the endogenous rodent β2M gene.

In exemplary embodiment 673, provided herein is the method of any one of embodiments 670 to 672, wherein the nucleic acid sequence comprises exons 2-4 of a human β2M gene.

In exemplary embodiment 674, provided herein is the method of any one of embodiments 670 to 673, wherein the rodent does not express a rodent β2M polypeptide.

In exemplary embodiment 675, provided herein is the method of any one of embodiments 560 to 674, wherein the rodent is heterozygous for the engineered β2M locus.

In exemplary embodiment 676, provided herein is the method of any one of embodiments 560 to 674, wherein the rodent is homozygous for the engineered β2M locus.

In exemplary embodiment 677, provided herein is the method of any one of embodiments 519 to 676, further comprising in its genome an engineered Fc epsilon receptor 1 alpha (FcεR1α) locus comprising a nucleic acid sequence encoding an FcεR1α polypeptide comprising a human extracellular domain.

In exemplary embodiment 678, provided herein is the method of embodiment 677, wherein the FcεR1α polypeptide further comprises a rodent transmembrane domain.

In exemplary embodiment 679, provided herein is the method of embodiment 677, wherein the FcεR1α polypeptide further comprises a human transmembrane domain.

In exemplary embodiment 680, provided herein is the method of any one of embodiments 677 to 679, wherein the FcεR1α polypeptide further comprises a rodent cytoplasmic domain.

In exemplary embodiment 681, provided herein is the method of any one of embodiments 677 to 679, wherein the FcεR1α polypeptide further comprises a human cytoplasmic domain.

In exemplary embodiment 682, provided herein is the method of any one of embodiments 677 to 681, wherein the nucleic acid sequence encoding the FcεR1α polypeptide is positioned at an endogenous rodent FcεR1α locus.

In exemplary embodiment 683, provided herein is the method of embodiment 682, wherein the nucleic acid sequence encoding the FcεR1α polypeptide replaces all or part of an endogenous rodent FcεR1α gene.

In exemplary embodiment 684, provided herein is the method of embodiment 683, wherein the FcεR1α polypeptide comprises a human extracellular domain, a human transmembrane domain and a human cytoplasmic domain In exemplary embodiment 685, provided herein is the method of embodiment 677, wherein the nucleic acid sequence encoding the human FcεR1α extracellular domain replaces an endogenous nucleic acid sequence encoding a rodent FcεR1α extracellular domain.

In exemplary embodiment 686, provided herein is the method of any one of embodiments 677 to 685, wherein the rodent does not express a rodent FcεR1α.

In exemplary embodiment 687, provided herein is the method of any one of embodiments 677 to 686, wherein the rodent is heterozygous for the engineered FcεR1α locus.

In exemplary embodiment 688, provided herein is the method of any one of embodiments 677 to 686, wherein the rodent is homozygous for the engineered FcεR1α locus.

In exemplary embodiment 689, provided herein is the method of any one of embodiments 519 to 688, further comprising in its genome an engineered Fc gamma receptor 1a (FcγR1a) locus comprising a nucleic acid sequence encoding an FcγR1a polypeptide comprising a human extracellular domain.

In exemplary embodiment 690, provided herein is the method of embodiment 689, wherein the FcγR1a polypeptide further comprises a rodent transmembrane domain.

In exemplary embodiment 691, provided herein is the method of embodiment 689, wherein the FcγR1a polypeptide further comprises a human transmembrane domain.

In exemplary embodiment 692, provided herein is the method of any one of embodiments 689 to 691, wherein the FcγR1a polypeptide further comprises a rodent cytoplasmic domain.

In exemplary embodiment 693, provided herein is the method of any one of embodiments 689 to 691, wherein the FcγR1a polypeptide further comprises a human cytoplasmic domain.

In exemplary embodiment 694, provided herein is the method of any one of embodiment 689 to 693, wherein the nucleic acid sequence encoding the FcγR1a polypeptide is positioned at an endogenous rodent FcγR1a locus.

In exemplary embodiment 695, provided herein is the method of embodiment 694, wherein the nucleic acid sequence encoding the FcγR1a polypeptide replaces all or part of an endogenous rodent FcγR1a gene.

In exemplary embodiment 696, provided herein is the method of embodiment 689, wherein the nucleic acid sequence encoding the human FcγR1a extracellular domain replaces an endogenous nucleic acid sequence encoding a rodent FcγR1a extracellular domain.

In exemplary embodiment 697, provided herein is the method of any one of embodiments 689 to 696, wherein the rodent does not express a rodent FcγR1a.

In exemplary embodiment 698, provided herein is the method of any one of embodiments 689 to 697, wherein the rodent is heterozygous for the engineered FcγR1a locus.

In exemplary embodiment 699, provided herein is the method of any one of embodiments 689 to 697, wherein the rodent is homozygous for the engineered FcγR1a locus.

In exemplary embodiment 700, provided herein is the method of any one of embodiments 519 to 699, further comprising in its genome an engineered Fc gamma receptor 2a (FcγR2a) locus comprising a nucleic acid sequence encoding a human FcγR2a polypeptide.

In exemplary embodiment 701, provided herein is the method embodiment 700, wherein the nucleic acid sequence encoding the FcγR2a polypeptide is positioned at an endogenous rodent low affinity FcγR locus.

In exemplary embodiment 702, provided herein is the method of embodiment 701, wherein the nucleic acid sequence encoding the human FcγR2a polypeptide replaces all or part of an endogenous rodent low affinity FcγR gene.

In exemplary embodiment 703, provided herein is the method of any one of embodiments 700 to 702, wherein the rodent is heterozygous for the engineered FcγR2a locus.

In exemplary embodiment 704, provided herein is the method of any one of embodiments 700 to 702, wherein the rodent is homozygous for the engineered FcγR2a locus.

In exemplary embodiment 705, provided herein is the method of any one of embodiments 519 to 704, further comprising in its genome an engineered Fc gamma receptor 2b (FcγR2b) locus comprising a nucleic acid sequence encoding a human FcγR2b polypeptide.

In exemplary embodiment 706, provided herein is the method embodiment 705, wherein the nucleic acid sequence encoding the FcγR2b polypeptide is positioned at an endogenous rodent low affinity FcγR locus.

In exemplary embodiment 707, provided herein is the method of embodiment 706, wherein the nucleic acid sequence encoding the human FcγR2b polypeptide replaces all or part of endogenous rodent low affinity FcγR gene.

In exemplary embodiment 708, provided herein is the method of any one of embodiments 705 to 707, wherein the rodent is heterozygous for the engineered FcγR2b locus.

In exemplary embodiment 709, provided herein is the method of any one of embodiments 705 to 707, wherein the rodent is homozygous for the engineered FcγR2b locus.

In exemplary embodiment 710, provided herein is the method of any one of embodiments 519 to 709, further comprising in its genome an engineered Fc gamma receptor 3a (FcγR3a) locus comprising a nucleic acid sequence encoding a human FcγR3a polypeptide.

In exemplary embodiment 711, provided herein is the method embodiment 710, wherein the nucleic acid sequence encoding the FcγR3a polypeptide is positioned at an endogenous rodent low affinity FcγR locus.

In exemplary embodiment 712, provided herein is the method of embodiment 711, wherein the nucleic acid sequence encoding the human FcγR3a polypeptide replaces all or part of endogenous rodent low affinity FcγR gene.

In exemplary embodiment 713, provided herein is the method of any one of embodiments 710 to 712, wherein the rodent is heterozygous for the engineered FcγR3a locus.

In exemplary embodiment 714, provided herein is the method of any one of embodiments 710 to 712, wherein the rodent is homozygous for the engineered FcγR3a locus.

In exemplary embodiment 715, provided herein is the method of any one of embodiments 519 to 714, further comprising in its genome an engineered Fc gamma receptor 3b (FcγR3b) locus comprising a nucleic acid sequence encoding a human FcγR3b polypeptide.

In exemplary embodiment 716, provided herein is the method of embodiment 715, wherein the nucleic acid sequence encoding the FcγR3b polypeptide is positioned at an endogenous rodent low affinity FcγR locus.

In exemplary embodiment 717, provided herein is the method of embodiment 716, wherein the nucleic acid sequence encoding the human FcγR3b polypeptide replaces all or part of endogenous rodent low affinity FcγR gene.

In exemplary embodiment 718, provided herein is the method of any one of embodiments 715 to 717, wherein the rodent is heterozygous for the engineered FcγR3b locus.

In exemplary embodiment 719, provided herein is the method of any one of embodiments 715 to 717, wherein the rodent is homozygous for the engineered FcγR3b locus.

In exemplary embodiment 720, provided herein is the method of any one of embodiments 519 to 719, further comprising in its genome an engineered Fc gamma receptor 2c (FcγR2c) locus comprising a nucleic acid sequence encoding a human FcγR2c polypeptide.

In exemplary embodiment 721, provided herein is the method of embodiment 720, wherein the nucleic acid sequence encoding the FcγR2c polypeptide is positioned at an endogenous rodent low affinity FcγR locus.

In exemplary embodiment 722, provided herein is the method of embodiment 721, wherein the nucleic acid sequence encoding the human FcγR2c polypeptide replaces all or part of endogenous rodent low affinity FcγR gene.

In exemplary embodiment 723, provided herein is the method of any one of embodiments 720 to 722, wherein the rodent does not express a rodent FcγR2c.

In exemplary embodiment 724, provided herein is the method of any one of embodiments 720 to 723, wherein the rodent is heterozygous for the engineered FcγR2c locus.

In exemplary embodiment 725, provided herein is the method of any one of embodiments 720 to 723, wherein the rodent is homozygous for the engineered FcγR2c locus.

In exemplary embodiment 726, provided herein is a method of making a rodent comprising in its genome an engineered neonatal Fc receptor (FcRn) locus comprising a nucleic acid sequence encoding a FcRn polypeptide comprising a human extracellular domain, the method comprising modifying the genome of a rodent so that it comprises a neonatal Fc receptor (FcRn) locus comprising a nucleic acid sequence encoding an FcRn polypeptide comprising a human extracellular domain.

In exemplary embodiment 727, provided herein is the method of embodiment 726, wherein the FcRn polypeptide further comprises a rodent transmembrane domain.

In exemplary embodiment 728, provided herein is the method of embodiment 726, wherein the FcRn polypeptide further comprises a human transmembrane domain.

In exemplary embodiment 729, provided herein is the method of any one of embodiments 726 to 728, wherein the FcRn polypeptide further comprises a rodent cytoplasmic domain.

In exemplary embodiment 730, provided herein is the method of any one of embodiments 726 to 728, wherein the FcRn polypeptide further comprises a human cytoplasmic domain.

In exemplary embodiment 731, provided herein is the method of any one of embodiment 726 to 730, wherein the nucleic acid sequence encoding the FcRn polypeptide is positioned at an endogenous rodent FcRn locus.

In exemplary embodiment 732, provided herein is the method of embodiment 731, wherein the nucleic acid sequence encoding the FcRn polypeptide replaces all or part of an endogenous rodent FcRn gene.

In exemplary embodiment 733, provided herein is the method of embodiment 732, wherein the nucleic acid sequence encoding the human FcRn extracellular domain replaces an endogenous nucleic acid sequence encoding a rodent FcRn extracellular domain.

In exemplary embodiment 734, provided herein is the method of any one of embodiments 726 to 733, wherein the rodent does not express a rodent FcRn.

In exemplary embodiment 735, provided herein is the method of any one of embodiments 726 to 734, wherein the rodent is heterozygous for the engineered FcRn locus.

In exemplary embodiment 736, provided herein is the method of any one of embodiments 726 to 734, wherein the rodent is homozygous for the engineered FcRn locus.

In exemplary embodiment 737, provided herein is the method of any one of embodiments 726 to 736, further comprising in its genome an engineered β-2-microglobulin (β2M) locus comprising a nucleic acid sequence encoding a human or humanized β-2-microglobulin (β2M) polypeptide.

In exemplary embodiment 738, provided herein is the method of embodiment 737, wherein the nucleic acid sequence encoding a human or humanized β2M polypeptide is positioned at an endogenous rodent β2M locus.

In exemplary embodiment 739, provided herein is the method of embodiment 738, wherein the nucleic acid sequence encoding a human or humanized β2M polypeptide replaces all or part of the endogenous rodent β2M gene.

In exemplary embodiment 740, provided herein is the rodent of any one of embodiments 737 to 739, wherein the nucleic acid sequence comprises exons 2-4 of a human β2M gene.

In exemplary embodiment 741, provided herein is the method of any one of embodiments 737 to 740, wherein the rodent does not express a rodent β2M polypeptide.

In exemplary embodiment 742, provided herein is the method of any one of embodiments 737 to 741, wherein the rodent is heterozygous for the engineered β2M locus.

In exemplary embodiment 743, provided herein is the method of any one of embodiments 737 to 741, wherein the rodent is homozygous for the engineered β2M locus.

In exemplary embodiment 744, provided herein is a method of making a rodent comprising in its genome an engineered Fc epsilon receptor 1 alpha (FcεR1α) locus comprising a nucleic acid sequence encoding an FcεR1α polypeptide comprising a human extracellular domain, the method comprising modifying the genome of a rodent so that it comprises an engineered FcεR1α locus comprising a nucleic acid sequence encoding an FcεR1α polypeptide comprising a human extracellular domain.

In exemplary embodiment 745, provided herein is the method of embodiment 744, wherein the FcεR1α polypeptide further comprises a rodent transmembrane domain.

In exemplary embodiment 746, provided herein is the method of embodiment 744, wherein the FcεR1α polypeptide further comprises a human transmembrane domain.

In exemplary embodiment 747, provided herein is the method of any one of embodiments 744 to 746 wherein the FcεR1α polypeptide further comprises a rodent cytoplasmic domain.

In exemplary embodiment 748, provided herein is the method of any one of embodiments 744 to 746, wherein the FcεR1α polypeptide further comprises a human cytoplasmic domain.

In exemplary embodiment 749, provided herein is the method of any one of embodiments 744 to 748, wherein the nucleic acid sequence encoding the FcεR1α polypeptide is positioned at an endogenous rodent FcγR1 locus.

In exemplary embodiment 750, provided herein is the method of embodiment 749, wherein the nucleic acid sequence encoding the FcεR1α polypeptide replaces all or part of an endogenous rodent FcεR1α gene.

In exemplary embodiment 751, provided herein is the method of embodiment 750, wherein the FcεR1α polypeptide comprises a human extracellular domain, a human transmembrane domain and a human cytoplasmic domain.

In exemplary embodiment 752, provided herein is the method of embodiment 744, wherein the nucleic acid sequence encoding the human FcεR1α extracellular domain replaces an endogenous nucleic acid sequence encoding a rodent FcεR1α extracellular domain.

In exemplary embodiment 753, provided herein is the method of any one of embodiments 744 to 752, wherein the rodent does not express a rodent FcεR1α.

In exemplary embodiment 754, provided herein is the method of any one of embodiments 744 to 753, wherein the rodent is heterozygous for the engineered FcεR1α locus.

In exemplary embodiment 755, provided herein is the method of any one of embodiments 744 to 753, wherein the rodent is homozygous for the engineered FcεR1α locus.

In exemplary embodiment 756, provided herein is the method of any one of embodiments 519 to 755, wherein the rodent is a mouse.

In exemplary embodiment 757, provided herein is the method of any one of embodiments 519 to 755, wherein the rodent is a rat.

EXAMPLES

Example 1

Genetic Engineering of Mice Comprising Humanized Immunoglobulin Constant Regions This example illustrates exemplary methods of constructing a series of targeting vectors for insertion into the genome of a non-human animal such as a rodent (e.g., a mouse). The methods described in this example demonstrate the production of non-human animals whose genomes comprise an engineered immunoglobulin heavy chain constant region and/or an engineered immunoglobulin light chain (kappa or lambda) constant region. In particular, this example demonstrates the construction of targeting vectors for engineering immunoglobulin heavy constant regions so that the non-human animals express and/or produce antibodies that include immunoglobulin heavy chains having human variable domains and constant domains that are human, in whole or in part (e.g., comprise a human portion and a rodent portion). It also demonstrates the construction of targeting vectors for engineering immunoglobulin light constant regions so that the non-human animals express and/or produce antibodies that include immunoglobulin light chains having human variable domains and constant domains that are human, in whole or in part (e.g., comprise a human portion and a rodent portion). Further, such antibodies are contemplated to form functional B cell receptors on the surface of B cells in the non-human animal. A schematic summary of various rodent strains containing selected, engineered immunoglobulin heavy chain constant regions is set forth in FIG. 1A, and containing selected, engineered immunoglobulin light chain constant regions is set forth in FIG. 2A. For simplicity, human $V_H$ gene segments are not shown; only a small number of gene segments are represented schematically—for a full repertoire of possible present V(D)J gene segments see imgt.org; Lefranc, M.-P., Exp. Clin. Immunogenet., 18, 100-116 (2001); Lefranc, M.-P. and Lefranc, G., The Immunoglobulin FactsBook, Academic Press, London, 458 pages (2001); U.S. Pat. Nos. 8,642,835 and 8,697,940; or Macdonald et al. *PNAS* (2014) vol. 111 (14):5147-5152, all incorporated herein by reference in their entireties.

DNA constructs and targeting vectors containing human immunoglobulin constant region coding sequences for insertion into selected rodent immunoglobulin constant regions were created from human and mouse bacterial artificial chromosomes (BAC) using VELOCIGENE® technology (see, e.g., U.S. Pat. No. 6,586,251 and Valenzuela et al., 2003, Nature Biotech. 21(6):652-9; incorporated herein by reference) and molecular biology techniques known in the art. The methods described in this example can be employed to utilize any human immunoglobulin constant region coding sequence, or combination of coding sequences (or sequence fragments) as desired.

The targeted BAC DNA was used to electroporate mouse ES cells to create modified ES cells for generating mice that express human or chimeric mouse/human immunoglobulin constant region coding sequences as depicted in FIGS. 1A an 2A. ES cells containing appropriate modifications were identified by a quantitative TAQMAN™ assay (see, e.g., Lie and Petropoulos, 1998. Curr. Opin. Biotechnology 9:43-48, incorporated herein by reference). Specific primer sets and probes were designed for detecting insertion of human sequences (gain-of-allele, GOA) and deletion of mouse sequences (loss-of-allele, LOA).

Targeted ES cells were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing the modified allele were identified by genotyping using a modification of allele assay that detects the presence of the unique gene sequences, e.g., human gene sequences. Selected heterozygous mice bearing the modified allele were bred to homozygosity.

Example 1.1

Genetic Engineering of Mice Comprising Human Heavy Chain Variable Regions and Chimeric or Fully Human Heavy Chain Constant Regions To generate rodents that can be used for human antibody testing (e.g., pharmacokinetic and dosing studies of therapeutic antibodies), several approaches were implemented. In the first approach, mice were generated that comprised human heavy chain variable regions and heavy chain constant regions that contained either chimeric (human $C_H1$-H-$C_H2$-$C_H3$ coding sequences and mouse M1-M2 coding sequences) or fully human ($C_H1$-H-$C_H2$-$C_H3$-M1-M2 coding sequences) heavy chain constant region gene segments. Such mice could be used, for example, to test therapeutic antibodies which isotype matched the immunoglobulin constant domain (i.e., the $C_H1$-H-$C_H2$-$C_H3$ portion of the constant domain) which is encoded by the modified gene segment (e.g., testing IgG1 antibodies in mice comprising a genetically engineered IgG1 constant).

In one example, mice were constructed that comprised human heavy chain variable region sequences and a chimeric human (human $C_H1$-H-$C_H2$-$C_H3$)—mouse (mouse M1-M2) constant region sequence where the $C_H1$-H-$C_H2$-$C_H3$ coding sequence of the human IgG1 was operably linked with the M1-M2 coding sequence of mouse IgG2a at the endogenous IgG2a locus (FIG. 1A, mouse locus 1). Briefly, a plasmid was constructed using a DNA fragment that included human IgG1 $C_H1$-H-$C_H2$-$C_H3$ synthetic gene from Blue Heron and flanked by regions of overlap with a mouse IgG2a constant region gene. The resulting plasmid was cloned via several steps of digestion/ligation/CRIPSR-Cas9 isothermal assembly to generate a BAC clone so that the human IgG1 $C_H1$-H-$C_H2$-$C_H3$ sequence was operably linked to the transmembrane and cytoplasmic-encoding sequences (i.e., M1 and M2 exons) of a mouse IgG2a constant region gene. The BAC clone also contained both mouse IgG2a switch region (Sγ2a) and mouse IgE switch region (Sε), as well as mouse IgE constant region gene segment. The clone was introduced via electroporation into mouse ES cells to generate modified ES cells that could be used to generate mice comprising the immunoglobulin locus depicted in FIG. 1A, locus 1, where a nucleic acid sequence encoding human IgG1 extracellular portion of the constant domain is operably linked to a nucleic acid sequence encoding mouse IgG2a connecting, transmembrane and cytoplasmic portions of the constant domain at the endogenous mouse IgG2a locus. The remaining heavy chain constant region isotype sequences were fully mouse. The mouse ES cells used for electroporation comprised human heavy chain variable gene segments (human $V_H$, D, and $J_H$ variable gene segments) operably linked to a mouse heavy chain constant region, including inserted murine Adam6-encoding sequence; see, e.g., U.S. Pat. Nos. 8,642,835 and 8,697,940, incorporated herein by reference.

In another example, mice were constructed that comprised human heavy chain variable region sequences and fully human IgG1 constant region sequence (human $C_H1$-H-$C_H2$-$C_H3$-M1-M2) at the endogenous mouse IgG2a locus (FIG. 1A, mouse locus 2). Briefly, human M1-M2 sequences were amplified using BAC clone RP11-448n5 (Thermo Fisher Scientific) as a template, and in the course of several steps of genetic engineering introduced into the BAC clone used to generate mouse locus 1 described above in place of the endogenous mouse IgG2a M1-M2 sequence. The resultant BAC clone for use in introducing into ES cells contained a DNA fragment that contained human IgG1 $C_H1$-H-$C_H2$-$C_H3$-M1-M2 coding sequences, mouse IgG2a (Sγ2a) and IgE (Sε) switch regions, and a mouse IgE constant region gene segment. The mouse generated from the genetically modified ES cells comprised the immunoglobulin locus depicted in FIG. 1A, locus 2, where a nucleic acid sequence encoding human IgG1 constant domain replaced nucleic acid sequence encoding endogenous mouse IgG2a constant domain at the endogenous mouse IgG2a gene segment locus. The remaining heavy chain constant region isotype sequences were fully mouse. The mouse ES cells used herein comprised human heavy chain variable gene segments (human $V_H$, D, and $J_H$ variable gene segments) operably linked to a mouse heavy chain constant region, including inserted murine Adam6-encoding sequence; see, e.g., U.S. Pat. Nos. 8,642,835 and 8,697,940, incorporated herein by reference.

In yet another example, mice were constructed that comprised human heavy chain variable region sequences and a chimeric human (human $C_H1$-H-$C_H2$-$C_H3$)—mouse (mouse M1-M2) constant region sequence where the $C_H1$-H-$C_H2$-$C_H3$ coding sequence of the human IgG4 was operably linked with the M1-M2 coding sequence of mouse IgG1 at the endogenous IgG1 locus (FIG. 1A, mouse locus 3). Briefly, using BAC CTD-3034B12 (Thermo Fisher Scientific) as a template, a plasmid was constructed that included a DNA fragment encoding human IgG4 $C_H1$-H-$C_H2$-$C_H3$, flanked by regions of overlap with a mouse IgG1 constant region gene. The resulting plasmid was cloned via several steps of digestion/ligation/CRIPSR-Cas9 isothermal assembly into BMQ-263J18 (The Sanger Centre) to generate a BAC clone so that the human IgG4 $C_H1$-H-$C_H2$-$C_H3$ sequence was operably linked to the transmembrane and cytoplasmic-encoding sequences (i.e., M1 and M2 exons) of a mouse IgG1 constant region gene. This BAC clone also contained mouse IgG1 switch region (Sγ1), and a mouse IgG2b constant region gene segment. The clone was introduced via electroporation into mouse ES cells to generate modified ES cells for generating mice comprising the immunoglobulin locus depicted in FIG. 1A, locus 3, where a nucleic acid sequence encoding human IgG4 extracellular portion of the constant domain is operably linked to a nucleic acid sequence encoding mouse IgG1 transmembrane portion of the constant domain at the endogenous mouse IgG1 gene segment locus. The remaining heavy chain constant region isotype sequences were fully mouse. The mouse ES cells used for electroporation comprised human heavy chain variable gene segments (human $V_H$, D, and $J_H$ variable gene segments) operably linked to a mouse heavy chain constant region, including inserted murine Adam6-encoding sequence; see, e.g., U.S. Pat. Nos. 8,642,835 and 8,697,940, incorporated herein by reference.

In yet another example, mice were constructed that comprised human heavy chain variable region sequences and fully human IgG4 constant region sequence (human $C_H1$-H-$C_H2$-$C_H3$-M1-M2) at the endogenous mouse IgG1 locus (FIG. 1A, mouse locus 4). Briefly, human $C_H1$-H-$C_H2$-$C_H3$-M1-M2 sequences were amplified using BAC clone CTD-3034B12 (Thermo Fisher Scientific) as a template, and in the course of several steps of genetic engineering introduced into the BAC clone BMQ-263J18 (The Sanger Centre) in place of the endogenous mouse IgG1 $C_H1$-H-$C_H2$-$C_H3$-M1-M2 sequence. The resultant BAC clone for use in introducing into ES cells contained a DNA fragment that contained human IgG4 $C_H1$-H-$C_H2$-$C_H3$-M1-M2 coding sequences and a mouse IgG1 (Sγ1) switch region, and a mouse IgG2b constant region gene segment. The mouse generated from the genetically modified ES cells comprised the immunoglobulin locus depicted in FIG. 1A, 4, where a nucleic acid sequence encoding human IgG4 constant domain replaced nucleic acid encoding endogenous mouse IgG1 constant domain at the endogenous mouse IgG1 gene segment locus. The remaining heavy chain constant region isotype sequences were fully mouse. The mouse ES cells used for electroporation comprised human heavy chain variable gene segments (human $V_H$, D, and $J_H$ variable gene segments) operably linked to a mouse heavy chain constant region, including inserted murine Adam6-encoding sequence; see, e.g., U.S. Pat. Nos. 8,642,835 and 8,697,940, incorporated herein by reference.

Mice were also constructed that comprised a human heavy chain variable region and a constant region comprising fully human IgM, IgD, IgG3, and IgG1 gene segments at the endogenous mouse immunoglobulin heavy chain locus (FIG. 1A, mouse 5).

In order to generate a construct for targeting mouse ES cells that comprised human heavy chain variable regions and human heavy chain constant regions, first a construct was generated that comprised a deletion of the entire mouse IgH constant region (IgM, IgD, IgG3, IgG1, IgG2b, IgG2a, IgE, and IgA) between intronic enhancer (Eμ) and 3' regulatory region (3'RR) that was then targeted into the VELOCIMMUNE® ES Cells.

Briefly, a BAC designated 3hVh BACvec, previously described in Macdonald et al. PNAS (2014) vol. 111 (14): 5147-5152 (incorporated herein by reference) was modified by removal of the 3' mouse IgM gene of 3hVH by bacterial homologous recombination (BHR) and selection cassette swap, and removal of 5' mouse homology arm. A 3' mouse homology arm was made by two BHR modifications of BAC RP23-351j19 (Thermo Fisher Scientific), which included deletion of the mouse IgG2b, IgG2a, IgE, and IgA genes was from the 5' end of RP23-351j19, and incorporation of unique restriction sites. A restriction fragment of this second construct was ligated into the first construct to make the final LTVEC (MAID6022). MAID6022 contained from 5' to 3': EM7 hyg cassette, human IGHDs/IGHJs, mouse IgM enhancer from BAC CT7-302a07, synthetic linker, a unique I-CeuI site, a lox2372-ub-neo-lox2372 cassette with a unique AscI site 5' of the 3' lox2372 site, a 40.5 kb region of the mouse IgH locus beginning in the 3' UTR of the IgA gene and ending downstream of the 3' RR, and a unique PI-SceI site.

This vector was designated MAID6022 (FIG. 1B), and was used for introducing human heavy chain variable region sequences in the next engineering step.

Next, human DNA from BAC RP11-448n5 (Thermo Fisher Scientific) was modified by BHR to trim the 3' end of the BAC and insert a lox2372-ub-hyg-lox2372 cassette. The cassette contained a unique AscI site 5' of the 3' lox2372 site. The human-lox2372 junction was 3.7 kb downstream of the IgG1 polyA signal. This construct was designated VI694. A 3' mouse homology arm was obtained from mouse BAC RP23-351j19 Thermo Fisher Scientific via several steps of BHR and ligated onto the human BAC. The resultant BAC clone comprised the following sequences, listed in Table 1:

TABLE 1

Genome Coordinates for a Targeting Vector Used to Generate Mouse Locus 5 (MAID 6993)

| Region | Genome coordinates (mouse: GRCm38, or human: GRCh38) | kb |
| --- | --- | --- |
| 5' human homology arm | 14: 105,888,576-105,862,976 (−stand) | ~33 |
| Human | 14: 105,862,975-105,732,864 (−strand) | ~130 |
| 3' mouse homology arm | 12: 113,215,726-113,256,185 (−strand) | ~40.4 |

Figure 1B:
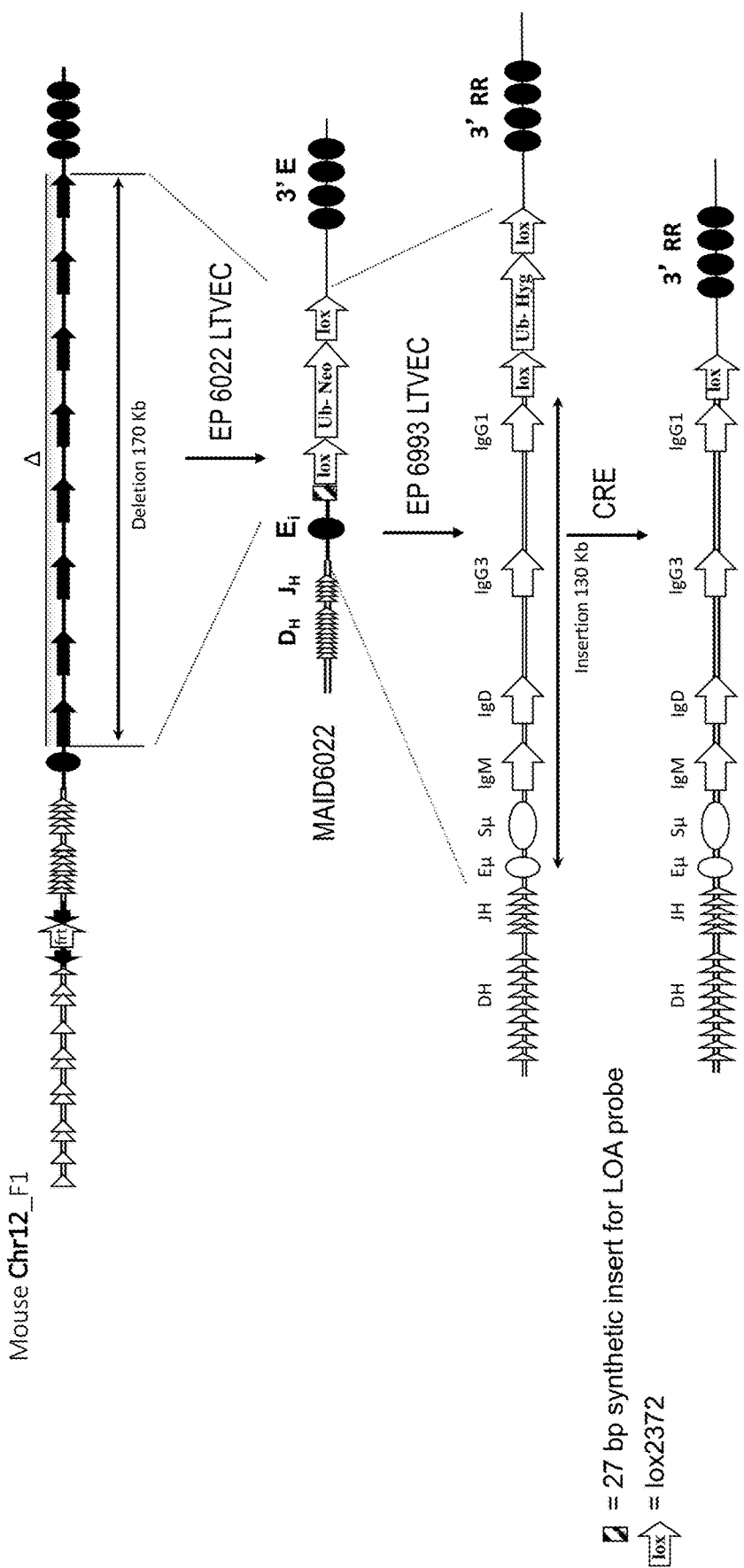
FIG. 1B shows a schematic summary, not to scale, of an exemplary method for the creation of exemplary modified immunoglobulin heavy chain locus 5 depicted in FIG. 1A as described in Example 1.1. For simplicity, human $V_H$ gene segments and mouse Adam6 gene are not shown in every schematic diagram. Unless otherwise indicated (e.g., for lox sites, etc.), empty shapes and double lines represent human sequences and filled shapes and single lines represent mouse sequences.
Figure 1C:
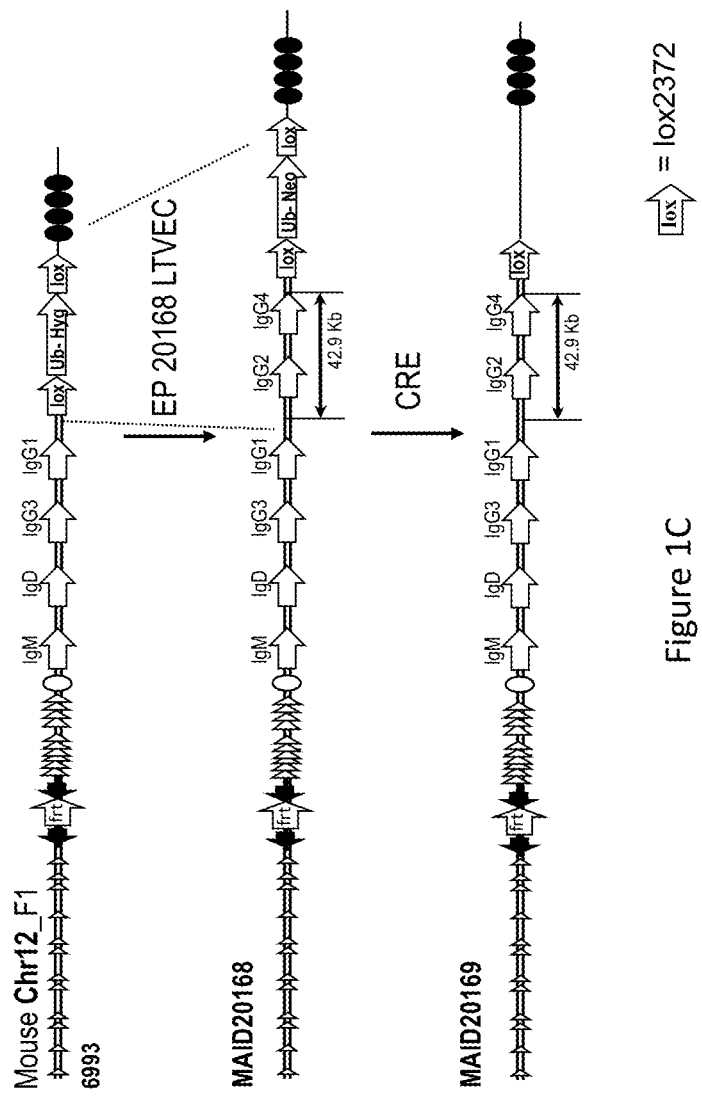
FIG. 1C shows a schematic summary, not to scale, of an exemplary method for the creation of exemplary modified immunoglobulin heavy chain locus 6 depicted in FIG. 1A as described in Example 1.1. For simplicity, human $V_H$ gene segments and mouse Adam6 gene are not shown in every schematic diagram. Unless otherwise indicated (e.g., for lox sites, etc.), empty shapes and double lines represent human sequences and filled shapes and single lines represent mouse sequences.
Figure 1D:
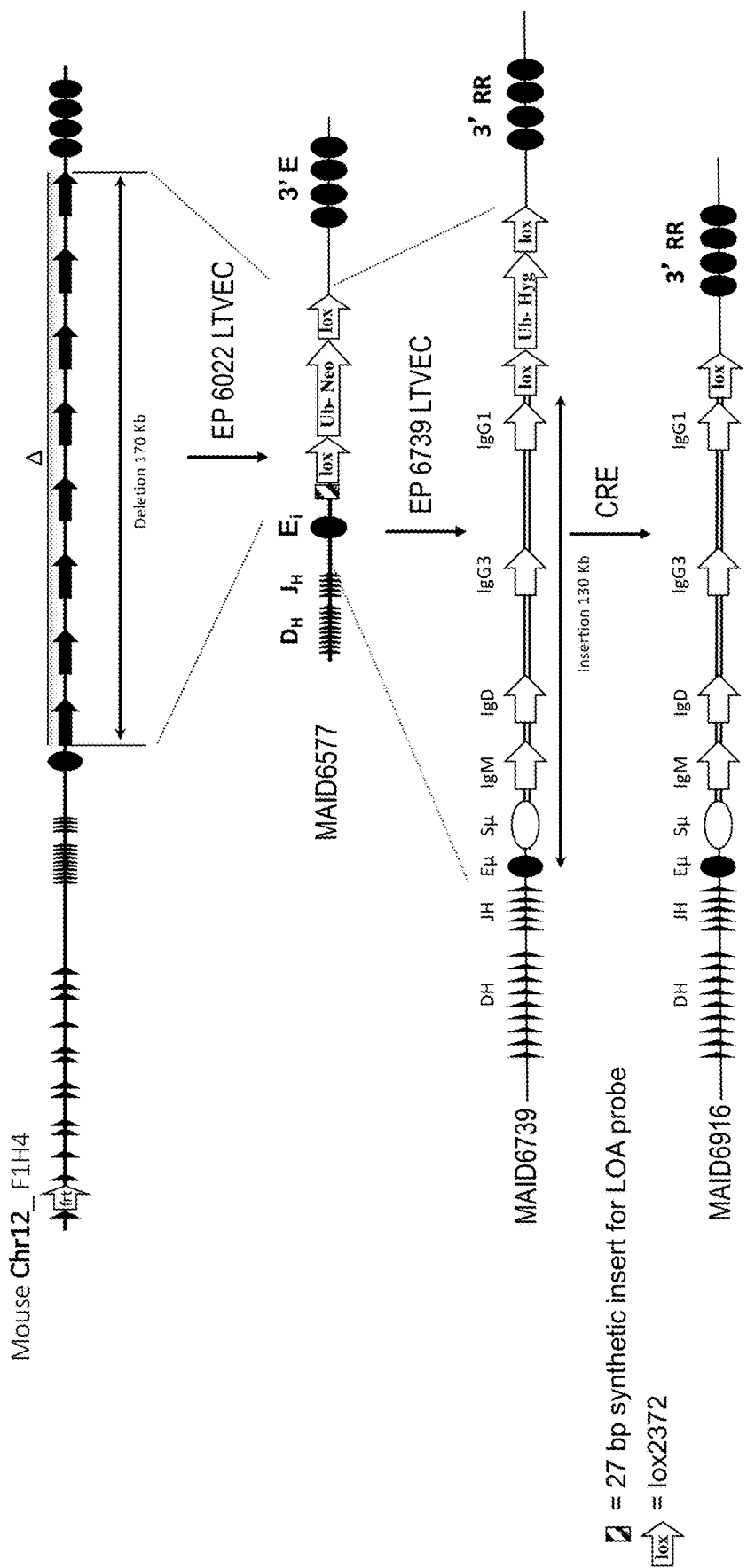
FIG. 1D shows a schematic summary, not to scale, of an exemplary method for the creation of exemplary modified immunoglobulin heavy chain locus 7 depicted in FIG. 1A as described in Example 1.2. For simplicity, mouse $V_H$ gene segments are not shown in every schematic diagram. Unless otherwise indicated (e.g., for lox sites, etc.), empty shapes and double lines represent human sequences and filled shapes and single lines represent mouse sequences.

The resultant large targeting vector was electroporated into ES cells comprising human heavy chain variable gene segments, inserted murine Adam6-encoding sequence, and a 170 Kb deletion of the mouse heavy chain constant region sequence (See FIG. 1B). Subsequent to the introduction of the human constant region sequences, the selection cassette was removed using Cre recombinase. The junction of various sequences of modified allele of the mouse locus 5 from FIG. 1A, prior to selection cassette deletion, are listed in Table 2 below.

TABLE 2

Junctions of Genetically Modified Allele of Mouse Locus 5

| Junction | Sequence | SEQ ID NO: |
| --- | --- | --- |
| 5' human homology arm/ Human gene IgM | TGGGACTCAGGTTGGGTGCGTCTGATGGAGTAACTGAGCC TGGGGGCTTGGGGAGCCACATTTGGACGAGATGCCTGAAC | 1 |

TABLE 2-continued

Junctions of Genetically Modified Allele of Mouse Locus 5

| Junction | Sequence | SEQ ID NO: |
|---|---|---|
| Human gene IgG1 sequence/ AgeI/5' lox2372 | TAACAGAGAATGGAGAATGGCGATGACTTCTACCAAGC <u>ACCGGT</u>*ATAACTTCGTATAAGGTATCCTATACGAAGTTAT* | 2 |
| AscI/3' lox2372/ XhoI/3' mouse sequence | <u>GGCGCGCC</u>*ATAACTTCGTATAAGGTATCCTATACGAAGTTAT*<u>CTCGAG</u> AGGTGGCAGTCATGGAGATGGTGGGGTACAGGGTGGGGGC | 3 |

Regular font represents mouse sequences, bold font represents human sequences, restriction enzyme sites/vector sequences are underlined, and loxp sites are in Italics.

The mouse generated from the genetically modified ES cells comprised the immunoglobulin locus depicted in FIG. 1A, locus 5, where a nucleic acid sequence encoding human IgM, IgD, IgG3, IgG1 constant region gene segments replaced nucleic acid encoding endogenous mouse heavy chain constant region gene segments at the endogenous mouse heavy chain constant region locus.

Mice were also constructed that comprised additional human heavy chain constant region sequences, such as human IgM, IgD, IgG3, IgG1, IgG2, and IgG4 sequences at the endogenous heavy chain locus. These mice, depicted in FIG. 1A, mouse 6, comprised human heavy chain variable region and fully human IgM, IgD, IgG3, IgG1, IgG2, and IgG4 sequences at the endogenous mouse immunoglobulin heavy chain locus.

Briefly, 42.9 Kb of human DNA sequence comprising IgG2 and IgG4 sequences were obtained from human BAC CTD-3034B12 (Thermo Fisher Scientific) and modified via several steps of bacterial homologous recombination, digestion and ligation to add 5' and 3' human homology arms. The genome coordinates for the resulting BAC clone are listed in Table 3 below.

TABLE 3

Genome Coordinates for a Targeting Vector Used to Generate Mouse Locus 6 (MAID 20168)

| Region | Genome coordinates (mouse: GRCm38, or human: GRCh38) | kb |
|---|---|---|
| 5' human homology arm | 14: 105,732,663-105,751,156 (−strand) | ~18.5 |
| Human gene IGG2 and IGG4 | 14: 105,614,742-105,657,695 (−strand) | ~42.9 |
| 3' mouse homology arm | 12: 113,215,726-113,256,185 (−strand) | ~40.4 |

The resultant large targeting vector was electroporated into ES cells comprising human heavy chain variable regions and human heavy chain IgM, IgD, IgG3, and IgG1 constant region gene segments of mouse locus 5 described above (see FIG. 1C). The various junctions of the resulting allele are described in Table 4 below. The selection cassette was removed by Cre recombinase.

TABLE 4

Junctions of Genetically Modified Allele of Mouse Locus 6

| Junction | Sequence | SEQ ID NO: |
|---|---|---|
| 5' human homology arm/ MreI/ Human gene IGG2 | TCTGTGCCTAGTTAACAGAGAATGGAGAATGGCGATGACTTCTACCAAGC <u>CGCCGGCG</u> ACTCATCACCAAGGGGAAGATGCTCAATCATTCATGAGGGATCTGCCCCC | 4 |
| Human gene IGG4/ AgeI/5' lox2372 | ATGCTCTTTATCTTATTAACTAAGGTGTCGTAACCAGTTCAAAGTGGAATT <u>ACCGGT</u> *ATAACTTCGTATAAGGTATCCTATACGAAGTTAT* | 5 |
| 3' lox2372/ NotI/ mouse 3' RR | *ATAACTTCGTATAAGGTATCCTATACGAAGTTAT* <u>CTCGAGGCGGCCGC</u> AGGTGGCAGTCATGGAGATGGTGGGGTACAGGGTGGGGGCAGGGGCACTC | 6 |

Regular font represents mouse sequences, bold font represents human sequences, restriction enzyme sites/vector sequences are underlined, and loxp sites are in Italics.

Figure 6:
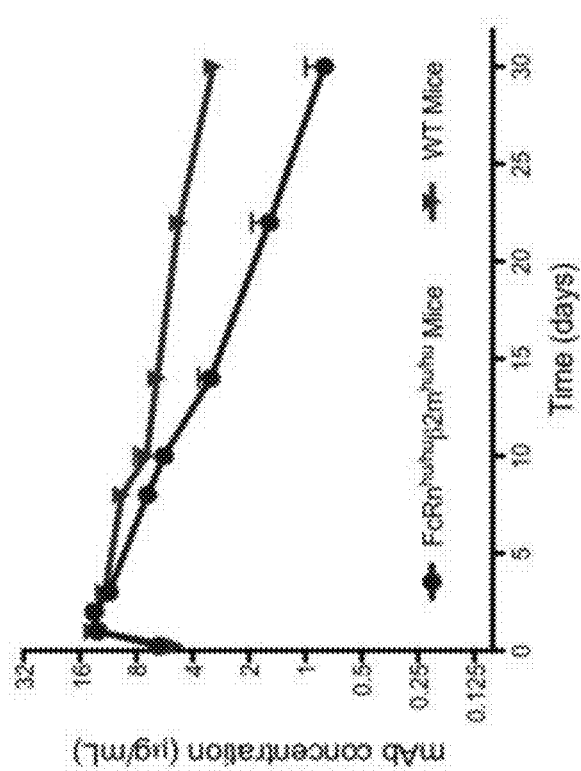
FIG. 6 shows the antibody clearance (depicted as antibody concentration) of a human antibody by mice comprising exemplary modified FcRn and β2M loci, compared to wild-type mice.

The mouse generated from the genetically modified ES cells comprised the immunoglobulin locus depicted in FIG. 1A, 6, where a nucleic acid sequence encoding human IgM, IgD, IgG3, IgG1, IgG2, and IgG4 constant region gene segments replaced nucleic acid encoding endogenous mouse heavy chain constant region gene segments at the endogenous mouse heavy chain constant region locus.

All genetically modified ES cells, comprising human heavy chain variable regions and chimeric or fully human heavy chain constant regions generated in this Example were used to make genetically modified mice using VELOCIMOUSE® method described above.

Example 1.2

Genetic Engineering of Mice Comprising Mouse Heavy Chain Variable Regions and Human Heavy Chain Constant Regions In order to generate a construct for targeting mouse ES cells that comprised mouse heavy chain variable regions and human heavy chain constant regions, first a construct was generated that comprised a deletion of the entire mouse IgH constant region (IgM, IgD, IgG3, IgG1, IgG2b, IgG2a, IgE, and IgA) between the intronic enhancer (Eµ) and the 3' regulatory region (3'RR).

Briefly, a 5.2 kb 5' mouse homology arm was amplified by PCR from BAC clone BMQ-451A16 (The Sanger Centre) and cloned using isothermal assembly into a plasmid with an R6K origin of replication and a lox2372-ub-neo cassette. The resulting plasmid contains from 5' to 3': the 392 bp R6K ori, a unique I-CeuI site, a 5.2 kb region of the mouse IgH locus including DQ52, JH1-4, and Eµ, a unique NotI site, the lox2372-ub-neo cassette, and a unique AscI site. This plasmid was digested, and a I-CeuI-AscI fragment of the plasmid was ligated into a vector derived from mouse BAC clone RP23-351j19 (Thermo Fisher Scientific) that contained from 5' to 3': a unique I-CeuI site, a lox2372-ub-hyg-lox2372 cassette with a unique AscI site 5' of the 3' lox2372 site, a 40.5 kb region of the mouse IgH locus beginning in the 3' UTR of the IgA gene and ending downstream of the 3' RR, a unique PI-SceI site, and a spectinomycin-resistance (Spec) cassette. The resulting vector contained from 5' to 3': a unique I-CeuI site, a 5.2 kb 5' mouse homology arm (including DQ52, JH1-4, and Eµ), a unique NotI site, a lox2372-ub-neo-lox2372 cassette, a 40.5 kb 3' mouse homology arm (including the IgH 3'RR), a unique PI-SceI site, and a Spec cassette. This vector (depicted as MAID6577 in FIG. 1D), was used for introducing human heavy chain variable region sequences in the next engineering step, and also for electroporation into mouse ES cells to generate ES cells with a deletion of the entire mouse entire mouse IgH constant region.

In the next engineering step, human BAC clone RP11-448n5 was modified by BHR to replace 5.3 kb of the human insert plus the CM cassette with a lox2372-ub-hyg-lox2372 cassette. The cassette contained a unique AscI site 5' of the 3' lox2372 site. The human-lox2372 junction was 3.7 kb downstream of the IgG1 polyA signal. This construct was designated VI694. Subsequently, VI694 was modified by BHR to replace 34.3 kb of the human insert with a CM cassette and unique NotI site. The NotI-human junction was 3' of Eµ and 5' of the IgM switch region (Sµ). This construct was designated VI695. The 131.7 kb NotI-AscI fragment of VI695 (human insert and lox2372-ub-hyg cassette) was ligated into MAID6577 to make the final targeting vector MAID6739 (mouse locus 7 in FIG. 1A). MAID6739 contains, from 5' to 3': a unique I-CeuI site, a 5.2 kb 5' mouse homology arm (including DQ52, JH1-4, and Eµ), a unique NotI site, a 130 kb region of the human IgH constant gene locus (including the IgM, IgD, IgG3, and IgG1 genes), a lox2372-ub-hyg-lox2372 cassette, a 40.5 kb 3' mouse homology arm (beginning in the 3' UTR of IgA, and ending 3' of the 3' RR), a unique PI-SceI site, and a Spec cassette. The genomic coordinates for the targeting vector are depicted in Table 5 and the junction sequences of the modified allele are listed in Table 6.

TABLE 5

Genomic Coordinates for a Targeting Vector Used to Generate Mouse Locus 7 (MAID 6739)

| Region | Genome coordinates (mouse: GRCm38, or human: GRCh38) | kb |
| --- | --- | --- |
| 5' mouse homology arm | Chr12: 113,432,184-113,426,948 (−strand) | ~5.2 |
| Human IgHC region | Chr14: 105,861,617-105,732,663 (−strand) | ~130 |
| 3' mouse homology arm | Chr12: 113,256,185-113,215,726 (−strand) | ~40.5 |

TABLE 6

Junctions of Genetically Modified Allele of Mouse Locus 7

| Junction | Sequence | SEQ ID NO |
| --- | --- | --- |
| 5' mouse arm/ human IgHC | TTAAATGAATGCAATTATCTAGACTTATTTCAGTTGAACATGCTGGTTGG <u>GCGGCCGC</u> TGGCATAAGAGAAAACTCAATCAGATAGTGCTGAAGACAGGACTGTGGAG | 7 |
| human IgHC/5' lox2372 | TCTGTGCCTAGTTAACAGAGAATGGAGAATGGCGATGACTTCTACCAAGC <u>ACCGGT</u> *ATAACTTCGTATAAGGTATCCTATACGAAGTTAT* | 8 |
| 3' lox2372/ 3' mouse arm | *ATAACTTCGTATAAGGTATCCTATACGAAGTTAT* <u>CTCGAG</u> AGGTGGCAGTCATGGAGATGGTGGGGTACAGGGTGGGGGCAGGGGCACTC | 9 |

Regular font represents mouse sequences, bold font represents human sequences, restriction enzyme sites/vector sequences are underlined, and loxp sites are in Italics.

The resultant large targeting vector was electroporated into mouse ES cells that comprised a deletion of the entire mouse IgH constant region (MAID 6577) in order to insert the human IgM, IgD, IgG3, and IgG1 gene segments. Selection cassette was removed by Cre recombinase.

The mouse generated from the genetically modified ES cells comprised the immunoglobulin locus depicted in FIG. 1A, locus 7, where a nucleic acid sequence encoding human IgM, IgD, IgG3, IgG1 constant region gene segments replaced nucleic acid encoding endogenous mouse heavy chain constant region gene segments at the endogenous mouse heavy chain constant region locus.

Figure 1E:
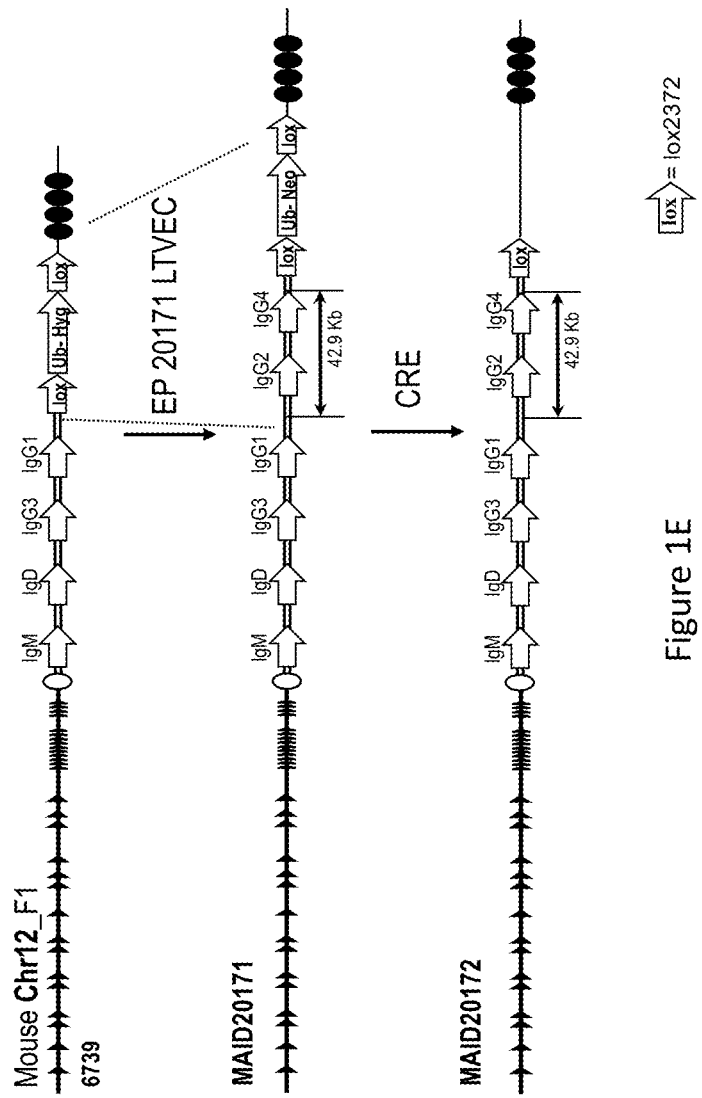
FIG. 1E shows a schematic summary, not to scale, of an exemplary method for the creation of exemplary modified immunoglobulin heavy chain locus 8 depicted in FIG. 1A as described in Example 1.2. For simplicity, mouse $V_H$ gene segments are not shown in every schematic diagram. Unless otherwise indicated (e.g., for lox sites, etc.), empty shapes and double lines represent human sequences and filled shapes and single lines represent mouse sequences.

Subsequent to generating ES cells and mice comprising the mouse locus depicted in FIG. 1A, locus 7, mice were generated that comprised additional human heavy chain constant region sequences, such as human IgM, IgD, IgG3, IgG1, IgG2, and IgG4 sequences at the endogenous heavy chain locus. These mice, depicted in FIG. 1A, locus 8, comprised mouse heavy chain variable region and fully human IgM, IgD, IgG3, IgG1, IgG2, and IgG4 region gene segments at the endogenous mouse immunoglobulin heavy chain locus. In order to generate these mice, the same targeting vectors and protocols were used as described above for constructing mouse locus 6, as depicted in FIG. 1E.

All genetically modified ES cells, comprising mouse heavy chain variable regions and chimeric or human heavy chain constant regions generated in this Example were used to make genetically modified mice using VELOCI-MOUSE® method described above.

Example 1.3

Genetic Engineering of Mice Comprising Human Light Chain Constant Regions

Genetically engineered mice comprising human light chain constant regions were generated as follows.

First, to generate a mouse comprising a human kappa light chain constant region, 0.5 Kb of human IGKC gene was synthesized by BlueHeron, and contained genomic nucleic acid sequence from 5'UTR at the distal end of IGKC gene to the 3' end downstream of the polyA tail. A loxP-Ub-Neo-loxP selection cassette was added at the 3' end of this sequence. CRISPR/Cas9 and isothermal assembly techniques were used to introduce the human IGKC sequence into mouse BAC BMQ-126m16 (The Sanger Centre). The 5' CM cassette and mouse IgKJs were then removed by BHR using a spec selection cassette. The genome coordinates of the resulting BAC clone are described in Table 7 and the junction sequences of the modified allele are listed in Table 8.

TABLE 7

Genomic Coordinates for a Targeting Vector Used to Generate a Mouse Comprising Human IgKC

| Region | Genome coordinates (mouse: GRCm38, or human: GRCh38) | kb |
|---|---|---|
| 5' mouse homology arm | 6: 707,24,056-70,726,317 (+strand) | ~2.3 |
| Human gene (5'UTR-polyA) | 2: 88,857,079-88,857,800 (−strand) | ~0.7 |
| 3' mouse homology arm | 6: 70,727,061-707,56,817 (+strand) | ~29.7 |

TABLE 8

Junctions of Genetically Modified Mouse Allele Comprising Human IgKC

| Junction | Sequence | SEQ ID NO: |
|---|---|---|
| Mouse 5' UTR/ human 5' UTR | AAACAACAAGATTGTATATATGTGCATCCTGGCCCCATTGTTCCTTATCT GGGATAAGCATGCTGTTTTCTGTCTGTCCCTAACATGCCCTGTGATTATC | 10 |
| human/ 5' loxp | TCTGTTGTTTTACCAACTACTCAATTTCTCTTATAAGGGACTAAATATGT<u>ACCGGT</u> *ATAACTTCGTATAATGTATGCTATACGAAGTTAT* | 11 |
| 3' loxp/ I-CeuI/ mouse 3' UTR | *ATAACTTCGTATAATGTATGCTATACGAAGTTAT* <u>GTCGACCTCGAG</u> AATCCACCACACTTAAAGGATAAATAAAACCCTCCACTTGCCCTGGTTGGCTGTCCACTA | 12 |

Regular font represents mouse sequences, bold font represents human sequences, restriction enzyme sites/vector sequences are underlined, and loxp sites are in Italics.

Figure 2B:
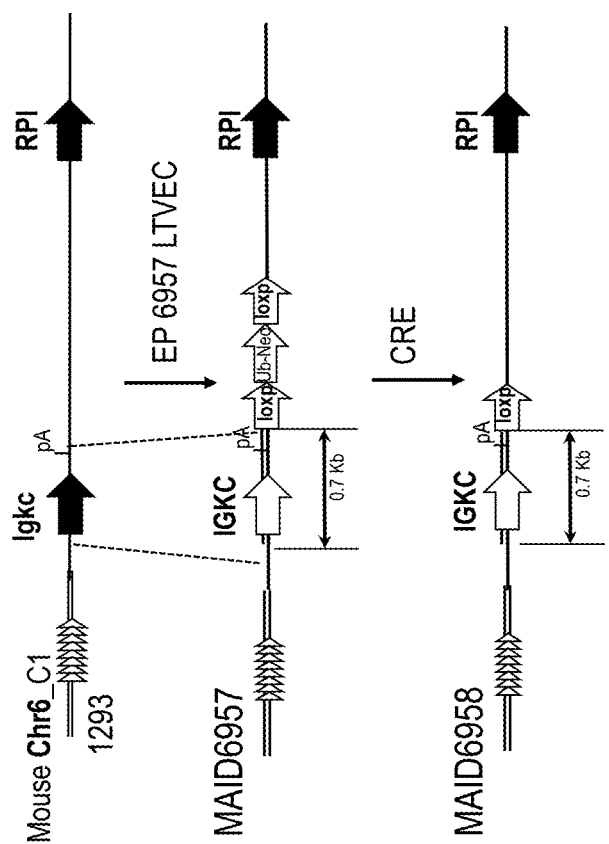
FIG. 2B shows a schematic summary, not to scale, of an exemplary method for the creation of exemplary modified immunoglobulin kappa chain locus depicted in FIG. 2A as described in Example 1.3. Unless otherwise indicated (e.g., for loxp sites, etc.), empty shapes and double lines represent human sequences and filled shapes and single lines represent mouse sequences.

As shown in FIG. 2B, the resultant large targeting vector comprising human IgKC region sequence was electroporated into ES cells comprising an immunoglobulin locus with human kappa light chain variable gene segments operably linked to a mouse constant kappa constant region (See, e.g., Macdonald et al. *PNAS* (2014) vol. 111 (14):5147-5152, incorporated herein by reference). The selection cassette was removed by Cre recombinase. The genetically modified ES cells were used to make genetically modified mice using VELOCIMOUSE® method described above.

Finally, in another example, a mouse comprising human lambda constant region sequences is described in U.S. Ser. No. 15/803,513, filed Nov. 3, 2017 (published as US 2018/0125043), incorporated herein by reference in its entirety.

Example 1.4

Generation of a Mouse Comprising Human Heavy and Light Chain Constant Regions Mice bearing an engineered heavy chain constant region, e.g., comprising either fully human or chimeric heavy chain constant region sequences at the endogenous mouse immunoglobulin heavy chain locus described in, e.g., Examples 1.1-1.2, are bred with mice comprising human IgK constant region sequence and/or human IgL constant region sequence described in Example 1.3. Breeding is performed by standard techniques recognized in the art. Mouse strains bearing desired engineered loci are screened for presence of the human heavy chain constant region sequence(s) and human light chain constant region sequence(s). Thus, mice comprising human heavy chain variable gene segment sequences and human or chimeric human/mouse heavy chain constant region sequences at the endogenous immunoglobulin heavy chain locus are bred with mice comprising human kappa light chain variable gene segment sequences and human kappa light chain constant region sequences and/or human lambda light chain variable gene segment sequences and human lambda light chain constant region sequence described in this Example.

Example 2

Mouse Models for Pharmacokinetic and Dosing Studies of Human Therapeutics

Mouse Anti-Human Antibody (MAHA), an immune response generated by a mouse against a human antibody, can result in fast clearance of circulating human monoclonal antibodies that are dosed for pharmacokinetic and/or efficacy experiments. In order to obtain more relevant PK and dosing studies of fully human antibodies in mouse models, mice comprising human IgH constant regions described in Example 1 above were tested for their ability to circumvent the MAHA response. Mice heterozygous for human IgH constant regions exhibited normal B cell development, expressed both human and mouse IgM/IgD, and demonstrated intact allelic exclusion.

In one example, mice homozygous for human heavy chain variable region and heterozygous for human IgM, IgD, IgG3, and IgG1 constant region gene segments as depicted in FIG. 1A, locus 5 were tested for reduction of MAHA response. For these experiments, all mice were housed and bred in a pathogen-free facility at Regeneron Pharmaceuticals. Naïve VELOCIMMUNE® control mice (age 16 weeks, male, n=2) and nave hVs, hIgM, hIgD, hIgG3 and hIgG1 (locus 5 in FIG. 1A, age 20 weeks, male, n=4) mice were sacrificed, and blood and spleens were harvested. Spleens were lysed with ACK lysis buffer, followed by washing with RPMI medium with 5% FBS. Blood was collected into serum separator tubes (BD, cat #365956) and serum was collected as per manufacturer's directions. Normal human serum (Quidel, cat #A113) was used as a positive control for ELISA.

Figure 3A:
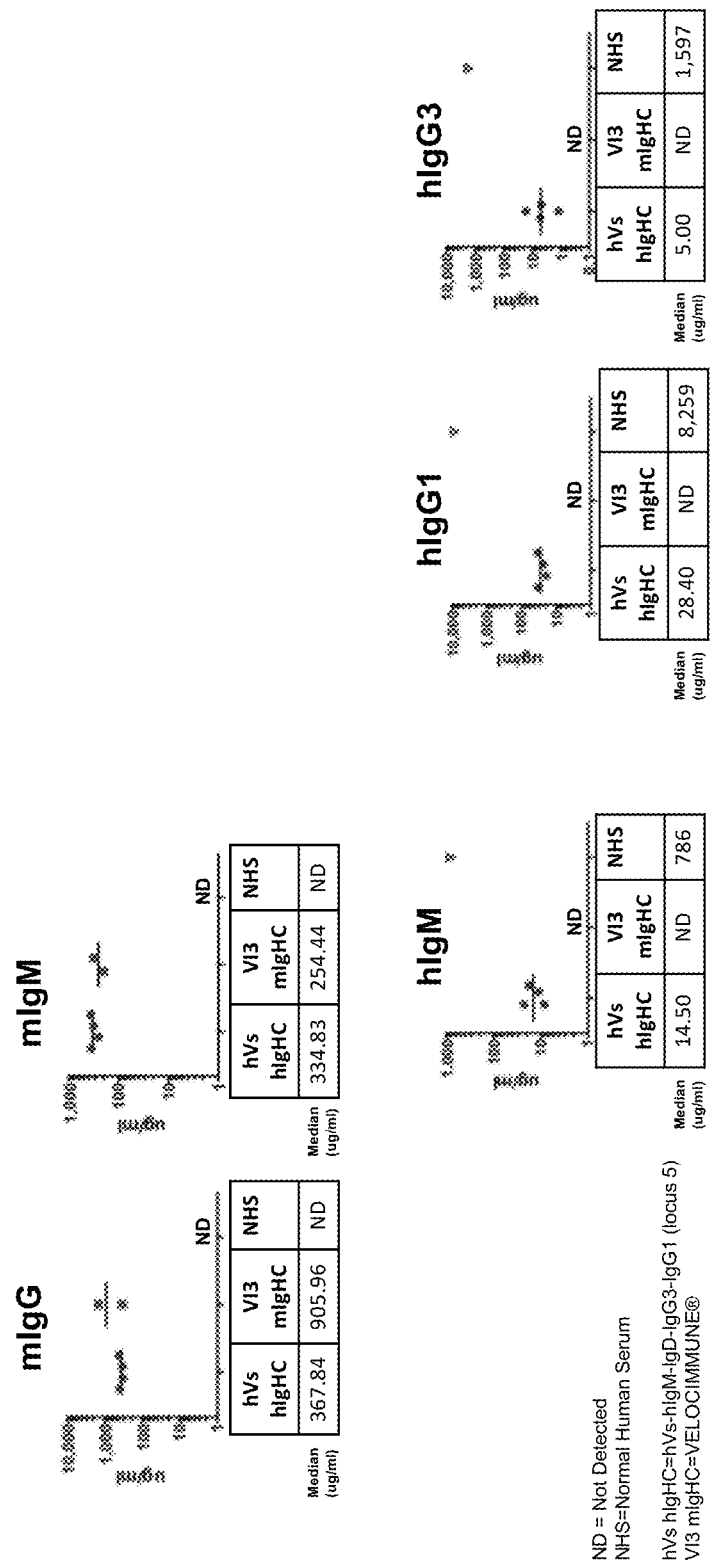
FIG. 3A shows the levels of mouse IgG, mouse IgM, human IgM, human IgG1 and human IgG3 present in the serum of hVs-hIgM-hIgD-hIgG3-hIgG1 mice (locus 5), VELOCIMMUNE® mice and in normal human serum.

Total human IgM antibody was assayed using ELISA as follows. Plates were coated overnight at 4 degrees C. with 2 ug/ml rabbit anti-human IgM antibody (Jackson ImmunoResearch cat #309-005-095), washed, blocked with 1% BSA in PBS-T. ChromPure Human IgM standard (Jackson ImmunoResearch cat #009-000-012) was serially diluted from 600 ng/ml to 0.823 ng/ml in PBS-T and added to wells. Wells were incubated with diluted serum samples, washed, and incubated with HRP conjugated-anti-human IgM antibody (Jackson ImmunoResearch #309-035-095). Plates were washed and developed with Opt EIA TMB substrate reagent set (BD cat #555214). Reaction was stopped with 1N Sulfuric Acid and blank-corrected OD was measured at 450 nm with a Molecular Devices Spectramax M5 microplate reader and SoftMax Pro software. Data was analyzed using Prism Software. Data represented are duplicate points. Further, human IgG1 and human IgG3 ELISAs were conducted according to the manufacturer's directions (Invitrogen cat #BMS2092 and BMS2094, respectively). The results for Ig isotype levels, shown in FIG. 3A, demonstrate that introduced human heavy chain constant isotypes were expressed in serum of the genetically modified mice of mouse locus 5.

Figure 3B:
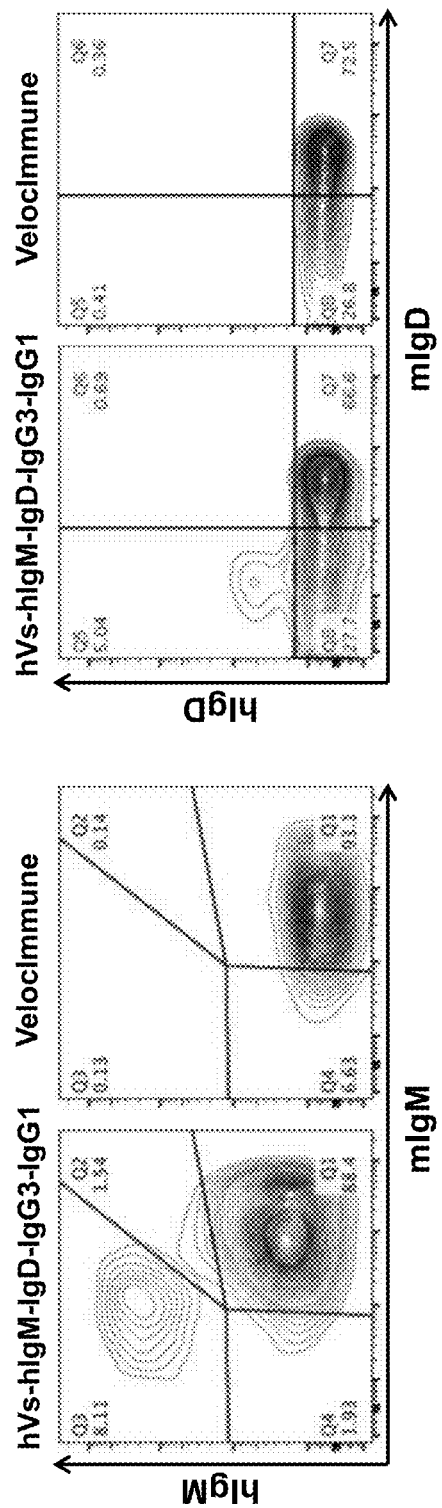
FIG. 3B shows FACS plots for hIgM vs mIgM and hIgD vs mIgD to show allele utilization and presence of allelic exclusion in hVs-hIgM-hIgD-hIgG3-hIgG1 mice (locus 5) and VELOCIMMUNE® mice.

For the flow cytometry experiments, $1\times10^6$ cells were incubated with anti-mouse CD16/CD32 (2.4G2, BD) on ice for 10 minutes. Cells were subsequently labeled with the following antibody panel for 30 min on ice: anti-mouse FITC-CD3 (17A2, BD), A700-CD19 (1D3, BD), Pe-Cy7-IgM (11/41, eBioscience), PerCP-Cy5.5-IgD (11-26c.2a, BioLegend), anti-human PE-IgD (IA6-2, BioLegend) and BV421-IgM (G20-127, BD). Following staining, cells were washed and fixed in 2% formaldehyde. Data acquisition was performed on a BD LSRFortessa flow cytometer and analyzed with FlowJo. B cells (CD19+), were plotted for hIgM vs mIgM and hIgD vs mIgD to show allele utilization and presence of allelic exclusion (FIG. 3B).

The molecular weights of the antibodies in the serum obtained from several versions of mice heterozygous for immunoglobulin human constant region (e.g., locus 1, 4, 6 and 8 mice depicted in FIG. 1A) were assayed by Western blotting. The samples were run on a 4-12% Tris-Glycine gel (Invitrogen), transferred to a membrane, blocked overnight at 4 degrees C., and then the antibodies were detected using an HRP conjugated anti-human IgG (Thermo #31412) and an HRP conjugated anti-mouse IgG (Thermo 31439) and developed with ELC Western Blotting Detection Reagents (GE Health Care #RPN2106). The Western blots showed that the molecular weights of the antibodies comprising human immunoglobulin constant region as detected by anti-human IgG antibody in serum of heterozygous human Ig constant region mice were similar to the molecular weights of the antibodies in the normal human serum (data not shown). The molecular weights of antibodies comprising mouse immunoglobulin constant region as detected by anti-mouse IgG in serum of heterozygous human Ig constant region mice were also similar when compared to the molecular weights of antibodies in the mouse serum of wild type and reverse chimeric VELOCIMMUNE® mice (data not shown).

When tested for MAHA responses against a relevant isotype antibody, mice heterozygous for hIgM, hIgD, hIgG3 and hIgG1 (locus 5) exhibited reduced MAHA responses compared to control mice (data not shown).

Figure 3C:
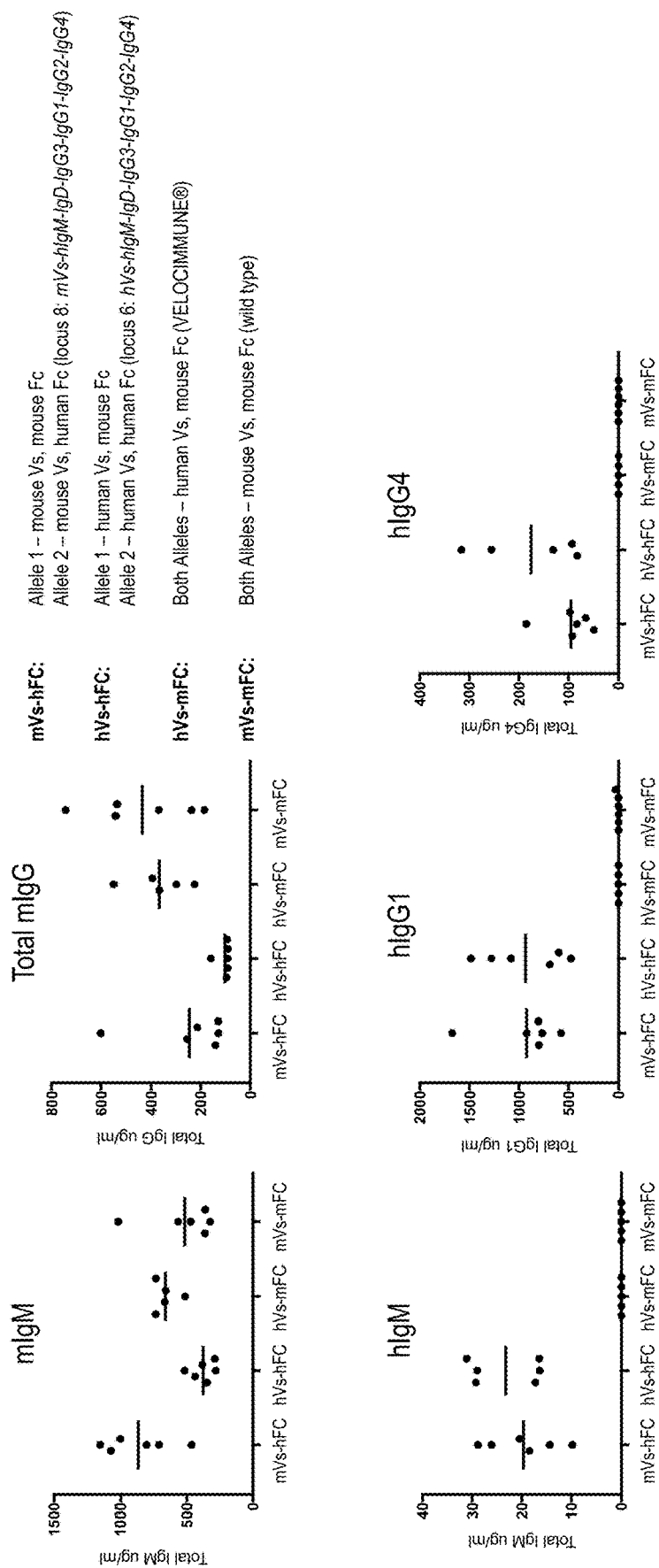
FIG. 3C shows the levels of mouse IgG, mouse IgM, human IgM, human IgG1 and human IgG4 present in the serum of mice indicated.
Figure 3D:
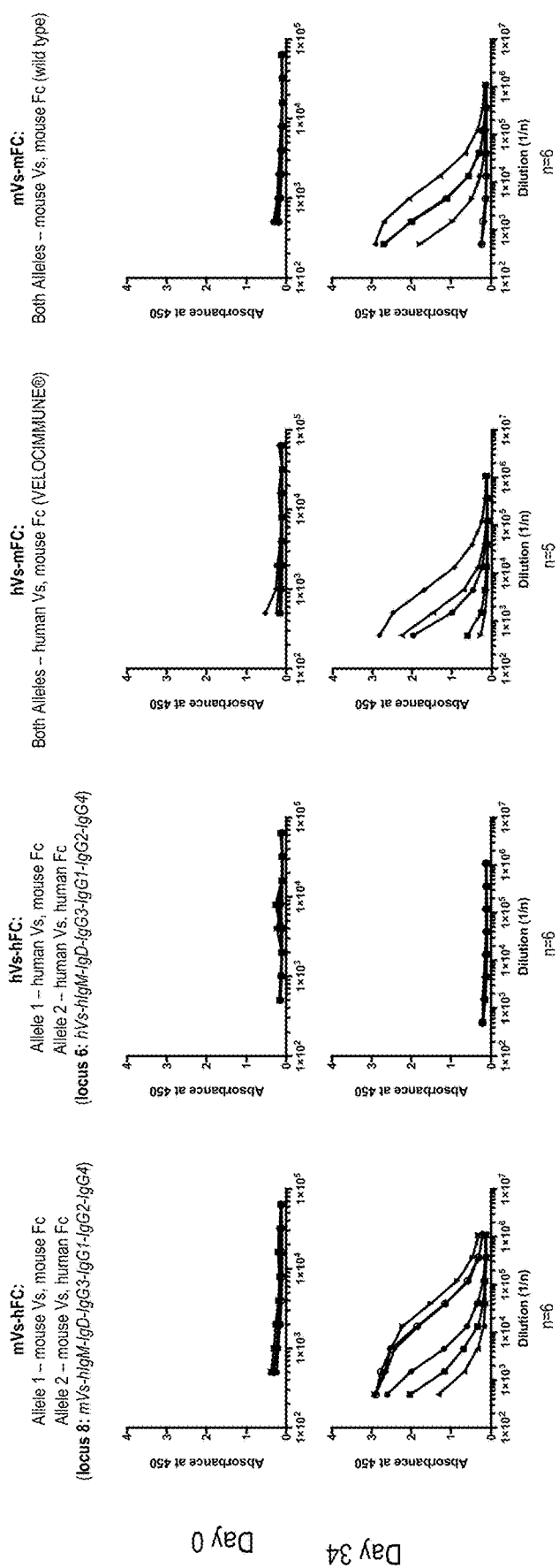
FIG. 3D shows the concentrations of mouse against human antibodies at day 0 and day 34 in the indicated mice following injection of a human IgG4 antibody.

In another example, mice homozygous for human heavy chain variable region and heterozygous for human IgM, IgD, IgG3, IgG1, IgG2, and IgG4 constant regions as depicted in FIG. 1A, locus 6, or homozygous for mouse heavy chain variable region and heterozygous for human IgM, IgD, IgG3, IgG1, IgG2, and IgG4 constant regions as depicted in FIG. 1A, locus 8, were tested for reduction of MAHA response. For these experiments, all mice were housed and bred in the specific pathogen-free facility at Regeneron Pharmaceuticals. Both mice comprising (1) mouse heavy chain variable region and human heavy chain constant region (mVs-hFC; mouse locus 8 in FIG. 1A) and (2) human heavy chain variable region and human heavy chain constant region (hVs-hFC; mouse locus 6 in FIG. 1A) were homozygous for mouse or human variable region, respectively, and heterozygous for human heavy chain constant region. The VELOCIMMUNE® mice (hVs-mFc; see U.S. Pat. Nos. 8,642,835 and 8,697,940, incorporated herein by reference) were homozygous for human heavy chain variable region and homozygous for mouse heavy chain constant region. Naïve WT control mice (age 15 weeks, female, n=6); hVs-mFc mice (age 14 weeks, male, n=5); hVs-hFc mice: human variables, hIgM, hIgD, hIgG3, hIgG1, hIgG2, and hIgG4 mice (age 11 weeks, male, n=6); and mVs-hFc: mouse variables, hIgM, hIgD, hIgG3, hIgG1, hIgG2, and hIgG4 mice (age 11 weeks, female, n=6) were bled before the antibody injection in order to determine serum antibody isotype concentrations (FIG. 3C) and initial mouse against human antibody titers (FIG. 3D, day 0). Blood was collected into serum separator tubes (BD, cat #365956) and serum was collected as per manufacturer's directions. A fully human IgG4 antibody was injected subcutaneously at a concentration of 1 mg/kg diluted in Dulbecco's PBS. The mice were bled at 7 days, 15 days, 22 days, and 34 days after injection to test for MAHA (FIG. 3D; only day 34 data is shown).

Measurements of total antibody isotype (mouse IgM, total mouse IgG, human IgM and human IgG1, and human IgG4 ELISAs were conducted according to the manufacturer's directions (Invitrogen, mIgM: 88-50470-88, total mIgG: 88-50400-88, hIgM: 8850620-88, hIgG1: 88-50560-22, hIgG4: 88-50590-22). The majority of the mice characterizations are summarized in FIG. 3C (some data are not shown). In sum, there appeared to be similar serum levels for mouse IgM and IgG between the humanized Fc mice and wild type mice, and the levels of hIgM, hIgG1, and hIgG4 were similar between the two versions of humanized heavy chain constant region mice (mVs-hFc: locus 8, and hVs-hFc: locus 6).

For MAHA studies, heterozygous mice were given a single subcutaneous injection of a hIgG4 antibody and then MAHA ELISAs were run as described below. Maxisorb plates (Nunc cat. #430341) were coated overnight at 4 degrees C. with 1 ug/ml dosed human IgG4 antibody, blocked, and incubated overnight with diluted serum samples, followed by incubation with HRP conjugated-anti-mouse IgG antibody (Jackson ImmunoResearch, code #115-035-164) for 1HR at room temp. Plates were developed with Opt EIA TMB substrate reagent set (BD cat #555214). Reaction was stopped with 1N Sulfuric Acid and OD was measured at 450 nm with a Molecular Devices Spectramax M5 microplate reader and SoftMax Pro software. Data was analyzed using Prism Software.

As shown in FIG. 3D, mice with humanized IgH variables and IgH constants (hVs-hIgM-hIgD-hIgG3-hIgG1-hIgG2-hIgG4; locus 6), have significantly lower MAHA titers against a fully human IgG4 antibody on day 34 post-injection as compared to any of the other three mice tested. Reduced MAHA responses were also observed in other mice (e.g., other mice depicted in FIG. 1A) comprising human heavy chain variable regions and either chimeric mouse-human (when human antibody injected was the same as the humanized constant gene) or fully human heavy chain constant region (data not shown).

The concentration of dosed antibody remaining in the serum was determined by ELISA on serum at day 0, 2 days, 7 days, 15 days, 22 days and 34 days for the same mice as described in FIG. 3D above. Maxisorb plates (Nunc cat. #430341) were coated overnight at 4 degrees C. with 1 ug/ml of the antigen, blocked with BSA in PBS, and incubated with diluted serum samples, followed by incubation with HRP conjugated-anti-human IgG antibody (Jackson ImmunoResearch, code #109-035-098) for 1HR at room temp. Plates were developed with Opt EIA TMB substrate reagent set (BD cat #555214). Reaction was stopped with 1N Sulfuric Acid and OD was measured at 450 nm with a Molecular Devices Spectramax M5 microplate reader and SoftMax Pro software. Data was analyzed using Prism Software. The concentration was determined using the dosed antibody as the standard.

Figure 3E:
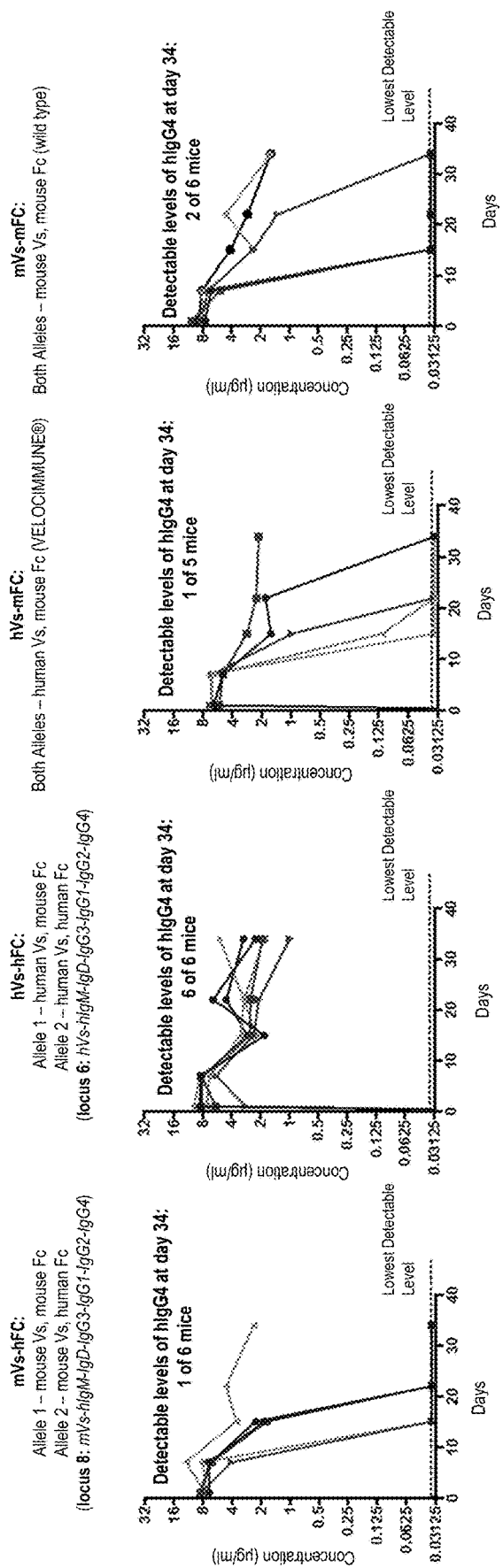
FIG. 3E shows the concentrations of human IgG4 antibody in the indicated mice during the first 34 days following its injection.

Mice that had a strong MAHA response had faster clearance of the dosed antibody compared to mice with no MAHA response (FIG. 3E). The number of mice that had a MAHA response from each genotype is as follows; 5 of 6 mice with mVs-hFc, 0 of 6 mice with hVs-hFC, 4 of 5 mice with hVs-mFc, and 4 of 6 mice with mVs-mFc. Mice with no MAHA response still had detectable levels of the dosed antibody in serum at day 34.

Example 3

A Mouse Comprising Humanized Neonatal Fc Receptor (FcRn) as an In Vivo Model for Studying Human Antibody Recycling The mouse FcRn locus, located on mouse chromosome 7, was humanized by construction of unique targeting vectors from human and mouse bacterial artificial chromosomes (BAC) DNA using VELOCIGENE® technology (see, e.g., U.S. Pat. No. 6,586,251 and Valenzuela et al. (2003)), High-throughput engineering of the mouse genome couple with high-resolution expression analysis. Nat. Biotech. 21(6): 652-659, both incorporated herein by reference). DNA from mouse BAC RP23-19D22 (Invitrogen-Thermo Fisher) was modified by homologous recombination to delete 8.3 Kb of mouse genomic DNA encoding the extracellular portion of mouse FcRn and subsequently to insert 11.5 Kb of corresponding human FcRn sequence. Thus, the mouse exons encoding alpha 1, alpha 2, and alpha 3 domains (exons 3, 4, and 5) of the mouse FcRn gene were replaced with human exons encoding alpha 1, alpha 2, and alpha 3 domains (exons 3, 4, and 5) of the human FcRn gene (see FIG. 4). The resulting chimeric FcRn gene comprised mouse exon 1 (non-coding exon), mouse exon 2 (comprising nucleic acid sequence encoding the signal peptide), human exons 3-6, mouse exons 6 and 7 (encoding transmembrane and cytoplasmic domains).

Specifically, to generate humanized FcRn mice, the large targeting vector used in construction of the chimeric gene comprised the nucleic acid sequences listed in Table 9 below. LoxP-Ub-Neo-LoxP cassette was inserted in intron 5 of the vector.

TABLE 9

Genome Coordinates for the FcRn Large Targeting Vector DNA

| Region | Genome coordinates (mouse: GRCm38, or human: GRCh38) | kb |
|---|---|---|
| 5' mouse homology arm | 7: 45,165,536-45,102,749 (−strand) | ~63 |
| Human region (ectodomain) | 19: 49,513,756-49,525,253 (+strand) | ~11.5 |
| 3' mouse homology arm | 7: 45,094,477-44,974,225 | ~120 |

The targeted BAC DNA was used to electroporate mouse ES cells comprising a deletion in mouse FcRn exons to create modified ES cells for generating mice that express humanized FcRn (FIG. 4). ES cells containing insertions of human FcRn exon sequences were identified by a quantitative TAQMAN™ assay (see, e.g., Lie and Petropoulos, 1998. Curr. Opin. Biotechnology 9:43-48, incorporated herein by reference).

Specific primer sets and probes were designed for detecting insertion of human sequences (gain-of-allele, GOA) and deletion of mouse sequences (loss-of-allele, LOA) (not shown).

The selection cassette may be removed by methods known by the skilled artisan. For example, ES cells bearing the humanized FcRn locus may be transfected with a construct that expresses Cre in order to remove floxed cassette. The selection cassette may optionally be removed by breeding to mice that express Cre recombinase. Optionally, the selection cassette is retained in the mice. The junctions of the humanized FcRn allele prior to the selection cassette deletion are presented in Table 10 below.

TABLE 10

Junctions of the Humanized FcRn allele

| Junction | Sequence | SEQ ID NO: |
|---|---|---|
| mouse/<br>human<br>(intron 2) | CTTTCTGGGTGTCTGTCCCCTTCTCTCTGGAGGATCATGGCACTTCAGAT<br>CTGTCCCCTCTCTCTGAATCTGTCCCCCTCCCTCCATAATAGATTCTTCT | 13 |
| human/<br>5' loxp<br>(intron 5) | TCTCCCCACTGCACTGGCACAGCCCCGCCTTGCCGCTGCTGATCCATTGCCGGTGTGACC<br><u>CGGGCTCGATAACTATAACGGTCCTAAGGTAGCGACTCGAG</u><br>*ATAACTTCGTATAATGTATGCTATACGAAGTTAT* | 14 |
| 3' loxp/<br>mouse<br>(intron 5) | *ATAACTTCGTATAATGTATGCTATACGAAGTTAT*<br><u>CCTAGGTTGGAGCTC</u><br>GTGTGAGAGGGGAGAGCAGAGGTGAGTCTGTGCCATGGGATACTTGTGGCG | 15 |

Bold sequences represent human DNA, underlined sequences are restriction enzyme sites or vector sequences, italicized sequences are loxP site sequences.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a humanized FcRn were identified by genotyping using a modification of allele assay (see above) that detects the presence of the unique human FcRn gene sequences. Heterozygous mice bearing a chimeric FcRn gene were bred to homozygosity.

The sequence of the resultant chimeric FcRn protein expressed by the genetically modified mice is depicted below (SEQ ID NO:16), with alpha 1, 2, and 3 domains italicized and the signal peptide and transmembrane domain bolded and underlined. The mature chimeric protein starts at amino acid 22 of the sequence depicted below, and the mouse-human and human-mouse boundaries are designated with an asterisk(*). For reference, exemplary Genbank Accession Numbers for human and mouse protein and mRNA sequences are listed in Table 11 below.

SEQUENCE OF CHIMERIC PROTEIN
(SEQ ID NO: 16)
MGMPLPWALS LLLVLLPOTW GS\*ESHLSLLY HLTAVSSPAP

GTPAFWVSGW LGPQQYLSYN SLRGEAEPCG AWVWENQVSW

YWEKETTDLR IKEKLFLEAF KALGGKGPYT LQGLLGCELG

PDNTSVPTAK FALNGEEFMN FDLKQGTWGG DWPEALAISQ

RWQQQDKAAN KELTFLLFSC PHRLREHLER GRGNLEWKEP

PSMRLKARPS SPGFSVLTCS AFSFYPPELQ LRFLRNGLAA

GTGQGDFGPN SDGSFHASSS LTVKSGDEHH YCCIVQHAGL

AQPLRVEL*DS SARS<u>SVPVVG</u> IVLGLLLVVV AIAGGVLLWG

RMRSGLPAPW LSLSGDDSGD LLPGGNLPPE AEPQGANAFP ATS

TABLE 11

Genbank Accession Numbers for FcRn (FCGRT)

| Species | Protein | mRNA |
|---|---|---|
| mouse | NP_034319 | NM_010189 |
| human | NP_001129491 | NM_001136019 |

Mice comprising a chimeric FcRn gene were bred with mice comprising a humanized B2M gene at the endogenous mouse B2M locus (FIG. 5), described in detail in U.S. patent application publication No. 2013/0111617, incorporated herein in its entirely by reference. Mice were bred for homozygosity at both loci.

To detect expression of chimeric FcRn and humanized B2M, mice were sacrificed, and spleens collected. After treatment with ACK lysis buffer (Gibco), the spleens were dissociated, cells centrifuged, washed and placed in plates, and fixed with IC Fixation Buffer (eBioscience), and permeabilized with buffer containing Fc block (BD) to prepare for staining. To detect FcRn, cells were stained with either in-house anti-human FcRn primary antibody or anti-mouse FcRn primary antibody (R&D AF6775), followed by staining with an appropriate secondary antibody (ThermoFisher 1885920 or ThermoFisher 1915848). Cells were washed and samples analyzed on a LSRFortessa X-20 (BD) FACS machine. To detect B2M, cells were stained with either anti-mouse B2M PE-Labelled antibody (BioLegend clone A16041A) or anti-human B2M PE-labelled antibody (BioLegend clone 2M2). Cells were washed and samples analyzed on a LSRFortessa X-20 (BD) FACS machine.

Humanized FcRn/B2M mice expressed detectable levels of the chimeric protein (data not shown). However, since human FcRn cannot bind mouse IgG, it was determined that mice homozygous for human FcRn and humanized B2M exhibited significantly reduced levels of mouse IgG in the blood (data not shown). Humanized FcRn/B2M mice expressed a humanized B2M protein (data not shown).

It is known that mouse FcRn binds human Ig with higher affinity than human FcRn. To test whether the mice expressing chimeric mouse/human FcRn exhibited human antibody recycling properties similar to that of humans, three of each wild type mice and mice homozygous for the chimeric FcRn and humanized B2M described above were dosed with human IgG4 antibody subcutaneously at 1 mg/kg, and antibody drug levels in serum were measured at 6 hours, 1, 2, 3, 8, 10, 14, 22, and 30 days post injection using a Gyros immunoassay. As shown in FIG. 6, mice homozygous for both chimeric FcRn (FcRn hu/hu) and humanized B2M (B2M hu/hu) demonstrated a faster antibody clearance than wild type mice that did not express humanized proteins. Therefore, mice expressing chimeric FcRn and humanized B2M serve as a model for studying human therapeutic antibody recycling that is more similar to that of a human, and therefore, serve as a great model to study pharmacokinetic and pharmacodynamic profile of a therapeutic.

Example 4

A Mouse Comprising Humanized High and Low Affinity FcGamma Receptors and Human Heavy Chain Immunoglobulin Constant Regions Humanized mice comprising high and low affinity Fcγ receptors and humanized constant regions were generated. For these experiments, mice comprising high affinity Fcγ receptors and low affinity Fcγ receptors (the generation of these mice were described in U.S. Pat. Nos. 8,658,154; 9,056,130; 8,658,853; 8,883,496; 9,687,566; 9,089,599; 9,221,894 and 9,474,255, which are incorporated herein by reference in the entirety) were combined together with mice comprising human heavy chain constant regions (e.g., mouse locus 7 in FIG. 1A) by breeding or retargeting ES cells in accordance with the known techniques in the art. The resultant mice are bred to homozygosity. Various exemplary embodiments of the humanized loci described herein are presented in FIG. 7.

Upon completion of gene targeting, ES cells or genetically modified non-human animals were screened to confirm successful incorporation of exogenous nucleotide sequence of interest or expression of exogenous polypeptide. Numerous techniques are known to those skilled in the art, and include (but are not limited to) Southern blotting, long PCR, quantitative PCR (e.g., real-time PCR using TAQMAN), fluorescence in situ hybridization, Northern blotting, flow cytometry, Western analysis, immunocytochemistry, immunohistochemistry, etc. For example, mice bearing the genetic modification of interest, i.e. human high affinity FcgR and low affinity FcgR and human heavy chain constant regions, can be identified by screening for gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

Figure 7:
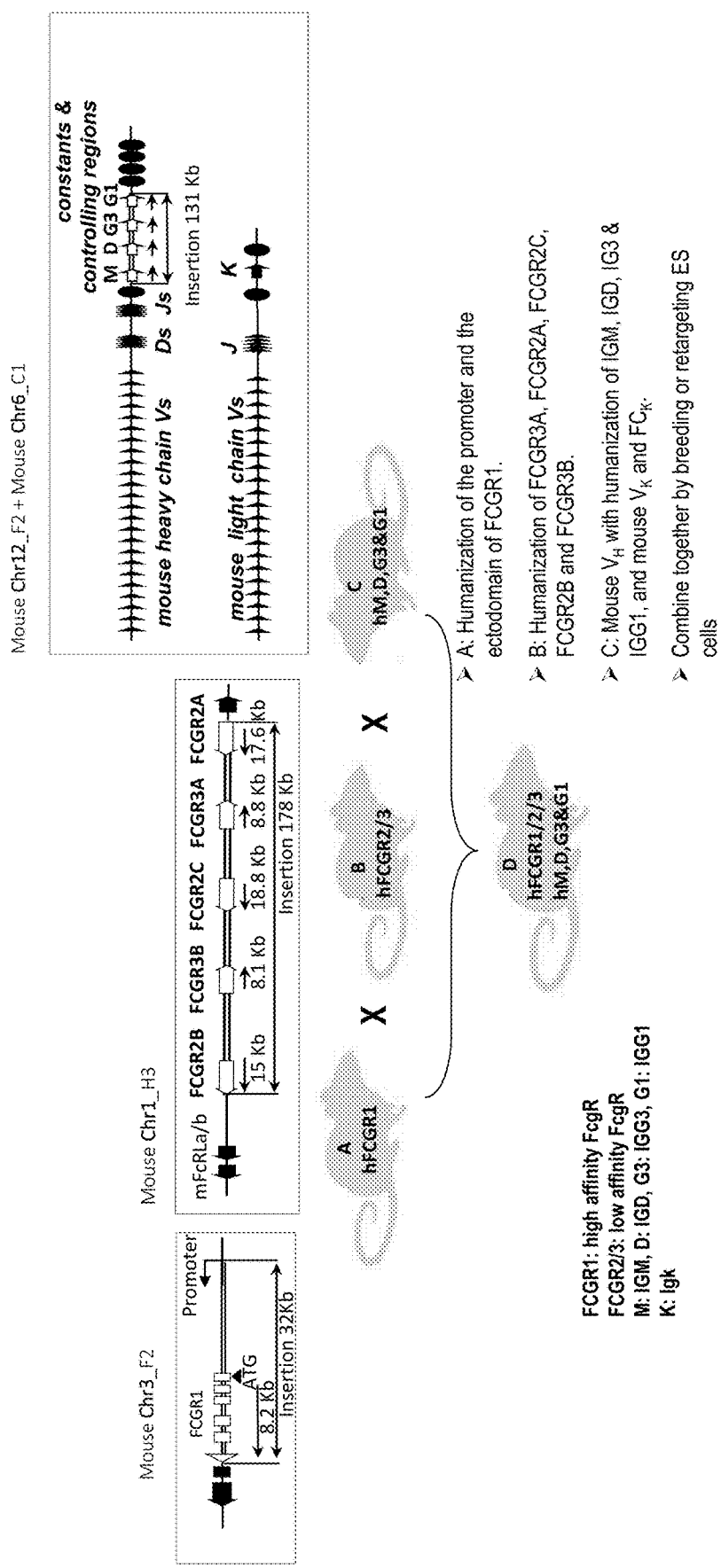
FIG. 7 shows a schematic summary, not to scale, of an exemplary method for the creation of mice comprising exemplary modified FcγR1α (shown as FCGR1 in the figure), FcγRIIIa, FcγRIIa, FcγRIIc, FcγRIIb, FcγRIIIb and heavy chain loci as described in Example 4. Empty shapes and double lines represent human sequences and filled shapes and single lines represent mouse sequences.

Once breedings or ES cells retargeting were complete as described in FIG. 7, the resultant mice were characterized. For these experiments, all mice were housed and bred in the specific pathogen-free facility at Regeneron Pharmaceuticals. Naïve WT control mice (age 26-36 weeks, male and female, n=2) and nave high- and low-affinity hFcgR, hIgM, hIgD, hIgG3 & hIgG1 (locus 7 in FIG. 1A, age 19-22 weeks, male and female, n=5) mice were sacrificed, and blood and spleens were harvested. Red blood cells from blood and spleens were lysed with ACK lysis buffer, followed by washing with RPMI medium with 5% FBS. Blood was also collected into serum separator tubes (BD, cat #365956) and serum was collected as per manufacturer's directions. Normal human serum (Quidel, cat #A113) was used as a positive control for ELISA.

Total human IgM antibody was assayed using ELISA as follows. Plates were coated overnight at 4 deg C. with 2 ug/ml donkey anti-human IgM antibody (Jackson ImmunoResearch cat #709-005-073), washed, blocked with 1% BSA in PBS-T. ChromPure Human IgM standard (Jackson ImmunoResearch cat #009-000-012) was serially diluted from 500 ng/ml to 0.49 ng/ml in PBS-T and added to wells. Wells were incubated with diluted serum samples, washed, and incubated with HRP conjugated-anti-human IgM antibody (Jackson ImmunoResearch #009-035-073. Plates were washed and developed with Opt EIA TMB substrate reagent set (BD cat #555214). Reaction was stopped with 1N Sulfuric Acid and blank-corrected OD was measured at 450 nm with a Molecular Devices Spectramax M5 microplate reader and SoftMax Pro software. Data was analyzed using Prism Software. Data represented are duplicate points. Further, human IgG1 and human IgG3 ELISAa were conducted according to the manufacturer's directions (Invitrogen cat #BMS2092 and BMS2094, respectively). (FIG. 8C)

For the flow cytometry experiments, $1\times10^6$ cells were stained with Fixable Viability Dye eFluor 455UV (ThermoFisher cat #65-0868-14) and following washing were incubated with anti-mouse CD16/CD32 (2.4G2, BD) on ice for 10 minutes. Cells were subsequently labeled with the following antibody panel for 30 min on ice: anti-mouse FITC-CD3 (17A2, BD), A700-CD19 (1D3, BD), Pe-Cy7-IgM (11/41, eBioscience), PerCP-Cy5.5-IgD (11-26c.2a, BioLegend) and anti-human PE-IgD (IA6-2, BioLegend) and BV421-IgM (G20-127, BD). Following staining, cells were washed and fixed in 2% formaldehyde. Data acquisition was performed on a BD LSRFortessa flow cytometer and analyzed with FlowJo. B cells (CD19+), mature B cells (CD19+ IgD-high IgM-int), transitional/immature B cells (CD19+ IgD-int IgM-high). (FIGS. 8A and 8B).

Figure 8A:
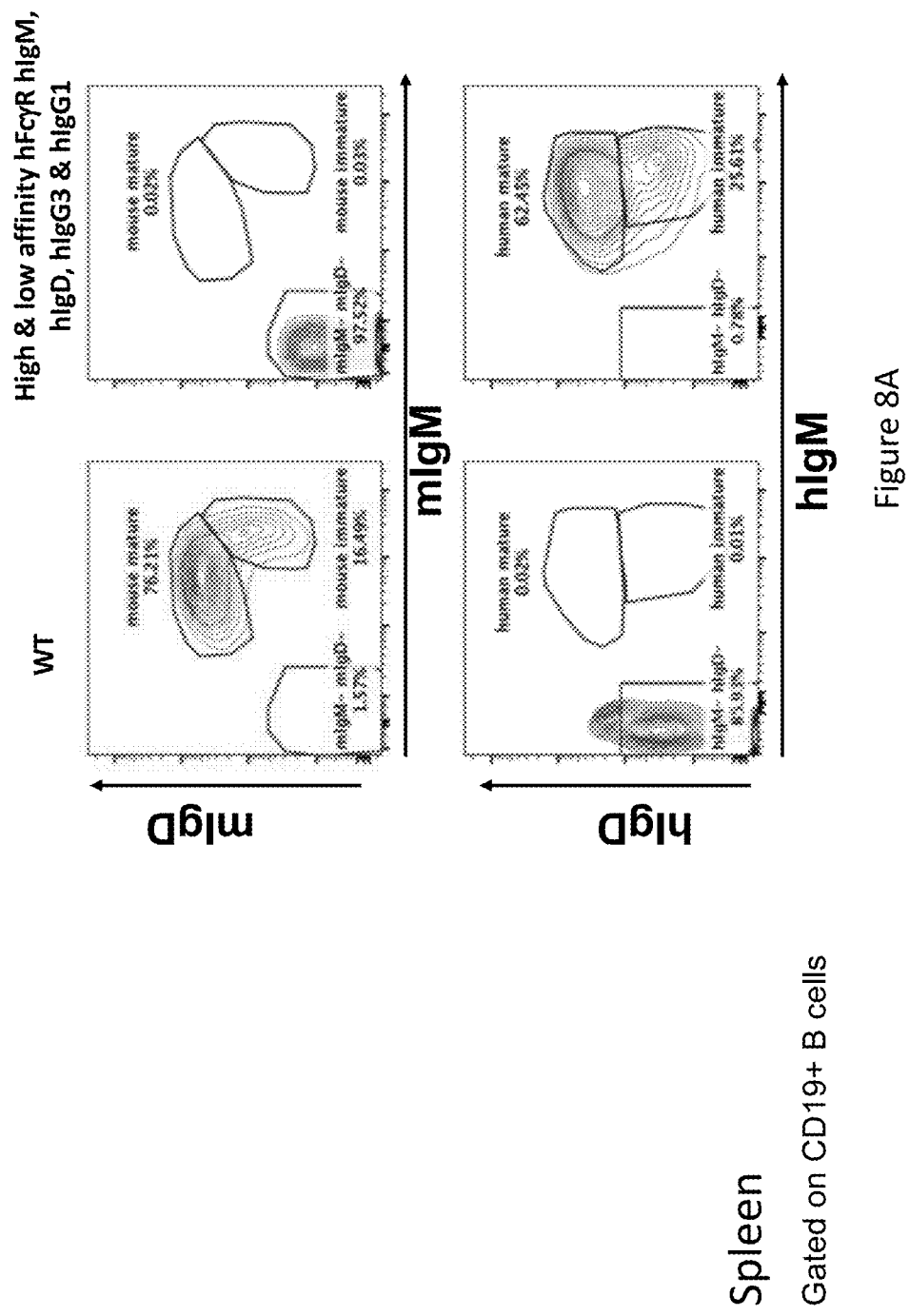
FIG. 8A shows FACS plots depicting the utilization of mouse IgD vs mouse IgM, human IgD vs human IgM in mice bearing human high affinity FcγR and human low affinity FcγR and human heavy chain constant regions.
Figure 8B:
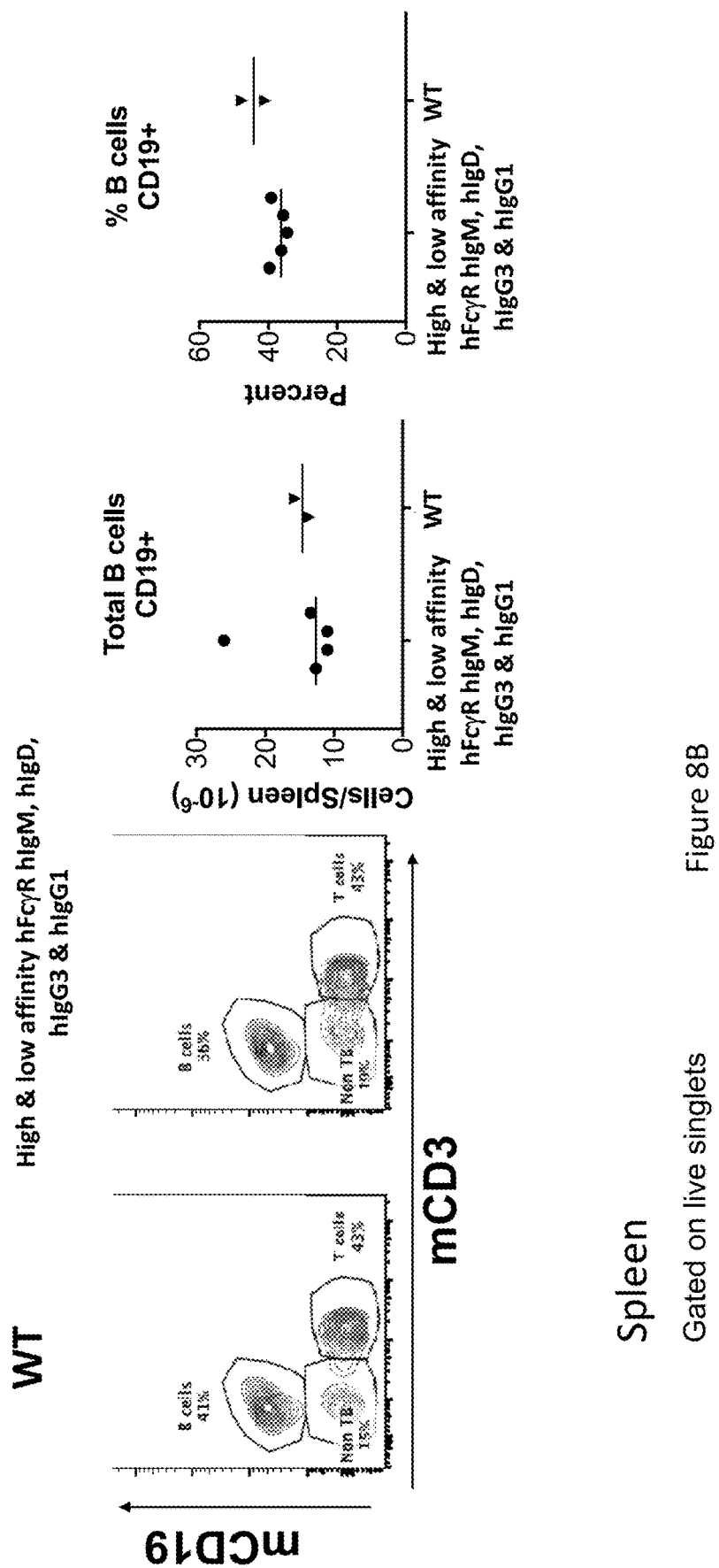
FIG. 8B shows the number or percentage of T cells (mCD3 positive) and B cells (mCD19 positive) present in the spleens of mice bearing human high affinity FcγR and human low affinity FcγR and human heavy chain constant regions compared to wild-type mice.
Figure 8C:
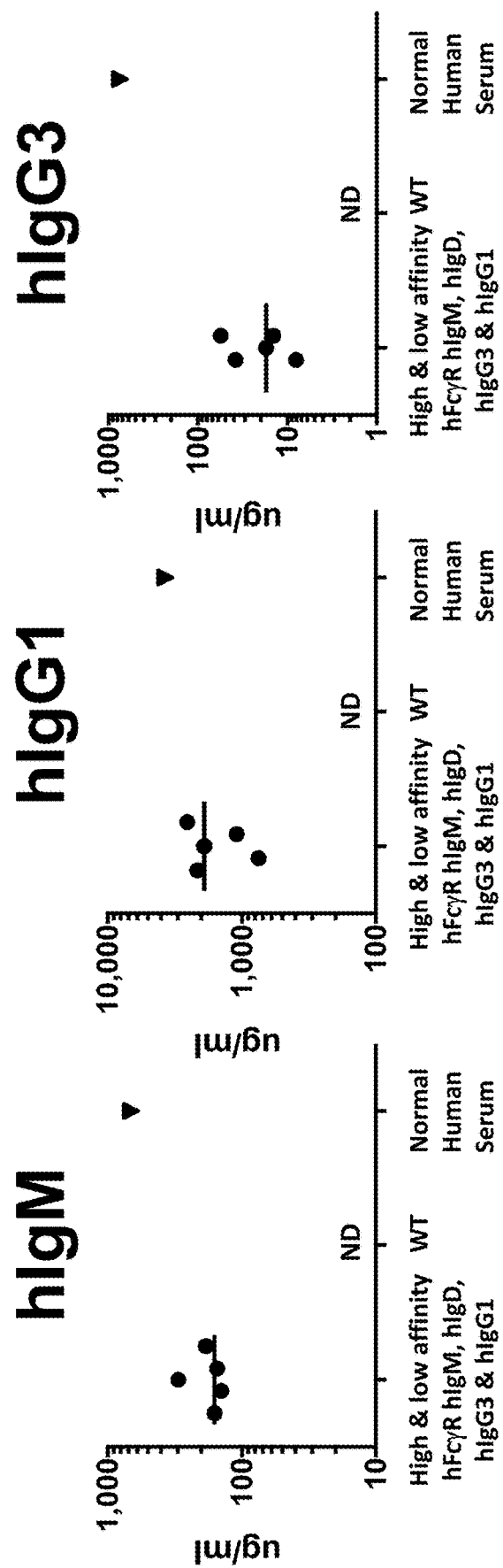
FIG. 8C shows the serum concentration of human IgM, human IgG1 and human IgG3 in mice bearing human high affinity FcγR and human low affinity FcγR and human heavy chain constant regions compared to normal human serum.

As summarized in FIGS. 8A, 8B, and 8C, there is significant gain of human IgM and human IgD surface expression in B cells of humanized high and low affinity Fcγ receptors and humanized IgM, IgD, IgG3 and IgG1 mice. Further, these mice exhibit normal splenic B cell population and normal serum antibody levels. These mice, which exhibit precise humanization of high and low affinity hFCγR and humanization of heavy chain constant regions, represent a novel model to study human Fc receptor effector function.

Example 5

A Mouse Comprising Humanized Fc ε Receptor Alpha (Fc εRα) for Studying Human IgE Antibody Interactions The FcεR protein consists of a single α subunit, a β subunit, and two γ subunits. The extracellular portion of the α subunit, FcεRIα, comprises two immunoglobulin-like domains and binds IgE with high affinity, even in the absence of the other subunits. Therefore, in the strategy outlined below, FcεRIα, the α subunit of the FcεR was humanized.

The mouse FcεRIα locus, located on mouse chromosome 1, was humanized by construction of unique targeting vectors from human and mouse bacterial artificial chromosomes (BAC) DNA using VELOCIGENE® technology (see, e.g., U.S. Pat. No. 6,586,251 and Valenzuela et al. (2003) High-throughput engineering of the mouse genome couple with high-resolution expression analysis. Nat. Biotech. 21(6):652-659, both incorporated herein by reference). DNA from mouse BAC RP23-332i14 (Invitrogen-Thermo Fisher) was modified by homologous recombination to delete 5.7 Kb of mouse genomic DNA encoding the coding region of the mouse FcεRIα, and subsequently to insert 6.1 Kb of human FcεRIα coding sequence and human 3' untranslated region from BAC CTD-3064h17 (Invitrogen-Thermo Fisher) (FIG. 9). Thus, part of mouse coding exon 1, coding exon 2, coding exon 3, coding exon 4, and coding exon 5 of the mouse FcεRIα were replaced by part of human coding exon 1, coding exon 2, coding exon 3, coding exon 4, and coding exon 5 of the human FcεRIα gene. The resulting chimeric FcεRIα gene comprised chimeric mouse/human exon 1 (comprising mouse promoter and 5' UTR), human coding exons 2-5 through the stop codon, human 3'UTR and polyA, followed by the mouse 3'UTR and polyA. Chimeric gene exons 1 (partial) and 2 encode the signal peptide, exon 3 and 4 encode the two Ig-like domains of FcεRIα that are believed to interact with IgE, and exon 5 encodes the cytoplasmic and transmembrane domains of the protein (see FIG. 9).

Specifically, to generate humanized FcεRIα mice, the large targeting vector used in construction of the chimeric gene comprised the nucleic acid sequences listed in Table 12 below. Self-deleting neomycin cassette was inserted 3' of the last coding exon.

TABLE 12

Genome Coordinates for the FcεRIα Large Targeting Vector DNA

| Region | Genome coordinates (mouse: GRCm38, or human: GRCh38) | kb |
|---|---|---|
| 5' mouse homology arm | 1: 173,309,806-173,227,174 (−strand) | ~82.6 |
| Human gene (ATG-polyA) | 1: 159,302,358-159,308,425 (+strand) | ~6.1 |
| 3' mouse homology arm | 1: 173,221,426-173,138,062 (−strand) | ~83.4 |

The targeted BAC DNA was used to electroporate mouse ES cells comprising a deletion in mouse FcεRIα exons to create modified ES cells for generating mice that express humanized FcεRIα (FIG. 9). ES cells containing insertions of human FcεRIα exon sequences were identified by a quantitative TAQMAN™ assay (see, e.g., Lie and Petropoulos, 1998. Curr. Opin. Biotechnology 9:43-48, incorporated herein by reference). Specific primer sets and probes were designed for detecting insertion of human sequences (gain-of-allele, GOA) and deletion of mouse sequences (loss-of-allele, LOA) (not shown).

The junctions of the humanized FcεRIα allele prior to the selection cassette deletion are presented in Table 13 below.

TABLE 13

Junctions of the Humanized FcεRIα allele

| Junction | Sequence | SEQ ID NO: |
|---|---|---|
| Mouse 5' UTR/ human ATG | TTTTCGAAGCCATAGCTCTCTGGTGCAGTTAGCACCTGAAGGTGCAGGGGCG ATGAAGAAGATGGCTCCTGCCATGGAATCCCCTACTCTACTGTGTGTAGCCT | 17 |
| human/ 5' loxp | TCTTCTTCAGCTTACTAAATATGAACTTTCAGTTCTTGGCAGAATCAGGG <u>CTCGAG</u> *ATAACTTCGTATAATGTATGCTATACGAAGTTAT* | 18 |
| 3' loxp/ I-CeuI/ mouse 3' UTR | *ATAACTTCGTATAATGTATGCTATACGAAGTTAT* <u>GCTAGGTAACTATAACGGTCCTAAGGTAGCGAGCTAGC</u> CCTCAATAGCTTCTCCACTGTCAAAGGCCACTCATGTGATCCCTAGAAAA | 19 |

Bold sequences represent human DNA, underlined sequences are restriction enzyme sites or vector sequences, italicized sequences are loxP site sequences.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a humanized FcεRIα were identified by genotyping using a modification of allele assay (see above) that detects the presence of the unique human FcεRIα gene sequences. Heterozygous mice bearing a chimeric FcεRIα gene were bred to homozygosity.

The resultant FcεRIα protein expressed by the mice is completely human, and the sequence of the human FcεRIα protein expressed by the genetically modified mice is depicted below (SEQ ID NO:20), with Ig-like domains italicized and the signal peptide and transmembrane domain bold and underlined. The mature protein starts at amino acid 26 of the sequence depicted below. For reference, exemplary Genbank Accession Numbers for human and mouse protein and mRNA sequences are listed in Table 14 below.

SEQUENCE OF HUMAN PROTEIN (SEQ ID NO: 20)
<u>MAPAMESPTL LCVALLFFAP DGVLA</u>VPQKP *KVSLNPPWNR*

*IFKGENVTLT CNGNNFFEVS STKWFHNGSL SEETNSSLNI*

*VNAKFEDSGE YKCQHQQVNE SEPVYLEVFS DWLLLQASAE*

*VVMEGQPLFL RCHGWRNWDV YKVIYYKDGE ALKYWYENHN*

-continued

ISITNATVED SGTYYCTGKV WQLDYESEPL NITVIKAPRE

KYWLQFFIPL LVVILFAVDT GLFISTQQQV TFLLKIKRTR

KGFRLLNPHP KPNPKNN

TABLE 14

Genbank Accession Numbers for FCER1A

| Species | Protein | mRNA |
|---------|---------|------|
| Mouse | NP_034314 | NM_010184 |
| Human | NP_001992 | NM_002001 |

Figure 10:
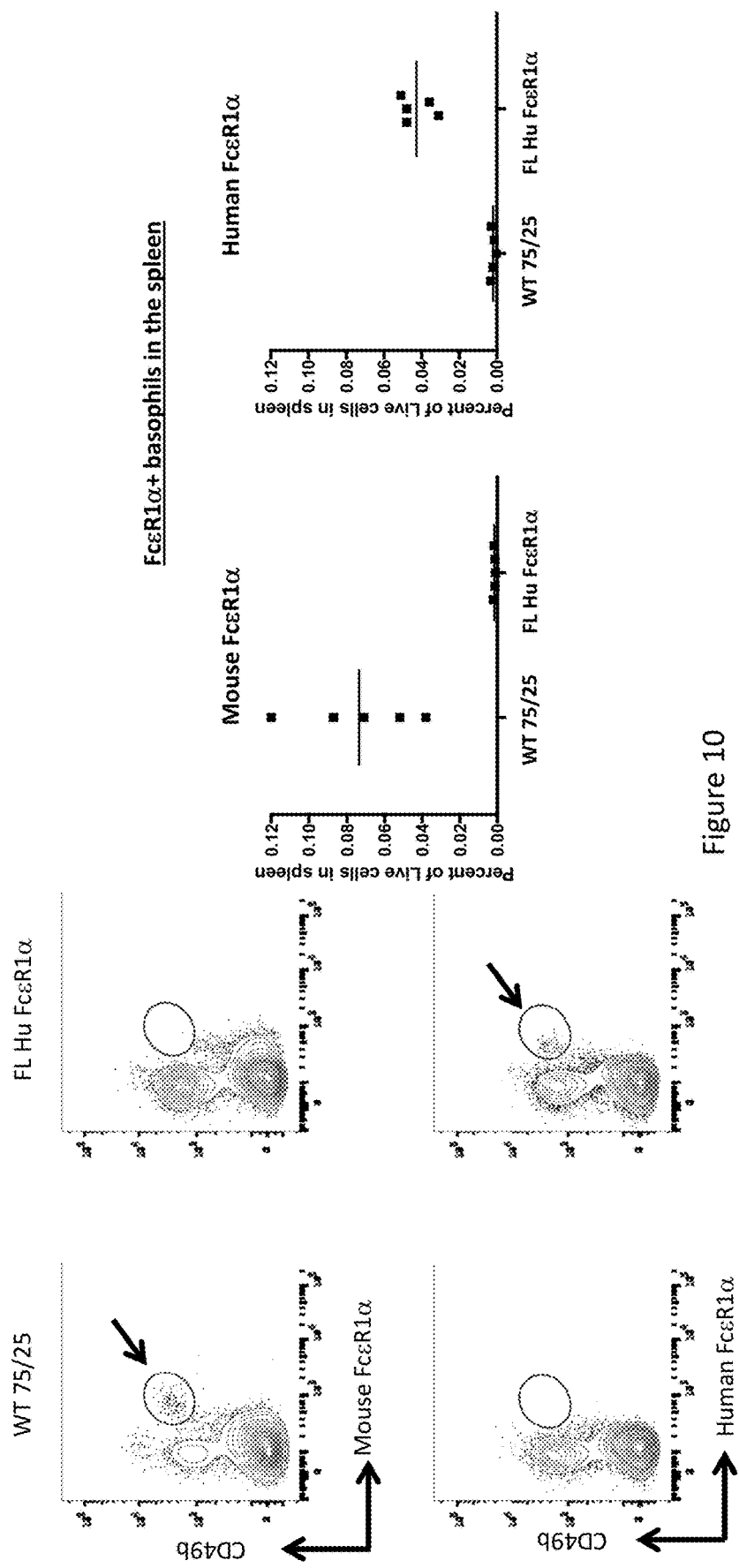
FIG. 10, on the left panel, shows a FACS plot demonstrating that humanized FcεR1α is expressed on the surface of basophils in exemplary mice comprising the humanized FcεR1α locus disclosed herein. On the right panel, the figure shows the percentage of mouse or human FcεR1α+ basophils present in the spleens of mice comprising the humanized FcεR1α locus disclosed herein compared to wild-type mice.

To validate expression of humanized FcεRIα on the surface of splenic basophils from humanized FcεRIα mice, wild type (WT) or homozygous humanized FcεRIα mice were sacrificed, the spleens were harvested and single cell suspensions were prepared following red blood cell lysis (Sigma). The cells were then stained with a live/dead cell marker, blocked by Fc block, followed by antibody staining with one of two antibody mixes: (1) mix 1: anti-mouse CD49b antibody (PECy7 conjugated, EBioscience clone DX5), anti-mouse TCRβ (APC conjugated, BD clone H57-597), anti-mouse B220 (BUV395 conjugated, BD clone RA3-682) and anti-mouse FcεRIα (eFluor 450 conjugated, EBioscience clone MAR-1) or (2) mix 2: anti-mouse CD49b antibody (PECy7 conjugated, EBioscience clone DX5), anti-mouse TCRβ (APC conjugated, BD clone H57-597), anti-mouse B220 (BUV395 conjugated, BD clone RA3-682) and anti-human FcεRIα (eFluor 450 conjugated, EBioscience clone AER-37(CRA1)). The cells were acquired in an LSRFortessa instrument and analyzed using FlowJo software. Basophils were identified as TCRβ– B220– CD49b+ FcεRIα+. The FACS plots in FIG. 10 show the TCRβ– B220– population, with the basophil population identified by arrows. This population is positive for mouse FcεRIα only in WT mice, and positive for human FcεRIα only in humanized FcεRIα mice. The graphs show the quantification of human or mouse FcεRIα+ basophils as percent of live cells in the spleens of 5 mice from of each genotype (FIG. 10).

Figure 11:
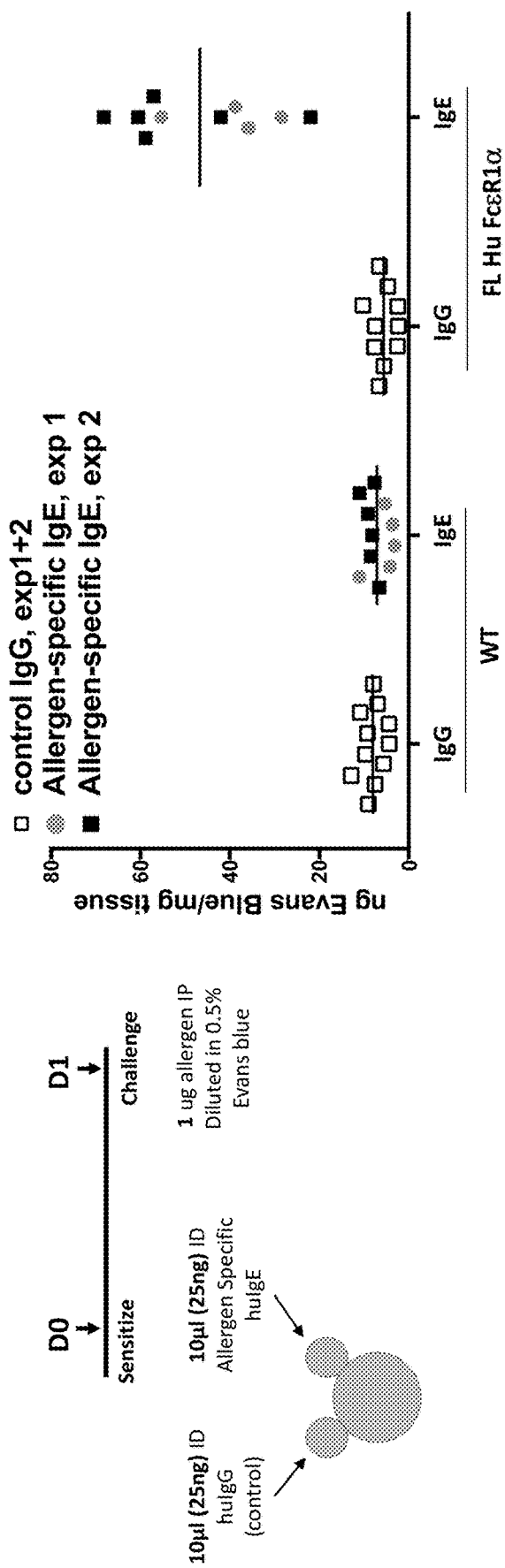
FIG. 11 shows that an exemplary humanized FcεR1α locus provided herein is functional. Mice were sensitized by intradermal ear injections with either human allergen-specific IgEs or IgG as a negative control. After 1 day, mice were challenged IV with allergen diluted in Evans blue dye. Evans blue dye extravasation in the ear was measured as a readout of mast cell degranulation. As human IgE does not bind to mouse FcεR1, the response in the mouse comprising the humanized FcεR1α locus indicates that a functional FcεR1α was produced.

FcεRIα humanized mice were validated in passive cutaneous anaphylaxis (PCA) model. On day 1, groups of WT or humanized mice received an intradermal injection with a cocktail of two allergen-specific human IgE antibodies, or an irrelevant IgG antibody (negative control) into the right and left ears, respectively, thus allowing allergen-specific IgE to bind FcεR on mast cells. After twenty-four hours, the mice were challenged by intravenous (IV) injection of 1 μg of allergen diluted in 0.5% Evan's blue dye. One hour after allergen challenge, mice were sacrificed, Evan's blue dye was extracted from ear tissue and spectrophotometrically quantitated using a standard curve. Ears were then dried and weighed. The results show Evan's blue dye extravasation in the tissue quantified as ng Evan's blue/mg tissue as a measure of local mast cell degranulation. The data, shown in FIG. 11, demonstrate that the human allergen-specific IgE can mediate a local anaphylactic response in humanized FcεRIα mice, but not in WT mice.

Figure 12:
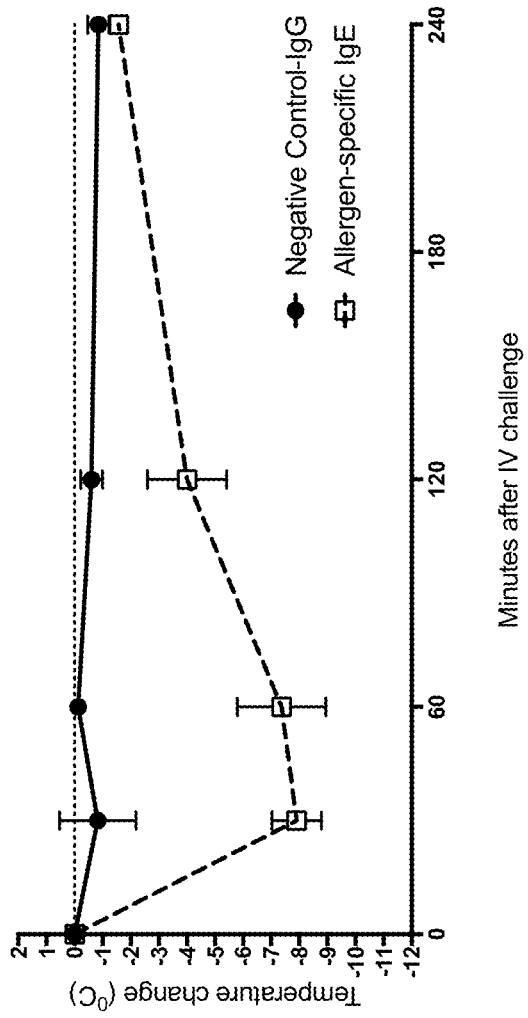
FIG. 12 shows that an exemplary humanized FcεR1α locus provided herein is functional. Mice were sensitized with an IV injection of human allergen-specific IgE. After 1 day, mice were challenged with an IV injection of allergen and temperature changes were monitored over a 4 hour time period after the injection. Temperature drop is a readout of systemic anaphylaxis.

FcεRIα humanized mice were also validated in passive systemic anaphylaxis (PSA) model. On day 1, groups of humanized FcεRIα mice received an intravenous (IV) injection with a cocktail of two allergen-specific human IgE antibodies, or an irrelevant IgG antibody (negative control), allowing allergen-specific IgE to bind FcεR1-expressing cells systemically. After twenty-four hours, basal core temperature measurements were taken for all the mice, followed by IV injection of 1 μg of allergen. Core temperature measurements were then taken for all the mice at 30, 60, 120 and 240 minutes after the allergen challenge, and changes in core temperature at each time point relative to basal temperature were calculated. A decrease in core temperature is a readout for systemic anaphylaxis. The data, shown in FIG. 12, demonstrate that the human allergen-specific IgE can mediate the systemic anaphylactic response in humanized FcεRIα mice, as measured by a significant drop in core temperature 30-60 minutes after challenge.

Example 6

Figure 13:
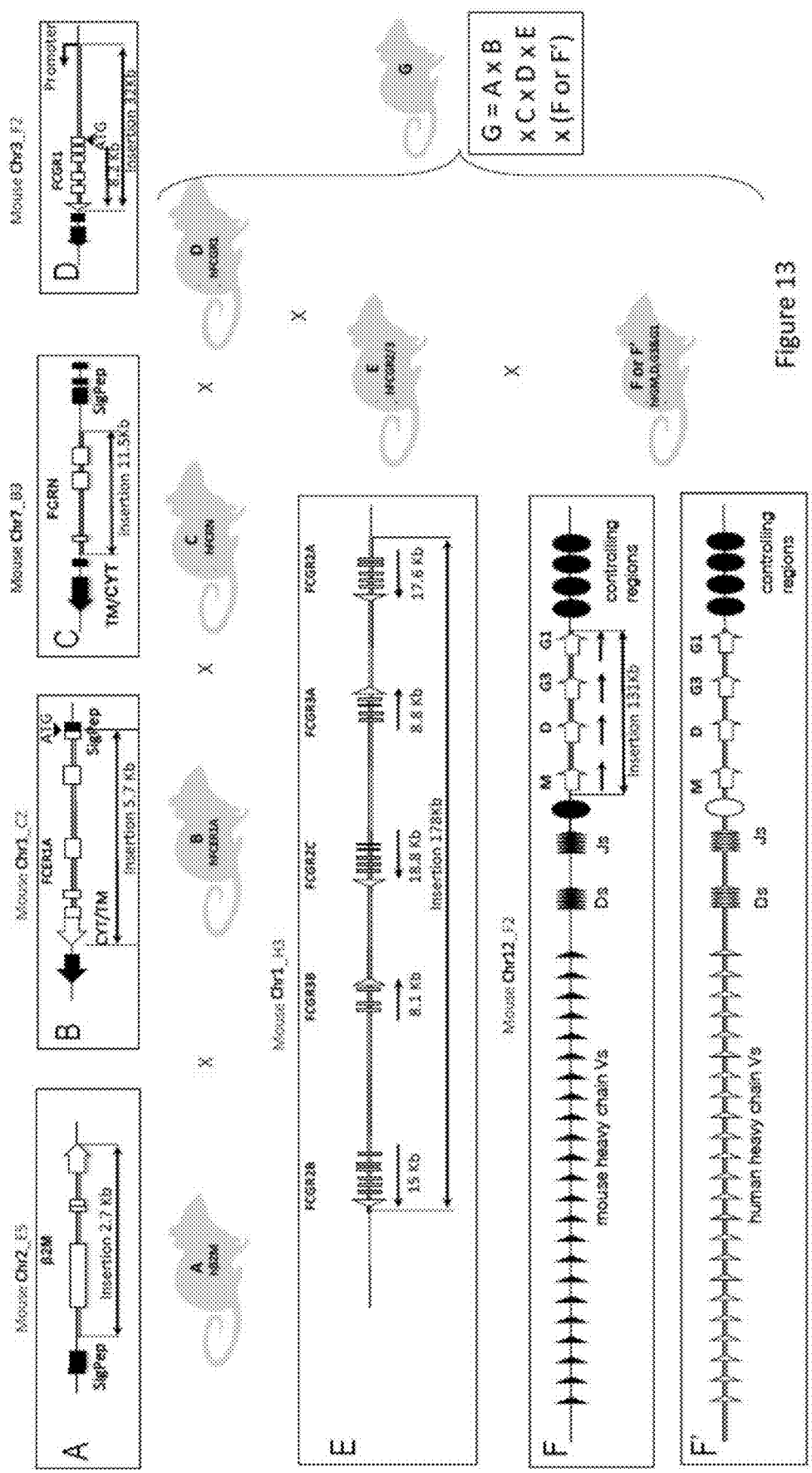
FIG. 13 shows a schematic summary, not to scale, of an exemplary method for the creation of mice comprising exemplary humanized FcRn, β2M, FcεR1α, FcγR1α (shown as FCGR1 in the figure), FcγRIIIa, FcγRIIa, FcγRIIc, FcγRIIb, FcγRIIIb, heavy chain constant region loci, and heavy chain variable region loci as described in Example 6. For simplicity, in loci F and F' only a small number of gene segments are represented schematically—for a full repertoire of possible present V, D, and J gene segments see imgt.org, Lefranc, M.-P., Exp. Clin. Immunogenet., 18, 100-116 (2001), and Lefranc, M.-P. and Lefranc, G., The Immunoglobulin FactsBook, Academic Press, London, 458 pages (2001), incorporated herein by reference. Empty shapes and double lines represent human sequences and filled shapes and single lines represent mouse sequences.

A Master Mouse for Studying Human Fc Receptor Interactions and Efficacy of Human Therapeutic Antibodies In order to obtain better model for studying fully human monoclonal antibodies in a mouse model and human Fc receptor effector function, mice A (humanized hβ2M; see Example 3), mice B (hFCER1A; see Example 5), mice C (hFCRN; See Example 3), mice D (hFCGR1), mice E (hFCGR2/3) and mice F (mVs, hIgM, hIgD, IgG3 and IgG1; mouse locus 7 of FIG. 1A) or alternatively mice F' (hVs, hIgM, hIgD, IgG3 and IgG1; mouse locus 5 of FIG. 1A) as described in FIG. 13, are combined together by breeding or retargeting of ES cells in accordance with the techniques described herein and known in the art. The resultant mice may be heterozygous or homozygous for any or all of these genes. Various exemplary embodiments of the humanized loci described herein are depicted in FIG. 13. Other mice with human heavy chain constant regions depicted in FIG. 1A may be bred to the remaining mice (mice A-E) in FIG. 13, Thus, mice A (humanized hb2M; see Example 3), mice B (hFCER1A; see Example 5), mice C (hFCRN; See Example 3), mice D (hFCGR1), mice E (hFCGR2/3) and mice (mVs, hIgM, hIgD, IgG3, IgG1, IgG2, and IgG4; mouse locus 8 of FIG. 1A) or alternatively mice (hVs, hIgM, hIgD, IgG3 IgG1, IgG2, and IgG4; mouse locus 6 of FIG. 1A) are combined together by breeding or retargeting of ES cells in accordance with the techniques described herein and known in the art. These may also be bred to light chain mice depicted in FIG. 2A. Additional human immunoglobulin constant regions are added via genetic engineering techniques described in Example 1 and known in the art.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of using a genetically modified mouse to determine the therapeutic effect of a human immunoglobulin G1 (IgG1) antibody, the method comprising:
   (a) administering the human IgG1 antibody to a genetically modified mouse whose genome comprises a replacement of an endogenous nucleic acid sequence encoding immunoglobulin G2a (IgG2a) heavy chain constant domain 1 ($C_H1$), hinge (H), heavy chain constant domain 2 ($C_H2$), and heavy constant domain 1 ($C_H3$) with nucleic acids encoding human IgG1 $C_H1$, H, $C_H2$, and $C_H3$ domains, wherein the mouse functionally expresses IgG antibodies comprising the human IgG1 $C_H1$, H, $C_H2$, and $C_H3$ domains, has decreased mouse-anti-human antibody response to human IgG1 antibodies compared to a mouse that does not functionally express IgG antibodies comprising the human IgG1 $C_H1$, H, $C_H2$, and $C_H3$ domains, and has a disease symptom; and
   (b) determining the therapeutic effect of the human IgG1 antibody on the disease symptom.

2. The method of claim 1, wherein the genome of the mouse further comprises a replacement of nucleic acid sequence encoding an endogenous IgG2a transmembrane (TM) domain and an IgG2a cytoplasmic (CYT) domain with a nucleic acid sequence encoding human IgG1 TM and CYT domains.

3. The method of claim 1, wherein the genome of the mouse further comprises a full repertoire of endogenous mouse heavy chain variable, heavy chain diversity, and heavy chain joining gene segments operably linked to the nucleic acid sequence encoding the IgG1 $C_H1$, H, $C_H2$, and $C_H3$ domains.

4. The method of claim 3, wherein the mouse functionally expresses IgG antibodies comprising a mouse heavy chain variable domain and the human IgG1 $C_H1$, H, $C_H2$, and $C_H3$ domains.

5. The method of claim 1, wherein the genome of the mouse further comprises a full repertoire of human heavy chain variable, heavy chain diversity, and heavy chain joining gene segments operably linked to the nucleic acid sequence encoding the IgG1 $C_H1$, H, $C_H2$, and $C_H3$ domains.

6. The method of claim 5, wherein the mouse functionally expresses IgG antibodies comprising a human heavy chain variable domain and the human IgG1 $C_H1$, H, $C_H2$, and $C_H3$ domains.

7. The method of claim 1, wherein the method further comprises measuring the immune response generated by the mouse against the human IgG1 antibody.

8. The method of claim 1, wherein the mouse further comprises in its genome a replacement of an endogenous kappa constant region gene with a human kappa constant region gene, wherein the mouse functionally expresses an antibody comprising a human kappa constant domain and the human IgG1 antibody comprises a human κ light chain.

9. A method of using a genetically modified mouse to determine the therapeutic effect of a human immunoglobulin G4 (IgG4) antibody, the method comprising:
   (a) administering the human IgG4 antibody to a genetically modified mouse whose genome comprises a replacement of an endogenous nucleic acid sequence encoding immunoglobulin G1 (IgG1) heavy chain constant domain 1 ($C_H1$), hinge (H), heavy chain constant domain 2 ($C_H2$), and heavy constant domain 1 ($C_H3$) with nucleic acids encoding human IgG4 $C_H1$, H, $C_H2$, and $C_H3$ domains, wherein the mouse functionally expresses IgG antibodies comprising the human IgG4 $C_H1$, H, $C_H2$, and $C_H3$ domains, has decreased mouse-anti-human antibody response to human IgG4 antibodies compared to a mouse that does not functionally express IgG antibodies comprising the human IgG4 $C_H1$, H, $C_H2$, and $C_H3$ domains, and has a disease symptom; and
   (b) determining the therapeutic effect of the human IgG1 antibody on the disease symptom.

10. The method of claim 9, wherein the genome of the mouse further comprises a replacement of nucleic acid sequence encoding an endogenous IgG4 transmembrane (TM) domain and an IgG4 cytoplasmic (CYT) domain with a nucleic acid sequence encoding human IgG1 TM and CYT domains.

11. The method of claim 9, wherein the genome of the mouse further comprises a full repertoire of endogenous mouse heavy chain variable, heavy chain diversity, and heavy chain joining gene segments operably linked to the nucleic acid sequence encoding the IgG4 $C_H1$, H, $C_H2$, and $C_H3$ domains.

12. The method of claim 11, wherein the mouse functionally expresses IgG antibodies comprising a mouse heavy chain variable domain and the human IgG4 $C_H1$, H, $C_H2$, and $C_H3$ domains.

13. The method of claim 9, wherein the genome of the mouse further comprises a full repertoire of human heavy chain variable, heavy chain diversity, and heavy chain joining gene segments operably linked to the nucleic acid sequence encoding the IgG4 $C_H1$, H, $C_H2$, and $C_H3$ domains.

14. The method of claim 13, wherein the mouse functionally expresses IgG antibodies comprising a human heavy chain variable domain and the human IgG4 $C_H1$, H, $C_H2$, and $C_H3$ domains.

15. The method of claim 9, wherein the method further comprises measuring the immune response generated by the mouse against the human IgG4 antibody.

16. The method of claim 9, wherein the mouse further comprises in its genome a replacement of an endogenous kappa constant region gene with a human kappa constant region gene, wherein the mouse functionally expresses an antibody comprising a human kappa constant domain and the human IgG4 antibody comprises a human κ light chain.

17. A method of using a genetically modified mouse to determine the therapeutic effect of a human antibody, the method comprising:
(a) administering the human antibody to a genetically modified mouse whose genome comprises a replacement of an endogenous nucleic acid sequence comprising immunoglobulin (Ig) constant mu ($C_\mu$), constant delta ($C_\delta$), constant gamma 3 ($C_{\gamma 3}$), constant gamma 1 ($C_{\gamma 1}$), constant gamma 2b ($C_{\gamma 2b}$), a constant gamma 2a ($C_{\gamma 2a}$), constant epsilon ($C_\varepsilon$), and constant alpha ($C_\alpha$) heavy chain genes with a nucleic acid sequence comprising human $C_\mu$, $C_\delta$, $C_{\gamma 3}$, $C_{\gamma 1}$ heavy chain genes,
wherein the mouse functionally expresses IgM antibodies comprising a human constant domain, IgD antibodies comprising a human constant domain, IgG3 antibodies comprising a human constant domain, and IgG1 antibodies comprising a human constant domain, has decreased mouse-anti-human-antibody response to human kW antibodies, human IgD antibodies, human IgG3 antibodies, and human IgG1 antibodies as compared to a mouse that does not functionally expresses IgM antibodies comprising a human constant domain, IgD antibodies comprising a human constant domain, IgG3 antibodies comprising a human constant domain, and IgG1 antibodies comprising a human constant domain, and has a disease symptom;
(b) determining the therapeutic effect of the human antibody on the disease symptom.

18. The method of claim 17, wherein the replacement further comprises a nucleic acid sequence comprising human Ig constant gamma 2 ($C_{\gamma 2}$) and constant gamma 4 ($C_{\gamma 4}$) genes, the mouse functionally expresses IgG2 antibodies comprising a human constant domain and IgG4 antibodies comprising a human constant domain, and has decreased mouse-anti-human-antibody response to human IgG2 antibodies and human IgG4 antibodies as compared to a mouse that does not functionally expresses IgG2 antibodies comprising a human constant domain and IgG4 antibodies comprising a human constant domain.

19. The method of claim 17, wherein the human antibody is a human IgD antibody, a human IgM antibody, a human IgG1 antibody, or a human IgG3 antibody.

20. The method of claim 18, wherein the human antibody is a human IgD antibody, a human IgM antibody, a human IgG1 antibody, a human IgG3 antibody, a human IgG2 antibody or a human IgG4 antibody.

* * * * *

SEQUENCE LISTING

<160> NUMBER OF SEQ ID NOS: 20

<210> SEQ ID NO 1
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgggactcag gttgggtgcg tctgatggag taactgagcc tgggggcttg gggagccaca    60
tttggacgag atgcctgaac                                                80

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taacagagaa tggagaatgg cgatgacttc taccaagcac cggtataact tcgtataagg    60
tatcctatac gaagttat                                                  78

<210> SEQ ID NO 3
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcgcgccat aacttcgtat aaggtatcct atacgaagtt atctcgagag gtggcagtca    60
tggagatggt ggggtacagg gtggggc                                        88

<210> SEQ ID NO 4
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
tctgtgccta gttaacagag aatggagaat ggcgatgact tctaccaagc cgccggcgac    60
tcatcaccaa ggggaagatg ctcaatcatt catgagggat ctgccccc               108

<210> SEQ ID NO 5
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgctcttta tcttattaac taaggtgtcg taaccagttc aaagtggaat taccggtata    60
acttcgtata aggtatccta tacgaagtta t                                   91

<210> SEQ ID NO 6

-continued

```
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ataacttcgt ataaggtatc ctatacgaag ttatctcgag gcggccgcag gtggcagtca    60
tggagatggt ggggtacagg gtgggggcag gggcactc                           98

<210> SEQ ID NO 7
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ttaaatgaat gcaattatct agacttattt cagttgaaca tgctggttgg gcggccgctg    60
gcataagaga aaactcaatc agatagtgct gaagacagga ctgtggag               108

<210> SEQ ID NO 8
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tctgtgccta gttaacagag aatggagaat ggcgatgact tctaccaagc accggtataa    60
cttcgtataa ggtatcctat acgaagttat                                    90

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ataacttcgt ataaggtatc ctatacgaag ttatctcgag aggtggcagt catggagatg    60
gtggggtaca gggtgggggc aggggcactc                                    90

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
aaacaacaag attgtatata tgtgcatcct ggccccattg ttccttatct gggataagca    60
tgctgttttc tgtctgtccc taacatgccc tgtgattatc                        100

<210> SEQ ID NO 11
<211> LENGTH: 90
<212> TYPE: DNA
<213> ORGANISM: Artificial Sequence
<220> FEATURE:
```

<223> OTHER INFORMATION: Description of Artificial Sequence: Synthetic
       oligonucleotide

<400> SEQUENCE: 11
tctgttgttt taccaactac tcaatttctc ttataaggga ctaaatatgt accggtataa    60
cttcgtataa tgtatgctat acgaagttat                                     90

<210> SEQ ID NO 12
<211> LENGTH: 106
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 12
ataacttcgt ataatgtatg ctatacgaag ttatgtcgac ctcgagaatc caccacactt    60
aaaggataaa taaaccctc acttgccct ggttggctgt ccacta                    106

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 13
ctttctgggt gtctgtcccc ttctctctgg aggatcatgg cacttcagat ctgtcccctc    60
tctctgaatc tgtcccctc cctccataat agattcttct                         100

<210> SEQ ID NO 14
<211> LENGTH: 135
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 14
tctccccact gcactggcac agccccgcct tgccgctgct gatccattgc cggtgtgacc    60
cgggctcgat aactataacg gtcctaaggt agcgactcga gataacttcg tataatgtat   120
gctatacgaa gttat                                                   135

<210> SEQ ID NO 15
<211> LENGTH: 100
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 15
ataacttcgt ataatgtatg ctatacgaag ttatcctagg ttggagctcg tgtgagaggg    60
gagagcagag gtgagtctgt gccatgggat acttgtggcg                        100

<210> SEQ ID NO 16
<211> LENGTH: 363
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 16

Met Gly Met Pro Leu Pro Trp Ala Leu Ser Leu Leu Val Leu Leu
1               5                   10                  15

Pro Gln Thr Trp Gly Ser Glu Ser His Leu Ser Leu Leu Tyr His Leu
            20                  25                  30

Thr Ala Val Ser Ser Pro Ala Pro Gly Thr Pro Ala Phe Trp Val Ser
            35                  40                  45

Gly Trp Leu Gly Pro Gln Gln Tyr Leu Ser Tyr Asn Ser Leu Arg Gly
50                  55                  60

Glu Ala Glu Pro Cys Gly Ala Trp Val Trp Glu Asn Gln Val Ser Trp
65                  70                  75                  80

Tyr Trp Glu Lys Glu Thr Thr Asp Leu Arg Ile Lys Glu Lys Leu Phe
                85                  90                  95

Leu Glu Ala Phe Lys Ala Leu Gly Gly Lys Gly Pro Tyr Thr Leu Gln
            100                 105                 110

Gly Leu Leu Gly Cys Glu Leu Gly Pro Asp Asn Thr Ser Val Pro Thr
        115                 120                 125

Ala Lys Phe Ala Leu Asn Gly Glu Glu Phe Met Asn Phe Asp Leu Lys
130                 135                 140

Gln Gly Thr Trp Gly Gly Asp Trp Pro Glu Ala Leu Ala Ile Ser Gln
145                 150                 155                 160

Arg Trp Gln Gln Gln Asp Lys Ala Ala Asn Lys Glu Leu Thr Phe Leu
                165                 170                 175

Leu Phe Ser Cys Pro His Arg Leu Arg Glu His Leu Glu Arg Gly Arg
            180                 185                 190

Gly Asn Leu Glu Trp Lys Glu Pro Pro Ser Met Arg Leu Lys Ala Arg
        195                 200                 205

Pro Ser Ser Pro Gly Phe Ser Val Leu Thr Cys Ser Ala Phe Ser Phe
210                 215                 220

Tyr Pro Pro Glu Leu Gln Leu Arg Phe Leu Arg Asn Gly Leu Ala Ala
225                 230                 235                 240

Gly Thr Gly Gln Gly Asp Phe Gly Pro Asn Ser Asp Gly Ser Phe His
                245                 250                 255

Ala Ser Ser Ser Leu Thr Val Lys Ser Gly Asp Glu His His Tyr Cys
            260                 265                 270

Cys Ile Val Gln His Ala Gly Leu Ala Gln Pro Leu Arg Val Glu Leu
        275                 280                 285

Asp Ser Ser Ala Arg Ser Ser Val Pro Val Val Gly Ile Val Leu Gly
290                 295                 300

Leu Leu Leu Val Val Val Ala Ile Ala Gly Val Leu Leu Trp Gly
305                 310                 315                 320

Arg Met Arg Ser Gly Leu Pro Ala Pro Trp Leu Ser Leu Ser Gly Asp
                325                 330                 335

Asp Ser Gly Asp Leu Leu Pro Gly Gly Asn Leu Pro Pro Glu Ala Glu
            340                 345                 350

Pro Gln Gly Ala Asn Ala Phe Pro Ala Thr Ser
        355                 360

<210> SEQ ID NO 17
<211> LENGTH: 104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
ttttcgaagc catagctctc tggtgcagtt agcacctgaa ggtgcagggg cgatgaagaa    60
gatggctcct gccatggaat cccctactct actgtgtgta gcct                    104

<210> SEQ ID NO 18
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcttcttcag cttactaaat atgaactttc agttcttggc agaatcaggg ctcgagataa    60
cttcgtataa tgtatgctat acgaagttat                                    90

<210> SEQ ID NO 19
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ataacttcgt ataatgtatg ctatacgaag ttatgctagg taactataac ggtcctaagg    60
tagcgagcta gccctcaata gcttctccac tgtcaaaggc cactcatgtg atccctagaa    120
aa                                                                  122

<210> SEQ ID NO 20
<211> LENGTH: 257
<212> TYPE: PRT
<213> ORGANISM: Homo sapiens

<400> SEQUENCE: 20

Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys

-continued

```
                165                 170                 175
Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
        210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn
```